(12) United States Patent
Senger et al.

(10) Patent No.: US 10,731,169 B2
(45) Date of Patent: Aug. 4, 2020

(54) GENE EXPRESSION OR ACTIVITY ENHANCING ELEMENTS

(71) Applicant: BASF PLANT SCIENCE COMPANY GMBH, Ludwigshafen (DE)

(72) Inventors: Toralf Senger, Durham, NC (US); Joerg Bauer, Durham, NC (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 105 days.

(21) Appl. No.: 14/902,715

(22) PCT Filed: Jul. 3, 2014

(86) PCT No.: PCT/IB2014/062816
§ 371 (c)(1),
(2) Date: Jan. 4, 2016

(87) PCT Pub. No.: WO2015/001505
PCT Pub. Date: Jan. 8, 2015

(65) Prior Publication Data
US 2016/0168584 A1    Jun. 16, 2016

(30) Foreign Application Priority Data
Jul. 5, 2013  (EP) ..................... 13175398

(51) Int. Cl.
C12N 15/82    (2006.01)
C12N 15/113   (2010.01)

(52) U.S. Cl.
CPC ........ *C12N 15/8216* (2013.01); *C12N 15/113* (2013.01)

(58) Field of Classification Search
None
See application file for complete search history.

(56) References Cited

U.S. PATENT DOCUMENTS

| | | | |
|---|---|---|---|
| 4,945,050 A | 7/1990 | Sanford et al. | |
| 7,473,820 B2* | 1/2009 | Qiu ..................... | C07K 14/415 435/134 |
| 7,544,859 B2 | 6/2009 | Heinz et al. | |
| 8,049,064 B2 | 11/2011 | Cirpus et al. | |
| 8,134,046 B2 | 3/2012 | Cirpus et al. | |
| 8,455,035 B2* | 6/2013 | Rein ..................... | A23D 9/00 426/601 |
| 8,648,183 B2 | 2/2014 | Suzuki et al. | |
| 8,710,299 B2 | 4/2014 | Bauer et al. | |
| 8,785,163 B2* | 7/2014 | Senger ............... | C12N 15/8247 435/134 |
| 8,853,383 B2 | 10/2014 | Bauer et al. | |
| 8,901,374 B2* | 12/2014 | Bauer ................ | C12N 15/8247 435/134 |
| 9,090,902 B2* | 7/2015 | Bauer ..................... | C12N 9/00 |
| 9,150,871 B2 | 10/2015 | Kuhn et al. | |
| 9,428,757 B2 | 8/2016 | Senger et al. | |
| 9,433,228 B2 | 9/2016 | Zank et al. | |
| 2003/0159174 A1* | 8/2003 | Qiu ..................... | C07K 14/415 800/281 |
| 2003/0172398 A1 | 9/2003 | Browse | |
| 2008/0076166 A1 | 3/2008 | Cirpus et al. | |
| 2010/0227924 A1 | 9/2010 | Cirpus et al. | |
| 2010/0263088 A1 | 10/2010 | Bauer et al. | |
| 2011/0035841 A1* | 2/2011 | Plesch ................ | C12N 15/8242 800/281 |
| 2011/0039010 A1* | 2/2011 | Rein ........................ | A23D 9/00 426/607 |
| 2012/0167248 A1 | 6/2012 | Kuhn et al. | |
| 2013/0263330 A1 | 10/2013 | Loyall et al. | |
| 2014/0230087 A1 | 8/2014 | Hartig et al. | |
| 2015/0052636 A1 | 2/2015 | Hartig et al. | |
| 2017/0335338 A1* | 11/2017 | Andre ................ | C12N 15/8247 |

FOREIGN PATENT DOCUMENTS

| CA | 2559360 | 9/2005 |
|---|---|---|
| CN | 1650009 A | 8/2005 |

(Continued)

OTHER PUBLICATIONS

Benfey et al. Tissue-specific expression from CaMV 35S enhancer subdomains in early stages of plant development. The EMBO Journal. 1990. 9(6): 1677-1684.*

Kim et al. Seed-specific expression of sesame microsomal oleic acid desaturase is controlled by combinatorial properties between negative cis-regulatory elements in the SeFAD2 promoter and enhancers in the 5'-UTR intron. Molecular Genetics and Genomics. 2006. 274(4): 351-368.*

(Continued)

*Primary Examiner* — Ashley K Buran
(74) *Attorney, Agent, or Firm* — Marshall, Gerstein & Borun LLP

(57) ABSTRACT

The present invention relates to transgenic nucleic acids, expression cassettes, vectors, plant cells, plant organs and plants. The invention also relates to methods for increasing expression or activity of a target gene, particularly in a plant cell or plant organ, and also to uses of recombinant nucleic acids and expression cassettes to increase expression or activity of a target gene or for manufacturing of a vector, plant cell, plant organ or plant. Incidentally, the invention relates to enhancers for achieving increased expression or activity of a target gene, particularly in a plant cell or plant organ, when operably linked to a promoter functional in such plant cell, plant organ or plant. The invention is described herein with reference to the technical field of production of polyunsaturated fatty acids (PUFAs), without being limited to this technical field.

For the production of desired molecules in plant cells, e.g. PUFAs, it is frequently required to express a target gene heterologous to the plant cell, or to overexpress a target gene naturally found in said plant cell.

8 Claims, 49 Drawing Sheets

Specification includes a Sequence Listing.

(56) References Cited

FOREIGN PATENT DOCUMENTS

| | | | |
|---|---|---|---|
| CN | 102643840 A | 8/2012 | |
| WO | WO-01/012316 A1 | 2/2001 | |
| WO | WO-01/16340 A1 | 3/2001 | |
| WO | WO2001016340 * | 3/2001 | ............ C12N 15/82 |
| WO | WO-01/059128 A2 | 8/2001 | |
| WO | WO-01/85968 A2 | 11/2001 | |
| WO | WO-02/26946 A2 | 4/2002 | |
| WO | WO-02/077213 A2 | 10/2002 | |
| WO | WO-02/102970 A2 | 12/2002 | |
| WO | WO-2005/012316 A2 | 2/2005 | |
| WO | WO-2005/083093 A2 | 9/2005 | |
| WO | WO-2006/069710 A1 | 7/2006 | |
| WO | WO-2006/100241 A2 | 9/2006 | |
| WO | WO-2007/017419 A2 | 2/2007 | |
| WO | WO-2007/042510 A2 | 4/2007 | |
| WO | WO-2007/051577 A2 | 5/2007 | |
| WO | WO-2007/096387 A1 | 8/2007 | |
| WO | WO-2007/133425 A2 | 11/2007 | |
| WO | WO-2008/040787 A2 | 4/2008 | |
| WO | WO-2009/077478 | 6/2009 | |
| WO | WO-2009/130291 A2 | 10/2009 | |
| WO | WO-2010/000708 A2 | 1/2010 | |
| WO | WO-2011/023537 A1 | 3/2011 | |
| WO | WO-2011/023539 A1 | 3/2011 | |
| WO | WO-2011/023800 A1 | 3/2011 | |
| WO | WO-2012/077020 A1 | 6/2012 | |
| WO | WO-2013/005152 A1 | 1/2013 | |
| WO | WO-2013/038294 A1 | 3/2013 | |

OTHER PUBLICATIONS

McElroy et al. Construction of expression vectors based on the rice actin 1 (Act1) 5' region for use in monocot transformation. Molecular and General Genetics MCG. 1991. 231(1): 150-160.*

Sandhu et al. A/T-rich sequences act as quantative enhancers of gene expression expression in transgenic tobacco and potato plants. Plant Molecular Biology. 1998. 37: 885-896.*

Li et al. Bi-directional Duplex Promoters with Duplicated Enhancers Significantly Increase Transgene Expression in Grape and Tobacco. Transgenic Research. 2004. 13(2): 143-154.*

Rombauts et al. PlantCARE, a plant cis-acting regulatory element database. Nucleic Acids Research. 1999. 27(1): 295-296.*

Ross et al. Activation of the Oryza sativa non-symbiotic haemoglobin-2 promoter by the cytokinin-regulated transcription factor, ARR1. Journal of Experimental Biology. 2004. 55(403): 1721-1731.*

Deblaere et al., Efficient octopine Ti plasmid-derived vectors for Agrobacterium-mediated gene transfer to plants, Nucleic Acids Res., 13(13):4777-88 (1985).

Heckman et al., Gene splicing and mutagenesis by PCR-driven overlap extension, Nat. Protoc., 2(4):924-32 (2007).

Hellens et al., Technical Focus:a guide to Agrobacterium binary Ti vectors, Trends Plant Sci., 5(10):446-51 (2000).

International Preliminary Report on Patentability, International Application No. PCT/IB2014/062816, dated Jan. 5, 2016.

International Search Report and Written Opinion, International Application No. PCT/IB2014/062816, dated Jan. 6, 2015.

Kozak, An analysis of 5'-noncoding sequences from 699 vertebrate messenger RNAs, Nucleic Acids Res., 15(20):8125-48 (1987).

Luo et al., Construction and application of an *Escherichia coli* high effective expression vector with an enhancer (English-language abstract), Chinese J. Biotechnol., 16(5):578-81 (2000).

Moloney et al., High efficiency transformation of *Brassica napus* usingAgrobacterium vectors, Plant Cell Rep., 8(4):238-42 (1989).

Murashige et al., A revised medium for rapid growth and bio assays with tobacco tissue cultures, Physiol. Plant., 15:473-97 (1962).

Van der Geest et al., A 68 bp element of the beta-phaseolin promoter functions as a seed-specific enhancer, Plant Mol. Biol., 32(4):579-88 (1996).

Xie et al., Bidirectionalization of polar promoters in plants, Nat. Biotechnol., 19(7):677-9 (2001).

Extended European Search Report, European patent application No. 14819406.1, dated Mar. 8, 2017.

"P-LuCnINEENAss14 fusion DNA SEQ ID:3", EBI Accession No. GSN:AZF58412 (Apr. 14, 2011).

* cited by examiner

Figure 1: Schematical figure of the different enzymatic activities leading to the production of ARA and EPA. The conversion efficiency of the delta-5-desaturase reporter gene used in this invention is calculated as desaturation products / (sum of desaturation substrates and products)

Figure 2 Strategy employed for stepwise buildup of plant expression plasmids of the invention

Figure 4: List of sequences

>SEQ-1;promoter_plus_untranslated_region_incl_enhancer
ttagcagatatttggtgtctaaatgtttattttgtgatatgttcatgtttgaaatggtggtttcgaaaccagggacaacgttgggatctgatagggtgtcaaagagt
attatggattgggacaatttcggtcatgagttgcaaattcaagtatatcgttcgattatgaaaattttcgaagaatatcccatttgagagagtctttacctcattaat
gtttttagattatgaaattttatcatagttcatcgtagtcttttggtgtaaaggctgtaaaaagaaattgttcacttttgttttcgtttatgtgaaggctgtaaaagattgt
aaaagactattttggtgttttggataaaatgatagtttttatagattcttttgctttagaagaaatacatttgaaattttttccatgttgagtataaaataccgaaatcg
attgaagatcatagaaatattttaactgaaaacaaatttataactgattcaattctctccattttatacctatttaaccgtaatcgattctaatagatgatcgattttt
atataatcctaattaaccaacggcatgtattggataattaaccgatcaactctcacccctaatagaatcagtatttccttcgacgttaattgatcctacactatgt
aggtcatatccatcgttttaattttggccaccattcaattctgtcttgcctttagggatgtgaatatgaacggccaaggtaagagaataaaaataatccaaatt
aaagcaagagaggccaagtaagataatccaaatgtacacttgtcattgccaaaattagtaaaatactcggcatattgtatcccacacattattaaaatacc
gtatatgtattggctgcatttgcatgaataatactacgtgtaagcccaaaagaacccacgtgtagcccatgcaaagttaacactcacgaccccattcctcag
tctccactatataaacccaccatccccaatctcaccaaacccaccacacaactcacaactcactctcacaccttaaagaaccaatcaccaccaaaaa >SEQ-2;promoter_1039_plus_38pb_without_enhancer
ttagcagatatttggtgtctaaatgtttattttgtgatatgttcatgtttgaaatggtggtttcgaaaccagggacaacgttgggatctgatagggtgtcaaagagt
attatggattgggacaatttcggtcatgagttgcaaattcaagtatatcgttcgattatgaaaattttcgaagaatatcccatttgagagagtctttacctcattaat
gtttttagattatgaaattttatcatagttcatcgtagtcttttggtgtaaaggctgtaaaaagaaattgttcacttttgttttcgtttatgtgaaggctgtaaaagattgt
aaaagactattttggtgttttggataaaatgatagtttttatagattcttttgctttagaagaaatacatttgaaattttttccatgttgagtataaaataccgaaatcg
attgaagatcatagaaatattttaactgaaaacaaatttataactgattcaattctctccattttatacctatttaaccgtaatcgattctaatagatgatcgattttt
atataatcctaattaaccaacggcatgtattggataattaaccgatcaactctcacccctaatagaatcagtatttccttcgacgttaattgatcctacactatgt
aggtcatatccatcgttttaattttggccaccattcaattctgtcttgcctttagggatgtgaatatgaacggccaaggtaagagaataaaaataatccaaatt
aaagcaagagaggccaagtaagataatccaaatgtacacttgtcattgccaaaattagtaaaatactcggcatattgtatcccacacattattaaaatacc
gtatatgtattggctgcatttgcatgaataatactacgtgtaagcccaaaagaacccacgtgtagcccatgcaaagttaacactcacgaccccattcctcag
tctccactatataaacccaccatccccaatctcaccaaacccaccacacaactcacaactcactctcacaccttctagaggatctgatatcgcggccgcg
gcgcgccacc >SEQ-3
ttagcagatatttggtgtctaaatgtttattttgtgatatgttcatgtttgaaatggtggtttcgaaaccagggacaacgttgggatctgatagggtgtcaaagagt
attatggattgggacaatttcggtcatgagttgcaaattcaagtatatcgttcgattatgaaaattttcgaagaatatcccatttgagagagtctttacctcattaat
gtttttagattatgaaattttatcatagttcatcgtagtcttttggtgtaaaggctgtaaaaagaaattgttcacttttgttttcgtttatgtgaaggctgtaaaagattgt
aaaagactattttggtgttttggataaaatgatagtttttatagattcttttgctttagaagaaatacatttgaaattttttccatgttgagtataaaataccgaaatcg
attgaagatcatagaaatattttaactgaaaacaaatttataactgattcaattctctccattttatacctatttaaccgtaatcgattctaatagatgatcgattttt
atataatcctaattaaccaacggcatgtattggataattaaccgatcaactctcacccctaatagaatcagtatttccttcgacgttaattgatcctacactatgt
aggtcatatccatcgttttaattttggccaccattcaattctgtcttgcctttagggatgtgaatatgaacggccaaggtaagagaataaaaataatccaaatt
aaagcaagagaggccaagtaagataatccaaatgtacacttgtcattgccaaaattagtaaaatactcggcatattgtatcccacacattattaaaatacc
gtatatgtattggctgcatttgcatgaataatactacgtgtaagcccaaaagaacccacgtgtagcccatgcaaagttaacactcacgaccccattcctcag
tctccactatataaacccaccatccccaatctcaccaaacccaccacacaactcacaactcactctcacacctcc >SEQ-4;p-BnNapin
taaggatgacctacccattcttgagacaaatgttacattttagtatcagagtaaaatgtgtacctataactcaaattcgattgacatgtatccattcaacataaa
attaaaccagcctgcacctgcatccacatttcaagtattttcaaaccgttcggctcctatccaccgggtgtaacaagacggattccgaatttggaagatttga
ctcaaattcccaatttatattgaccgtgactaaatcaactttaacttctataattctgattaagctcccaatttatattcccaacggcactacctccaaaatttatag
actctcatcccttttaaaccaacttagtaaacgttttttttttaattttatgaagttaagttttaccttgttttaaaaagaatcgttcataagatgccatgccagaac
attagctacacgttacacatagcatgcagccgcggagaattgttttcttcgccacttgtcactcccttcaaacacctaagagcttctctctcacagcacacac

Figure 4 (continued)

atacaatcacatgcgtgcatgcattattacacgtgatcgccatgcaaatctcctttatagcctataaattaactcatcggcttcactctttactcaaaccaaaact
catcaatacaaacaagattaaaaaca >SEQ-5;p-LuPXR
cacgggcaggacatagggactactacaagcatagtatgcttcagacaaagagctaggaaagaactcttgatggaggttaagagaaaaaagtgctaga
ggggcatagtaatcaaacttgtcaaaaccgtcatcatgatgagggatgacataatataaaaagttgactaaggtcttggtagtactctttgattagtattatat
attggtgagaacatgagtcaagaggagacaagaaaccgaggaaccatagtttagcaacaagatggaagttgcaaagttgagctagccgctcgattagt
tacatctcctaagcagtactacaaggaatggtctctatactttcatgtttagcacatggtagtgcggattgacaagttagaaacagtgcttaggagacaaag
agtcagtaaaggtattgaaagagtgaagttgatgctcgacaggtcaggagaagtccctccgccagatggtgactaccaagggggttggtatcagctgaga
cccaaataagattcttcggttgaaccagtggttcgaccgagactcttagggtgggatttcactgtaagatttgtgcatttttgttgaatataaaattgacaattttttta
tttaattatagattatttagaatgaattacatatttagtttctaacaaggatagcaatggatgggtatgggtacaggttaaacatatctattacccacccatctagt
cgtcgggttttacacgtacccacccgtttacataaaccagaccggaattttaaaccgtacccgtccgttagcgggtttcagatttacccgtttaatcgggtaaa
acctgattactaaatatatatttttatttgataaacaaaacaaaaatgttaatattttcatattggatgcaatttaagaaacacatattcataaatttccatatttgt
aggaaaataaaaagaaaaatatattcaagaacacaaatttcaccgacatgactttattacagagttggaattagatctaacaattgaaaaattaaaatta
agatagaatatgttgaggaacatgacatagtataatgctgggttacccgtcgggtaggtatcgaggcggatactactaaatccatcccactcgctatccgat
aatcactggtttcgggtatacccattcccgtcaacaggccttttaaccggataatttcaacttatagtgaatgaattttgaataaatagttagaataccaaaatc
ctggattgcatttgcaatcaaattttgtgaaccgttaaattttgcatgtacttgggatagatataatagaaccgaattttcattagtttaatttataacttactttgttca
aagaaaaaaatatctatccaatttacttataataaaaaataatctatccaagttacttattataatcaacttgtaaaaaggtaagaatacaaatgtggtagc
gtacgtgtgattatatgtgacgaaatgttatatctaacaaaagtccaaattcccatggtaaaaaaaatcaaaatgcatggcaggctgtttgtaaccttggaat
aagatgttggccaattctggagccgccacgtacgcaagactcagggccacgttctcttcatgcaaggatagtagaacaccactccacccacctcctatatt
agacctttgcccaacccctccccaactttcccatcccatccacaaagaaaccgacattttatcataaatc >SEQ-6;p-PvArc
tactatagaaaatgtgttatatcgacatgaccagacaaaggggcaacagttaacaaaacaattaattctttcatttgagattaaggaaggtaaggtactaa
aaagattaaaaaaaatgagcttatctctttgtttctgtaataataatataagtgtgataaacttttaatataataattgtaattaggttttctacagatgagcaccac
tcagagacaagataagaagaaaacaattttgttaaacatgattatagaaacttttagttaagtcttgaagtatcaatataacaaaaaaaagtacacacgac
tatgacaataaacccactaccgtcaggttatcatttcgatgaaatgttttgatatcattaaatataacagtcacaaaaaatcatctaattataacaatataactt
atacatatatttaactaaaaacttagagttttgtaatgattctaattgatgattagagtttatagaaatacaattaaataaaaaatataatttaaaaaaacatag
taaagtcaatgagatcctctctgacctcagtgatcatttagtcatgtatgtacaacaatcattgttcatcacatgactgtaaaataaataaggataaacttggg
aatatatataatatattgtattaaataaaaaagggaaatacaaatatcaattttagattcccgagttgacacaactcaccatgcacgctgccacctcagctcc
cagctctcgtcacatgtctcatgtcagttaggtctttggttttttagtctttgacacaactcgccatgcatgttgccacgtgagctcgttcctcttcccatgatctcacc
actgggcatgcatgctgccacctcagctggcacctcttctctatatgtccctagaggccatgcacagtgccacctcagcactcctctcagaacccatacgta
cctgccaatcggcttctctccataaatatctatttaaattataactaattatttcatatacttaattgatgacgtggatgcattgccatcgttgtttaataattgttaatta
cgacatgataaataaaatgaaagtaaaaagtacgaaagattttccatttgttgttgtataaatagagaagtgagtgatgcataatgcatgaatgcatga >SEQ-7;p-VfSBP
tcgacggcccggactgtatccaacttctgatctttgaatctctctgttccaacatgttctgaaggagttctaagacttttcagaaagcttgtaacatgctttgtaga
ctttctttgaattactcttgcaaactctgattgaacctacgtgaaaactgctccagaagttctaaccaaattccgtcttgggaaggcccaaaatttattgagtactt
cagtttcatggacgtgtcttcaaagatttataacttgaaatcccatcattttaagagaagttctgttccgcaatgtcttagatctcattgaaatctacaactcttgtg
tcagaagttcttccagaatcaacttgcatcatggtgaaaatctggccagaagttctgaacttgtcatatttcttaacagttagaaaaatttctaagtgtttagaatt
ttgacttttccaaagcaaacttgacttttgactttcttaataaaacaaacttcatattctaacatgtcttgatgaaatgtgattcttgaaatttgatgttgatgcaaaa
gtcaaagtttgacttttcagtgtgcaattgaccattttgctcttgtgccaattccaaacctaaattgatgtatcagtgctgcaaacttgatgtcatggaagatcttat
gagaaaattcttgaagactgagaggaaaaattttgtagtacaacacaaagaatcctgttttcatagtcggactagacacattaacataaaacaccacttc
attcgaagagtgattgaagaaggaaatgtgcagttacctttctgcagttcataagagcaacttacagacactttttactaaaatactacaaagaggaagattt
aacaacttagagaagtaatgggagttaaagagcaacacattaaggggggagtgttaaaattaatgtgttgtaaccaccactacctttagtaagtattataag

Figure 4 (continued)

aaaattgtaatcatcacattataattattgtccttatttaaaattatgataaagttgtatcattaagattgagaaaaccaaatagtcctcgtcttgatttttgaattatt
gttttctatgttacttttcttcaagcctatataaaaactttgtaatgctaaattgtatgctggaaaaaaatgtgtaatgaattgaatagaaattatggtatttcaaagt
ccaaaatccatcaatagaaatttagtacaaaacgtaactcaaaaatattctcttattttaaattttacaacaatataaaaatattctcttattttaaattttacaata
ataatttatcacctgtcacctttagaataccaccaacaatattaatacttagatattttattcttaataattttgagatctctcaatatatctgatatttattttatatttg
tgtcatattttcttatgttttagagttaacccttatatcttggtcaaactagtaattcaatatatgagtttgtgaaggacacattgacatcttgaaacattggttttaacc
ttgttggaatgttaaaggtaataaaacattcagaattatgaccatctattaatatacttcctttgtcttttaaaaaagtgtgcatgaaaatgctctatggtaagcta
gagtgtcttgctggcctgtgtatatcaattccatttccagatggtagaaactgccactacgaataattagtcataagacacgtatgttaacacacgtccccttgc
atgttttttgccatatattccgtctctttcttttcttcacgtataaaacaatgaactaattaatagagcgatcaagctgaac >SEQ-8;p-BnFAE1
aagctttacaacgctacacaaaacttataaccgtaatcaccattcattaacttaactactatcacatgcattcatgaattgaaacgagaaggatgtaaatagt
tgggaagttatctccacgttgaagagatcgttagcgagagctgaaagaccgagggaggagacgccgtcaacacggacagagtcgtcgaccctcacat
gaagtaggaggaatctccgtgaggagccagagagacgtctttggtcttcggtttcgatccttgatctgacggagaagacgagagaagtgcgactggactc
cgtgaggaccaacagagtcgtcctcggtttcgatcgtcggtattggtggagaaggcggaggaatctccgtgacgagccagagagatgtcgtcggtcttcg
gtttcgatccttgatctgacggagaagacgagagaagtgcgacgagactccgtgaggaccaacagagttgtcctcggtttcgatcgtcggtttcggcgga
gaaggcggaggaatctccgtgaggagccagagagacgtcgttggtcttcggtttcgatccttgatctgttggagaagacgagacaagtgggacgagact
caacgacggagtcagagacgtcgtcggtcttcggtttcggccgagaaggcggagtcggtcttcggtttcggccgagaaggcggaggagacgtcttcgat
ttgggtctctcctcttgacgaagaaaacaaagaacacgagaaataatgagaaagagaacaaaagaaaaaaaaataaaaataaaaataaaatttggt
cctcttatgtggtgacacgtggtttgaaacccaccaaataatcgatcacaaaaaacctaagttaaggatcggtaataaccttctaattaattttgatttatatta
aatcactcttttatttataaaccccactaaattatgcgatattgattgtctaagtacaaaaattctctcgaattcaatacacatgtttcatatatttagccctgttcatt
taatattactagcgcatttttaatttaaaattttgtaaactttttggtcaaagaacattttttaattagagacagaaatctagactctttatttggaataatagtaata
aagatatattaggcaatgagtttatgatgttatgtttatatagtttatttcatttttaaattgaaaagcattattttttatcgaaatgaatctagtatacaatcaatatttatg
ttttttcatcagatacttttcctatttttttggcacctttcatcggactactgatttatttcaatgtgtatgcatgcatgagcatgagtatacacatgtctttttaaaatgcatgt
aaagcgtaacggaccacaaaagaggatccatacaaatacatctcatcgcttcctctactattctccgacacacacactgagca >SEQ-9;p-VfUSP
ctgcagcaaatttacacattgccactaaacgtctaaacccttgtaatttgttttgtttttactatgtgtgttatgtatttgatttgcgataaattttatatttggtactaaat
ttataacaccttttatgctaacgtttgccaacacttagcaatttgcaagttgattaattgattctaaattattttttgtcttctaaatacatatactaatcaactggaaat
gtaaatatttgctaatatttctactataggagaattaaagtgagtgaatatggtaccacaaggtttggagatttaattgttgcaatgctgcatggatggcatatac
accaaacattcaataattcttgaggataataatggtaccacacaagatttgaggtgcatgaacgtcacgtggacaaaaggtttagtaattttcaagacaac
aatgttaccacacacaagttttgaggtgcatcatggatgccctgtgaaagtttaaaaatatttttggaaatgatttgcatggaagccatgtgtaaaaccatg
acatccacttggaggatgcaataatgaagaaaactacaaatttacatgcaactagttatgcatgtagtctatataatgaggattttgcaatactttcattcatac
acactcactaagttttacacgattataatttcttcatagccagt >SEQ-10;d5Des_Tc_GA
atgggaaaaggatctgagggaagatctgctgctagagagatgactgctgaggctaacggagataagagaaagaccatcctcattgagggagtgttgta
cgatgctaccaacttcaaacacccaggaggttccattattaacttcctcaccgagggagaagctggagttgatgctacccaagcttacagagagttccatc
agagatccggaaaggctgataagtacctcaagtccctcccaaagttggatgcttctaaggtggagtctaggttctctgctaaggagcaggctagaaggga
cgctatgaccagggattacgctgctttcagagaggagttggttgctgagggatacttcgatccatctatcccacacatgatctacagagtggtggagattgtg
gctttgttcgctttgtctttctggttgatgtctaaggcttctccaacctcttggttttgggagtggtgatgaacggaatcgctcaaggaagatgcggatggttatg
catgagatgggacacggatctttcactggagttatctggctcgatgataggatgtgcgagttcttctacggagttggatgtggaatgtctggacactactgga
agaaccagcattctaagcaccatgctgctccaaacagattggagcacgatgtggatttgaacaccttgccactcgttgctttcaacgagagagttgtgagg
aaggttaagccaggatctttgttggctttgtggctcagagttcaggctatttgttcgctccagtgtcttgcttgttgatcggattgggatggaccttgtacttgcacc
caagatatatgctcaggaccaagagacatatggagtttgtggatcttcgctagatatcggatggtctccttgatggagctttgggatattctcctggaa
cttctgtgggaatgtacctctgctcttcggacttggatgcatctacatcttcctccaattcgctgtgtctcatacccatttgccagttaccaacccagaggatcaa

Figure 4 (continued)

ttgcattggcttgagtacgctgctgatcataccgtgaacatctctaccaagtcttggttggttacctggtggatgtctaacctcaacttccaaatcgagcatcattt
gttcccaaccgctccacaattcaggttcaaggagatctctccaagagttgaggctctcttcaagagacataacctcccttactacgatttgccatacacctct
gctgtttctactaccttcgctaacctctactctgttggacattctgttggagctgataccaagaagcaggattga >SEQ-11;d5Des_Tc
MGKGSEGRSAAREMTAEANGDKRKTILIEGVLYDATNFKHPGGSIINFLTEGEAGVDATQAYREFHQRSGKA
DKYLKSLPKLDASKVESRFSAKEQARRDAMTRDYAAFREELVAEGYFDPSIPHMIYRVVEIVALFALSFWLMS
KASPTSLVLGVVMNGIAQGRCGWVMHEMGHGSFTGVIWLDDRMCEFFYGVGCGMSGHYWKNQHSKHHA
APNRLEHDVDLNTLPLVAFNERVVRKVKPGSLLALWLRVQAYLFAPVSCLLIGLGWTLYLHPRYMLRTKRHM
EFVWIFARYIGWFSLMGALGYSPGTSVGMYLCSFGLGCIYIFLQFAVSHTHLPVTNPEDQLHWLEYAADHTV
NISTKSWLVTWWMSNLNFQIEHHLFPTAPQFRFKEISPRVEALFKRHNLPYYDLPYTSAVSTTFANLYSVGHS
VGADTKKQD >SEQ-12;d5Des_Tc_GA2
atgggaaaaggatctgagggaagatctgctgctagagagatgactgctgaggctaacggagataagagaaagaccatcctcattgagggagtgttgta
cgatgctaccaacttcaaacacccaggaggttccattattaacttcctcaccgagggagaagctggagttgatgctacccaagcttacagagagttccatc
agagatccgaaaggctgataagtacctcaagtcccctcccaaagttggatgcttcaaggtggagtctaggttctctgctaaggagcaggctagaaggga
cgctatgaccagggattacgctgctttcagagaggagttggttgctgagggatacttcgatccatctatcccacacatgatctacagagtggtggagattgtg
gctttgttcgctttgtctttctggttgatgtctaaggcttctccaacctctttggttttgggagtggtgatgaacggaatcgctcaaggaagatgcggatgggttatg
cacgagatgggacacggatctttcactggagttatctggctcgatgataggatgtgcgagttcttctacggagttggatgtgaatgtctggacactactgga
agaaccagcactctaagcaccacgctgctccaaacagattggagcacgatgtggatttgaacaccttgccactcgttgctttcaacgagagagttgtgag
gaaggttaagccaggatctttgttggctttgtggctcagagttcaggcttatttgttcgctccagtgtcttgcttgttgatcggattgggatggaccttgtacttgcac
ccaagatatatgctcaggaccaagagacacatggagtttgtgtggatcttcgctagatatatcggatggtctccttgatgggagctttgggatattctcctgga
acttctgtgggaatgtacctctgctctttcggacttggatgcatctacatcttcctccaattcgctgtgtctcacacccacttgccagttaccaacccagaggatc
aattgcactggcttgagtacgctgctgatcacaccgtgaacatctctaccaagtcttggttggttacctggtggatgtctaacctcaacttccaaatcgagcac
cacttgttcccaaccgctccacaattcaggttcaaggagatctctccaagagttgaggctctcttcaagagacacaacctcccttactacgatttgccataca
cctctgctgtttctactaccttcgctaacctctactctgttggacactctgttggagctgataccaagaagcaggattga >SEQ-13;o3Des_Cp_GA
atggctgctactacctctgctatgagcaaggatgctgttcttagaagaactgctgctgctactactgctatcgatcacgaaagctctacctctgcttctccagct
gattctcctagactctctgcttcttctacctctctctcttctctcagctctctcgacgctaaggataaggatgatgagtacgctggacttcttgatacttacggaaac
gctttcaccccctcctgatttcactatcaaggatatcagagatgctatccctaagcactgcttcgagcgttctgctatcaagggatacgcttatatcctcagagat
gtggcttgcctttctaccactttctacctcttccacaacttcgttacccctgagaacgttccttacacccctcttagagttttcctctggggagtttacactgctcttca
gggacttttcggaactggactctggattatcgctcacgagtgtggacacggtgctttctctccttctaccctcactaacgatcttactggatgggttctccactctg
ctcttctcgtgccttacttctcttggaagttctctcactctgctcaccacaagggaaccggaaatatggaaagggatatggctttcctccctagaactagggctc
aatacgctaccagattcggaagagctatggatcagcttggagatctttgcgaggaaaccccatctatacactgctggattccttgttttccagcagcttcttggat
ggccttcttacttgatcgctaacgttactggacacgatcttcacgagagacagagagagggaagaggaaagggaaagaagaacggattcggaggaa
ctgttaaccacttcgaccctcgttctcctatcttcgatgacaagcacgctaagtttatcgttctcagcgatatcggacttggacttgctatcgctgctcttgttacct
cggaaacagattcggatgggctaacgttgctgtttggtacttcgttccttacctctgggttaaccactggatcgttgctatcactttccttcagcacactgatccta
ctcttcctcactacactgctgaggaatggaacttcgttcgtggagctgctgctacaatcgatagagagatgggatttatcggtagacacctcttccacggaat
cgttgagactcacgtgcttcaccactacgtttcttcaatcccttctacaacgctgatgaggcttctgaggctatcaagcctgttatgggaaagcactaccgttct
gagactaaggatggacctatggttttatcagggctttgtggaaaactgctagatggtgtcaatggttgagccttctgctgatgctcaaggtgctggtgaag
gtgttctcttcttcaggaacagaaacggacttggaactaagcctatctctatgaggacccagtga >SEQ-14;o3Des_Cp

Figure 4 (continued)

MAATTSAMSKDAVLRRTAAATTAIDHESSTSASPADSPRLSASSTSLSSLSSLDAKDKDDEYAGLLDTYGNAF
TPPDFTIKDIRDAIPKHCFERSAIKGYAYILRDVACLSTTFYLFHNFVTPENVPYTPLRVFLWGVYTALQGLFGT
GLWIIAHECGHGAFSPSTLTNDLTGWVLHSALLVPYFSWKFSHSAHHKGTGNMERDMAFLPRTRAQYATRF
GRAMDQLGDLCEETPIYTAGFLVFQQLLGWPSYLIANVTGHDLHERQREGRGKGKKNGFGGTVNHFDPRSP
IFDDKHAKFIVLSDIGLGLAIAALVYLGNRFGWANVAVWYFVPYLWVNHWIVAITFLQHTDPTLPHYTAEEWNF
VRGAAATIDREMGFIGRHLFHGIVETHVLHHYVSSIPFYNADEASEAIKPVMGKHYRSETKDGPMGFIRALWK
TARWCQWVEPSADAQGAGEGVLFFRNRNGLGTKPISMRTQ

>SEQ-15;o3Des_Cp_GA2_V282L
atggctgctaccacttctgcaatgtctaaggacgctgttctgcggcgcactgctgccgcaacgactgccatcgatcacgagtcgtcgacctctgccagtcca
gccgactcgcctagactctcagcctcgtccacgtcgctttcgtcgcttcttctctcgatgcgaaggacaaggacgacgagtatgccggccttcttgacacat
acggaaacgccttcacaccccccgacttcactatcaaggacatccgtgatgccatacccaagcattgcttcgaacgctctgccatcaagggatacgcata
tattcttcgcgacgtcgcctgtctttctactacgttctacctgttccacaacttcgtgacgcccgagaacgtccctacactccccttcgtgtctttctctgggtgtt
tacactgccctgcaaggtctatttggaactggactctggattattgcccacgaatgtggccacggagccttctcttcctccaacttgaccaacgaccttaccg
gctgggtccttcactcagctctccttgttccctatttcagctggaagttttcccacagtgcgcatcacaaaggaactggaaacatggagcgcgacatggctttc
cttccccgcacacgtgcgcagtatgccactcgatttggacgtgcgatggatcaacttggtgacctttgcgaagagacacccatttacacggctgggttcttgg
ttttccagcagctcctaggctggcctagctatcttatagcgaacgtcacaggtcacgacctccacgaacgccagcgtgagggtcgaggtaagggcaaga
agaacggtttcgggggcaccttaaatcactttgatccccgcagcccctattttcgatgacaaacacgccaagttcattgttctctctgacatcggcctgggtcttg
ctatcgctgctctggtgtatcttggcaaccgtttcggctgggctaacgtggctgtttggtatttcgtgccctatctttgggtgaatcactggatcgttgccatcacgtt
cctccagcatacggatccaactctgccgcattacaccgccgaagagtggaactttgttcgcggtgccgctgctaccattgatcgcgagatgggcttcattgg
ccgccaccttttccacgcattgtcgagacccatgtcctccatcactatgtcagctctataccgttctacaacgcggacgaagcctccgaggccataaaac
cggttatgggcaagcactatcgatctgaaaccaaagacggacctatggatttatccgcgctctttggaagactgctcgctggtgccagtgggtagagcct
agtgccgatgcgcaaggtgctggagagggcgtgttgttcttccgcaaccgaaatggtctcggcacgaaacccattcgatgagaactcagtag >SEQ-16;o3Des_Cp_V282L
MAATTSAMSKDAVLRRTAAATTAIDHESSTSASPADSPRLSASSTSLSSLSSLDAKDKDDEYAGLLDTYGNAF
TPPDFTIKDIRDAIPKHCFERSAIKGYAYILRDVACLSTTFYLFHNFVTPENVPYTPLRVFLWGVYTALQGLFGT
GLWIIAHECGHGAFSPSTLTNDLTGWVLHSALLVPYFSWKFSHSAHHKGTGNMERDMAFLPRTRAQYATRF
GRAMDQLGDLCEETPIYTAGFLVFQQLLGWPSYLIANVTGHDLHERQREGRGKGKKNGFGGTLNHFDPRSP
IFDDKHAKFIVLSDIGLGLAIAALVYLGNRFGWANVAVWYFVPYLWVNHWIVAITFLQHTDPTLPHYTAEEWNF
VRGAAATIDREMGFIGRHLFHGIVETHVLHHYVSSIPFYNADEASEAIKPVMGKHYRSETKDGPMGFIRALWK
TARWCQWVEPSADAQGAGEGVLFFRNRNGLGTKPISMRTQ >SEQ-17;o3Des(Pi_GA2)
atggctacaaaggaggcttacgttttcccaactctcaccgagatcaagagatctctcccaaaggattgcttcgaggcttctgtgcctttgtctctctactacact
gtgagatgcttggttattgctgtggctttgaccttcggattgaactacgctagagctttgccagaggttgagtcttctgggctttggatgctgctttgtgcactggat
atatcctcctccagggaattgtgttctggggattcttcactgttggacacgatgctggacacggagctttctctagataccacctcttgaacttcgttgtgggaac
cttcatgcactctctcatcttgaccccattcgagtcttggaagttgacccacagacaccaccacaagaacaccggaaacatcgatagagatgaggtgttct
acccacagagaaaggctgatgatcacccattgtccaggaacttgatcttggctttgggagctgcttggcttgcttatttggtggagggattcccaccaagaa
aggtgaaccacttcaacccattcgagccacttttgtgagacaagtgtccgctgtggttatctctttgctcgctcacttcttcgttgctggactctctatctacttgtct
ctccagttgggacttaagaccatggctatctactactacggaccagttttcgtgttcggatctatgttggtgattaccaccttcttgcaccacaacgatgaggag
actccatggtatgctgattctgagtggacttacgtgaagggaaacttgtcctctgtggatagatcttacggtgctctcatcgataacctctcccacaacatcgg
aactcaccagatccaccacctcttcccaattatcccacactacaagctcaagaaggctactgctgctttccaccaagctttcccagagcttgtgagaaagtc
cgatgagccaatcatcaaggctttcttcagagtggaaggttgtatgctaactacggagtggttgatcaagaggctaagctcttcactttgaaggaggctaa
ggctgctactgaagctgctgctaagaccaagtctacctga

Figure 4 (continued)

>SEQ-18;o3Des(Pi_GA2)
MATKEAYVFPTLTEIKRSLPKDCFEASVPLSLYYTVRCLVIAVALTFGLNYARALPEVESFWALDAALCTGYILL
QGIVFWGFFTVGHDAGHGAFSRYHLLNFVVGTFMHSLILTPFESWKLTHRHHHKNTGNIDRDEVFYPQRKAD
DHPLSRNLILALGAAWLAYLVEGFPPRKVNHFNPFEPLFVRQVSAVVISLLAHFFVAGLSIYLSLQLGLKTMAIY
YYGPVFVFGSMLVITTFLHHNDEETPWYADSEWTYVKGNLSSVDRSYGALIDNLSHNIGTHQIHHLFPIIPHYK
LKKATAAFHQAFPELVRKSDEPIIKAFFRVGRLYANYGVVDQEAKLFTLKEAKAATEAAAKTKST

>SEQ-19;o3Des_Pi_GA
atggctacaaaggaggcttacgttttcccaactctcaccgagatcaagagatctctcccaaaggattgcttcgaggcttctgtgcctttgtctctactacact
gtgagatgcttggttattgctgtggctttgaccttcggattgaactacgctagagctttgccagaggttgagtctttctgggctttggatgctgctttgtgcactggat
atatcctcctccagggaattgtgttctggggattcttcactgttggacacgatgctggacatggagctttctctagataccacctcttgaacttcgttgtgggaac
cttcatgcattctctcatcttgaccccattcgagtcttggaagttgacccatagacaccatcataagaacaccggaaacatcgatagagatgaggtgttctac
ccacagagaaaggctgatgatcatccattgtccaggaacttgatcttggctttgggagctgcttggcttgcttatttggtggagggattcccaccaagaaagg
tgaaccacttcaacccattcgagccactttttgtgagacaagtgtccgctgtggtatctctttgctcgctcacttcttcgttgctggactctctatctacttgtctctcc
agttgggacttaagaccatggctatctactactacggaccagttttcgtgttcggatctatgttggtgattaccaccttcttgcaccataacgatgaggagactc
catggtatgctgattctgagtggacttacgtgaagggaaacttgtcctctgtggatagatcttacggtgctctcatcgataacctctcccataacatcggaactc
atcagatccatcacctcttcccaattatcccacactacaagctcaagaaggctactgctgctttccatcaagctttcccagagcttgtgagaaagtccgatga
gccaatcatcaaggctttcttcagagtgggaaggttgtatgctaactacggagtggttgatcaagaggctaagctcttcactttgaaggaggctaaggctgct
actgaagctgctgctaagaccaagtctacctga >SEQ-20;enhancer_end_sequence_according_to_invention
accaatcaccaccaaaaa >SEQ-21;artificial_5'_untranslated_region_based_on_6-tuples
aatcaccaccaccaaaaa >SEQ-22;artificial_5'_untranslated_region_based_on_6-tuples
accaccaatcaccaaaaa >SEQ-23;artificial_5'_untranslated_region_based_on_6-tuples
caccaccaccaccaaaaa >SEQ-24;artificial_5'_untranslated_region_based_on_5-tuples
aaagaaccaccaccaaaa >SEQ-25;artificial_5'_untranslated_region_based_on_5-tuples
aaccaatcacaccaaaaa >SEQ-26;artificial_5'_untranslated_region_based_on_5-tuples
aactcaccaccaccaaaa >SEQ-27;artificial_5'_untranslated_region_based_on_5-tuples
aatcaccaccaccaaaaa

Figure 4 (continued)

>SEQ-28;artificial_5'_untranslated_region_based_on_5-tuples
accaatcacacaccaaaa

>SEQ-29;artificial_5'_untranslated_region_based_on_5-tuples
actcacacaccaccaaaa

>SEQ-30;artificial_5'_untranslated_region_based_on_5-tuples
caactcaccacaccaaaa

>SEQ-31;artificial_5'_untranslated_region_based_on_5-tuples
caatcacaccaccaaaaa

>SEQ-32;artificial_5'_untranslated_region_based_on_5-tuples
cacaactcacaccaaaaa

>SEQ-33;artificial_5'_untranslated_region_based_on_5-tuples
cacaactcaccaccaaaa

>SEQ-34;artificial_5'_untranslated_region_based_on_5-tuples
caccaccaatcaccaaaa

>SEQ-35;artificial_5'_untranslated_region_based_on_5-tuples
ccaatcaccaccaaaaaa

>SEQ-36;artificial_5'_untranslated_region_based_on_5-tuples
ccaccaatcacaccaaaa

>SEQ-37;artificial_5'_untranslated_region_based_on_4-tuples
accacactcacaaccaaa

>SEQ-38;artificial_5'_untranslated_region_based_on_4-tuples
actcaccacaaccaaaaa

>SEQ-39;artificial_5'_untranslated_region_based_on_4-tuples
cacaaccactcaccaaaa

>SEQ-40;artificial_5'_untranslated_region_based_on_4-tuples
cacaactcaccaccaaaa

>SEQ-41;artificial_5'_untranslated_region_based_on_4-tuples
caccacacaatcaccaaa

>SEQ-42;artificial_5'_untranslated_region_based_on_4-tuples
caccaccacacaaccaaa

Figure 4 (continued)

>SEQ-43;artificial_5'_untranslated_region_based_on_4-tuples
ccaactcacaccacaaaa

>SEQ-44;artificial_5'_untranslated_region_based_on_4-tuples
ccaccaactcacaccaaa

>SEQ-45;artificial_5'_untranslated_region_based_on_4-tuples
ctcacaccacaccacaaa

>SEQ-46;longer_enhancer
ccaccacacaactcacaactcactctcacaccttaaagaaccaatcaccaccaaaaa >SEQ-47;artificial_5'_untranslated_region_based_on_6-tuples
acaactcacaactcacaccttaaagaaccaatcaccaatcaccaccaccaccaaaaa >SEQ-48;artificial_5'_untranslated_region_based_on_6-tuples
acaactcacaactcactctcacaactcacaccttaaagaaccaatcaccaccaaaaa >SEQ-49;artificial_5'_untranslated_region_based_on_6-tuples
acaactcacaactcactctcacaccttaaagaaccaatcaccaccaatcaccaaaaa >SEQ-50;artificial_5'_untranslated_region_based_on_6-tuples
actctcacaccttaaagaaccaatcaccaatcaccaatcaccaatcaccaccaaaaa >SEQ-51;artificial_5'_untranslated_region_based_on_6-tuples
atcaccacacaactcactctcacaccttaaagaaccaatcaccaccaccaccaaaaa >SEQ-52;artificial_5'_untranslated_region_based_on_6-tuples
caccttaaagaaccaatcaccaccacaccttaaagaaccaatcaccaccaccaaaaa >SEQ-53;artificial_5'_untranslated_region_based_on_6-tuples
ccaatcaccacacaactcactctcacaactcactctcacaccttaaagaaccaaaaa >SEQ-54;artificial_5'_untranslated_region_based_on_6-tuples
tcacacaactcacaccttaaagaaccaatcaccaccaccaccaatcaccaaaaa >SEQ-55;artificial_5'_untranslated_region_based_on_5-tuples
aactcactctcacaactctcacacaactcacaccaatcaccaccaatcacaccaaaa >SEQ-56;artificial_5'_untranslated_region_based_on_5-tuples
acacaactctcactcacaactcacaactcacaactcactcacaactcaccaccaaaa >SEQ-57;artificial_5'_untranslated_region_based_on_5-tuples
actcacaactctcaccaccacaactctcacaccttaaagaaccaatcacaccaaaaa

Figure 4 (continued)

>SEQ-58;artificial_5'_untranslated_region_based_on_5-tuples
actcactcacaactcacaactctcacacaccaccacaccaatcaccaccaccaaaaa >SEQ-59;artificial_5'_untranslated_region_based_on_5-tuples
agaaccaatcactcaccaatcaccttaaagaaccaccaccaatcacaccaccaaaaa >SEQ-60;artificial_5'_untranslated_region_based_on_5-tuples
atcacaactctcactcaccaccaatcactcacaccaatcaccaatcacacaccaaaa >SEQ-61;artificial_5'_untranslated_region_based_on_5-tuples
caatcaccacacacaactcactcactcacaactctcacaccaatcaccaccaaaaaa >SEQ-62;artificial_5'_untranslated_region_based_on_5-tuples
cacacacacaactcacacaccaatcactctcaccaatcacaactcaccacaccaaaa >SEQ-63;artificial_5'_untranslated_region_based_on_5-tuples
ccacaactctcaccacaactcaccaccttaaagaaccaatcacaactctcaccaaaa >SEQ-64;artificial_5'_untranslated_region_based_on_5-tuples
ccaccaatcactcaccacaccacaactctcacaactcacaaccaccaatcaccaaaa >SEQ-65;artificial_5'_untranslated_region_based_on_5-tuples
ccttaaagaaccaatcacaactcacacaccaatcactctcacaactcacaccaaaaa >SEQ-66;artificial_5'_untranslated_region_based_on_5-tuples
cttaaagaaccaatcacaccaatcactctcacaactcacaactcaccaccaccaaaa >SEQ-67;artificial_5'_untranslated_region_based_on_5-tuples
caaccaccttaaagaaccacaactcacaccttaaagaaccaccaccaatcaccaaaa >SEQ-68;artificial_5'_untranslated_region_based_on_5-tuples
tcacaactctcactcactcactctcacaactcacaccttaaagaaccaccaccaaaa >SEQ-69;artificial_5'_untranslated_region_based_on_5-tuples
tctcacaactcacaccacaactcactctcaccaatcacaactcacacaccaccaaaa >SEQ-70;artificial_5'_untranslated_region_based_on_4-tuples
aactcacaaccaactcacactcaccacaaccacaaccacaccacactcacaaccaaa >SEQ-71;artificial_5'_untranslated_region_based_on_4-tuples
aagaactcacacaatcaccacaatcaccaccacacaactcacaaccactcaccaaaa >SEQ-72;artificial_5'_untranslated_region_based_on_4-tuples
aagaactctctcacacaaagaactcaccactctcaccaccacaactcaccaccaaaa

Figure 4 (continued)

>SEQ-73;artificial_5'_untranslated_region_based_on_4-tuples
acacaactcacacaccaccaaagaactcaccaactctcacaccacacaatcaccaaa >SEQ-74;artificial_5'_untranslated_region_based_on_4-tuples
accaccaaagaaccaatcaccaccaccaactctcaccaaccaactcacaccacaaaa >SEQ-75;artificial_5'_untranslated_region_based_on_4-tuples
cacaactcaccacaactctctctcactcacaccacaccaccaccaactcacaccaaa >SEQ-76;artificial_5'_untranslated_region_based_on_4-tuples
caccaatcaccaatcacaatcactcaccacaatcacaatcaccaccacacaaccaaa >SEQ-77;artificial_5'_untranslated_region_based_on_4-tuples
caccacaaccaatcaccttaaagaactcaccttaaaagaactcaccacaaccaaaaa >SEQ-78;artificial_5'_untranslated_region_based_on_4-tuples
caccacactctcaccaccaactcacactcaccacaccaactcacaccacaccacaaa >SEQ-79;artificial_5'_untranslated_region_based_on_4-tuples
ccacaactcactcacacaccaccaaaaagaactcaccaatcacacaatcacaaaaaa >SEQ-80;artificial_5'_untranslated_region_based_on_4-tuples
ccaatcaccttaaagaactcaccttaaagaactcacaatcacaccaccaaccacaaa >SEQ-81;artificial_5'_untranslated_region_based_on_4-tuples
ccacaccacaactcaccacacaatcacaactcaccaagaactctctcaccaccaaaa >SEQ-82;artificial_5'_untranslated_region_based_on_4-tuples
ccactcacaactcacaacaccaccaactcaccacaactcacaccaactcaccttaaa >SEQ-83;artificial_5'_untranslated_region_based_on_4-tuples
ctcaccaccacaatcaccactcacaactctctcacacaccaaccaatcaccaccaaa >SEQ-84;tuples_at_end_of_5'_untranslated_region
ccaat >SEQ-85;tuples_at_end_of_5'_untranslated_region
ccaaa >SEQ-86;tuples_at_end_of_5'_untranslated_region
caaaa >SEQ-87;tuples_at_end_of_5'_untranslated_region
aaaaa

Figure 4 (continued)

>SEQ-88;tuples_at_end_of_5'_untranslated_region
accaa

>SEQ-89;tuples_at_end_of_5'_untranslated_region
waaag

>SEQ-90;tuples_in_5'_untranslated_region
actc

>SEQ-91;tuples_in_5'_untranslated_region
caactc

>SEQ-92;tuples_in_5'_untranslated_region
acaactc

>SEQ-93;tuples_in_5'_untranslated_region
cacaact

>SEQ-94;5'_untranslated_region
gaaccaatcaccaccaaaaa

>SEQ-95;5'_untranslated_region
agaaccaatcaccaccaaaaa

>SEQ-96;longer_5'_untranslated_region
actctcacaccttaaagaaccaatcaccaccaaaaa

>SEQ-97;longer_5'_untranslated_region
actctcacaccttaa

>SEQ-98;longer_5'_untranslated_region
actctcacaccttaaa

>SEQ-99;longer_5'_untranslated_region
actctcacaccttaaagaa

>SEQ-100;CCAAT-Box_core
ccaa

>SEQ-101;CCAAT-Box
aaccaatca

>SEQ-102;Dof1_core
aaag

Figure 4 (continued)

>SEQ-103;Dof1
cacaccttaaagaacca

>SEQ-104;SEF3,_Soybean_embryo_factor_3
tataaacccaccatc

>SEQ-105;SEF3,_Soybean_embryo_factor_3
accaaacccaccaca

>SEQ-106;SEF3,_Soybean_embryo_factor_3_core
accc

>SEQ-107;Plant_TATA_box
cactatataaacccaccat

>SEQ-108;Plant_TATA_box_core
tataa

>SEQ-109;RY_and_Sph_motifs_conserved_in_seed-specific_promoters
gtgtagcccatgcaaagttaacactca >SEQ-110;RY_and_Sph_motifs_conserved_in_seed-specific_promoters_core
catg >SEQ-111;Prolamin_box,_conserved_in_cereal_seed_storage_protein_gene_promoters
gcccatgcaaagttaac >SEQ-112;Prolamin_box,_conserved_in_cereal_seed_storage_protein_gene_promoters_core
aaag >SEQ-113;Common_plant_regulatory_factor_(CPRF)_from_parsley
aagaacagcccat >SEQ-114;Common_plant_regulatory_factor_(CPRF)_from_parsley_core
acgt >SEQ-115;TCP_class_I_transcription_factor_(Arabidopsis)
gtaagcccaaaag >SEQ-116;TCP_class_I_transcription_factor_(Arabidopsis)_core
gccc >SEQ-117;bZIP_protein_G-Box_binding_factor_1
ataatactacgtgtaagccca

Figure 4 (continued)

\>SEQ-118;bZIP_protein_G-Box_binding_factor_1_core
acgt

\>SEQ-119;Cis-element_in_the_GAPDH_promoters_conferring_light_inducibility
ttgcatgaataatac \>SEQ-120;Cis-element_in_the_GAPDH_promoters_conferring_light_inducibility_core
atga \>SEQ-121;SBF-1
cacattattaaaatacc \>SEQ-122;SBF-1_core
ttaa \>SEQ-123;Sunflower_homeodomain_leucine-zipper_protein_Hahb-4
cacattattaa \>SEQ-124;Sunflower_homeodomain_leucine-zipper_protein_Hahb-4_core
atta \>SEQ-125;Transcriptional_repressor_BELLRINGER
aaaattagtaa \>SEQ-126;Transcriptional_repressor_BELLRINGER_core
atta \>SEQ-127;Floral_homeotic_protein_APETALA1
cattgccaaaattagtaaaat \>SEQ-128;Floral_homeotic_protein_APETALA1_core
caaa \>SEQ-129;ICE_(inducer_of_CBF_expression_1),_AtMYC2_(rd22BP1)
aatgtacacttgtca \>SEQ-130;ICE_(inducer_of_CBF_expression_1),_AtMYC2_(rd22BP1)_core
acac \>SEQ-131;bZIP_factors_DPBF-1_and_2_(Dc3_promoter_binding_factor-1_and_2)
tacacttgtca \>SEQ-132;bZIP_factors_DPBF-1_and_2_(Dc3_promoter_binding_factor-1_and_2)_core
acac

Figure 4 (continued)

\>SEQ-133;Class_I_GATA_factors
agtaagataatccaaat

\>SEQ-134;Class_I_GATA_factors_core
gata

\>SEQ-135;Dof2_-_single_zinc_finger_transcription_factor
tccaaattaaagcaaga

\>SEQ-136;Dof2_-_single_zinc_finger_transcription_factor_core
aaag

\>SEQ-137;Transcription_factor_binding_site_box_enhancer
cacaccttaaagaaccaatca

\>SEQ-138;Transcription_factor_binding_site_box_short_promoter
ataatactacgtgtaagcccaaaagaacccacgtgtagcccat \>SEQ-139;Transcription_factor_binding_site_box_long_promoter
tccaaattaaagcaagagaggccaagtaagataatccaaatgtacacttgtcattgccaaaattagtaa \>SEQ-140;spacer
ccccaatctcaccaaac \>SEQ-141;98nt_promoter
ataatactacgtgtaagcccaaaagaacccacgtgtagcccatgcaaagttaacactcacgacccattcctcagtctccactatataaacccaccat \>SEQ-142;98nt_promoter_with_spacer
ataatactacgtgtaagcccaaaagaacccacgtgtagcccatgcaaagttaacactcacgacccattcctcagtctccactatataaacccaccatccccaatctcaccaaac \>SEQ-143;98nt_promoter_with_spacer_and_enhancer
ataatactacgtgtaagcccaaaagaacccacgtgtagcccatgcaaagttaacactcacgacccattcctcagtctccactatataaacccaccatccccaatctcaccaaacccaccacacaactcacaactcactctcacaccttaaagaaccaatcaccaccaaaaa \>SEQ-144;142nt_promoter
cacattattaaaataccgtatatgtattggctgcatttgcatgaataatactacgtgtaagcccaaaagaacccacgtgtagcccatgcaaagttaacactcacgacccattcctcagtctccactatataaacccaccat \>SEQ-145;142nt_promoter_with_spacer
cacattattaaaataccgtatatgtattggctgcatttgcatgaataatactacgtgtaagcccaaaagaacccacgtgtagcccatgcaaagttaacactcacgacccattcctcagtctccactatataaacccaccatccccaatctcaccaaac \>SEQ-146;142nt_promoter_with_spacer_and_enhancer

Figure 4 (continued)

cacattattaaaataccgtatatgtattggctgcatttgcatgaataatactacgtgtaagcccaaaagaacccacgtgtagcccatgcaaagttaacactc
acgaccccattcctcagtctccactatataaacccaccatccccaatctcaccaaacccaccacacaactcacaactcactctcacaccttaaagaacca
atcaccaccaaaaa >SEQ-147;160nt_promoter
cggcatattgtattcccacacattattaaaataccgtatatgtattggctgcatttgcatgaataatactacgtgtaagcccaaaagaacccacgtgtagccca
tgcaaagttaacactcacgaccccattcctcagtctccactatataaacccaccat >SEQ-148;160nt_promoter_with_spacer
cggcatattgtattcccacacattattaaaataccgtatatgtattggctgcatttgcatgaataatactacgtgtaagcccaaaagaacccacgtgtagccca
tgcaaagttaacactcacgaccccattcctcagtctccactatataaacccaccatccccaatctcaccaaac >SEQ-149;160nt_promoter_with_spacer_and_enhancer
cggcatattgtattcccacacattattaaaataccgtatatgtattggctgcatttgcatgaataatactacgtgtaagcccaaaagaacccacgtgtagccca
tgcaaagttaacactcacgaccccattcctcagtctccactatataaacccaccatccccaatctcaccaaacccaccacacaactcacaactcactctca
caccttaaagaaccaatcaccaccaaaaa >SEQ-150;197nt_promoter
aatgtacacttgtcattgccaaaattagtaaaatactcggcatattgtattcccacacattattaaaataccgtatatgtattggctgcatttgcatgaataatact
acgtgtaagcccaaaagaacccacgtgtagcccatgcaaagttaacactcacgaccccattcctcagtctccactatataaacccaccat >SEQ-151;197nt_promoter_with_spacer
aatgtacacttgtcattgccaaaattagtaaaatactcggcatattgtattcccacacattattaaaataccgtatatgtattggctgcatttgcatgaataatact
acgtgtaagcccaaaagaacccacgtgtagcccatgcaaagttaacactcacgaccccattcctcagtctccactatataaacccaccatccccaatctc
accaaac >SEQ-152;197nt_promoter_with_spacer_and_enhancer
aatgtacacttgtcattgccaaaattagtaaaatactcggcatattgtattcccacacattattaaaataccgtatatgtattggctgcatttgcatgaataatact
acgtgtaagcccaaaagaacccacgtgtagcccatgcaaagttaacactcacgaccccattcctcagtctccactatataaacccaccatccccaatctc
accaaacccaccacacaactcacaactcactctcacaccttaaagaaccaatcaccaccaaaaa >SEQ-153;235nt_promoter
tccaaattaaagcaagagaggccaagtaagataatccaaatgtacacttgtcattgccaaaattagtaaaatactcggcatattgtattcccacacattatta
aaataccgtatatgtattggctgcatttgcatgaataatactacgtgtaagcccaaaagaacccacgtgtagcccatgcaaagttaacactcacgacccca
ttcctcagtctccactatataaacccaccat >SEQ-154;235nt_promoter_with_spacer
tccaaattaaagcaagagaggccaagtaagataatccaaatgtacacttgtcattgccaaaattagtaaaatactcggcatattgtattcccacacattatta
aaataccgtatatgtattggctgcatttgcatgaataatactacgtgtaagcccaaaagaacccacgtgtagcccatgcaaagttaacactcacgacccca
ttcctcagtctccactatataaacccaccatccccaatctcaccaaac >SEQ-155;235nt_promoter_with_spacer_and_enhancer
tccaaattaaagcaagagaggccaagtaagataatccaaatgtacacttgtcattgccaaaattagtaaaatactcggcatattgtattcccacacattatta
aaataccgtatatgtattggctgcatttgcatgaataatactacgtgtaagcccaaaagaacccacgtgtagcccatgcaaagttaacactcacgacccca

Figure 4 (continued)

ttcctcagtctccactatataaacccaccatccccaatctcaccaaacccaccacacaactcacaactcactctcacaccttaaagaaccaatcaccacc
aaaaa >SEQ-156;240nt_promoter
aataatccaaattaaagcaagagaggccaagtaagataatccaaatgtacacttgtcattgccaaaattagtaaaatactcggcatattgtattcccacac
attattaaaataccgtatatgtattggctgcatttgcatgaataatactacgtgtaagcccaaaagaacccacgtgtagcccatgcaaagttaacactcacg
accccattcctcagtctccactatataaacccaccat >SEQ-157;240nt_promoter_with_spacer
aataatccaaattaaagcaagagaggccaagtaagataatccaaatgtacacttgtcattgccaaaattagtaaaatactcggcatattgtattcccacac
attattaaaataccgtatatgtattggctgcatttgcatgaataatactacgtgtaagcccaaaagaacccacgtgtagcccatgcaaagttaacactcacg
accccattcctcagtctccactatataaacccaccatccccaatctcaccaaac >SEQ-158;240nt_promoter_with_spacer_and_enhancer
aataatccaaattaaagcaagagaggccaagtaagataatccaaatgtacacttgtcattgccaaaattagtaaaatactcggcatattgtattcccacac
attattaaaataccgtatatgtattggctgcatttgcatgaataatactacgtgtaagcccaaaagaacccacgtgtagcccatgcaaagttaacactcacg
accccattcctcagtctccactatataaacccaccatccccaatctcaccaaacccaccacacaactcacaactcactctcacaccttaaagaaccaatc
accaccaaaaa >SEQ-159;1064nt_promoter
ttagcagatatttggtgtctaaatgtttattttgtgatatgttcatgtttgaaatggtggtttcgaaaccagggacaacgttgggatctgataggtgtcaaagagt
attatggattgggacaatttcggtcatgagttgcaaattcaagtatatcgttcgattatgaaaattttcgaagaatatcccatttgagagagtctttacctcattaat
gttttagattatgaaatttatcatagttcatcgtagtcttttggtgtaaaggctgtaaaaagaaattgttcacttttgttttcgtttatgtgaaggctgtaaaagattgt
aaaagactattttggtgttttggataaaatgatagttttatagattctttgcttttagaagaaatacatttgaaatttttccatgttgagtataaaataccgaaatcg
attgaagatcatagaaatattttaactgaaaacaaatttataactgattcaattctctccatttttatacctatttaaccgtaatcgattctaatagatgatcgattttt
atataatcctaattaaccaacggcatgtattggataattaaccgatcaactctcacccctaatagaatcagtattttccttcgacgttaattgatcctacactatgt
aggtcatatccatcgttttaattttggccaccattcaattctgtcttgcctttagggatgtgaatatgaacggccaaggtaagagaataaaaataatccaaatt
aaagcaagagaggccaagtaagataatccaaatgtacacttgtcattgccaaaattagtaaaatactcggcatattgtattcccacacattattaaaatacc
gtatatgtattggctgcatttgcatgaataatactacgtgtaagcccaaaagaacccacgtgtagcccatgcaaagttaacactcacgaccccattcctcag
tctccactatataaacccaccat >SEQ-160;1064nt_promoter_with_spacer_but_without_enhancer
ttagcagatatttggtgtctaaatgtttattttgtgatatgttcatgtttgaaatggtggtttcgaaaccagggacaacgttgggatctgataggtgtcaaagagt
attatggattgggacaatttcggtcatgagttgcaaattcaagtatatcgttcgattatgaaaattttcgaagaatatcccatttgagagagtctttacctcattaat
gttttagattatgaaatttatcatagttcatcgtagtcttttggtgtaaaggctgtaaaaagaaattgttcacttttgttttcgtttatgtgaaggctgtaaaagattgt
aaaagactattttggtgttttggataaaatgatagttttatagattctttgcttttagaagaaatacatttgaaatttttccatgttgagtataaaataccgaaatcg
attgaagatcatagaaatattttaactgaaaacaaatttataactgattcaattctctccatttttatacctatttaaccgtaatcgattctaatagatgatcgattttt
atataatcctaattaaccaacggcatgtattggataattaaccgatcaactctcacccctaatagaatcagtattttccttcgacgttaattgatcctacactatgt
aggtcatatccatcgttttaattttggccaccattcaattctgtcttgcctttagggatgtgaatatgaacggccaaggtaagagaataaaaataatccaaatt
aaagcaagagaggccaagtaagataatccaaatgtacacttgtcattgccaaaattagtaaaatactcggcatattgtattcccacacattattaaaatacc
gtatatgtattggctgcatttgcatgaataatactacgtgtaagcccaaaagaacccacgtgtagcccatgcaaagttaacactcacgaccccattcctcag
tctccactatataaacccaccatccccaatctcaccaaac >SEQ-161;ProPer_98nt_promoter_with_spacer_and_enhancer

Figure 4 (continued)

ataatactacgtgtaagcccaaaagaacccacgtgtagcccatgcaaagttaacactcatgaccccattcctcagtctccactatataaacccaccatccc
ctatctcaccaaacccaccacacaactcacaactcactctcacaccttaaagaaccaatcaccaccaaaaa >SEQ-162;ProPer_98nt_promoter_with_spacer_and_enhancer
ataatactacgtgtaagcccaaaagaacccacgtgtagcccatgcaaagttaacactcacaaccccattcctcagtctccactatataaacccaccatctt
acttctcaccaaacccaccacacaactcacaactcactctcacaccttaaagaaccaatcaccaccaaaaa >SEQ-163;ProPer_98nt_promoter_with_spacer_and_enhancer
ataatactacgtgtaagcccaaaagaacccacgtgtagcccatgcaaagttaacactcaagaccccattcctcagtctccactatataaacccaccatcc
atcgtctcaccaaacccaccacacaactcacaactcactctcacaccttaaagaaccaatcaccaccaaaaa >SEQ-164;ProPer_98nt_promoter_with_spacer_and_enhancer
ataatactacgtgtaagcccaaaagaacccacgtgtagcccatgcaaagttaacactcataaccccattcctcagtctccactatataaacccaccatcat
ctctctcaccaaacccaccacacaactcacaactcactctcacaccttaaagaaccaatcaccaccaaaaa >SEQ-165;ProPer_98nt_promoter_with_spacer_and_enhancer
ataatactacgtgtaagcccaaaagaacccacgtgtagcccatgcaaagttaacactcattaccccattcctcagtctccactatataaacccaccatcga
atttctcaccaaacccaccacacaactcacaactcactctcacaccttaaagaaccaatcaccaccaaaaa >SEQ-166;ProPer_98nt_promoter_with_spacer_and_enhancer
ataatactacgtgtaagcccaaaagaacccacgtgtagcccatgcaaagttaacactcagcaccccattcctcagtctccactatataaacccaccatcct
cgctctcaccaaacccaccacacaactcacaactcactctcacaccttaaagaaccaatcaccaccaaaaa >SEQ-167;ProPer_98nt_promoter_with_spacer_and_enhancer
ataatactacgtgtaagcccaaaagaacccacgtgtagcccatgcaaagttaacactcaggaccccattcctcagtctccactatataaacccaccatcg
gatgtctcaccaaacccaccacacaactcacaactcactctcacaccttaaagaaccaatcaccaccaaaaa >SEQ-168;ProPer_98nt_promoter_with_spacer_and_enhancer
ataatactacgtgtaagcccaaaagaacccacgtgtagcccatgcaaagttaacactcaccaccccattcctcagtctccactatataaacccaccatca
catctctcaccaaacccaccacacaactcacaactcactctcacaccttaaagaaccaatcaccaccaaaaa >SEQ-169;ProPer_98nt_promoter_with_spacer_and_enhancer
ataatactacgtgtaagcccaaaagaacccacgtgtagcccatgcaaagttaacactcaggaccccattcctcagtctccactatataaacccaccatca
acaatctcaccaaacccaccacacaactcacaactcactctcacaccttaaagaaccaatcaccaccaaaaa >SEQ-170;ProPer_98nt_promoter_with_spacer_and_enhancer
ataatactacgtgtaagcccaaaagaacccacgtgtagcccatgcaaagttaacactcactaccccattcctcagtctccactatataaacccaccatcca
acatctcaccaaacccaccacacaactcacaactcactctcacaccttaaagaaccaatcaccaccaaaaa >SEQ-171;synthetic_160nt_promoter_with_spacer
attaaaataccgtatataaacccacgtgtagcccatgcaaagttaacactcacgaccccattcccacacattattaaaatactacgtgtaagcccatgcaa
agttaacactcaccatcccattcccacacattattaaaataccgtatataaacccaccaaaagaacccaccaaac >SEQ-172;synthetic_160nt_promoter_with_spacer

Figure 4 (continued)

acgtgtaagcccaatctcaccatccccattcctcagtctccactatataaacccacgtgtagcccatgcaaagttaacactcacgaccccatgcaaagtta
acactcacgaccccaatctcaccatccccattcctcagtctccactatataaacccaccaaaagaacccaccaaac >SEQ-173;synthetic_160nt_promoter_with_spacer
ctacgtgtaagcccaatctcacgaccccatgcaaagttaacactcaccaaaagaacccaccaaaagaacccacgtgtagcccaatctcacgaccccatt
cctcagtctccactatataaacccacacattattaaaataccgtatataaacccacgtgtagcccaatctcaccaaac >SEQ-174;synthetic_160nt_promoter_with_spacer
tcctcagtctccactatatgtattgtattcctcagtctccactatataaacccacgtgtagcccattcccacacattattaaaatactacgtgtagcccatgcaaa
gttaacactcaccatccccattcccacacattattaaaataccgtatataaacccacgtgtaagcccaaac >SEQ-175;synthetic_160nt_promoter_with_spacer
tgtaagcccatgcaaagttaacactcacgaccccattcccacacattattaaaataccgtatataaacccaccatccccaaaagaacccacgtgtagccc
atgcaaagttaacactcacgaccccattcccacacattattaaaataccgtatataaacccacgtgtaagcccaaac >SEQ-176;synthetic_160nt_promoter_with_spacer
acattattaaaataccgtatatgtattggctgcatgaataatactacgtgtagcccatgcaaagttaacactcaccatccccattcccacgtgtagcccatgc
aaagttaacactcaccatccccattcctcagtctccactatataaacccacgtgtaagcccaatctcaccaaac >SEQ-177;synthetic_160nt_promoter_with_spacer
cgaccccatgcaaagttaacactcacgaccccaatctcaccaaaagaacccaccatccccatgcaaagttaacactcaccatccccatgcaaagttaa
cactcaccatccccaaaagaacccacgtgtaagcccattcctcagtctccactatataaacccacgtgtaagcccaaac >SEQ-178;synthetic_160nt_promoter_with_spacer
aacactcacgaccccaatctcacgaccccaaaagaacccacgtgtagcccaatctcacgaccccatgcaaagttaacactcaccatccccattcctca
gtctccactatatgtattgtattcccacgtgtagcccattcctcagtctccactatataaacccacgtgtagcccaaac >SEQ-179;synthetic_160nt_promoter_with_spacer
aaaagaacccacacattattaaaataccgtatataaacccacgtgtaagcccaaaagaacccacacattattaaaatactacgtgtaagcccatgcaaa
gttaacactcaccaaaagaacccacacattattaaaataccgtatataaacccacgtgtaagcccaatctcaccaaac >SEQ-180;synthetic_160nt_promoter_with_spacer
cccacgtgtaagcccaatctcacgaccccattcccacacattattaaaatactacgtgtaagcccattcccacgtgtagcccatgcaaagttaacactcac
gaccccattcctcagtctccactatatgtattcctcagtctccactatataaacccaccaaaagaacccaccaaac >SEQ-181;synthetic_160nt_promoter_with_spacer
aacccacacattattaaaataccgtatatgtattcccaccatccccatgcaaagttaacactcaccatccccaaaagaacccacacattattaaaataccg
tatatgtattcccacgtgtagcccattcctcagtctccactatataaacccacgtgtaagcccattcccaccaaac >SEQ-182;synthetic_160nt_promoter_with_spacer
cccatgcaaagttaacactcacgaccccaaaagaacccacacattattaaaataccgtatatgtattcctcagtctccactatataaacccacgtgtaagc
ccattcccacacattattaaaataccgtatatgtattcctcagtctccactatataaacccacgtgtagcccaaac >SEQ-183;synthetic_160nt_promoter_with_spacer

Figure 4 (continued)

cgtatatgtattgtattcccacgtgtaagcccaatctcacgaccccatgcaaagttaacactcacgaccccatgcaaagttaacactcaccaaaagaacc
cacacattattaaaatactacgtgtagcccattcctcagtctccactatataaacccaccaaaagaacccaccaaac >SEQ-184;synthetic_160nt_promoter_with_spacer
acacattattaaaataccgtatataaacccacgtgtagcccatgcaaagttaacactcacgaccccaaaagaacccacacattattaaaatactacgtgt
aagcccattcctcagtctccactatatgtattgtattcctcagtctccactatataaacccacgtgtaagcccaaac >SEQ-185;synthetic_160nt_promoter_with_spacer
tatatgtattcccacacattattaaaatactacgtgtagcccattcccacacattattaaaatactacgtgtaagcccattcctcagtctccactatataaaccca
cgtgtagcccattcccacacattattaaaataccgtatataaacccacgtgtaagcccattcccaccaaac >SEQ-186;synthetic_160nt_promoter_with_spacer
taaacccaccatccccattcctcagtctccactatataaacccacgtgtagcccatgcaaagttaacactcaccatccccaatctcaccatccccaatctca
cgaccccatgcaaagttaacactcacgaccccattcctcagtctccactatataaacccacgtgtaagcccaaac >SEQ-187;synthetic_160nt_promoter_with_spacer
ctacgtgtagcccattcccacgtgtaagcccaatctcacgaccccattcccacgtgtaagcccattcccacgtgtagcccatgcaaagttaacactcaccat
ccccaatctcaccatccccaatctcacgaccccattcctcagtctccactatataaacccacgtgtagcccaaac >SEQ-188;synthetic_160nt_promoter_with_spacer
atgcaaagttaacactcacgaccccatgcaaagttaacactcaccaaaagaacccacacattattaaaatactacgtgtagcccattcccacgtgtaagc
ccattcctcagtctccactatatgtattcctcagtctccactatataaacccacgtgtaagcccaatctcaccaaac >SEQ-189;synthetic_160nt_promoter_with_spacer
gaacccacacattattaaaatactacgtgtagcccaatctcaccatccccaaaagaacccacacattattaaaataccgtatatgtattgtattgtattggctg
catttgcatgaataatactacgtgtaagcccattcctcagtctccactatataaacccacgtgtagcccaaac >SEQ-190;synthetic_160nt_promoter_with_spacer
cctcagtctccactatataaacccacgtgtagcccaatctcaccatccccatgcaaagttaacactcaccatccccaaaagaacccacacattattaaaat
accgtatatgtattgtattcccacacattattaaaataccgtatataaacccacgtgtagcccaatctcaccaaac >SEQ-191;synthetic_160nt_promoter_with_spacer
agttaacactcacgaccccaatctcaccatccccattcccacgtgtagcccaatctcacgaccccaatctcacgaccccaatctcaccaaaagaaccca
cgtgtaagcccatgcaaagttaacactcacgaccccattcctcagtctccactatataaacccacgtgtagcccaaac >SEQ-192;synthetic_160nt_promoter_with_spacer
gcccatgcaaagttaacactcaccatccccattcctcagtctccactatatgtattcccacacattattaaaataccgtatataaacccacgtgtagcccatgc
aaagttaacactcacgaccccattcctcagtctccactatataaacccacgtgtaagcccaatctcaccaaac >SEQ-193;synthetic_160nt_promoter_with_spacer
cattattaaaataccgtatatgtattcccacgtgtaagcccaatctcacgaccccatgcaaagttaacactcaccatccccaatctcacgaccccattcctca
gtctccactatatgtattgtattgtattcctcagtctccactatataaacccaccatccccaatctcaccaaac >SEQ-194;synthetic_160nt_promoter_with_spacer

Figure 4 (continued)

cccattcccacgtgtaagcccatgcaaagttaacactcacgaccccaatctcacgaccccattcccaccaaaagaacccacacattattaaaataccgt
atatgtattggctgcatgaataataccgtatatgtattcctcagtctccactatataaacccacgtgtaagcccaaac >SEQ-195;synthetic_160nt_promoter_with_spacer
atgtattggctgcatgaataataccgtatatgtattcctcagtctccactatatgtattcctcagtctccactatatgtattggctgcatgaataatactacgtgtaa
gcccaatctcacgaccccattcctcagtctccactatataaacccacgtgtagcccaatctcaccaaac >SEQ-196;synthetic_160nt_promoter_with_spacer
ccatccccattcctcagtctccactatataaacccacacattattaaaatactacgtgtagcccattcccacgtgtagcccatgcaaagttaacactcacgac
cccaatctcaccaaaagaacccaccatccccattcctcagtctccactatataaacccacgtgtaagcccaaac >SEQ-197;synthetic_160nt_promoter_with_spacer
accccatgcaaagttaacactcacgaccccattcccacacattattaaaataccgtatatgtattcctcagtctccactatataaacccaccaaaagaaccc
acacattattaaaataccgtatatgtattggctgcatgaataataccgtatataaacccacgtgtaagcccaaac >SEQ-198;synthetic_160nt_promoter_with_spacer
cactatatgtattggctgcatttgcatttgcatgaataatactacgtgtaagcccaatctcacgaccccaaaagaacccacacattattaaaataccgtatata
aacccacacattattaaaataccgtatatgtattcctcagtctccactatataaacccacgtgtagcccaaac >SEQ-199;synthetic_160nt_promoter_with_spacer
cacgaccccaaaagaacccacgtgtaagcccaatctcacgaccccatgcaaagttaacactcaccatccccatgcaaagttaacactcaccaaaaga
acccacacattattaaaatactacgtgtagcccattcctcagtctccactatataaacccaccaaaagaacccaccaaac >SEQ-200;synthetic_160nt_promoter_with_spacer
actacgtgtagcccattcctcagtctccactatatgtattgtattcccacgtgtaagcccatgcaaagttaacactcacgaccccaaaagaacccacacatt
attaaaatactacgtgtaagcccattcccacacattattaaaataccgtatataaacccacgtgtaagcccaaac >SEQ-201;synthetic_160nt_promoter_with_spacer
aataataccgtatatgtattggctgcatttgcatgaataatactacgtgtaagcccaatctcaccatccccattcctcagtctccactatataaacccacacatt
attaaaataccgtatatgtattggctgcatgaataataccgtatataaacccaccaaaagaacccaccaaac >SEQ-202;synthetic_160nt_promoter_with_spacer
accgtatatgtattggctgcatttgcatgaataataccgtatataaacccacgtgtaagcccatgcaaagttaacactcaccatccccattcctcagtctccac
tatatgtattcctcagtctccactatatgtattcctcagtctccactatataaacccacgtgtaagcccaaac >SEQ-203;synthetic_160nt_promoter_with_spacer
ccaaaagaacccacgtgtaagcccatgcaaagttaacactcaccatccccaatctcaccatccccattcccacacattattaaaataccgtatataaacc
cacacattattaaaatactacgtgtagcccattcctcagtctccactatataaacccaccaaaagaacccaccaaac >SEQ-204;synthetic_160nt_promoter_with_spacer
atgcaaagttaacactcacgaccccatgcaaagttaacactcaccatccccatgcaaagttaacactcaccaaaagaacccaccatccccatgcaaag
ttaacactcaccatccccattcccacacattattaaaataccgtatataaacccacgtgtaagcccaatctcaccaaac >SEQ-205;synthetic_160nt_promoter_with_spacer

Figure 4 (continued)

atactacgtgtaagcccattcctcagtctccactatatgtattcccacgtgtaagcccaaaagaacccacgtgtaagcccatgcaaagttaacactcacga
ccccaatctcaccatccccaatctcacgaccccattcctcagtctccactatataaacccacgtgtaagcccaaac >SEQ-206;synthetic_160nt_promoter_with_spacer
cactcacgaccccatgcaaagttaacactcacgaccccatgcaaagttaacactcacgaccccaatctcacgaccccattcccacacattattaaaatac
cgtatataaacccaccaaaagaacccaccatccccattcctcagtctccactatataaacccacgtgtagcccaaac >SEQ-207;synthetic_160nt_promoter_with_spacer
acattattaaaataccgtatataaacccacacattattaaaatactacgtgtaagcccaaaagaacccaccatccccaatctcacgaccccaatctcacg
accccattcctcagtctccactatataaacccacacattattaaaataccgtatataaacccacgtgtagcccaaac >SEQ-208;synthetic_160nt_promoter_with_spacer
aaaataccgtatataaacccacgtgtaagcccaatctcaccatccccatgcaaagttaacactcacgaccccaatctcacgaccccatgcaaagttaac
actcacgaccccattcctcagtctccactatatgtattcctcagtctccactatataaacccacgtgtaagcccaaac >SEQ-209;synthetic_160nt_promoter_with_spacer
taagcccaatctcaccatccccattcctcagtctccactatatgtattcccacgtgtaagcccaatctcacgaccccatgcaaagttaacactcacgaccccc
aaaagaacccaccatccccaaaagaacccacacattattaaaataccgtatataaacccacgtgtaagcccaaac >SEQ-210;synthetic_160nt_promoter_with_spacer
acattattaaaatactacgtgtaagcccatgcaaagttaacactcaccatccccaatctcaccaaaagaacccacgtgtaagcccaatctcaccatcccc
atgcaaagttaacactcacgaccccattcctcagtctccactatataaacccacgtgtaagcccattcccaccaaac >SEQ-211;synthetic_160nt_promoter_with_spacer
cactcaccaaaagaacccaccatccccaaaagaacccacgtgtagcccaatctcacgaccccattcccaccatccccatgcaaagttaacactcacg
accccattcccacacattattaaaataccgtatatgtattcctcagtctccactatataaacccacgtgtaagcccaaac >SEQ-212;synthetic_160nt_promoter_with_spacer
acccacgtgtagcccatgcaaagttaacactcaccatccccaaaagaacccacgtgtaagcccattcccacacattattaaaataccgtatatgtattcctc
agtctccactatataaacccacacattattaaaataccgtatataaacccacgtgtaagcccaatctcaccaaac >SEQ-213;synthetic_160nt_promoter_with_spacer
atgtattcctcagtctccactatatgtattcccacgtgtaagcccaatctcaccatccccaaaagaacccaccaaaagaacccacacattattaaaatacta
cgtgtagcccaatctcacgaccccattcctcagtctccactatataaacccacgtgtagcccaatctcaccaaac >SEQ-214;synthetic_160nt_promoter_with_spacer
attaaaataccgtatatgtattggctgcatgaataataccgtatataaacccacgtgtaagcccaaaagaacccacacattattaaaataccgtatataaac
ccacgtgtagcccaaaagaacccacacattattaaaataccgtatataaacccaccatccccaatctcaccaaac >SEQ-215;synthetic_160nt_promoter_with_spacer
cactatatgtattcctcagtctccactatataaacccacacattattaaaataccgtatatgtattggctgcatgaataatactacgtgtagcccatgcaaagtta
acactcaccatccccaaaagaacccacacattattaaaataccgtatataaacccacgtgtaagcccaaac >SEQ-216;synthetic_160nt_promoter_with_spacer

Figure 4 (continued)

actacgtgtaagcccatgcaaagttaacactcacgaccccatgcaaagttaacactcacgaccccaatctcacgaccccattcctcagtctccactatata
aacccacgtgtaagcccattcccacgtgtagcccattcctcagtctccactatataaacccacgtgtagcccaaac >SEQ-217;synthetic_160nt_promoter_with_spacer
aagaacccacacattattaaaataccgtatataaacccacacattattaaaataccgtatatgtattcctcagtctccactatataaacccaccatccccatg
caaagttaacactcacgaccccattcctcagtctccactatataaacccacgtgtaagcccaatctcaccaaac >SEQ-218;synthetic_160nt_promoter_with_spacer
acattattaaaatactacgtgtaagcccaatctcaccaaaagaacccacgtgtaagcccaatctcacgaccccatgcaaagttaacactcaccaaaaga
acccacgtgtaagcccaaaagaacccacacattattaaaataccgtatataaacccaccatccccattcccaccaaac >SEQ-219;synthetic_160nt_promoter_with_spacer
ctcacgaccccattcccacgtgtagcccatgcaaagttaacactcaccatccccaatctcaccaaaagaacccaccatccccaaaagaacccacacat
tattaaaatactacgtgtaagcccaaaagaacccacacattattaaaataccgtatataaacccacgtgtagcccaaac >SEQ-220;synthetic_160nt_promoter_with_spacer
tccccatgcaaagttaacactcaccatccccaatctcaccaaaagaacccacacattattaaaataccgtatataaacccacacattattaaaatactacg
tgtaagcccatgcaaagttaacactcacgaccccattcctcagtctccactatataaacccacgtgtagcccaaac >SEQ-221;ProPer_160nt_promoter_with_spacer_and_enhancer
aaggcatcgctgaaagagcacattattaaaataccgtatatgtattggctgcatttgcatgaataatactacgtgtaagcccaaaagaacccacgtgtagc
ccatgcaaagttaacactcaggaccccattcctcagtctccactatataaacccaccatcggggttctcaccaaacccaccacacaactcacaactcact
ctcacaccttaaagaaccaatcaccaccaaaaa >SEQ-222;ProPer_160nt_promoter_with_spacer_and_enhancer
gaggcgagggtctgtcgacacattattaaaataccgtatatgtattggctgcatttgcatgaataatactacgtgtaagcccaaaagaacccacgtgtagcc
catgcaaagttaacactcactaccccattcctcagtctccactatataaacccaccatcctctctctcaccaaacccaccacacaactcacaactcactctc
acaccttaaagaaccaatcaccaccaaaaa >SEQ-223;ProPer_160nt_promoter_with_spacer_and_enhancer
ctggtgatgccagggttgcacattattaaaataccgtatatgtattggctgcatttgcatgaataatactacgtgtaagcccaaaagaacccacgtgtagccc
atgcaaagttaacactcaaaaccccattcctcagtctccactatataaacccaccatcaacattctcaccaaacccaccacacaactcacaactcactctc
acaccttaaagaaccaatcaccaccaaaaa >SEQ-224;ProPer_160nt_promoter_with_spacer_and_enhancer
cgagtgggaaccgttcctcacattattaaaataccgtatatgtattggctgcatttgcatgaataatactacgtgtaagcccaaaagaacccacgtgtagccc
atgcaaagttaacactcataacccattcctcagtctccactatataaacccaccatcagccctctcaccaaacccaccacacaactcacaactcactctc
acaccttaaagaaccaatcaccaccaaaaa >SEQ-225;ProPer_160nt_promoter_with_spacer_and_enhancer
attctacggttccctcaacacattattaaaataccgtatatgtattggctgcatttgcatgaataatactacgtgtaagcccaaaagaacccacgtgtagccca
tgcaaagttaacactcaccaccccattcctcagtctccactatataaacccaccatctctcttctcaccaaacccaccacacaactcacaactcactctcac
accttaaagaaccaatcaccaccaaaaa >SEQ-226;ProPer_160nt_promoter_with_spacer_and_enhancer

Figure 4 (continued)

agatccgcggcacaaagccacattattaaaataccgtatatgtattggctgcatttgcatgaataatactacgtgtaagcccaaaagaacccacgtgtagc
ccatgcaaagttaacactcagcaccccattcctcagtctccactatataaacccaccatcggcaatctcaccaaacccaccacacaactcacaactcact
ctcacaccttaaagaaccaatcaccaccaaaaa >SEQ-227;ProPer_160nt_promoter_with_spacer_and_enhancer
agatacgcacccaccctacacattattaaaataccgtatatgtattggctgcatttgcatgaataatactacgtgtaagcccaaaagaacccacgtgtagcc
catgcaaagttaacactcattaccccattcctcagtctccactatataaacccaccatctgacttctcaccaaacccaccacacaactcacaactcactctc
acaccttaaagaaccaatcaccaccaaaaa >SEQ-228;ProPer_160nt_promoter_with_spacer_and_enhancer
gacggtgccctgcgtggccacattattaaaataccgtatatgtattggctgcatttgcatgaataatactacgtgtaagcccaaaagaacccacgtgtagcc
catgcaaagttaacactcaacaccccattcctcagtctccactatataaacccaccatcctagatctcaccaaacccaccacacaactcacaactcactct
cacaccttaaagaaccaatcaccaccaaaaa >SEQ-229;ProPer_160nt_promoter_with_spacer_and_enhancer
cctgggagaggtctcttacacattattaaaataccgtatatgtattggctgcatttgcatgaataatactacgtgtaagcccaaaagaacccacgtgtagccc
atgcaaagttaacactcaaaaccccattcctcagtctccactatataaacccaccatctgtaatctcaccaaacccaccacacaactcacaactcactctc
acaccttaaagaaccaatcaccaccaaaaa >SEQ-230;ProPer_160nt_promoter_with_spacer_and_enhancer
gcagctttccgttacgggcacattattaaaataccgtatatgtattggctgcatttgcatgaataatactacgtgtaagcccaaaagaacccacgtgtagccc
atgcaaagttaacactcaccaccccattcctcagtctccactatataaacccaccatccttcctctcaccaaacccaccacacaactcacaactcactctca
caccttaaagaaccaatcaccaccaaaaa >SEQ-231;synthetic_240nt_promoter_with_spacer
ccaaattaaagcaagagaggccaagtaaaattagtaaaatactacgtgtagcccattcccaccatccccaatctcaccatcccattcctcagtctccact
atatgtattgtattcccacgtgtagcccatgcaaagttaacactcacgaccccaaattaaaatactcggcatattgtattcctcagtctccactatataaaccca
cgtgtagcccaaac >SEQ-232;synthetic_240nt_promoter_with_spacer
gtgtaagcccaaattaaaataccgtatataaacccacacattattaaagcaagagaggccaaaatactacgtgtagcccaaaattaaaataccgtatata
aacccacgtgtagcccaatctcacgaccccatgcaaagttaacactcacgaccccaaaagaacccacacattattaaagcaagagaggccaaatgta
ttgtattcctcagtctccactatataaacccacgtgtaagataatccaaac >SEQ-233;synthetic_240nt_promoter_with_spacer
gcatttgcatgaataatccaaaataccgtatatgtacacttgtcattgccaagtaaaattaaaattaaagcaagagaggccaaattaaaatactacgtgtaa
gcccattcccacgtgtagcccatgcaaagttaacacttgtcattgccaaattaaaatactcggcatattggctgcatgaataatactacgtgtagcccaatct
cacgaccccaaaatactacgtgtaagataataccgtatataaacccacgtgtagcccaatctcaccaaac >SEQ-234;synthetic_240nt_promoter_with_spacer
cacacattattaaagcaagagaggccaaaagaacccacacattattaaagcaagagaggccaagtaagataatccaaattaaaatactacgtgtagc
ccattcccacgtgtaagcccaatctcacgaccccattcctcagtctccactatataaacccaccatccccatgcaaagttaacacttgtcattgccaagtaa
aattagtaaaatactacgtgtaagcccattcccacacattattaaaataccgtatataaacccacgtgtaagataatccaaac >SEQ-235;synthetic_240nt_promoter_with_spacer

Figure 4 (continued)

accaaaagaacccacgtgtaagcccaaaagaacccacgtgtaagcccaaatgtattcccacacattattaaagcaagagaggccaagtaaaatacta
cgtgtagcccatgcaaagttaacactcaccaaatgtattcccaccaaattagtaaaatactacgtgtaagcccattcccaccaaaagaacccacgtgtag
cccatgcaaagttaacacttgtcattgccaagtaaaatactcggcatattggctgcatgaataataccgtatataaacccacgtgtaagcccaatctcacca
aac >SEQ-236;synthetic_240nt_promoter_with_spacer
tcagtctccactatataaacccacacattattaaagcaagagaggccaaaatactacgtgtaagcccattcccacgtgtagcccaaattagtaagcccat
gcaaagttaacactcacgaccccattcccacgtgtaagataatccaaattagtaaaatactcggcatattgtattggctgcatgaataatccaaaatactcg
gcatattgtattgtattcccaccaaaatactcggcatattgtattgtattcctcagtctccactatatgtattgtattcctcagtctccactatataaacccacgtgta
agataatccaaac >SEQ-237;synthetic_240nt_promoter_with_spacer
tgaataatccaaaagaacccacgtgtaagataatactcggcatattgtattggctgcatgaataatccaaaagaacccacacattattaaagcaagagag
gccaaaatactacgtgtagcccaaatgtacacttgtcattgccaaaagaacccacgtgtagcccattcccacacattattaaagcaagagaggccaagt
aagcccatgcaaagttaacactcacgaccccattcccacgtgtagcccaaattagtaagataatccaaaataccgtatatgtacacttgtcattgccaagt
aagataataccgtatataaacccacgtgtaagataatccaaac >SEQ-238;synthetic_240nt_promoter_with_spacer
tttgcatgaataatactcggcatattgtattggctgcatttgcatttgcatttgcatgaataatccaaaagaacccaccaaaattaaaattaaagcaagagag
gccaagtaagataatactcggcatattgtattggctgcatgaataatactcggcatattgtattggctgcatgaataatccaaaatactacgtgtagcccattc
ctcagtctccactatatgtacactcacgaccccattcctcagtctccactatataaacccacgtgtaagcccatgcaaagttaacactcacgaccccaaaat
accgtatataaacccacgtgtaagataatccaaac >SEQ-239;synthetic_240nt_promoter_with_spacer
taccgtatataaacccacacattattaaagcaagagaggccaagtaagataatccaaatgtacacttgtcattgccaagtaaaattagtaaaatactcggc
atattggctgcatttgcatgaataataccgtatataaacccaccaaaattaaaataccgtatataaacccacacattattaaaattaaaatactacgtgtagc
ccatgcaaagttaacacttgtcattgccaaaagaacccacgtgtaagcccatgcaaagttaacacttgtcattgccaaaagaacccacgtgtaagcccat
cccacacattattaaaataccgtatataaacccacgtgtagcccaatctcaccaaac >SEQ-240;synthetic_240nt_promoter_with_spacer
aagcaagagaggccaagtaagataatccaaatgtattcccacgtgtagcccatgcaaagttaacacttgtcattgccaagtaagcccaatctcaccatcc
ccattcctcagtctccactatatgtacacttgtcattgccaagtaaaattaaaataccgtatataaacccaccatccccatgcaaagttaacactcacgaccc
caaaattaaagcaagagaggccaagtaaaatactacgtgtagcccaatctcaccaaatgtattcccaccatccccattcccacgtgtagcccatgcaaa
gttaacactcaccaaattagtaaaataccgtatataaacccacgtgtaagataatccaaac >SEQ-241;synthetic_240nt_promoter_with_spacer
cacattattaaaattaaagcaagagaggccaagtaagcccaaatgtacacttgtcattgccaaattaaaatactcggcatattgtattgtattcccacacatt
attaaaatactcggcatattgtattggctgcatttgcatttgcatgaataatactacgtgtaagataatccaaaatactacgtgtagcccatgcaaagttaacac
tcaccaaaagaacccacgtgtaagcccatgcaaagttaacactcaccaaatgtattcccacacattattaaaattaaaattagtaaaataccgtatatgtat
tcccacgtgtaagcccattcctcagtctccactatataaacccacgtgtagcccaaac >SEQ-242;synthetic_240nt_promoter_with_spacer
agcccaatctcaccaaaagaacccacgtgtagcccatgcaaagttaacacttgtcattgccaaaagaacccacgtgtaagcccattcccacacattatta
aagcaagagaggccaagtaagcccaaatgtacacttgtcattgccaagtaaaatactacgtgtagcccatgcaaagttaacactcaccatccccaatct

Figure 4 (continued)

cacgaccccattcccacgtgtaagataatccaaattaaagcaagagaggccaaatgtattcctcagtctccactatataaacccaccatcoccatgcaaa
gttaacacttgtcattgccaaattagtaagataataccgtatataaacccacgtgtaagataatccaaac >SEQ-243;synthetic_240nt_promoter_with_spacer
aataatactcggcatattggctgcatgaataatactcggcatattgtattgtattggctgcatttgcatgaataatactcggcatattgtattgtattgtattcccac
acattattaaagcaagagaggccaagtaaaatactcggcatattggctgcatgaataatccaaattaaagcaagagaggccaaaatactacgtgtagc
ccaaattaaaatactcggcatattgtattcccaccaaatgtattcctcagtctccactatatgtattgtattcctcagtctccactatataaacccacgtgtagccc
atgcaaagttaacacttgtcattgccaagtaaaataccgtatataaacccacgtgtaagcccaaac >SEQ-244;synthetic_240nt_promoter_with_spacer
cattcccaccatccccaaaagaacccacacattattaaagcaagagaggccaaaatactacgtgtagcccattcctcagtctccactatatgtattggctg
catttgcatttgcatttgcatttgcatttgcatttgcatgaataataccgtatataaacccaccaaaagaacccacacattattaaaatactcggcatatt
gtattcccacgtgtagcccaatctcaccaaatgtattggctgcatgaataatactacgtgtaagcccaatctcacgaccccaatctcaccatccccatgcaa
agttaacacttgtcattgccaaatgtattcccacgtgtaagataataccgtatataaacccacgtgtagcccaaac >SEQ-245;synthetic_240nt_promoter_with_spacer
attaaagcaagagaggccaagtaaaatactacgtgtagcccaatctcaccatccccattcctcagtctccactatatgtattcccacacattattaaagcaa
gagaggccaagtaaaataccgtatataaacccaccatccccattcccacgtgtagcccatgcaaagttaacacttgtcattgccaaatgtacactcaccat
ccccaaattagtaaaataccgtatataaacccaccaaatgtacactcacgaccccattcccaccatccccatgcaaagttaacactcaccatccccattcc
caccaaaagaacccacgtgtagcccaatctcacgaccccattcctcagtctccactatataaacccacgtgtaagcccaaac >SEQ-246;synthetic_240nt_promoter_with_spacer
ctcagtctccactatataaacccacacattattaaagcaagagaggccaagtaaaatactacgtgtaagcccaaatgtacactcaccaaaagaaccca
ccatccccaaaagaacccacgtgtagcccatgcaaagttaacactcacgaccccatgcaaagttaacactcaccatccccattcctcagtctccactatat
gtacacttgtcattgccaagtaagcccaatctcacgaccccaatctcacgaccccaaatgtattcctcagtctccactatatgtattgtattcccaccaaattag
taaaatactacgtgtagcccaatctcaccatccccattcctcagtctccactatataaacccacgtgtaagataatccaaac >SEQ-247;synthetic_240nt_promoter_with_spacer
ttgtattcctcagtctccactatataaacccacacattattaaagcaagagaggccaaaatactacgtgtagcccaaatgtattcccacgtgtagcccaaaa
gaacccacgtgtaagcccattcccacgtgtaagcccattcccacacattattaaagcaagagaggccaagtaaaataccgtatatgtattcctcagtctcc
actatatgtacacttgtcattgccaagtaaaatactcggcatattgtattgtattcctcagtctccactatataaacccaccatccccaaaattagtaagcccat
gcaaagttaacacttgtcattgccaagtaagataatccaaattaaaataccgtatataaacccacgtgtagcccaaac >SEQ-248;synthetic_240nt_promoter_with_spacer
gataatactcggcatattggctgcatgaataatccaaattagtaaaattaaagcaagagaggccaagtaaaatactacgtgtaagataatactacgtgta
gcccattcctcagtctccactatataaacccacgtgtagcccatgcaaagttaacactcacgaccccaaatgtacacttgtcattgccaagtaaaattagta
aaattagtaagataatccaaaatactacgtgtagcccaatctcaccatccccattcctcagtctccactatataaacccaccatccccattcccacacattatt
aaaattagtaaaataccgtatataaacccacacattattaaaataccgtatataaacccacgtgtaagataatccaaac >SEQ-249;synthetic_240nt_promoter_with_spacer
attaaagcaagagaggccaagtaaaatactacgtgtaagataatactacgtgtagcccaatctcacgaccccaaaatactcggcatattggctgcatga
ataatactacgtgtagcccaaatgtattgtattcctcagtctccactatatgtattcctcagtctccactatataaacccacgtgtagcccatgcaaagttaacac
tcaccatccccaatctcacgaccccattcctcagtctccactatataaacccacacattattaaaataccgtatataaacccacgtgtaagcccatgcaaag
ttaacactcaccatccccaaatgtacacttgtcattgccaaattaaaataccgtatataaacccacgtgtagcccaaac

Figure 4 (continued)

>SEQ-250;synthetic_240nt_promoter_with_spacer
taaacccacacattattaaagcaagagaggccaagtaaaattaaaatactacgtgtaagcccaatctcacgaccccaatctcaccaaatgtacacttgtc
attgccaagtaaaatactcggcatattggctgcatttgcatgaataatactacgtgtagcccattcctcagtctccactatataaacccacgtgtagcccatgc
aaagttaacacttgtcattgccaagtaagataatactacgtgtaagataatccaaaagaacccacgtgtagcccatgcaaagttaacactcaccaaatgt
attcctcagtctccactatataaacccacacattattaaaataccgtatataaacccaccaaattagtaagataatccaaac >SEQ-251;synthetic_240nt_promoter_with_spacer
ccactatataaacccacacattattaaagcaagagaggccaaattagtaaaattaaagcaagagaggccaaaatactacgtgtaagcccaaatgtaca
ctcaccaaaagaacccaccaaaagaacccacgtgtaagataatactacgtgtaagcccaatctcaccatccccatgcaaagttaacactcaccatccc
cattcccacgtgtagcccaatctcacgaccccatgcaaagttaacactcacgaccccattcctcagtctccactatataaacccacgtgtaagcccatgca
aagttaacactcacgaccccaatctcaccaaatgtattgtattcctcagtctccactatataaacccaccatccccattcccaccaaac >SEQ-252;synthetic_240nt_promoter_with_spacer
tagcccaatctcaccaaaataccgtatatgtattcctcagtctccactatatgtattggctgcatgaataatccaaaattaaagcaagagaggccaagtaaa
atactacgtgtaagcccaatctcacgaccccattcccaccaaaagaacccacgtgtagcccaatctcaccaaaattagtaagataatccaaaatactac
gtgtaagcccatgcaaagttaacacttgtcattgccaaatgtacacttgtcattgccaaattaaagcaagagaggccaagtaagcccatgcaaagttaac
acttgtcattgccaaaatactacgtgtaagcccattcctcagtctccactatataaacccacgtgtaagcccaatctcaccaaac >SEQ-253;synthetic_240nt_promoter_with_spacer
attattaaagcaagagaggccaagtaaaatactacgtgtagcccattcccacgtgtagcccatgcaaagttaacactcaccatccccatgcaaagttaac
acttgtcattgccaaattaaaatactcggcatattggctgcatttgcatttgcatttgcatttgcatttgcatgaataatccaaaagaacccaccatccccattcct
cagtctccactatatgtacactcacgaccccaatctcaccatccccatgcaaagttaacactcaccaaaagaacccacgtgtaagcccaatctcaccaa
attaaagcaagagaggccaaattaaaatactacgtgtaagataataccgtatataaacccacgtgtaagataatccaaac >SEQ-254;synthetic_240nt_promoter_with_spacer
accccattcccaccatccccaatctcacgaccccatgcaaagttaacacttgtcattgccaagtaagcccattcctcagtctccactatatgtacacttgtcatt
gccaaatgtattcccaccatccccattcctcagtctccactatataaacccacacattattaaagcaagagaggccaaattagtaaaattagtaagcccatt
cccaccaaaataccgtatatgtattgtattgtattcccacgtgtaagataatactacgtgtagcccattcccacgtgtaagcccatgcaaagttaacactcacc
atccccaatctcacgaccccaaattagtaagataataccgtatataaacccacgtgtagcccaatctcaccaaac >SEQ-255;synthetic_240nt_promoter_with_spacer
gtaaaattaaagcaagagaggccaaaatactacgtgtagcccaatctcacgaccccaaattaaaataccgtatatgtacactcacgaccccaatctcac
gaccccatgcaaagttaacactcacgaccccattcccacgtgtaagcccatgcaaagttaacactcaccatccccattcccaccaaatgtattcctcagtct
ccactatataaacccacacattattaaaatactacgtgtaagcccaatctcacgaccccatgcaaagttaacacttgtcattgccaagtaagcccaaattaa
aataccgtatatgtattggctgcatgaataatccaaaattagtaaaataccgtatataaacccacgtgtaagataatccaaac >SEQ-256;synthetic_240nt_promoter_with_spacer
attaaaattaaagcaagagaggccaagtaagataatactacgtgtagcccattcccaccatccccaatctcaccaaaattaaaattagtaaaatactcgg
catattgtattgtattggctgcatttgcatttgcatgaataatactcggcatattgtattcctcagtctccactatataaacccacacattattaaagcaagagagg
ccaagtaagcccatgcaaagttaacacttgtcattgccaaaataccgtatataaacccacgtgtagcccaatctcacgaccccaaaataccgtatataaa
cccacgtgtagcccatgcaaagttaacacttgtcattgccaagtaaaataccgtatataaacccacgtgtagcccaaac >SEQ-257;synthetic_240nt_promoter_with_spacer
ttggctgcatttgcatgaataatccaaattaaagcaagagaggccaaattaaaatactacgtgtagcccatgcaaagttaacactcaccatccccaatctc
acgaccccattcctcagtctccactatataaacccacgtgtagcccaatctcaccatccccattcctcagtctccactatataaacccaccatccccaatctc

Figure 4 (continued)

accatccccaatctcaccatccccatgcaaagttaacactcaccatccccaaaatactcggcatattgtattcctcagtctccactatatgtacacttgtcattg
ccaagtaagcccaaatgtattggctgcatttgcatgaataataccgtatataaacccacgtgtaagataatccaaac >SEQ-258;synthetic_240nt_promoter_with_spacer
agagaggccaagtaaaataccgtatatgtattcccacacattattaaaatactacgtgtagcccaaaagaacccacacattattaaagcaagagaggcc
aagtaagcccaaaatactacgtgtagcccatgcaaagttaacacttgtcattgccaagtaagcccattcccacacattattaaaattaaagcaagagagg
ccaaatgtacacttgtcattgccaaatgtattgtattcctcagtctccactatataaacccacgtgtagcccatgcaaagttaacacttgtcattgccaagtaaa
atactcggcatattgtattcctcagtctccactatatgtattcctcagtctccactatataaacccacgtgtaagcccaaac >SEQ-259;synthetic_240nt_promoter_with_spacer
tgcaaagttaacacttgtcattgccaagtaagataatccaaattagtaagcccaaatgtacactcaccatccccaatctcaccaaatgtattcccaccatcc
ccatgcaaagttaacactcacgaccccaatctcacgaccccaaaattaaagcaagagaggccaaaagaacccacacattattaaagcaagagagg
ccaagtaaaattaaaatactcggcatattgtattggctgcatgaataatactacgtgtagcccaatctcaccaaaagaacccacgtgtaagcccaaaaga
acccacgtgtaagcccatgcaaagttaacactcaccatccccattcctcagtctccactatataaacccacgtgtaagataatccaaac >SEQ-260;synthetic_240nt_promoter_with_spacer
attaaaatactcggcatattggctgcatgaataataccgtatataaacccacacattattaaagcaagagaggccaaaatactcggcatattgtattgtattg
gctgcatgaataatccaaaataccgtatatgtacacttgtcattgccaagtaaaattagtaagataatactacgtgtagcccaatctcaccaaaattagtaag
ataatactcggcatattgtattcccacgtgtaagcccaatctcaccatccccattccaccatccccaaatgtacactcaccaaaagaacccacgtgtaag
cccatgcaaagttaacacttgtcattgccaaattaaaataccgtatataaacccacgtgtaagcccaatctcaccaaac >SEQ-261;synthetic_240nt_promoter_with_spacer
attgccaagtaagataatccaaatgtattcccaccaaaatactcggcatattggctgcatgaataataccgtatataaacccacacattattaaagcaaga
gaggccaagtaaaatactcggcatattggctgcatttgcatgaataatccaaattaaagcaagagaggccaaattagtaaaatactacgtgtaagccca
aaattaaaatactcggcatattgtattgtattgtattggctgcatttgcatgaataatccaaatgtacacttgtcattgccaaaagaacccacgtgtagcccatg
caaagttaacacttgtcattgccaaatgtattgtattcctcagtctccactatataaacccaccaaaagaacccaccaaac >SEQ-262;synthetic_240nt_promoter_with_spacer
acattattaaaattaaagcaagagaggccaaatgtacacttgtcattgccaagtaagataatccaaattagtaagataatccaaaagaacccacacatta
ttaaagcaagagaggccaaattaaaatactacgtgtaagcccaaattagtaaaattaaaattagtaagataatccaaattaaaatactacgtgtagcccat
gcaaagttaacactcacgaccccattcctcagtctccactatataaacccaccaaaatactacgtgtaagcccattcctcagtctccactatataaacccac
gtgtagcccatgcaaagttaacacttgtcattgccaaatgtattcctcagtctccactatataaacccacgtgtagcccaaac >SEQ-263;synthetic_240nt_promoter_with_spacer
acattattaaagcaagagaggccaaattaaaattagtaaaatactacgtgtaagataatactcggcatattgtattcctcagtctccactatataaacccacg
tgtaagcccatgcaaagttaacactcacgaccccattcctcagtctccactatataaacccacgtgtagcccatgcaaagttaacactcacgaccccatgc
aaagttaacacttgtcattgccaagtaagataataccgtatatgtattgtattcccacgtgtagcccaatctcacgaccccaaaagaacccacacattattaa
agcaagagaggccaaaatactacgtgtagcccattcctcagtctccactatataaacccacgtgtaagataatccaaac >SEQ-264;synthetic_240nt_promoter_with_spacer
ggcatattggctgcatgaataatccaaattaaagcaagagaggccaagtaaaattagtaaaatactacgtgtaagataatccaaaattagtaagcccaa
aatactcggcatattggctgcatttgcatgaataatccaaatgtattgtattgtattcctcagtctccactatatgtacactcacgaccccaaattaaaatactac
gtgtaagataatccaaattagtaagcccaaaagaacccacgtgtagcccaaaagaacccaccatccccaaattagtaagcccatgcaaagttaacact
tgtcattgccaagtaaaataccgtatatgtattgtattgtattcctcagtctccactatataaacccacgtgtaagcccaaac

Figure 4 (continued)

\>SEQ-265;synthetic_240nt_promoter_with_spacer
gaccccaatctcaccatccccatgcaaagttaacacttgtcattgccaagtaagcccaaaagaacccaccaaatgtattgtattcccacacattattaaag
caagagaggccaaatgtattcccaccaaaagaacccaccatccccaatctcacgaccccaatctcaccaaattagtaagataatactacgtgtaagcc
cattcctcagtctccactatataaacccaccatccccaatctcacgacccccattcctcagtctccactatataaacccacacattattaaaataccgtatataa
acccacgtgtagcccatgcaaagttaacactcaccatccccattcctcagtctccactatataaacccacgtgtagcccaaac \>SEQ-266;synthetic_240nt_promoter_with_spacer
cccatgcaaagttaacactcacgaccccaatctcaccatccccaatctcaccaaaagaacccaccatccccatgcaaagttaacactcacgaccccatt
cccacacattattaaagcaagagaggccaaattagtaagataataccgtatatgtacactcaccaaattaaagcaagagaggccaagtaagataatact
acgtgtagcccaaaattaaagcaagagaggccaagtaagataatccaaattagtaaaatactacgtgtagcccaatctcaccatccccaaaagaaccc
acgtgtaagcccatgcaaagttaacacttgtcattgccaaaattagtaagataataccgtatataaacccacgtgtaagataatccaaac \>SEQ-267;synthetic_240nt_promoter_with_spacer
ccacgtgtaagataatactcggcatattggctgcatttgcatttgcatttgcatttgcatgaataataccgtatatgtattcccacgtgtaagataatccaaattag
taaaatactcggcatattggctgcatgaataatactacgtgtaagataataccgtatataaacccacacattattaaagcaagagaggccaagtaagata
atccaaattagtaaaatactacgtgtaagcccattcccacgtgtagcccatgcaaagttaacactcaccaaaatactcggcatattggctgcatgaataatc
caaattagtaagcccaatctcaccatccccattcctcagtctccactatataaacccacgtgtaagataatccaaac \>SEQ-268;synthetic_240nt_promoter_with_spacer
tccactatatgtacactcacgaccccaaatgtacacttgtcattgccaaatgtattggctgcatgaataatccaaatgtattcccacacattattaaagcaaga
gaggccaagtaagataataccgtatatgtattggctgcatgaataatccaaattagtaaaattagtaagataatactacgtgtagcccattcctcagtctcc
actatataaacccacgtgtagcccatgcaaagttaacactcacgaccccaatctcacgaccccaaaagaacccaccaaaagaacccacacattattaa
agcaagagaggccaaatgtacactcacgaccccaaattagtaaaataccgtatataaacccacgtgtaagataatccaaac \>SEQ-269;synthetic_240nt_promoter_with_spacer
ttaaaattaaagcaagagaggccaaatgtacactcacgaccccattcctcagtctccactatataaacccaccatccccatgcaaagttaacactcacca
aattagtaagcccatgcaaagttaacacttgtcattgccaagtaaaattagtaaaattagtaaaatactacgtgtagcccaaaattagtaaaattagtaagc
ccattcccaccaaaatactacgtgtagcccaaaagaacccacacattattaaaataccgtatataaacccacgtgtagcccatgcaaagttaacacttgtc
attgccaagtaagataatccaaattaaagcaagagaggccaagtaagataataccgtatataaacccacgtgtagcccaaac \>SEQ-270;synthetic_240nt_promoter_with_spacer
caaaagaacccacacattattaaagcaagagaggccaaatactacgtgtagcccattcccacacattattaaagcaagagaggccaagtaagataa
tccaaattagtaagcccaaaattaaaatactcggcatattgtattgtattcccacgtgtagcccatgcaaagttaacacttgtcattgccaaaatactcggcat
attgtattcccacacattattaaagcaagagaggccaagtaagcccatgcaaagttaacacttgtcattgccaagtaaaattagtaagcccaatctcacga
ccccaatctcacgaccccaaattaaaatactcggcatattgtattcctcagtctccactatataaacccacgtgtagcccaaac \>SEQ-271;synthetic_240nt_promoter_with_spacer
gtacactcaccaaaagaacccacacattattaaagcaagagaggccaagtaaaattaaaattagtaagcccatgcaaagttaacacttgtcattgccaa
aattagtaaaattaaaataccgtatataaacccacgtgtaagataatactacgtgtagcccaatctcacgaccccaatctcacgaccccattcccacacatt
attaaagcaagagaggccaagtaagcccatgcaaagttaacacttgtcattgccaagtaagataatccaaaagaacccacgtgtagcccatgcaaagt
taacacttgtcattgccaagtaaaatactacgtgtagcccattcctcagtctccactatataaacccacgtgtaagataatccaaac \>SEQ-272;synthetic_240nt_promoter_with_spacer
tcagtctccactatataaacccacacattattaaagcaagagaggccaagtaagataatactacgtgtagcccatgcaaagttaacactcaccatcccca
tgcaaagttaacacttgtcattgccaaaagaacccacgtgtaagcccatgcaaagttaacactcacgaccccaaattagtaagataatccaaatgtacac

Figure 4 (continued)

tcaccatccccaaaattagtaaaattagtaaaatactacgtgtagcccattcctcagtctccactatatataaacccaccaaatgtattcctcagtctccactatat
gtattccaccaaaataccgtatataaacccacacattattaaaataccgtatataaacccaccaaaagaacccaccaaac >SEQ-273;synthetic_240nt_promoter_with_spacer
tccactatataaacccacacattattaaagcaagagaggccaagtaaaatactacgtgtagcccaatctcacgaccccaatctcacgaccccaatctca
cgaccccatgcaaagttaacacttgtcattgccaagtaaaataccgtatataaacccacgtgtaagataatccaaattaaaataccgtatataaacccacc
atccccaatctcaccatccccatgcaaagttaacactcacgaccccatgcaaagttaacacttgtcattgccaaatgtacacttgtcattgccaaaataccgt
atatgtattgtattcctcagtctccactatatgtattggctgcatgaataataccgtatataaacccacgtgtaagcccaaac >SEQ-274;synthetic_240nt_promoter_with_spacer
attgccaaaagaacccaccaaatgtacacttgtcattgccaaaagaacccacacattattaaagcaagagaggccaaaagaacccacacattattaaa
attagtaagataatccaaaatactacgtgtagcccaatctcacgaccccatgcaaagttaacacttgtcattgccaagtaaaataccgtatataaacccac
gtgtagcccatgcaaagttaacactcacgaccccaatctcacgaccccattcctcagtctccactatataaacccacgtgtaagataatccaaatgtacact
tgtcattgccaaaatactacgtgtaagataatccaaattagtaagataataccgtatataaacccacgtgtaagataatccaaac >SEQ-275;synthetic_240nt_promoter_with_spacer
cacattattaaagcaagagaggccaaattaaaatactacgtgtagcccatgcaaagttaacactcacgaccccatgcaaagttaacactcaccatcccc
attccaccatccccattccaccatccccaatctcacgaccccattcctcagtctccactatataaacccacgtgtagcccatgcaaagttaacacttgtca
ttgccaagtaaaattagtaaaataccgtatatgtattggctgcatttgcatgaataataccgtatatgtacactcacgaccccaatctcacgaccccatgcaa
agttaacactcaccaaaatactacgtgtaagcccattcctcagtctccactatataaacccacgtgtaagataatccaaac >SEQ-276;ProPer_240nt_with_spacer_and_enhancer
aataatccaaattaaagcaagagtaggaaagtaagataatccaaatgtacacttgtcattgccaaaattagtaaaatactcggcatattgtagaagcgca
cattattaaaataccgtatatgtattggctgcatttgcatgaataatactacgtgtaagcccaaaagaacccacgtgtagcccatgcaaagttaacactcag
aacccattcctcagtctccactatataaacccaccatctttcatctcaccaaacccaccacacaactcacaactcactctcacaccttaaagaaccaatc
accaccaaaaa >SEQ-277;ProPer_240nt_with_spacer_and_enhancer
tataatccaaattaaagcaagacctcgcaagtaagataatccaaatgtacacttgtcattgccaaaattagtaaaatactcggcatattgtatgaggacaca
ttattaaaataccgtatatgtattggctgcatttgcatgaataatactacgtgtaagcccaaaagaacccacgtgtagcccatgcaaagttaacactcacga
ccccattcctcagtctccactatataaacccaccatcagcggtctcaccaaacccaccacacaactcacaactcactctcacaccttaaagaaccaatca
ccaccaaaaa >SEQ-278;ProPer_240nt_with_spacer_and_enhancer
tataatccaaattaaagcaagacagtctaagtaagataatccaaatgtacacttgtcattgccaaaattagtaaaatactcggcatattgtaatgcgtcacat
tattaaaataccgtatatgtattggctgcatttgcatgaataatactacgtgtaagcccaaaagaacccacgtgtagcccatgcaaagttaacactcaaaac
cccattcctcagtctccactatataaacccaccatcttgagtctcaccaaacccaccacacaactcacaactcactctcacaccttaaagaaccaatcacc
accaaaaa >SEQ-279;ProPer_240nt_with_spacer_and_enhancer
aataatccaaattaaagcaagatgcgaaaagtaagataatccaaatgtacacttgtcattgccaaaattagtaaaatactcggcatattgtattgtgccaca
ttattaaaataccgtatatgtattggctgcatttgcatgaataatactacgtgtaagcccaaaagaacccacgtgtagcccatgcaaagttaacactcactac
cccattcctcagtctccactatataaacccaccatcatttatctcaccaaacccaccacacaactcacaactcactctcacaccttaaagaaccaatcacc
accaaaaa

Figure 4 (continued)

\>SEQ-280;ProPer_240nt_with_spacer_and_enhancer
tataatccaaattaaagcaagacttttgcagtaagataatccaaatgtacacttgtcattgccaaaattagtaaaatactcggcatattgtactcactcacatta
ttaaaataccgtatatgtattggctgcatttgcatgaataatactacgtgtaagcccaaaagaacccacgtgtagcccatgcaaagttaacactcaagaccc
cattcctcagtctccactatataaacccaccatcttcggtctcaccaaacccaccacacaactcacaactcactctcacaccttaaagaaccaatcaccac
caaaaa \>SEQ-281;ProPer_240nt_with_spacer_and_enhancer
aataatccaaattaaagcaagaatatgtaagtaagataatccaaatgtacacttgtcattgccaaaattagtaaaatactcggcatattgtaatctgccacat
tattaaaataccgtatatgtattggctgcatttgcatgaataatactacgtgtaagcccaaaagaacccacgtgtagcccatgcaaagttaacactcatcacc
ccattcctcagtctccactatataaacccaccatctccactctcaccaaacccaccacacaactcacaactcactctcacaccttaaagaaccaatcacca
ccaaaaa \>SEQ-282;ProPer_240nt_with_spacer_and_enhancer
tataatccaaattaaagcaagatcgtggaagtaagataatccaaatgtacacttgtcattgccaaaattagtaaaatactcggcatattgtacttatccacatt
attaaaataccgtatatgtattggctgcatttgcatgaataatactacgtgtaagcccaaaagaacccacgtgtagcccatgcaaagttaacactcagtacc
ccattcctcagtctccactatataaacccaccatcccacttctcaccaaacccaccacacaactcacaactcactctcacaccttaaagaaccaatcacca
ccaaaaa \>SEQ-283;ProPer_240nt_with_spacer_and_enhancer
aataatccaaattaaagcaagagtacggcagtaagataatccaaatgtacacttgtcattgccaaaattagtaaaatactcggcatattgtagcaattcac
attattaaaataccgtatatgtattggctgcatttgcatgaataatactacgtgtaagcccaaaagaacccacgtgtagcccatgcaaagttaacactcagg
accccattcctcagtctccactatataaacccaccatcatctatctcaccaaacccaccacacaactcacaactcactctcacaccttaaagaaccaatca
ccaccaaaaa \>SEQ-284;ProPer_240nt_with_spacer_and_enhancer
aataatccaaattaaagcaagagcgacatagtaagataatccaaatgtacacttgtcattgccaaaattagtaaaatactcggcatattgtaaagtctcac
attattaaaataccgtatatgtattggctgcatttgcatgaataatactacgtgtaagcccaaaagaacccacgtgtagcccatgcaaagttaacactcacta
ccccattcctcagtctccactatataaacccaccatcaaacatctcaccaaacccaccacacaactcacaactcactctcacaccttaaagaaccaatca
ccaccaaaaa \>SEQ-285;ProPer_240nt_with_spacer_and_enhancer
aataatccaaattaaagcaagattagagaagtaagataatccaaatgtacacttgtcattgccaaaattagtaaaatactcggcatattgtaaggccccac
attattaaaataccgtatatgtattggctgcatttgcatgaataatactacgtgtaagcccaaaagaacccacgtgtagcccatgcaaagttaacactcatca
ccccattcctcagtctccactatataaacccaccatcgtaactctcaccaaacccaccacacaactcacaactcactctcacaccttaaagaaccaatcac
caccaaaaa \>SEQ-286;synthetic_1064_promoter_with_spacer
atgtgaaggctgtaaaatgatcgattgatcctaatagattatgaaaattttataaaaattaaagcaagagtatatgtattttaatgtttttatataactgaaaata
ctcggcatgtttgagttgcaaatgtacacttttattattttggccaccatccccaatctcaccatcgtttatagattattttggccaagtattttggtgtcatattggga
caattttcgtttatagatgatatgaatatcccacgtgtaaaatgttcatgagtattggattggataaaataccgaaattctctcaccattcaagtataactgattctt
ttaaccgtatatcgtttataaaatgtttttatataactgaaatgatcctaattaattgtaaaagatcaactctcaccattccttcgattatgaacggcatgtttgaaa
atatgtattattaaaatattttagaaatcgattgtattggctgtaaaggctgtaaaattttggccaaggtaagatattttttcctcattgcctttacctattttataaaa
atgttcacttttttgttcatgtttgaaaacaaatgatcgattctgtctaaatgatatgaaaacaaattaaaggctgtaaaagaataatccaaaagactatttttaac
caaattctaatactacgtgtaaaatacattaacactatgtattatggattggataaaattttggtgtaagattatgaaattgttcactttggataatagaatcagt
ctttagattctaattagtaagcccatgtttatatgttttagaagaacccacgtgtaaaggctgtaaaattgatcctaatagaaatcgattgtattggccaaggtaa

Figure 4 (continued)

gcccaatctcacgacccccatgcaaattctgtcttttaacacttgtcaaagttaatgttcacttttataaaataccgtaatcgattcaattctgtctttacctatttatag
aataatccaaaatactcggcatgaacggcatgagtataaaaagaacccacgtgtagcccaaac >SEQ-287;synthetic_1064_promoter_with_spacer
ccaaggtaagatcaactctccactatataaaagatcaactctccatttgcttttttatgaaaattctaataccgtaatcctaatagattatgaaatgatcctaatta
attaaagcaagagaataaaattttcgattatggataatagattatgtattggattggattggataatcgattttatgaataattagtaaaaatgatcgattatgaa
attaattgttcatgagttgcatgagttgcaaattttccatgcaaattctgtctaattttcgacgttgggatctgatagttcacttttgcaaagttaattgaaggctgtaa
aattttggataaaatttcgttcgaagattcaagtattaatttcgacgttaattaaaggctgtaagatcatagattctaaatgatatgtgatattgtttgaagaaccc
acgtgtagcccatgcaaatgtttgaaatttcgaagaaataccgtatatccccaatctcacgacccctaataccgaaaccagggacaacgttaactgattct
ctccatcgttttggtgtcaaagttaacactatgtacactcacgacccctaatagaaattgtaaaatactacgtgtagcccatgcaaatttaatgtacacttttttg
gtggtttcgtttatttttagatgatcctaatactacgtgtaaaataccgtaatcgattggataatccaaatgtattggccaccaaatttatatccccatgcaaattgta
aaagaaattaaccaacggcatatcccacgtgtaaagcaagagtcttttagaagaatatgtgatatgtgatagttcatcgttcgaagataatagaagatcata
gttttttgcttttgcaaagactatataatccaaaataccgaaatgtaggtcatgaaaataccgatcaactctccatcgttcgaagaaatggtgtcatgtacacttttt
aatgtatttaatgtttgaaaataaaaattaacactatataaaatatcgttcgacgttgggacaacgttaatgtttattttttccattcccatgcaaagaaatttttatat
cgttcgaaatcgattatgaatattttcgtttatacctcagtatataaaatactcggcatatccaaac >SEQ-288;synthetic_1064_promoter_with_spacer
aaagcaagagtattggataatcctaattttgtgaaggctgtaagagagtatatgtacactttttggtgtttgaaattaaagcaagagagtcttagaagaaatc
gattgtattattatgaataatcattatgtgaataatccaaattcaatttcgttcgaagaaattaaaattttatcatatcgttcgattggccaagtaagcccaatctc
acgacccccatgtacactatgtttttaacactatgtacactcacccctaatactacgtgtaaaatattttgcatgttttcgaaacccacacatttgagaggccaa
gtaaaggctgtaaaaagattgtaaaaagactattttttaggggtgtctaaatgtacactatatgaataatcctacactcaccatttgaaggctgcatttgcttttaa
ctgatattggataattagtaaaattttttatcatagatgatagttcatgtattgtaaaattctaattaaagcaagagtcttgcctttacctatttatacctcattgccaa
ggtaagcccaaaagaacccacacatttgaaatactcggcatgtattcccacacattattaaccgtaatcgattctaatagattgaaatgataggggtgtcaaa
gactatgtgaataaacccacgtgtaggtcatgaaattttatagaatcagtctttagggatctgatagggatctgataggggtgtcaaagactatgttttaaccga
tcaactctccatttgctttttagatgatagttcatgagttgcattttccttcgattttaactgatattggctgtaaaaagagtataaaaatactacgtgtaaaaagatc
aactctcacgacccccatttggtgtcaaagttaattaaaatacattaatgttgagaggccaaggtaagatcatagttttttataatccaaattaaccagggatct
gatatgaaatactacgtgtaaaagactatataaaagactatatccccaatctcacgacccccaatctcacgacccctaatagattgaaatactcggcatgtat
ttgaaaatgatcctacactcaccccaaaagaacccacacattgaaatcgattctaaatgttttttgtgatatttgcaaagttaacactcacgacccctaatta
attgtaaaggctgtaaagcaagagtctccatgcaaattttttgcttttataactgataggggacaattctctcaccccaaac >SEQ-289;synthetic_1064_promoter_with_spacer
tgttcatcgtagtcttttaaccgaaattttgcttttggtgtaagataaaccaacgttaatgtattgggacaacgttaatgtttgaaaacaaatttaactgatagttttc
gaagatcatattgggatgtgataggggatgtgatagttcatgtttttttggataatcctacactatatgaatatgaatatcccacacatttgaaatgtttttatgttttg
ttcacttgtcatatcgtttatcatatcgtagtcttgccaaatttaattttttttattaattagtaagattatgaacggccaaggtaagattattatgaatatttatcatag
ttcacttttggtgtaaaggctgtaagagtcttttatataactgaaaatgatagttttcggtcatagatgatagttcacttgtcattaaagcaagagtataattagta
aaaattttattaacacttttaaccgtaatcctacacttgtcatagttttggctgtaaaagactatgtacactcaccccatgttttggctgtaaaattgaagaaccc
acacattgaaatactacgtgtaggtcatagttttggtggtttcgaaacccacacatttgaaaattttgcttttggtgtagcccattccaccatcgtagtcttta
cctattttatagatgatcgattttcctcattgccaaattttttggtgtcaaagttaaccaaatttaattgtaaaatttcgacgttgggacaattctctccatttatacctc
attgcctttacctcattaaagcaagagagagtcttagggatgtgaaggctgcatgagttgcatttgagagagtctccatcccatttcgttcgacgttaacac
tcacgacccccatgcaaatgatcgatttgtttattttatgaacggccaaggtaagagaggccaagtatatccatttgcttttgctttgtgaatatcgtagtctcca
ctattttgttcatcgttttagaagaataatccattcccaccatcccatttgaaaataattgtaagattcaattctaatagatgatattgggacaattctgtctaatta
gtaagcccattccttcgaagaacccacgtgtagcccatgcaaattttcctcattattaaccgtaatcctacactatgttgagaggccaaggtaagagtatttaa
tgtttatttgcatttgaagaacccacgtgtagcccatttttataaaatacctcagtattcctcattgccaaac >SEQ-290;synthetic_1064_promoter_with_spacer

Figure 4 (continued)

ccatgttcactttttttttccttcgacgttgggacaacggccaagtaagcccatgcaaagttaattagtaagatcaactctccactatataactgatagttttccttc
gaaaccaaaataccgaaattctctcacgaccccaaaagactatgtatttgaaatactcggcatgtttatttgaaataccgtatatgaaaattgatcgattgtatt
gtttatcatatttaatttttcgttttcgtttatggataatccaaatgtacacttttgcttttggtgtagcccaaattaaaatggtgtaggtcatgaataaaaagagagg
ccaaggtaagagaatcagtcttgcctttacctcattattaaaagaaattttccatccccaatctcaccaaattaaaggctgcatgttttccatcgttttttcggtca
tatttgaaatcgattctaattaaagcaagagtcttttgtgaagaataatcgattcaattcttttggtgtaggtcattatggataatccaaaagaataatccaaattt
cgacgttaatgtattttccattcaagtattattatgaaatcgattgggacaacgttgggacaattctttagaatatcgttcgattctgtctttagaatcagtcttgcct
ttagaaatcgattgatcctacactatatccccatgcaaatggtgtagcccaaaatatgtattaaccgtaatccaaaatactacgtgtaagcccaaatgtttga
aaacaaatggtgtctaatagatgatagttttggtggtttcggtcatatttatataaaatactcggcatgtttgaagaaatttcgttcgaaataccgaaatactacg
tgtaaaaagaaattttcgttcgacgttaatttcgacgttaactgaaataattttcggtcatgagtattggccaccattcaattttggtgtctttacctcagtcttttggt
ggtttcgacgttgggatgtgaaggctgtaaaagatcatattttatgaatattttggtggtttcgacgttgggatgtgaagaacccacgtgtaaaattttaaccga
aaccaaaagaaattgttttaaccgtatataatcgatttttttagaagaacccacacatttgagtatatcccacacattaaagcaagagaatatccccatgcaa
agaacccaccattcaattttagaatcagtcttttataccgatcatagattctttatagaatcagtataaaatactacgtgtaagcccaaac >SEQ-291;synthetic_1064_promoter_with_spacer
gcaaattttttcctcattaaaggctgtaaaagagtattggctgtaaaagaacccacacattaaaggctgcattttagattctctcaccattcaagtaaaaatac
tacgtgtaaaagagtatataaaagagaataaaaattgatcgattatgaatatcgtagtctttagattgatcgattctctccatgcaaagaaattcaattcttttgt
gaataatccaaattaaccgaaacccaccatccccaatctcacgaccccctaatagatgatagttcatgtttgaaggctgcatgaaatggtgtaaaaatacatt
ttatcatatccccaatctcacgaccccatttagggatgtgaatatgtagcccatgcaaattaaaagaacccacgtgtaaagcaagagaatcagtcttttggt
ggtttcgaagataataccgtatatccaaaagattgggacaacggccaccatcgtttatgaataatccaaatttatggataatccatgcaaagaaattgtaaa
agaacccacgtgtaaaatactcggcatattttggtgtcaaagagtcttgcctttagaagaaatacctcattatgtgaaggctgtaaaagactattttaaccgt
ataaaccaacggcatgtattttcggtcatattttggtggtttcggtcattaaccgatcaactctccactatgtgaatattgttttgtgaagattgatcctacacttttgg
ccaccattcccatgtaggtcatagttcatgaaaacaaattgatcgattctctcaccaacgttgggacaacggcatgttcatcgttttatgaataaaatttcgttc
gaagattcaagtaaaggctgtaaaatactacgtgtaggtcatagaaatcgattttggataaaccaccatcgttcgacgttgggacaacgttgggacaac
ggccaaatttttaaccgtatatccaaatgatcgattatgaacggcatatcccatgtattaaaagaatcagtattcctcattgccaaggtaagcccaatctcac
gacccctaatacattatgaacggccaaaataattgaaaacaaatttcgaaacccacgtgtaaaaatttattaaccgaaattctttgcttttaatttcgacgttg
ggacaattcaattcaagtaaaatttcggtcatatttgaaattgaaatcgattgatcctacactatttgcatttgcttttatgtattttttaactgattctgtctaataga
agaatattggattgggacaacgttaactgattctctccatgcaaagaaatacctcattgcctttacctcagtataactgaaattaattttatatccaaac >SEQ-292;synthetic_1064_promoter_with_spacer
tctccatttgagaggccaaggtaagagagaatatcgtagtctccattcaattctctccactattttccttcgaagaacccacacattttgcaaatttattaacac
tatgtattttgtgaaggctgtaaagcaagagaatatccatgcaaattaattgatcctacacttgtcaaagaaatacatttgaaggctgtaaaagaatattttc
ggtcatgaaatactacgtgtaaaatacattatggattgtttatcatagttcatgttttggtgtaaaatgatcctacactcaccatcgtttagattgtaaaagatcat
attggccaccatcccacacattaacactcacgaccccctaatagatgatcgattttatacctcattaattgttcatcgttcgaaattaaccgatcaactctccact
attttggctgcatgagttgcattttatagaatcagtcttttattaattttgttttaaccgatcaactctccatcgtttatggataatcgattatgaatattgtaaagaa
ataatagatgatatgtagcccattcctcagtcttttgttcatcgtttatagaaatgtattgggacaattttggccaccatcgttcgaaattttggtgtcaaagagtat
tttggtgttttataaagaaattgatcctacactcaccccaaatttaattttagaagaatcagtattgggatctgattctgtcttgccaagtaaagcaagagagt
atataactgaaattaaaaatatccatccccaatctcacgaccccaaaataccgaaacccacgtgtagcccaaaagactatataactgatatggctgtaa
aaatggtgtcttgcctttagaatcagtcttgcctttagattgtattatgtaggtcatagttcacttgtcattgcctttacctatttaaccgtatatgttttatggataatag
aaatactcggcatgagttgcatgttttggtggtttcggtcattatgaaataatccatgcaaagagtatatgaatatgaaattttatcatagttcatgaaaatttttc
gaagaataaaaagaacccaccatcgttttatagaataatcctaattaaaattgatcctacactcaccccaatagaatcagtatataactgaaattttgcattt
gagagtatataactgaaatactacgtgtaagattgggacaattcaattcaagtattggattgaaaacaaatttatcatagaataatcgattttggataatccta
cacttttttaaccgtatataaaaataccgatcaactctcaccattttccttcgacgttgggacaattctctccatgcaaagtaatgtattaaaatactacgtgtag
gtcatgagtatataaaccagggacaacggcatatccaaac >SEQ-293;synthetic_1064_promoter_with_spacer

Figure 4 (continued)

ctatataaaccaaaatggtgtttgagagagaatattttattatgaacggcatgagttgcatttgcaaatgatagttcatgagtattcccaccaacgttaactgat
agggtgtaggtcatatccaaaataccgtaatccaaatttaacactattttcggtcatagattatttatgtgaataattaaagcaagagagtcttttatcatatccc
caaattaaaggctgtaagcccaaattttttaacactcacgaccccattttgtttttccttcgaaataatcctacactatgtacactcacgaccccatgtttatatcc
ccaaatggtggtttcgacgttgggacaacggccaccatcgttttggtgtcaaagttaacacttttggtgtttataccgtaatcctaatagattcaattctctcacca
acggcatgagttgcatttgcttttgcatttggtgtaaaagactatttgaaatactacgtgtaggtcattaatttaaccgtatatcgtttatagatgatcctacactca
ccccaatctcacgacccctaatttataccgtaatccaaattgtaaaagattcaattcaatttttttggtgtagcccatttttatgaaatggtgtaaaagaataatact
acgtgtaaaagaaatttatcatagattatgaaatttaaccgtaatcctaatagaaattctaaatgtttataccgatcatagttttgtgaataaaaagactattttat
agattcaattttataaaagagagaataaaagactatgtacacttgtcaaagttaactgattctctcaccccatgcaaattctttttaactgaaatttataatagatg
ataggggtgtcattgcctttacctcagtattccttcgaagaaataccgatcatagttcacttttcctcagtctccactatgtattttgtgaataaacccacgtgtaaa
atacattatgaaatatgtattcccattcctcattaaccgtaatccatgcaaagagtctttatatgaaatttatagattgtattccttcgaagaaatttcgtttatagat
gatcgattatgaatatcgttcgaagaaattctaattgtattccttcgattatttaacactatttataatactcggcatatcccattcaattttccattccattccttcga
agaaatttatataaaataccgatcatagttttagatgatcgattatggataatagatgatagttcatgttcatcgtttatatgaaaatacattatggataatcgattc
tgtcttttttggctgcatgttcatcgtagtctccactatgttttatagatgatattttttgtgaataatcctacacttgtcatagttcacttttttgttcatgagttgcaaagact
atgttttataattttattattatgaacggcatgaaaatttcgattctctcacgaccccctaattaaccgtatataaaccagggacaacggcatatccccaaac >SEQ-294;synthetic_1064_promoter_with_spacer
aatctcaccccattccttcgaagaacccaccaaaatggtgtcatagaagaatatcccatgcaaattaaaattttcctcattaaagcaagagaggccaagt
aagagtctttacctcattgccaagtaaaattttaacacttgtcaaagttaaccagggatgtgatagttcatgtacactatttgcatttgaaatcgatttttggattgg
ctgtaaaggctgtaaaaagactatatcccacacatttgcatgttgagagtctttacctattttttcgattcaatttttagggacaacgttgggatgtgaataatacta
cgtgtaaaatacatttgaaaacaaattaaaggctgtaaaagataatcgattctttagaagaataaacccacgtgtaagcccaatctcaccatcccacgtgt
aagcccatgcaaatgatatgtacactcacgaccccctaattttttggtggtttcgaaataatacattatgaaaatactacgtgtaagcccaatctcacgaccccca
aaataatccaaaagagagtattggctgtaaaatattttgcttttttgcttttggtgtttgaagaaatttttttaacacttgtcaaagttaaccgaaacccacgtgtaa
gcccatttgaagatcaactctcacgaccccaatctcacgaccccctaattaacacttttggtgtaaaagattatgaatatcgtttagaataatcctaatagaa
attgaaatttcgacgttgggatgtgaatatcccatttgaaataccgatcaactctcaccatttgcttttagaaatcgattctttttaactgataggggtgtaaaattt
atatgtattttaaccagggacaacgttgggatgtgaataaacccaccattccacgtgtaggtcatagattggataaaccaaaatactacgtgtaaaagag
tatttaactgaaatacctcattgcctttacctattttttaacactatataatccatcgtttatatccaaaagagagtctttgtgatattttccatcgtagtctttagaaga
aataccgtaatcctacacttttggataattagtaagatcatagttttgtgataaacccaccattcctcagtctccatcgtttataactgaaattttatcatatttttag
attggccaaggtaagagaatattttagggtgtttattaattaaaattaaccaaaagagagtataaaaatactcggcatatcgttttttagggatgtgaataaac
caacgttaactgaaaacaaattctgtctaaatggtggtttcgaagaaatactcggcatgagttgcaaattcaagtatatgtattcctcattaattaaagcaaga
gagtctttagattttttggtgtcaaagatcaactctcacgaccccattttccttcgacgttaattgtattgtaaaatggtgtcattaattaattgtaaaagagtatat
aaaatgatagggtgttttccatccccaaac >SEQ-295;synthetic_1064_promoter_with_spacer
cattcaattttttatcatagatgatagttttcgaaatcgattctaatagaaatactacgtgtaagagtattaatgtttttccattcaattcaattttagaagataaaag
aatatccccaaatttaaccgtaatcgattcaattctgtcttgccaagtatatgaataatccaaattagtaaagcaagagagtctccatttgaaggctgtaaagg
ctgtaaaggctgtaaaatactacgtgtaaaggctgtaaaagactatatgaataatcctaatagattatgaaatttcgttcgacgttgggatctgattctgtcttg
cctttacctatttaattgatcgattttcgacgttaatgtacactatatgttcacttttgtgaagaaatttttttagatgatcgattatgaaatactacgtgtaaaagaat
aattaaaagaaatcgattttattatgaaaacaaatttggtgtcatagaagataatttatagattgtaaaattaacactatgttcatgagtattggccaagtaag
cccattcccatttggataaaagactatatcccacgtgtaaaaataatcctacacttgtcaaagagaataaaagattatgtgaataattgaaggctgtaaaa
tactacgtgtaaagcaagagagtattggctgcatgagtataactgataggggtgtttatagattatgaaaatatcgttttcgttttggtgtcatatcccacgtgtaa
aatgtttgaaaacaaattttcggtcatagttttgcttttggtgttttatataatccaaatgtttatcatagttcacttgtcatagttttgttcatgttcatcgtagtctcca
ctatataaaatacctcagtattggctgtaaaagactattttgcattttggtgtcatatccccattcctcattaaccagggatctgattctctcacgaccccatttgc
atttggtggtttcgttcgaaatgtaggtcattatgtattcctcagtattaaaaatttcgattgggatctgattcaattctaatagattgtaaaaatggtgtctaaatg
ttcacttgtcaaagaacccacgtgtaggtcatatcccatgcaaagattgatcctaatactacgtgtaaaattttccatgtacactttggtgttttagggtgtcatg
agtattatggataatcgattgaaattttagggacaacggcatgaataatccaaatttcgattatgaacggccaagtattggccaccaacggccaagtattta

Figure 4 (continued)

gattattaaaagaaataacctcagtataaacccacgtgtaaaattgtattatgaaaacaaattaaaggctgcatttgaaggctgtaaagcaagagaataaa
agaataatcgattgaaaacaaatttatcatagttcacttgtcaaagttaattagtaagagagaggccaccatttgcaaattgatcctacactatataatccaa
attagtaagcccaaac >SEQ-296;synthetic_1064_promoter_with_spacer
gggacaatttatgaataatcctaatagattatggataatccatgttcatgtattttagggtgtttgaaattttgcttttggtgttttggtgtcaaagttaattttcggtca
ttgccaaggtaagatcaactctccactatataaaagaaatgtaggtcatgaatatgttgagttgcatgttgagagtattaaccaacggccaccaacgttggg
acaacgttgggatctgattctctccatttggtggtttcgattatgaaatggtgtttatagaagataatccatgcaaagttaatgtttgagtattcctcagtatatgtag
cccatgcaaatgttcatcgtagtcttttgtgatagggacaacggccaaggtaagcccatttgcttttggtgttttagaagatcatagttcacttgtcaaagagag
agaataatcgattatgaaatactacgtgtaaaatgatagggtgtcaaagaacccaccaaattaaagcaagagaggccaccattcaagtaaaatgatcg
attttagggatctgatagttttgttttggctgcatgaaaacaaattagtaagagagtctccactatttaaccgaaaccagggatctgattcaagtataaaagac
tatgtaggtcatagaagaatcagtcttttagattattttaaccgaaacccacgtgtaggtcattgccaaaatactcggcatatcgtttatttataatcctacact
atttttgtgaataattaaaggctgtaagattatgaaaatactacgtgtaagcccattcccacacatttttcgaagaacccacgtgtaggtcatgaaattctctcac
catcccaccattcaagtattgggacaattctaattaactgaaattaaaatatgtacactcacccctaatacattatggattgtaagcccatgtttgaaggctgc
atgagttgcaaattctgtctaatagattctaatagaaataatcgattgggatgtgaataatttttccatgtaggtcatatttatcatagaaattgtattggccaaggt
aagattgtaaaataatcgattattaaaggctgtaaaatacctatttataatagattctttagattgggatgtgaaggctgtaaaggctgtaaaataccatttatat
ccatcgttcgacgttaaccgtataaaagatcaactctcaccatttccttcgaagaataattttttatcatagttcacttgtcaaagttaatgtaggtcatagattca
agtaaaaagactatgtaggtcatgagtattcccatgcaaattgatcctaatttaatgttcatgtattgtaagatcatagaagaaattttggccaccattcaatttc
ggtcatgtattcccacgtgtaggtcatgtttataactgattctgtctaaatgttgagttgcaaatgtaggtcattgccaagtaaaataccgtatatgttttcgtttatat
aaaatactcggcatatccaaac >SEQ-297;synthetic_1064_promoter_with_spacer
actattttaacactattttggtgtcatagtttttggataatcgattattaattagtaagcccaatctcacgacccctaatagaagattctgtctaataccgtataactg
atatgtattcccatgtattccttcgaaacccacgtgtaaaagaacccaccatttagggtgtaaaagactatataaaattttcggtcatgtattaaccagggatc
tgatatgtattggataaacccaccatttgagagtattttggctgtaaaagagaataaaattagtaagagagaatatcgtttattaaaatgatagttttccttcgac
gttaattaaccaaaagactatgtacacttgtcattgcctttacctcattaacactatgtatttggataatcctaatagaataaaatggtgtaaaattaaccaggg
atctgattcttttataccgtatatccatcgttcgaaatatcgtagtcttgccaagtatataaaccagggacaacgttaattaaagcaagagtattatgaacggca
tgttgagtattccttcgattctaaatgtaggtcatagaataatcctacactatttataccatttttataccgtaatcgattctgtctaatactacgtgtagcccaatct
caccatttgaaatttagatgatcctaattgaaatttatcatagttcatcgttcgaaaccaaaagaacccacgtgtaagagagtcttttccatcgtttttaaccgt
ataaaataccgaaatattttttcggtcattgccaaggtaagcccaatctcaccccatttggataatcctaatagatgatcgattttccatgtagcccaaaagact
atttgagaggccaccaaaagaaatcgattatgaaattaaaagaaatactacgtgtaaaggctgtaaaagactatgtgaaggctgtaaaattttgtgaag
gctgtaaaagaatcagtctccactatttggtggtttcgaagattgaaatatcgtttatagattgaaatgtattaaccgtatataaaccagggatgtgatagttttt
aaccagggatgtgaataatccaaatgatcctaattgaaaatacctcagtctccattcaattcttttgcttttggtggttttcgaagaaattaaccgtataaaaga
aattagtaaaggctgcattttgtgaataaacccacgtgtagcccaatctcaccccatgcaaagatcaactctccatcccatttgaaatcgattttatgtattgt
attcctcattatgaacggcatatttgagttgcatgaacggcatgtttgaaggctgtaaaaattaatgttcatcgtagtcttgcctttacctatttgcttttagggaca
acggccaaggtaagattcttttaactgatagttcacttgtcaaagttaatgtttgaaaacaaattaaccgaaattaaaggctgtaaaagaatcagtctccact
ataattagtaagagaggccaaac >SEQ-298;synthetic_1064_promoter_with_spacer
aaggctgcatttgaaggctgtaagatcatagttcatcgtttatacctcattgcctttacctattttccatcgttcgaaattttcgtttatggataatagattgtaaaaa
gaaatcgattatgaataaaataaaagattattaattaattgaaggctgcatgttttagggtgtctaatactcggcatatcgtagtcttaacactattttggtgtct
tttataactgaaaacaaatttatagattctctcacgacccctaatagaatatcgttcgattcaattcaagtaagcccatgcaaagttaatttatgaataaaaga
ctattttccatcgttttatgaacggccaccatcgtagtctccactatgtatttgagtattccttcgattcttacctcagtattcccacacatttgaaatggtgtcatga
gtattgtaaagcaagagaggccaccatcgttttggtgtaagagtattcctcagtatataaacccacacattttattaaccgaaaccagggacaacggcatg
agtattaacacttttgtgatagggtgtaggtcatgttgagagagtataatccaaattctgtctaaatggtgttttggtggtttcgaaaccagggatctgattctaa

Figure 4 (continued)

atgatatgtgaagaaattaattttcgtttataccgtataactgattctaaatgttcacttttggataattaatttatatgtattgtatttaattttcgaaattttccatcccca
tgcaaagttaatgtttgaaataccgtatataaacccacgtgtaaaagaatatgaaaacaaattttcgaagaaattttttaaccaaattaaccgtaatccaaaa
gaaattttatggataatagatgatcctacacttttcgattggccaccaaattttagaagaaatcgattatgaacggccaaggtaagagtcttttggtgtaaag
gctgtaaaatactacgtgtaaaatactacgtgtaagcccatttgaaaacaaatgttcatcgtagtcttttgttcacttgtcaaagttaacacttgtcaaagttaat
gtttgagagtattgtttgagagaatcagtattaaaaatactacgtgtagcccatgttttcgattatgaatatgtacactttttggctgtaagagtcttgccaaggta
agagtattggctgtaaaatgttttggtgttttcgaaatgtttgaaatcgattatgaaataatcctacactatttaattgtaaaatactacgtgtaaaggctgtaaaat
atgttttttattttataaaattttcgaagaacccaccattcaattcaattctctccactatttaattgtaaaggctgtaaaagactatataaaagactatttatatgtatt
ggattgtaaaagaacccacgtgtaagcccatgcaaattttcgttttggattgggacaatttcgaagaaattttcgtttataatagaagatattggattggataat
ccaaac >SEQ-299;synthetic_1064_promoter_with_spacer
aactgattctgtcttttggccaccattcaagtaagagtcttttgttttggtgtttataccgatcaactctccactatgtgaatatcgtagtctccatgcaaattttggtg
taaaaagaatcagtatatcgtagtctttacctcagtcttgcctttacctattttataccgaaatttcgaaacccacacattatgaacggcatgaaattaattaaag
caagagaggccaaattgaaggctgcatgttgagagtattggataatagattcaattctgtctaatacattatgtttggataatcgattatgaataatccaaaat
accgaaacccaccaaaagaacccaccatcgtagtctccattcctcattaaaaatacctcagtatataaaatgtttatcatagttcatcgttttggccaagtatt
aaaataatcgattatgaaaataatagatgatagggtgtctaatactcggcatgaaattttcctcagtataaaattaaaaagattctgtctttagattctttttatatg
tattggccaccatttgcaaagttaatgtacactttttgtgaataatccatcgtagtcttttttccattttatatgtgaataaaccaaaagatatgaacggcatgtttatt
atgaatatgaaatattggctgcatttgaaaataatcgattggataatcgattttccttcgacgttgggacaacggccaagtattggattggccaaggtaagcc
caatctcacgacccctaattgtattcccatttgaaaatgatcctacactcaccccattcaattcaattttataccgtataactgattcttttggtgtaagagtctcca
ctatttaaccgtaatcctacactatttagaagaaatatgtacacttttggataatagaaatactacgtgtaaaatactacgtgtagcccaaaagactatataa
aatactcggcatgaatatgaataattaaaggctgtaaaatactacgtgtaaaatactacgtgtaaaagaaatactacgtgtaaaattctaatagaaattaaa
atgttgagttgcaaagttaaccagggacaatttatatcgttttttgtgatagggtgtttataaacccacgtgtagcccaaaattgtaaaaagataatccaaaata
ctacgtgtaaaattgatcgatttttggtgtcaaagttaattaaccgtataactgaaatcgattattaaccaaaatatttggataaacccaccatttggtgtctttac
ctcattatttccatgttcatcgttttagaagattatgaatatgtagcccatgcaaattttcgttcgattattaaaattgatcgattgaaaacaaattcgaagaacc
cacacattaatgtattatgtagcccaaatggtgtcatagaataatagaatatccaaaattttataactgaaatcgattgttcatgaacggcatgagtatataaa
cccaccaaattgtaagcccaaac >SEQ-300;synthetic_1064_promoter_with_spacer
cttcgaagatcaactctcacgacccctaattaaaggctgtaaagcaagagaggccaccatcccaccatttgaaatacattatgaaaacaaattttcctcatt
gccaaattctgtcttgcctttacctattttggtggtttcggtcatgaaatcgattatgaaatcgattgaaaattgtattggattgatcctacactcacgacccctaatt
agtaagagagaggccaaggtaagatcatagttcatcgtagtctccactatttgagaggccaagtattggctgtaagcccattcctcattatgaaaacaaat
tttcgattgatcgattttttgcttttggtgtttatggataatttcgttcgaaaccagggatgtgaatatcgttttataaaaatactacgtgtagcccattcaattcttttat
acctcagtatataaaatacattaattaatttttatggataatccatccccaatctcacccctaatagaagaacccacacattatgtgaagaatatcgtagtcttg
ccaaggtaagcccaaaatttaaccgtaatcgattttttaaccaaaataccgtataattaaaatacattaaccgtaatcctacactattttaatgttttccatgt
aggtcatgttgagaggccaaattagtaaaataatccattcctcattgcctttagaagaaataaaatacctcattatttgagaggccaaggtaagcccatgtat
tggctgtaaaatgatcgattgaaaatatttataccgaaacccacgtgtaagattcaattcaagtaagatcaactctcacgacccctaattttggtgtctaata
gattggctgtaaaatacctcagtctccactattttggtgtttcgaaatttataccttcattaaccagggacaacgttaaccgtaatccaaatgatatttaattaa
ccagggatgtgatagttcatgagttgcaaatggtgtcatatcccatttggtggtttcgaaatgtttgaaataaaagataatccaaatacaagagagtatttt
ggtggtttcgaagaaatgataggggatgtgaagaacccacgtgtaagcccaatctcacgacccctaattagtaagcccaatctcaccccattccacgtgt
aaaaatggtgttttggctgtaaaatggtgtaaaagaataatcgattggctgtaagcccaatctcaccccctaatagaatattgttcatgaataatccaaaatttat
agaataattaaccagggatgtgaaggctgcatgagttgcatttgcttttatataactgaaatacctcagtataaaccaaaataatcctacactcacgacccc
atgcaaagagagagtctccattcaatttcgacgttaaccagggatgtgatattggccaaatttaatttatgtattgtattgttttaactgaaatgtacactatatcgt
ttttataactgaaataaaataccgtaatccaaac >SEQ-301;ProPer_full_promoter_with_spacer_and_enhancer

Figure 4 (continued)

atcgcagatatttggtgtctaaatgtttattgtcctgtatgttcatttgggacaaattagctgaacagccagggacaacgttgggatctgatagggtgtcaaaga
gtattataaactgggacaatttcggtcatgagttgcaaattcaagtatatagctctgccgggggggattttcgaagaatatcccatttgacgagtcacctggctc
attaatgttttagattatgaaattttatcatagtaaggggacagttatttggtgtaaaggctgtaaaaagaaattgttcacttttgttttcgtttatgtgaaggcccta
aaagattgtgtaagactattttggtgttttggataaaatgatagttttttatagattcttttgcttttagaagaaatacatttgaaatttttttccatgttgagtataaacgc
atttatcgtattgaagatcatagaaatattttaactgaaaaataatttataactgattcaattctctccattttttatacctatttaaccgtaatcgtggcgagatccg
tcaggaccagccaagcatcctaattaaccaacggcatgtattggataattaaccgatcaactctcaccccctaatagaatcagagcgacacttcgacgtta
attgatcctacactacgggggtcatatccatcgtttttaattttttcgccaccattcaattctgtcttgcctttagggatgtgaatatgaacggccaaggtccgggtgc
aaaaataatccaaattaaagcaagaaaccgggagtaagataatccaaatgtacacttgtcattgccaaaattagtaaaatactcggcatattgtactagg
ccacattattaaaataccgtatatgtattggctgcatttgcatgaataatactacgtgtaagcccaaaagaacccacgtgtagcccatgcaaagttaacactc
aatacccccattcctcagtctccactatataaacccaccatcggcactctcaccaaacccaccacacaactcacaactcactctcacaccttaaagaacca
atcaccaccaaaaa >SEQ-302;ProPer_full_promoter_with_spacer_and_enhancer
acagcagatatttggtgtctaaatgtttattgttggctatgttcatgtgattctggttacgcaatgcttcagggacaacgttgggatctgatagggtgtcaaagagt
attgtgctctgggacaatttcggtcatgagttgcaaattcaagtatatacattagtcgcaccagatttcgaagaatatcccatttgacgacccacaatgctcatt
aatgttttagattatgaaattttatcatagttagaacacaatggtttggtgtaaaggctgtaaaaagaaattgttcacttttgttttcgtttatgtgaaggctataaa
agattgtataagactattttggtgttttggataaaatgatagttttttatagattcttttgcttttagaagaaatacatttgaaatttttttccatgttgagtataaagaccat
tgtataattgaagatcatagaaatattttaactgaaaactcatttataactgattcaattctctccattttttatacctatttaaccgtaatcgtaccctcggtactacg
ctaggaagcagccgtcctaattaaccaacggcatgtattggataattaaccgatcaactctcaccccctaatagaatcatctcgaaagttcgacgttaattgat
cctacactagtttggtcatatccatcgtttttaattttttgccaccattcaattctgtcttgcctttagggatgtgaatatgaacggccaagacggagagtaaaaaat
aatccaaattaaagcaagaaactggcagtaagataatccaaatgtacacttgtcattgccaaaattagtaaaatactcggcatattgtacaaggccacatt
attaaaataccgtatatgtattggctgcatttgcatgaataatactacgtgtaagcccaaaagaacccacgtgtagcccatgcaaagttaacactcatgacc
ccattcctcagtctccactatataaacccaccatcacgactctcaccaaacccaccacacaactcacaactcactctcacaccttaaagaaccaatcacc
accaaaaa >SEQ-303;ProPer_full_promoter_with_spacer_and_enhancer
tgtgcagatatttggtgtctaaatgtttatttcaaaatatgttcatgacgccgctgaacgaagaaaggacagggacaacgttgggatctgatagggtgtcaaa
gagtattagtcgatgggacaatttcggtcatgagttgcaaattcaagtatatggggtatctcagcaatctttcgaagaatatcccatttgaagcatttttactcctc
attaatgttttagattatgaaattttatcatagtataggggtgttttttggtgtaaaggctgtaaaaagaaattgttcacttttgttttcgtttatgtgaaggccctaaa
agattgtacaagactattttggtgttttggataaaatgatagttttttatagattcttttgcttttagaagaaatacatttgaaatttttttccatgttgagtataaagggtt
cttctccttgaagatcatagaaatattttaactgaaaacccatttataactgattcaattctctccattttttatacctatttaaccgtaatcgctaagttcgtcaagga
aataacttttaacctcctaattaaccaacggcatgtattggataattaaccgatcaactctcaccccctaatagaatcagtcgatgtcttcgacgttaattgatcct
acactacgtcggtcatatccatcgttttaattttttgccaccattcaattctgtcttgcctttagggatgtgaatatgaacggccaagctagttgtcgaaaaataat
ccaaattaaagcaagatagtctcagtaagataatccaaatgtacacttgtcattgccaaaattagtaaaatactcggcatattgtaattttgcacattattaaa
ataccgtatatgtattggctgcatttgcatgaataatactacgtgtaagcccaaaagaacccacgtgtagcccatgcaaagttaacactcactaccccattc
ctcagtctccactatataaacccaccatcagctatctcaccaaacccaccacacaactcacaactcactctcacaccttaaagaaccaatcaccaccaa
aaa >SEQ-304;ProPer_full_promoter_with_spacer_and_enhancer
cgtgcagatatttggtgtctaaatgtttattctggcatatgttcatttgtcatgatttatccgcccccttcagggacaacgttgggatctgatagggtgtcaaagagt
atttctgttgggacaatttcggtcatgagttgcaaattcaagtatatagttcgccgtgctgcgttttcgaagaatatcccatttgagactggtcgttcctcattaatg
ttttagattatgaaattttatcatagtcgcacccattgtcttggtgtaaaggctgtaaaaagaaattgttcacttttgttttcgtttatgtgaaggctgtaaaagattg
ttcaagactattttggtgttttggataaaatgatagttttttatagattcttttgcttttagaagaaatacatttgaaatttttttccatgttgagtataaacttgatcgttcggt
tgaagatcatagaaatattttaactgaaaagaaatttataactgattcaattctctccattttttatacctatttaaccgtaatcgaagccgaaatgagccaacgc
ctacgctatttcctaattaaccaacggcatgtattggataattaaccgatcaactctcaccccctaatagaatcaatttcccgcttcgacgttaattgatcctacac

Figure 4 (continued)

taggtgggtcatatccatcgttttaattttttagccaccattcaattctgtcttgcctttagggatgtgaatatgaacggccaagcaagctttgaaaaaataatcca
aattaaagcaagaaacaccaagtaagataatccaaatgtacacttgtcattgccaaaattagtaaaatactcggcatattgtagaacgccacattattaaa
ataccgtatatgtattggctgcatttgcatgaataatactacgtgtaagcccaaaagaacccacgtgtagcccatgcaaagttaacactcataacccatc
ctcagtctccactatataaacccaccatctcggatctcaccaaacccaccacacaactcacaactcactctcacaccttaaagaaccaatcaccaccaa
aaa >SEQ-305;ProPer_full_promoter_with_spacer_and_enhancer
agagcagatatttggtgtctaaatgtttattggttcgtatgttcatagtccgagtatgtacgagaaagccagggacaacgttgggatctgataggtgtcaaa
gagtattgtacgttgggacaatttcggtcatgagttgcaaattcaagtatatgctcaaggaagctcaagtttcgaagaatatcccatttgagacgaccgacgc
ctcattaatgttttagattatgaaattttatcatagttcaccccgaagattttggtgtaaaggctgtaaaagaaattgttcacttttgttttcgtttatgtgaaggcta
taaaagattgtataagactattttggtgttttggataaaatgatagttttatagattcttttgcttttagaagaaatacatttgaaattttttccatgttgagtataaaag
gcacgggagtgttgaagatcatagaaatattttaactgaaaaataatttataactgattcaattctctccattttataccctatttaaccgtaatcgcagtgatgga
cgcgggcatcggtaggactatcctaattaaccaacggcatgtattggataattaaccgatcaactctcaccccctaatagaatcagcaaataagttcgacgtt
aattgatcctacactatcagggtcatatccatcgttttaatttttggccaccattcaattctgtcttgcctttagggatgtgaatatgaacggccaaggactccatta
aaaaataatccaaattaaagcaagaactcttcagtaagataatccaaatgtacacttgtcattgccaaaattagtaaaatactcggcatattgtacagcccc
acattattaaaataccgtatatgtattggctgcatttgcatgaataatactacgtgtaagcccaaaagaacccacgtgtagcccatgcaaagttaacactca
gcaccccattcctcagtctccactatataaacccaccatctctttctcaccaaacccaccacacaactcacaactcactctcacaccttaaagaaccaatc
accaccaaaaa >SEQ-306;ProPer_full_promoter_with_spacer_and_enhancer
cgagcagatatttggtgtctaaatgtttattgtagtatatgttcattttaacttatgttaggtgtcaacagggacaacgttgggatctgataggtgtcaaagagt
attaataagtgggacaatttcggtcatgagttgcaaattcaagtatattcctactcgtagtgggttttcgaagaatatcccatttgaacgtaatcataactcatta
atgttttagattatgaaattttatcatagtagacatgctttgatttggtgtaaaggctgtaaaagaaattgttcacttttgttttcgtttatgtgaaggcggtaaaag
attgttcaagactattttggtgttttggataaaatgatagttttatagattcttttgcttttagaagaaatacatttgaaattttttccatgttgagtataaaaggcacga
atcaattgaagatcatagaaatattttaactgaaaagcgatttataactgattcaattctctccattttataccctatttaaccgtaatcgggtgcaccaactgaatt
gctttaatgatactcctaattaaccaacggcatgtattggataattaaccgatcaactctcaccccctaatagaatcagtagcggttttcgacgttaattgatccta
cactattagggtcatatccatcgttttaattttggccaccattcaattctgtcttgcctttagggatgtgaatatgaacggccaagcgcacgacgcaaaaataa
tccaaattaaagcaagacctgcaaagtaagataatccaaatgtacacttgtcattgccaaaattagtaaaatactcggcatattgtaatcgctcacattatta
aaataccgtatatgtattggctgcatttgcatgaataatactacgtgtaagcccaaaagaacccacgtgtagcccatgcaaagttaacactcacaacccca
ttcctcagtctccactatataaacccaccatcgaatttctcaccaaacccaccacacaactcacaactcactctcacaccttaaagaaccaatcaccacca
aaaa >SEQ-307;ProPer_full_promoter_with_spacer_and_enhancer
gatgcagatatttggtgtctaaatgtttattcgaggatatgttcatggggaccgtcaaggtagatgacacagggacaacgttgggatctgataggtgtcaa
agagtattccctgatgggacaatttcggtcatgagttgcaaattcaagtatatcggaacaggtcatgggctttcgaagaatatcccatttgatcgtttaaagga
ctcattaatgttttagattatgaaattttatcatagtagcgcgtgtccggtttggtgtaaaggctgtaaaagaaattgttcacttttgttttcgtttatgtgaaggcc
gtaaaagattgtaaaagactattttggtgttttggataaaatgatagttttatagattcttttgcttttagaagaaatacatttgaaattttttccatgttgagtataaa
cgtgaggttgtccttgaagatcatagaaatattttaactgaaaatctatttataactgattcaattctctccattttataccctatttaaccgtaatcgcacatttaagg
gatggcgacagcacccgcttcctaattaaccaacggcatgtattggataattaaccgatcaactctcaccccctaatagaatcagttttggtgttcgacgttaat
tgatcctacactatccgggtcatatccatcgttttaattttggccaccattcaattctgtcttgcctttagggatgtgaatatgaacggccaagcaatgccttgaa
aaataatccaaattaaagcaagatctctaaagtaagataatccaaatgtacacttgtcattgccaaaattagtaaaatactcggcatattgtagttctccacat
tattaaaataccgtatatgtattggctgcatttgcatgaataatactacgtgtaagcccaaaagaacccacgtgtagcccatgcaaagttaacactcaagac
cccattcctcagtctccactatataaacccaccatcatagctctcaccaaacccaccacacaactcacaactcactctcacaccttaaagaaccaatcacc
accaaaaa

Figure 4 (continued)

>SEQ-308;ProPer_full_promoter_with_spacer_and_enhancer
catgcagatatttggtgtctaaatgtttatttacccttatgttcattccacgctaggggagtgaatcaccagggacaacgttgggatctgatagggtgtcaaag
agtattctcccgtgggacaatttcggtcatgagttgcaaattcaagtatatgacagggctgggacacttttcgaagaatatcccatttgattaatcaagagact
cattaatgttttagattatgaaattttatcatagtgattctctgttactttggtgtaaaggctgtaaaaagaaattgttcacttttgttttcgtttatgtgaaggccctaa
aagattgtgcaagactattttggtgttttggataaaatgatagtttttatagattcttttgcttttagaagaaatacatttgaaattttttccatgttgagtataaaggcg
ggctgggtcttgaagatcatagaaatatttaactgaaaagccatttataactgattcaattctctccatttttatacctatttaaccgtaatcgcagcggaggaat
gtcactgacaaatgaacgtcctaattaaccaacggcatgtattggataattaaccgatcaactctcacccctaatagaatcagttccgtcattcgacgttaatt
gatcctacactacgacggtcatatccatcgtttaattttagccaccattcaattctgtcttgcctttagggatgtgaatatgaacgccaagttacgtcaacaa
aaataatccaaattaaagcaagaaaaccctagtaagataatccaaatgtacacttgtcattgccaaaattagtaaaatactcggcatattgtatcgagaca
cattattaaaataccgtatatgtattggctgcatttgcatgaataatactacgtgtaagcccaaaagaacccacgtgtagcccatgcaaagttaacactcaat
accccattcctcagtctccactatataaacccaccatcagccttctcaccaaacccaccacacaactcacaactcactctcacaccttaaagaaccaatca
ccaccaaaaa >SEQ-309;ProPer_full_promoter_with_spacer_and_enhancer
gtggcagatatttggtgtctaaatgtttattcctagatatgttcattgcggaattgcttctcaccgtgacagggacaacgttgggatctgatagggtgtcaaaga
gtatttcgacgtgggacaatttcggtcatgagttgcaaattcaagtatattcggtccaccttgttagtttcgaagaatatcccatttgacatgggcgcgcgctcat
taatgttttagattatgaaattttatcatagttagcgcctgcctatttggtgtaaaggctgtaaaaagaaattgttcacttttgttttcgtttatgtgaaggccgtaaa
agattgttaaagactattttggtgttttggataaaatgatagtttttatagattcttttgcttttagaagaaatacatttgaaattttttccatgttgagtataaagccga
actgacacttgaagatcatagaaatatttaactgaaaatacatttataactgattcaattctctccatttttatacctatttaaccgtaatcgggattagacgatat
ttccgcgtcatgccggtcctaattaaccaacggcatgtattggataattaaccgatcaactctcacccctaatagaatcagaatatttattcgacgttaattgat
cctacactaacatggtcatatccatcgtttaattttggccaccattcaattctgtcttgcctttagggatgtgaatatgaacggccaagatcccatttcaaaaat
aatccaaattaaagcaagatttcagtagtaagataatccaaatgtacacttgtcattgccaaaattagtaaaatactcggcatattgtatgtgttcacattatta
aaataccgtatatgtattggctgcatttgcatgaataatactacgtgtaagcccaaaagaacccacgtgtagcccatgcaaagttaacactcacgacccca
ttcctcagtctccactatataaacccaccatctgtagtctcaccaaacccaccacacaactcacaactcactctcacaccttaaagaaccaatcaccacca
aaaa >SEQ-310;ProPer_full_promoter_with_spacer_and_enhancer
atggcagatatttggtgtctaaatgtttattgggtggtatgttcatcttcaatttagtggtgtcaccggcagggacaacgttgggatctgatagggtgtcaaaga
gtattaaattttgggacaatttcggtcatgagttgcaaattcaagtatatcgacccgccccccaattatttcgaagaatatcccatttgagtggatagacgtctcat
taatgttttagattatgaaattttatcatagtaccggtaaccctgtttggtgtaaaggctgtaaaaagaaattgttcacttttgttttcgtttatgtgaaggcgttaaa
agattgttgaagactattttggtgttttggataaaatgatagtttttatagattcttttgcttttagaagaaatacatttgaaattttttccatgttgagtataaagaccgt
ggtatagttgaagatcatagaaatatttaactgaaaagcaatttataactgattcaattctctccatttttatacctatttaaccgtaatcgaataatcccaaaaa
gtatcgttagtttggctcctaattaaccaacggcatgtattggataattaaccgatcaactctcacccctaatagaatcattcgtcgctttcgacgttaattgatcc
tacactatcttggtcatatccatcgttttaatttttcgccaccattcaattctgtcttgcctttagggatgtgaatatgaacggccaagtgatccgcataaaaataat
ccaaattaaagcaagatatttcaagtaagataatccaaatgtacacttgtcattgccaaaattagtaaaatactcggcatattgtagcgactcacattattaa
aataccgtatatgtattggctgcatttgcatgaataatactacgtgtaagcccaaaagaacccacgtgtagcccatgcaaagttaacactcatgaccccatt
cctcagtctccactatataaacccaccatcggtgctctcaccaaacccaccacacaactcacaactcactctcacaccttaaagaaccaatcaccacca
aaaa >SEQ-311;WO0116340-GUS_data
tccactatgtaggtcatatccatcattttaattttgggcaccattcaattccatcttgcctttagggatgtgaatatgaacggccaaggtaagagaataaaaata
atccaaattaaagcaagagaggccaagtaagataatccaaatgtacacttgtcatcgccgaaattagtaaaatacgcggcatattgtattcccacacatta
ttaaaataccgtatatgtattggctgcatttgcatgaataatactacgtgtaagcccaaaagaacccacgtgtagcccatgcaaagttaacactcacgaccc
cattcctcagtctccactatataaacccaccatccccaatcttaccaaacccaccacacgactcacaactcgactctcacaccttaaag

Figure 4 (continued)

>SEQ-312;WO0116340-SEQ-006UTR
tccactatgtaggtcatatccatcattttaattttgggcaccattcaattccatcttgcctttagggatgtgaatatgaacggccaaggtaagagaataaaata
atccaaattaaagcaagagaggccaagtaagataatccaaatgtacacttgtcatcgccgaaattagtaaaatacgcggcatattgtattcccacacatta
ttaaaataccgtatatgtattggctgcatttgcatgaataatactacgtgtaagcccaaaagaacccacgtgtagcccatgcaaagttaacactcacgaccc
cattcctcagtctccactatataaacccaccatccccaatcttaccaaacccaccacacgactcacaactcgactctcacaccttaaagaaccaatcacc
accaaaaa >SEQ-313;WO0116340-SEQ-006
tccactatgtaggtcatatccatcattttaattttgggcaccattcaattccatcttgcctttagggatgtgaatatgaacggccaaggtaagagaataaaata
atccaaattaaagcaagagaggccaagtaagataatccaaatgtacacttgtcatcgccgaaattagtaaaatacgcggcatattgtattcccacacatta
ttaaaataccgtatatgtattggctgcatttgcatgaataatactacgtgtaagcccaaaagaacccacgtgtagcccatgcaaagttaacactcacgaccc
cattcctcagtctccactatataaacccaccatccccaatcttaccaaacccaccacacgactcacaactcgactctcacaccttaaagaaccaatcacc
accaaaaaatggcaaagctgatgagcctagcagccgtagcaacgcagttcctcttcctgatcgtggtggacgcatccgtccgaaccacagtgattatcg
acgaggagaccaaccaaggccgcggtggaggcaaggtggcagggacagcagcagtctgcgagcagcagatccagcagcgagacttcctgagga
gctgccagcagttcatgtgggagaaagtccagaggggcggccacagccactattacaaccagggccgtggaggaggcgaacagagccagtacttcg
aacagctgtttgtgacgaccttaagcaattgcgcaccgcggtgcaccatgccaggggacttgaagcgtgccatcggccaaatgaggcaggaaatccag
cagcagggacagcagcagggacagcagcaggaagttcagaggtggatccagcaagctaaacaaatcgctaaggacctccccggacagtgccgca
cccagcctagccaatgccagttccagggccagcagcaatctgcatggttttgaaggggtgatcgattatgagatcgtacaaagacactgctaggtgttaa
ggatggataataataataataatgagatgaatgtgttttaagttagtgtaacagctgtaataaagagagagagagagagagagagagagagagagag
agagagagagagagaggctgatgaaatgttatgtatgtttcttggttttaaaataaatgaaagcacatgctcgtgtggttcatcgaattattcggcggttc
ctgtgggaaaaagtccagaagggcggccgcagctactactacaaccaaggccgtggaggagggcaacagagccagcacttcgatagctgctgcgat
gatcttaagcaattgaggagcgagtgcacatgcaggggactggagcgtgcaatcggccagatgaggcaggacatccagcagcagggacagcagca
ggaagttgagaggtggtcccatcaatctaaacaagtcgctagggaccttccgggacagtgcggcacccagcctagccgatgccagctccaggggcag
cagcagtctgcatggttttgaagtggtgatcgatgagatcgtataaagacactgctaggtgttaaggatgggataataagatgtgttttaagtcattaaccgta
ataaaagagagagaggctgatggaatgttatgtatgtatgtttcttggttttaaaattaaatggaaagcacatgctcgtgtgggttctatc >SEQ-314;WO2002102970-pConlinin-1
caacggttccggcggtatagagttgggtaattcgaaaccgcacagatccaattcgattagcagatatttggtgtctaaatgtttattttgtgatatgttcatgtttg
aaatggtggtttcgaaaccagggacaacgttgggatctgataggggtgtcaaagagtattatggattgggacaatttcggtcatgagttgcaaattcaagtat
atcgttcgattatgaaaattttcgaagaatatcccatttgagagagtctttacctcattaatgttttttagattatgaaattttatcatagttcatcgtagtcttttggtgta
aaggctgtaaaaagaaattgttcacttttgttttcgtttatgtgaaggctgtaaaagattgtaaaagactattttggtgttttggataaaatgatagttttatagattc
ttttgcttttagaagaaatacatttgaaattttttccatgttgagtataaaataccgaaatcgattgaagatcatagaaatatttaactgaaaacaaatttataact
gattcaattctctccattttataccctatttaaccgtaatcgattctaatagatgatcgattttttatataatcctaattaaccaacggcatgtatggataattaaccga
tcaactctcacccctaatagaatcagtattttccttcgacgttaattgatcctacactatgtaggtcatatccatcgttttaattttggccaccattcaattctgtcttg
cctttagggatgtgaatatgaacggccaaggtaagagaataaaaataatccaaattaaagcaagagaggccaagtaagataatccaaatgtacacttgt
cattgccaaaattagtaaaatactcggcatattgtattcccacacattattaaaataccgtatatgtattggctgcatttgcatgaataatactacgtgtaagccc
aaaagaacccacgtgtagcccatgcaaagttaacactcacgaccccattcctcagtctccactatataaacccaccatccccaatctcaccaaacccac
cacacaactcacaactcactctcacaccttaaagaaccaatcaccaccaaaaatg >SEQ-315;WO2002102970-pConlinin-2
aactgatatatattactttgttggttggttaatagattaacctattttcataaaattataattaataaaaaaattgagtttttgaaattttgagctttcttgtattatgttgg
aacttcttgttccattgcaataaaatcagttataaaaaaattacaaacgaagtgcactcagtaattaaccacctcaaacagactctcacttactcatagtagg
atcaatattttccttcggcgataatcgttcctccactatgtaggtcattattttaattttggtgattattatgtgtctaattttaaaaattaattattcgataaatattacttt
tatgtattgttagtttgttttggaatttaaagtttgagttggtcttaagagttatcttgttaaccgatattaattgtaatactagaaaaataaagcttataaaaaacct
tttatttgtacatagatagggggaatcgaagaagaaaaaaaattcaaagtttaaattatttattttatatttatgttatttactttaaattttctaatttctattaaatattaat

Figure 4 (continued)

catatacgtcaaagcgtaatataatgggcaccttacacaaacattcgatagaagggatgtgaatatgaagggaccaaagtgagatcttgccctcagctcc
tagtgcgcctcttgctgttgctccacgtgttaatccaagtggcgagaaaaggagaataataacgcaaaaaaacaggccaagtaagataatccaagtgta
cacttgtcatcgccaaacttactaaaatacgcggcaaattgtatacccacacattattaccataccatatattggctgcatttgcatgtataatactacgtgtaa
gctcagaaaattccacgtgtcgcccatgcaaaattaacactcacgacccattcctaaatctccactatataaaccccactcccccatcttaccaaaccca
ccacacaactcacaacttagaaaaaccaatcataaccaaaatggcaaagctgatg >SEQ-316;WO02102970-SEQ-001-cDNA-Conlinin-1
gaaaaaccaatcataaccaaaatggcaaagctgatgagcctagcagccgtagcaacggcattcctcttcctcattgtggtggacgcatccgtccgaacc
acagtgatcatcgacgaggacaccaaccaaggccgcggtggccaaggtgggcaaggacagcagcagcaatgcgagaagcagatccaggagcaa
gactacctgaggagctgccagcagttcctgtgggagaaagtccagaagggcggccgcagctactactacaaccaaggccgtggaggagggcaaca
gagccagcacttcgatagctgctgcgatgatcttaagcaattgaggagcgagtgcacatgcaggggactggagcgtgcaatcggccagatgaggcag
gacatccagcagcagggacagcagcaggaagttgagaggtgggtccagcaagctaaacaagtcgctagggaccttccgggacagtgcggcaccca
gcctagccgatgccagctccaggggcagcagcagtctgcatggttttgaagtggtgatcgatgagatcgtataaagacacttgctaggtgttaaggatggg
ataataagatgtgttttaagtcattaacccgtaattaaaaggagagagagcttgatggaatggtattgatgttccttgggttttaaaaaaaaa >SEQ-317;WO02102970-UTR-SEQ-001-cDNA-Conlinin-1
gaaaaaccaatcataaccaaa >SEQ-318;WO02102970-SEQ-003-cDNA-Conlinin-2
aagaaccaatcaccaccaaaaaatggcaaagctgatgagcctggcagccgtagcaacggcattcctcttcctgatcgtggtggacgcatccgtccgaa
ccacagtgattatcgacgaggagaccaaccaaggccgcggtggaggccaaggtggccagggacagcagcagtcttgcgagcagcagatccagca
gcaagacttcctgaggagctgccagcagttcatgtgggagaaagtccagaggggcggccgcagccactattacaaccagggccgtggaggaggcga
acagagccagtacttcgacagctgttgtgacgaccttaagcaattgagcaccgggtgcacatgcaggggacttgagcgtgccatcggccaaatgaggc
aggaaatccagcagcagggacagcagcaggaagttcagaggtggatccagcaagctaaacaaatcgctaaggacctccccggacagtgccgacc
cagcctagccaatgccagttccagggccagcagcaatctgcatggttttgaaggggtgatcgattatgagatcgtacaaagacactgctaggtgttaagg
atggataataataataataatgagatggatgtgttttaagttaatgtaacagcttaataaagagagagagagagagagagagagagtcaaaaaa >SEQ-319;WO02102970-UTR-SEQ-003-cDNA-Conlinin-2
aagaaccaatcaccaccaaaaa >SEQ-320;WO2009130291-SEQ-026-pCnl1
ttagcagatatttggtgtctaaatgtttattttgtgatatgttcatgtttgaaatggtggtttcgaaaccagggacaacgttgggatctgataggtgtcaaagagt
attatggattgggacaatttcggtcatgagttgcaaattcaagtatatcgttcgattatgaaaattttcgaagaatatcccatttgagagagtctttacctcattaat
gtttttagattatgaaattttatcatagttcatcgtagtcttttggtgtaaaggctgtaaaagaaattgttcacttttgttttcgtttatgtgaaggctgtaaaagattgt
aaaagactattttggtgttttggataaaatgatagttttttatagattcttttgcttttagaagaaatacatttgaaattttttccatgttgagtataaaataccgaaatcg
attgaagatcatagaaatattttaactgaaaacaaatttataactgattcaattctctccatttttatacctatttaaccgtaatcgattctaatagatgatcgattttt
atataatcctaattaaccaacggcatgtattggataattaaccgatcaactctcacccctaatagaatcagtatttccttcgacgttaattgatcctacactatgt
aggtcatatccatcgttttaattttggccaccattcaattctgtcttgcctttagggatgtgaatatgaacggccaaggtaagagaataaaaataatccaaatt
aaagcaagagaggccaagtaagataatccaaatgtacacttgtcattgccaaaattagtaaaatactcggcatattgtattcccacacattattaaaatacc
gtatatgtattggctgcatttgcatgaataatactacgtgtaagcccaaaagaacccacgtgtagcccatgcaaagttaacactcacgacccattcctcag
tctccactatataaacccaccatccccaatctcaccaaacccaccacacaactcacaactcactctcacacct >SEQ-321;WO2009130291-SEQ-015-part
cccaccatccccaatctcaccaaacccaccacacaactcacaactcactctcacaccttaaagaaccaatcaccaccaaaaaaccatgggaaaagg
atctgagggaaga

Figure 4 (continued)

>SEQ-322;WO2009130291-SEQ-016-reverse_part
ttagcagatatttggtgtctaaatgtttattttgtgatatgttcatgtttgaaatggtggtttcgaaaccagggacaacgttgggatctgataggggtgtcaaagagt
attatggattgggacaatttcggtcatgagttgcaaattcaagtatatcgttcgattatgaaaattttcgaagaatatccctttgagagagtctttacctcattaat
gtttttagattatgaaatttatcatagttcatcgtagtcttttggtgtaaaggctgtaaaagaaattgttcacttttgttttcgtttatgtgaaggctgtaaaagattgt
aaaagactattttggtgttttggataaaatgatagtttttatagattcttttgcttttagaagaaatacatttgaaattttttccatgttgagtataaaataccgaaatcg
attgaagatcatagaaatattttaactgaaaacaaatttataactgattcaattctctccatttttatacctatttaaccgtaatcgattctaatagatgatcgattttt
atataatcctaattaaccaacggcatgtattggataattaaccgatcaactctcaccctaatagaatcagtattttccttcgacgttaattgatcctacactatgt
aggtcatatccatcgtttaattttggccaccattcaattctgtcttgcctttagggatgtgaatatgaacggccaaggtaagagaataaaaataatccaaatt
aaagcaagagaggccaagtaagataatccaaatgtacacttgtcattgccaaaattagtaaaatactcggcatattgtattcccacacattattaaaatacc
gtatatgtattggctgcatttgcatgaataatactacgtgtaagcccaaaagaacccacgtgtagcccatgcaaagttaacactcacgacccccattcctcag
tctccactatataaacccaccatccccaatctcaccaaacccaccacacaactcacaactcactctcacaccttaaagaaccaatcaccaccaaaaaa
ccatgggaaaaggatc >SEQ-323;AJ414732-Truska-Linum_mRNA_Cnl1
aagaaccaatcaccaccaaaaaatggcaaagctgatgagcctggcagccgtagcaacggcattcctcttcctgatcgtggtggacgcatccgtccgaa
ccacagtgattatcgacgaggagaccaaccaaggccgcggtggaggccaaggtggccagggacagcagcagtcttgcgagcagcagatccagca
gcaagacttcctgaggagctgccagcagttcatgtgggagaaagtccagaggggcggccgcagccactattacaaccagggccgtggaggaggcga
acagagccagtacttcgacagctgttgtgacgaccttaagcaattgagcaccgggtgcacatgcagggggacttgagcgtgccatcggccaaatgaggc
aggaaatccagcagcagggacagcagcaggaagttcagaggtggatccagcaagctaaacaaatcgctaaggacctccccggacagtgccgcac
ccagcctagccaatgccagttccagggccagcagcaatctgcatggttttgaaggggtgatcgattatgagatcgtacaaagacactgctaggtgttaag
gatggataataataataataatgagatggatgtgttttaagttaatgtaacagct >SEQ-324;p1039+38UTR
ccccaatctcaccaaacccaccacacaactcacaactcactctcacaccttctagaggatctgatatctgcggccgcggcgcgccacc >SEQ-325;p1039+38_differing_part
tctagaggatctgatatctgcggccgcggcgcgccacc >SEQ-326;p1039+2UTR
ccccaatctcaccaaacccaccacacaactcacaactcactctcacacctcc

SEQUENCE LISTING

<160> NUMBER OF SEQ ID NOS: 328

<210> SEQ ID NO 1
<211> LENGTH: 1063
<212> TYPE: DNA
<213> ORGANISM: Artificial Sequence
<220> FEATURE:
<223> OTHER INFORMATION: promoter plus untranslated region incl enhancer

<400> SEQUENCE: 1

```
ttagcagata tttggtgtct aaatgtttat tttgtgatat gttcatgttt gaaatggtgg      60
tttcgaaacc agggacaacg ttgggatctg atagggtgtc aaagagtatt atggattggg     120
acaatttcgg tcatgagttg caaattcaag tatatcgttc gattatgaaa attttcgaag     180
aatatcccat ttgagagagt ctttacctca ttaatgtttt tagattatga aattttatca     240
tagttcatcg tagtcttttt ggtgtaaagg ctgtaaaaag aaattgttca cttttgtttt     300
cgtttatgtg aaggctgtaa aagattgtaa aagactattt tggtgttttg gataaaatga     360 tagttttttat agattctttt gcttttagaa gaaatacatt tgaaattttt tccatgttga     420
gtataaaata ccgaaatcga ttgaagatca tagaaatatt ttaactgaaa acaaatttat     480
aactgattca attctctcca tttttatacc tatttaaccg taatcgattc taatagatga     540 tcgattttt atataatcct aattaaccaa cggcatgtat tggataatta accgatcaac     600
tctcacccct aatagaatca gtattttcct tcgacgttaa ttgatcctac actatgtagg     660
tcatatccat cgtttaatt tttggccacc attcaattct gtcttgcctt tagggatgtg     720
aatatgaacg gccaaggtaa gagaataaaa ataatccaaa ttaaagcaag agaggccaag     780
taagataatc caaatgtaca cttgtcattg ccaaaattag taaaatactc ggcatattgt     840
attcccacac attattaaaa taccgtatat gtattggctg catttgcatg aataatacta     900
cgtgtaagcc caaaagaacc cacgtgtagc ccatgcaaag ttaacactca cgaccccatt     960
cctcagtctc cactatataa acccaccatc cccaatctca ccaaacccac cacacaactc    1020
acaactcact ctcacaccctt aaagaaccaa tcaccaccaa aaa                     1063
```

<210> SEQ ID NO 2
<211> LENGTH: 1077
<212> TYPE: DNA

<213> ORGANISM: Artificial Sequence
<220> FEATURE:
<223> OTHER INFORMATION: promoter 1039 plus 38pb without enhancer

<400> SEQUENCE: 2

```
ttagcagata tttggtgtct aaatgtttat tttgtgatat gttcatgttt gaaatggtgg      60
tttcgaaacc agggacaacg ttgggatctg atagggtgtc aaagagtatt atggattggg     120
acaatttcgg tcatgagttg caaattcaag tatatcgttc gattatgaaa attttcgaag     180
aatatcccat ttgagagagt ctttacctca ttaatgtttt tagattatga aattttatca     240
tagttcatcg tagtcttttt ggtgtaaagg ctgtaaaaag aaattgttca cttttgtttt     300
cgtttatgtg aaggctgtaa aagattgtaa aagactattt tggtgttttg gataaaatga     360
tagttttat agattctttt gcttttagaa gaaatacatt tgaaattttt tccatgttga      420
gtataaaata ccgaaatcga ttgaagatca tagaaatatt ttaactgaaa acaaatttat     480
aactgattca attctctcca tttttatacc tatttaaccg taatcgattc taatagatga     540
tcgattttt atataatcct aattaaccaa cggcatgtat tggataatta accgatcaac      600
tctcacccct aatagaatca gtattttcct tcgacgttaa ttgatcctac actatgtagg     660
tcatatccat cgttttaatt tttggccacc attcaattct gtcttgcctt tagggatgtg     720
aatatgaacg gccaaggtaa gagaataaaa ataatccaaa ttaaagcaag agaggccaag     780
taagataatc caaatgtaca cttgtcattg ccaaaattag taaaatactc ggcatattgt     840
attcccacac attattaaaa taccgtatat gtattggctg catttgcatg aataatacta     900
cgtgtaagcc caaagaacc cacgtgtagc ccatgcaaag ttaacactca cgaccccatt      960
cctcagtctc cactatataa acccaccatc cccaatctca ccaaacccac cacacaactc    1020
acaactcact ctcacacctt ctagaggatc tgatatctgc ggccgcggcg cgccacc       1077
```

<210> SEQ ID NO 3
<211> LENGTH: 1041
<212> TYPE: DNA
<213> ORGANISM: Artificial Sequence
<220> FEATURE:
<223> OTHER INFORMATION: promoter 1039 without enhancer

<400> SEQUENCE: 3

```
ttagcagata tttggtgtct aaatgtttat tttgtgatat gttcatgttt gaaatggtgg      60
tttcgaaacc agggacaacg ttgggatctg atagggtgtc aaagagtatt atggattggg     120
acaatttcgg tcatgagttg caaattcaag tatatcgttc gattatgaaa attttcgaag     180
aatatcccat ttgagagagt ctttacctca ttaatgtttt tagattatga aattttatca     240
tagttcatcg tagtcttttt ggtgtaaagg ctgtaaaaag aaattgttca cttttgtttt     300
cgtttatgtg aaggctgtaa aagattgtaa aagactattt tggtgttttg gataaaatga     360
tagttttat agattctttt gcttttagaa gaaatacatt tgaaattttt tccatgttga      420
gtataaaata ccgaaatcga ttgaagatca tagaaatatt ttaactgaaa acaaatttat     480
aactgattca attctctcca tttttatacc tatttaaccg taatcgattc taatagatga     540
tcgattttt atataatcct aattaaccaa cggcatgtat tggataatta accgatcaac      600
tctcacccct aatagaatca gtattttcct tcgacgttaa ttgatcctac actatgtagg     660
tcatatccat cgttttaatt tttggccacc attcaattct gtcttgcctt tagggatgtg     720
aatatgaacg gccaaggtaa gagaataaaa ataatccaaa ttaaagcaag agaggccaag     780
taagataatc caaatgtaca cttgtcattg ccaaaattag taaaatactc ggcatattgt     840
```

```
attcccacac attattaaaa taccgtatat gtattggctg catttgcatg aataatacta    900
cgtgtaagcc caaaagaacc cacgtgtagc ccatgcaaag ttaacactca cgaccccatt    960
cctcagtctc cactatataa acccaccatc cccaatctca ccaaacccac cacacaactc   1020
acaactcact ctcacacctc c                                             1041
```

```
<210> SEQ ID NO 4
<211> LENGTH: 664
<212> TYPE: DNA
<213> ORGANISM: Artificial Sequence
<220> FEATURE:
<223> OTHER INFORMATION: promotor p-BnNapin

<400> SEQUENCE: 4
taaggatgac ctacccattc ttgagacaaa tgttacattt tagtatcaga gtaaaatgtg     60
tacctataac tcaaattcga ttgacatgta tccattcaac ataaaattaa accagcctgc    120
acctgcatcc acatttcaag tattttcaaa ccgttcggct cctatccacc gggtgtaaca    180
agacggattc cgaatttgga agattttgac tcaaattccc aatttatatt gaccgtgact    240
aaatcaactt taacttctat aattctgatt aagctcccaa tttatattcc caacggcact    300
acctccaaaa tttatagact ctcatcccct tttaaaccaa cttagtaaac gttttttttt    360
taattttatg aagttaagtt tttaccttgt ttttaaaaag aatcgttcat aagatgccat    420
gccagaacat tagctacacg ttacacatag catgcagccg cggagaattg tttttcttcg    480
ccacttgtca ctcccttcaa acacctaaga gcttctctct cacagcacac acatacaatc    540
acatgcgtgc atgcattatt acacgtgatc gccatgcaaa tctcctttat agcctataaa    600
ttaactcatc ggcttcactc tttactcaaa ccaaaactca tcaatacaaa caagattaaa    660
aaca                                                                 664
```

```
<210> SEQ ID NO 5
<211> LENGTH: 1727
<212> TYPE: DNA
<213> ORGANISM: Artificial Sequence
<220> FEATURE:
<223> OTHER INFORMATION: promotor  p-LuPXR

<400> SEQUENCE: 5
cacgggcagg acatagggac tactacaagc atagtatgct tcagacaaag agctaggaaa     60
gaactcttga tggaggttaa gagaaaaaag tgctagaggg gcatagtaat caaacttgtc    120
aaaaccgtca tcatgatgag ggatgacata atataaaaag ttgactaagg tcttggtagt    180
actctttgat tagtattata tattggtgag aacatgagtc aagaggagac aagaaaccga    240
ggaaccatag tttagcaaca agatggaagt tgcaaagttg agctagccgc tcgattagtt    300
acatctccta agcagtacta caaggaatgg tctctatact ttcatgttta gcacatggta    360
gtgcggattg acaagttaga aacagtgctt aggagacaaa gagtcagtaa aggtattgaa    420
agagtgaagt tgatgctcga caggtcagga gaagtccctc cgccagatgg tgactaccaa    480
ggggttggta tcagctgaga cccaaataag attcttcggt tgaaccagtg gttcgaccga    540
gactcttagg gtgggatttc actgtaagat ttgtgcattt tgttgaatat aaattgacaa    600
ttttttttat ttaattatag attatttaga atgaattaca tatttagttt ctaacaagga    660
tagcaatgga tgggtatggg tacaggttaa acatatctat tacccaccca tctagtcgtc    720
gggttttaca cgtacccacc cgtttacata aaccagaccg gaattttaaa ccgtacccgt    780
```

```
ccgttagcgg gtttcagatt tacccgttta atcgggtaaa acctgattac taaatatata    840 tttttattt gataaacaaa acaaaaatgt taatattttc atattggatg caattttaag    900
aaacacatat tcataaattt ccatatttgt aggaaaataa aaagaaaaat atattcaaga    960
acacaaattt caccgacatg acttttatta cagagttgga attagatcta acaattgaaa   1020
aattaaaatt aagatagaat atgttgagga acatgacata gtataatgct gggttacccg   1080
tcgggtaggt atcgaggcgg atactactaa atccatccca ctcgctatcc gataatcact   1140
ggtttcgggt atacccattc ccgtcaacag gccttttta ccggataatt tcaacttata   1200
gtgaatgaat tttgaataaa tagttagaat accaaaatcc tggattgcat ttgcaatcaa   1260
attttgtgaa ccgttaaatt ttgcatgtac ttgggataga tataatagaa ccgaattttc   1320
attagtttaa tttataactt actttgttca agaaaaaaa atatctatcc aatttactta   1380
taataaaaaa taatctatcc aagttactta ttataatcaa cttgtaaaaa ggtaagaata   1440
caaatgtggt agcgtacgtg tgattatatg tgacgaaatg ttatatctaa caaaagtcca   1500
aattcccatg gtaaaaaaaa tcaaaatgca tggcaggctg tttgtaacct tggaataaga   1560
tgttggccaa ttctggagcc gccacgtacg caagactcag ggccacgttc tcttcatgca   1620
aggatagtag aacaccactc cacccacctc ctatattaga cctttgccca accctcccca   1680
actttcccat cccatccaca aagaaaccga cattttatc ataaatc                  1727
```

<210> SEQ ID NO 6
<211> LENGTH: 1151
<212> TYPE: DNA
<213> ORGANISM: Artificial Sequence
<220> FEATURE:
<223> OTHER INFORMATION: promotor p-PvArc
<400> SEQUENCE: 6

```
tactatagaa aatgtgttat atcgacatga ccagacaaag gggcaacagt taacaaaaca     60
attaattctt tcatttgaga ttaaggaagg taaggtacta aaaagattaa aaaaaatgag    120
cttatctctt tgtttctgta ataataatat aagtgtgata aacttttaat ataataattg    180
taattaggtt ttctacagat gagcaccact cagagacaag ataagaagaa acaattttg     240 ttaaacatga ttatagaaac ttttagttaa gtcttgaagt atcaatataa caaaaaaaag    300
tacacacgac tatgacaata aacccactac cgtcaggtta tcatttcgat gaaatgtttt    360
gatatcatta aatataacag tcacaaaaaa tcatctaatt ataacaatat aacttataca    420
tatatttaac taaaaactta gagttttgt aatgattcta attgatgatt agagtttata    480
gaaatacaat taaataaaaa atataatttt aaaaaaacat agtaaagtca atgagatcct    540
ctctgacctc agtgatcatt tagtcatgta tgtacaacaa tcattgttca tcacatgact    600
gtaaaataaa taaggataaa cttgggaata tatataatat attgtattaa ataaaaaagg    660
gaaatacaaa tatcaatttt agattcccga gttgacacaa ctcaccatgc acgctgccac    720
ctcagctccc agctctcgtc acatgtctca tgtcagttag gtctttggtt tttagtcttt    780
gacacaactc gccatgcatg ttgccacgtg agctcgttcc tcttcccatg atctcaccac    840
tgggcatgca tgctgccacc tcagctggca cctcttctct atatgtccct agaggccatg    900
cacagtgcca cctcagcact cctctcagaa cccatacgta cctgccaatc ggcttctctc    960
cataaatatc tatttaaatt ataactaatt atttcatata cttaattgat gacgtggatg   1020
cattgccatc gttgtttaat aattgttaat tacgacatga taaataaaat gaaagtaaaa   1080
agtacgaaag attttccatt tgttgttgta taaatagaga agtgagtgat gcataatgca   1140
```
tgaatgcatg a                                                            1151

<210> SEQ ID NO 7
<211> LENGTH: 1799
<212> TYPE: DNA
<213> ORGANISM: Artificial Sequence
<220> FEATURE:
<223> OTHER INFORMATION: promotor

<400> SEQUENCE: 7
tcgacggccc ggactgtatc caacttctga tctttgaatc tctctgttcc aacatgttct      60
gaaggagttc taagactttt cagaaagctt gtaacatgct tgtagactt tctttgaatt     120
actcttgcaa actctgattg aacctacgtg aaaactgctc cagaagttct aaccaaattc    180
cgtcttggga aggcccaaaa tttattgagt acttcagttt catggacgtg tcttcaaaga    240
tttataactt gaaatcccat cattttaag agaagttctg ttccgcaatg tcttagatct     300
cattgaaatc tacaactctt gtgtcagaag ttcttccaga atcaacttgc atcatggtga    360
aaatctggcc agaagttctg aacttgtcat atttcttaac agttagaaaa atttctaagt    420
gtttagaatt ttgactttc caaagcaaac ttgacttttg actttcttaa taaaacaaac     480
ttcatattct aacatgtctt gatgaaatgt gattcttgaa atttgatgtt gatgcaaaag    540
tcaaagtttg acttttcagt gtgcaattga ccatttgct cttgtgccaa ttccaaacct     600
aaattgatgt atcagtgctg caaacttgat gtcatggaag atcttatgag aaaattcttg    660
aagactgaga ggaaaaattt tgtagtacaa cacaaagaat cctgttttc atagtcggac     720
tagacacatt aacataaaac accacttcat tcgaagagtg attgaagaag gaaatgtgca    780
gttaccttc tgcagttcat aagagcaact tacagacact tttactaaaa tactacaaag     840
aggaagattt taacaactta gagaagtaat gggagttaaa gagcaacaca ttaagggga     900
gtgttaaaat taatgtgttg taaccaccac taccttagt aagtattata agaaaattgt     960
aatcatcaca ttataattat tgtccttatt taaaattatg ataaagttgt atcattaaga   1020
ttgagaaaac caaatagtcc tcgtcttgat ttttgaatta ttgttttcta tgttactttt   1080
cttcaagcct atataaaaac tttgtaatgc taaattgtat gctggaaaaa aatgtgtaat   1140
gaattgaata gaaattatgg tatttcaaag tccaaaatcc atcaatagaa atttagtaca   1200
aaacgtaact caaaaatatt ctcttatttt aatttaca acaatataaa aatattctct    1260
tatttaaat tttacaataa tataattat cacctgtcac ctttagaata ccaccaacaa    1320
tattaatact tagatatttt attcttaata attttgagat ctctcaatat atctgatatt   1380
tattttatat ttgtgtcata ttttcttatg ttttagagtt aacccttata tcttggtcaa   1440
actagtaatt caatatatga gtttgtgaag gacacattga catcttgaaa cattggtttt   1500
aaccttgttg gaatgttaaa ggtaataaaa cattcagaat tatgaccatc tattaatata   1560
cttcctttgt cttttaaaaa agtgtgcatg aaaatgctct atggtaagct agagtgtctt   1620
gctggcctgt gtatatcaat tccatttcca gatggtagaa actgccacta cgaataatta   1680
gtcataagac acgtatgtta acacacgtcc ccttgcatgt ttttttgccat atattccgtc   1740
tcttttctttt tcttcacgta taaaacaatg aactaattaa tagagcgatc aagctgaac    1799

<210> SEQ ID NO 8
<211> LENGTH: 1430
<212> TYPE: DNA
<213> ORGANISM: Artificial Sequence
<220> FEATURE:

<223> OTHER INFORMATION: promotor p-BnFAE1

<400> SEQUENCE: 8

| | | | | | |
|---|---|---|---|---|---|
| aagctttaca | acgctacaca | aaacttataa | ccgtaatcac | cattcattaa | cttaactact | 60 |
| atcacatgca | ttcatgaatt | gaaacgagaa | ggatgtaaat | agttgggaag | ttatctccac | 120 |
| gttgaagaga | tcgttagcga | gagctgaaag | accgagggag | gagacgccgt | caacacggac | 180 |
| agagtcgtcg | accctcacat | gaagtaggag | gaatctccgt | gaggagccag | agagacgtct | 240 |
| ttggtcttcg | gtttcgatcc | ttgatctgac | ggagaagacg | agagaagtgc | gactggactc | 300 |
| cgtgaggacc | aacagagtcg | tcctcggttt | cgatcgtcgg | tattggtgga | gaaggcggag | 360 |
| gaatctccgt | gacgagccag | agagatgtcg | tcggtcttcg | gtttcgatcc | ttgatctgac | 420 |
| ggagaagacg | agagaagtgc | gacgagactc | cgtgaggacc | aacagagttg | tcctcggttt | 480 |
| cgatcgtcgg | tttcggcgga | gaaggcggag | gaatctccgt | gaggagccag | agagacgtcg | 540 |
| ttggtcttcg | gtttcgatcc | ttgatctgtt | ggagaagacg | agacaagtgg | gacgagactc | 600 |
| aacgacggag | tcagagacgt | cgtcggtctt | cggtttcggc | cgagaaggcg | gagtcggtct | 660 |
| tcggtttcgg | ccgagaaggc | ggaggagacg | tcttcgattt | gggtctctcc | tcttgacgaa | 720 |
| gaaaacaaag | aacacgagaa | ataatgagaa | agagaacaaa | agaaaaaaaa | ataaaaataa | 780 |
| aaataaaatt | tggtcctctt | atgtggtgac | acgtggtttg | aaacccacca | aataatcgat | 840 |
| cacaaaaaac | ctaagttaag | gatcggtaat | aaccttccta | attaattttg | atttatatta | 900 |
| aatcactctt | tttatttata | aaccccacta | aattatgcga | tattgattgt | ctaagtacaa | 960 |
| aaattctctc | gaattcaata | cacatgtttc | atatatttag | ccctgttcat | ttaatattac | 1020 |
| tagcgcattt | ttaatttaaa | attttgtaaa | cttttttggt | caaagaacat | tttttttaatt | 1080 |
| agagacagaa | atctagactc | tttatttgga | ataatagtaa | taaagatata | ttaggcaatg | 1140 |
| agtttatgat | gttatgttta | tatagtttat | ttcattttaa | attgaaaagc | attattttta | 1200 |
| tcgaaatgaa | tctagtatac | aatcaatatt | tatgttttt | catcagatac | tttcctattt | 1260 |
| tttggcacct | ttcatcggac | tactgattta | tttcaatgtg | tatgcatgca | tgagcatgag | 1320 |
| tatacacatg | tcttttaaaa | tgcatgtaaa | gcgtaacgga | ccacaaaaga | ggatccatac | 1380 |
| aaatacatct | catcgcttcc | tctactattc | tccgacacac | acactgagca | | 1430 |

<210> SEQ ID NO 9
<211> LENGTH: 684
<212> TYPE: DNA
<213> ORGANISM: Artificial Sequence
<220> FEATURE:
<223> OTHER INFORMATION: promotor p-VfUSP

<400> SEQUENCE: 9

| | | | | | |
|---|---|---|---|---|---|
| ctgcagcaaa | tttacacatt | gccactaaac | gtctaaaccc | ttgtaatttg | ttttttgtttt | 60 |
| actatgtgtg | ttatgtattt | gatttgcgat | aaatttttat | atttggtact | aaatttataa | 120 |
| caccttttat | gctaacgttt | gccaacactt | agcaatttgc | aagttgatta | attgattcta | 180 |
| aattattttt | gtcttctaaa | tacatatact | aatcaactgg | aaatgtaaat | atttgctaat | 240 |
| atttctacta | taggagaatt | aaagtgagtg | aatatggtac | cacaaggttt | ggagatttaa | 300 |
| ttgttgcaat | gctgcatgga | tggcatatac | accaaacatt | caataattct | tgaggataat | 360 |
| aatggtacca | cacaagattt | gaggtgcatg | aacgtcacgt | ggacaaaagg | tttagtaatt | 420 |
| tttcaagaca | acaatgttac | cacacacaag | ttttgaggtg | catgcatgga | tgccctgtgg | 480 |
| aaagtttaaa | aatatttttgg | aaatgatttg | catggaagcc | atgtgtaaaa | ccatgacatc | 540 |

| | | |
|---|---|---|
| cacttggagg atgcaataat gaagaaaact acaaatttac atgcaactag ttatgcatgt | 600 | |
| agtctatata atgaggattt tgcaatactt tcattcatac acactcacta agttttacac | 660 | |
| gattataatt tcttcatagc cagt | 684 | |

<210> SEQ ID NO 10
<211> LENGTH: 1320
<212> TYPE: DNA
<213> ORGANISM: Artificial Sequence
<220> FEATURE:
<223> OTHER INFORMATION: d5Des Tc GA delta 5 desaturase of
      Thraustochytrium, codon optimized

<400> SEQUENCE: 10

| | | |
|---|---|---|
| atgggaaaag atctgaggg aagatctgct gctagagaga tgactgctga ggctaacgga | 60 | |
| gataagagaa agaccatcct cattgaggga gtgttgtacg atgctaccaa cttcaaacac | 120 | |
| ccaggaggtt ccattattaa cttcctcacc gagggagaag ctggagttga tgctacccaa | 180 | |
| gcttacagag agttccatca gagatccgga aaggctgata agtacctcaa gtccctccca | 240 | |
| aagttggatg cttctaaggt ggagtctagg ttctctgcta aggagcaggc tagaagggac | 300 | |
| gctatgacca gggattacgc tgcttttcaga gaggagttgg ttgctgaggg atacttcgat | 360 | |
| ccatctatcc cacacatgat ctacagagtg gtggagattg tggctttgtt cgctttgtct | 420 | |
| ttctggttga tgtctaaggc ttctccaacc tctttggttt tgggagtggt gatgaacgga | 480 | |
| atcgctcaag gaagatgcgg atgggttatg catgagatgg gacacggatc tttcactgga | 540 | |
| gttatctggc tcgatgatag gatgtgcgag ttcttctacg gagttggatg tggaatgtct | 600 | |
| ggacactact ggaagaacca gcattctaag caccatgctg ctccaaacag attggagcac | 660 | |
| gatgtggatt tgaacacctt gccactcgtt gctttcaacg agagagttgt gaggaaggtt | 720 | |
| aagccaggat ctttgttggc tttgtggctc agagttcagg cttatttgtt cgctccagtg | 780 | |
| tcttgcttgt tgatcggatt gggatggacc ttgtacttgc acccaagata tatgctcagg | 840 | |
| accaagagac atatggagtt tgtgtggatc ttcgctagat atatcggatg ttctccttg | 900 | |
| atgggagctt gggatattc tcctggaact tctgtgggaa tgtacctctg ctctttcgga | 960 | |
| cttggatgca tctacatctt cctccaattc gctgtgtctc atacccattt gccagttacc | 1020 | |
| aacccagagg atcaattgca ttggcttgag tacgctgctg atcataccgt gaacatctct | 1080 | |
| accaagtctt ggttggttac ctggtggatg tctaacctca acttccaaat cgagcatcat | 1140 | |
| ttgttcccaa ccgctccaca attcaggttc aaggagatct ctccaagagt tgaggctctc | 1200 | |
| ttcaagagac ataacctccc ttactacgat ttgccataca cctctgctgt ttctactacc | 1260 | |
| ttcgctaacc tctactctgt tggacattct gttggagctg ataccaagaa gcaggattga | 1320 | |

<210> SEQ ID NO 11
<211> LENGTH: 439
<212> TYPE: PRT
<213> ORGANISM: Artificial Sequence
<220> FEATURE:
<223> OTHER INFORMATION: d5Des Tc GA delta 5 desaturase of
      Thraustochytrium, codon optimized

<400> SEQUENCE: 11

Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

-continued

Tyr Asp Ala Thr Asn Phe Lys His Pro Gly Gly Ser Ile Ile Asn Phe
          35                  40                  45

Leu Thr Glu Gly Glu Ala Gly Val Asp Ala Thr Gln Ala Tyr Arg Glu
 50                  55                  60

Phe His Gln Arg Ser Gly Lys Ala Asp Lys Tyr Leu Lys Ser Leu Pro
 65                  70                  75                  80

Lys Leu Asp Ala Ser Lys Val Glu Ser Arg Phe Ser Ala Lys Glu Gln
                 85                  90                  95

Ala Arg Arg Asp Ala Met Thr Arg Asp Tyr Ala Ala Phe Arg Glu Glu
             100                 105                 110

Leu Val Ala Glu Gly Tyr Phe Asp Pro Ser Ile Pro His Met Ile Tyr
         115                 120                 125

Arg Val Val Glu Ile Val Ala Leu Phe Ala Leu Ser Phe Trp Leu Met
     130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                 165                 170                 175

Ser Phe Thr Gly Val Ile Trp Leu Asp Asp Arg Met Cys Glu Phe Phe
             180                 185                 190

Tyr Gly Val Gly Cys Gly Met Ser Gly His Tyr Trp Lys Asn Gln His
         195                 200                 205

Ser Lys His His Ala Ala Pro Asn Arg Leu Glu His Asp Val Asp Leu
     210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                 245                 250                 255

Phe Ala Pro Val Ser Cys Leu Leu Ile Gly Leu Gly Trp Thr Leu Tyr
             260                 265                 270

Leu His Pro Arg Tyr Met Leu Arg Thr Lys Arg His Met Glu Phe Val
         275                 280                 285

Trp Ile Phe Ala Arg Tyr Ile Gly Trp Phe Ser Leu Met Gly Ala Leu
     290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                 325                 330                 335

Leu Pro Val Thr Asn Pro Glu Asp Gln Leu His Trp Leu Glu Tyr Ala
             340                 345                 350

Ala Asp His Thr Val Asn Ile Ser Thr Lys Ser Trp Leu Val Thr Trp
         355                 360                 365

Trp Met Ser Asn Leu Asn Phe Gln Ile Glu His His Leu Phe Pro Thr
     370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                 405                 410                 415

Val Ser Thr Thr Phe Ala Asn Leu Tyr Ser Val Gly His Ser Val Gly
             420                 425                 430

Ala Asp Thr Lys Lys Gln Asp
         435

```
<210> SEQ ID NO 12
<211> LENGTH: 1320
<212> TYPE: DNA
<213> ORGANISM: Artificial Sequence
<220> FEATURE:
<223> OTHER INFORMATION: d5Des Tc GA delta 5 desaturase of
      Thraustochytrium, codon optimized 2nd version

<400> SEQUENCE: 12
atgggaaaag gatctgaggg aagatctgct gctagagaga tgactgctga ggctaacgga    60
gataagagaa agaccatcct cattgaggga gtgttgtacg atgctaccaa cttcaaacac   120
ccaggaggtt ccattattaa cttcctcacc gagggagaag ctggagttga tgctacccaa   180
gcttacagag agttccatca gagatccgga aaggctgata agtacctcaa gtccctccca   240
aagttggatg cttctaaggt ggagtctagg ttctctgcta aggagcaggc tagaagggac   300
gctatgacca gggattacgc tgctttcaga gaggagttgg ttgctgaggg atacttcgat   360
ccatctatcc acacatgat ctacagagtg tggagattg tggctttgtt cgctttgtct    420
ttctggttga tgtctaaggc ttctccaacc tctttggttt tggagtggt gatgaacgga   480 atcgctcaag aagatgcgg atgggttatg cacgagatgg gacacggatc tttcactgga   540
gttatctggc tcgatgatag gatgtgcgag ttcttctacg gagttggatg tggaatgtct   600
ggacactact ggaagaacca gcactctaag caccacgctg ctccaaaacag attggagcac   660 gatgtggatt tgaacacctt gccactcgtt gctttcaacg agagagttgt gaggaaggtt   720
aagccaggat cttttgttggc tttgtggctc agagttcagg cttatttgtt cgctccagtg   780
tcttgcttgt tgatcggatt gggatggacc ttgtacttgc acccaagata tatgctcagg   840
accaagagac acatggagtt tgtgtggatc ttcgctagat atatcggatg gttctccttg   900
atgggagctt gggatatt c cctggaact tctgtgggaa tgtacctctg ctctttcgga   960
cttggatgca tctacatctt cctccaattc gctgtgtctc acccacactt gccagttacc   1020
aacccagagg atcaattgca ctggcttgag tacgctgctg atcaccgt gaacatctct   1080 accaagtctt ggttggttac ctggtggatg tctaacctca acttccaaat cgagcaccac   1140
ttgttcccaa ccgctccaca attcaggttc aaggagatct ctccaagagt tgaggctctc   1200
ttcaagagac acaacctccc ttactacgat ttgccataca cctctgctgt ttctactacc   1260
ttcgctaacc tctactctgt tggacactct gttggagctg ataccaagaa gcaggattga   1320

<210> SEQ ID NO 13
<211> LENGTH: 1434
<212> TYPE: DNA
<213> ORGANISM: Artificial Sequence
<220> FEATURE:
<223> OTHER INFORMATION: o3Des Cp GA omega 3 desaturase Claviceps
      purpurea; codon optimized

<400> SEQUENCE: 13
atggctgcta ctacctctgc tatgagcaag atgctgttc ttagaagaac tgctgctgct    60
actactgcta tcgatcacga aagctctacc tctgcttctc cagctgattc tcctagactc   120
tctgcttctt ctacctctct ctcttctctc agctctctcg acgctaagga taaggatgat   180
gagtacgctg acttcttga tacttacgga aacgctttca ccctcctga tttcactatc   240 aaggatatca gagatgctat ccctaagcac tgcttcgagc gttctgctat caagggatac   300
gcttatatcc tcagagatgt ggcttgcctt tctaccactt tctacctctt ccacaacttc   360
gttacccctg agaacgttcc ttacaccct cttagagttt tcctctgggg agtttacact   420
```

```
gctcttcagg gacttttcgg aactggactc tggattatcg ctcacgagtg tggacacggt    480
gctttctctc cttctaccct cactaacgat cttactggat gggttctcca ctctgctctt    540
ctcgtgcctt acttctcttg aagttctct cactctgctc accacaaggg aaccggaaat    600
atggaaaggg atatggcttt cctcccctaga actagggctc aatacgctac cagattcgga    660
agagctatgg atcagcttgg agatctttgc gaggaaaccc ctatctacac tgctggattc    720
cttgttttcc agcagcttct tggatggcct tcttacttga tcgctaacgt tactggacac    780
gatcttcacg agagacagag agagggaaga ggaaagggaa agaagaacgg attcggagga    840
actgttaacc acttcgaccc tcgttctcct atcttcgatg acaagcacgc taagtttatc    900
gttctcagcg atatcggact tggacttgct atcgctgctc ttgtttacct cggaaacaga    960
ttcggatggg ctaacgttgc tgtttggtac ttcgttcctt acctctgggt taaccactgg   1020
atcgttgcta tcactttcct tcagcacact gatcctactc ttcctcacta cactgctgag   1080
gaatggaact tcgttcgtgg agctgctgct acaatcgata gagagatggg atttatcggt   1140
agacacctct ccacggaat cgttgagact cacgtgcttc accactacgt tcttcaatc    1200 cctttctaca cgctgatga ggcttctgag gctatcaagc tgttatggg aaagcactac    1260 cgttctgaga ctaaggatgg acctatgggt tttatcaggg ctttgtggaa aactgctaga   1320
tggtgtcaat gggttgagcc ttctgctgat gctcaaggtg ctggtgaagg tgttctcttc   1380
ttcaggaaca gaaacggact tggaactaag cctatctcta tgaggaccca gtga         1434
```

<210> SEQ ID NO 14
<211> LENGTH: 477
<212> TYPE: PRT
<213> ORGANISM: Artificial Sequence
<220> FEATURE:
<223> OTHER INFORMATION: o3Des Cp GA omega 3 desaturase Claviceps
      purpurea; codon optimized

<400> SEQUENCE: 14

```
Met Ala Ala Thr Thr Ser Ala Met Ser Lys Asp Ala Val Leu Arg Arg
1               5                   10                  15

Thr Ala Ala Ala Thr Thr Ala Ile Asp His Glu Ser Ser Thr Ser Ala

```
                    180                 185                 190
Ala His His Lys Gly Thr Gly Asn Met Glu Arg Asp Met Ala Phe Leu
                195                 200                 205
Pro Arg Thr Arg Ala Gln Tyr Ala Thr Arg Phe Gly Arg Ala Met Asp
            210                 215                 220
Gln Leu Gly Asp Leu Cys Glu Glu Thr Pro Ile Tyr Thr Ala Gly Phe
225                 230                 235                 240
Leu Val Phe Gln Gln Leu Leu Gly Trp Pro Ser Tyr Leu Ile Ala Asn
                245                 250                 255
Val Thr Gly His Asp Leu His Glu Arg Gln Arg Glu Gly Arg Gly Lys
            260                 265                 270
Gly Lys Lys Asn Gly Phe Gly Gly Thr Val Asn His Phe Asp Pro Arg
        275                 280                 285
Ser Pro Ile Phe Asp Asp Lys His Ala Lys Phe Ile Val Leu Ser Asp
            290                 295                 300
Ile Gly Leu Gly Leu Ala Ile Ala Ala Leu Val Tyr Leu Gly Asn Arg
305                 310                 315                 320
Phe Gly Trp Ala Asn Val Ala Val Trp Tyr Phe Val Pro Tyr Leu Trp
                325                 330                 335
Val Asn His Trp Ile Val Ala Ile Thr Phe Leu Gln His Thr Asp Pro
            340                 345                 350
Thr Leu Pro His Tyr Thr Ala Glu Glu Trp Asn Phe Val Arg Gly Ala
        355                 360                 365
Ala Ala Thr Ile Asp Arg Glu Met Gly Phe Ile Gly Arg His Leu Phe
        370                 375                 380
His Gly Ile Val Glu Thr His Val Leu His His Tyr Val Ser Ser Ile
385                 390                 395                 400
Pro Phe Tyr Asn Ala Asp Glu Ala Ser Glu Ala Ile Lys Pro Val Met
                405                 410                 415
Gly Lys His Tyr Arg Ser Glu Thr Lys Asp Gly Pro Met Gly Phe Ile
            420                 425                 430
Arg Ala Leu Trp Lys Thr Ala Arg Trp Cys Gln Trp Val Glu Pro Ser
        435                 440                 445
Ala Asp Ala Gln Gly Ala Gly Glu Gly Val Leu Phe Phe Arg Asn Arg
    450                 455                 460
Asn Gly Leu Gly Thr Lys Pro Ile Ser Met Arg Thr Gln
465                 470                 475

<210> SEQ ID NO 15
<211> LENGTH: 1434
<212> TYPE: DNA
<213> ORGANISM: Artificial Sequence
<220> FEATURE:
<223> OTHER INFORMATION: o3Des Cp GA2 V282L; omega 3 desaturase
      Claviceps purpurea; mutation V282L; codon optimized

<400> SEQUENCE: 15
atggctgcta ccacttctgc aatgtctaag gacgctgttc tgcggcgcac tgctgccgca      60
acgactgcca tcgatcacga gtcgtcgacc tctgccagtc cagccgactc gcctagactc     120
tcagcctcgt ccacgtcgct ttcgtcgctt cttctctctcg atgcgaagga caaggacgac    180
gagtatgccg gccttcttga cacatacgga aacgccttca cacccccga cttcactatc     240 aaggacatcc gtgatgccat acccaagcat gtgcttcgaac gctctgccat caagggatac    300
gcatatattc ttcgcgacgt cgcctgtctt tctactacgt tctacctgtt ccacaacttc     360
```

```
gtgacgcccg agaacgtccc ctacactccc cttcgtgtct ttctctgggg tgtttac

-continued

His Ser Ala Leu Leu Val Pro Tyr Phe Ser Trp Lys Phe Ser His Ser
            180                 185                 190

Ala His His Lys Gly Thr Gly Asn Met Glu Arg Asp Met Ala Phe Leu
        195                 200                 205

Pro Arg Thr Arg Ala Gln Tyr Ala Thr Arg Phe Gly Arg Ala Met Asp
    210                 215                 220

Gln Leu Gly Asp Leu Cys Glu Glu Thr Pro Ile Tyr Thr Ala Gly Phe
225                 230                 235                 240

Leu Val Phe Gln Gln Leu Leu Gly Trp Pro Ser Tyr Leu Ile Ala Asn
                245                 250                 255

Val Thr Gly His Asp Leu His Glu Arg Gln Arg Glu Gly Arg Gly Lys
            260                 265                 270

Gly Lys Lys Asn Gly Phe Gly Gly Thr Leu Asn His Phe Asp Pro Arg
        275                 280                 285

Ser Pro Ile Phe Asp Asp Lys His Ala Lys Phe Ile Val Leu Ser Asp
    290                 295                 300

Ile Gly Leu Gly Leu Ala Ile Ala Ala Leu Val Tyr Leu Gly Asn Arg
305                 310                 315                 320

Phe Gly Trp Ala Asn Val Ala Val Trp Tyr Phe Val Pro Tyr Leu Trp
                325                 330                 335

Val Asn His Trp Ile Val Ala Ile Thr Phe Leu Gln His Thr Asp Pro
            340                 345                 350

Thr Leu Pro His Tyr Thr Ala Glu Glu Trp Asn Phe Val Arg Gly Ala
        355                 360                 365

Ala Ala Thr Ile Asp Arg Glu Met Gly Phe Ile Gly Arg His Leu Phe
    370                 375                 380

His Gly Ile Val Glu Thr His Val Leu His His Tyr Val Ser Ser Ile
385                 390                 395                 400

Pro Phe Tyr Asn Ala Asp Glu Ala Ser Glu Ala Ile Lys Pro Val Met
                405                 410                 415

Gly Lys His Tyr Arg Ser Glu Thr Lys Asp Gly Pro Met Gly Phe Ile
            420                 425                 430

Arg Ala Leu Trp Lys Thr Ala Arg Trp Cys Gln Trp Val Glu Pro Ser
        435                 440                 445

Ala Asp Ala Gln Gly Ala Gly Glu Gly Val Leu Phe Phe Arg Asn Arg
    450                 455                 460

Asn Gly Leu Gly Thr Lys Pro Ile Ser Met Arg Thr Gln
465                 470                 475

<210> SEQ ID NO 17
<211> LENGTH: 1086
<212> TYPE: DNA
<213> ORGANISM: Artificial Sequence
<220> FEATURE:
<223> OTHER INFORMATION: o3Des(Pi GA2); Phytophthora infestans; codon
      optimized, 2nd version

<400> SEQUENCE: 17

```
atggctacaa aggaggctta cgttttccca actctcaccg agatcaagag atctctccca     60
aaggattgct tcgaggcttc tgtgcctttg tctctctact acactgtgag atgcttggtt    120
attgctgtgg ctttgacctt cggattgaac tacgctagag ctttgccaga ggttgagtct    180
ttctgggctt tggatgctgc tttgtgcact ggatatatcc tcctccaggg aattgtgttc    240
tggggattct tcactgttgg acacgatgct ggacacggag ctttctctag ataccacctc    300
```

-continued

```
ttgaacttcg ttgtgggaac cttcatgcac tctctcatct tgaccccatt cgagtcttgg    360
aagttgaccc acagacacca ccacaagaac accggaaaca tcgatagaga tgaggtgttc    420
tacccacaga gaaaggctga tgatcaccca ttgtccagga acttgatctt ggctttggga    480
gctgcttggc ttgcttattt ggtggaggga ttcccaccaa gaaaggtgaa ccacttcaac    540
ccattcgagc cactttttgt gagacaagtg tccgctgtgg ttatctcttt gctcgctcac    600
ttcttcgttg ctggactctc tatctacttg tctctccagt tgggacttaa gaccatggct    660
atctactact acggaccagt tttcgtgttc ggatctatgt tggtgattac caccttcttg    720
caccacaacg atgaggagac tccatggtat gctgattctg agtggactta cgtgaaggga    780
aacttgtcct ctgtggatag atcttacggt gctctcatcg ataacctctc ccacaacatc    840
ggaactcacc agatccacca cctcttccca attatcccac actacaagct caagaaggct    900
actgctgctt tccaccaagc tttcccagag cttgtgagaa agtccgatga gccaatcatc    960
aaggctttct tcagagtggg aaggttgtat gctaactacg gagtggttga tcaagaggct   1020
aagctcttca ctttgaagga ggctaaggct gctactgaag ctgctgctaa gaccaagtct   1080
acctga                                                              1086
```

<210> SEQ ID NO 18
<211> LENGTH: 361
<212> TYPE: PRT
<213> ORGANISM: Artificial Sequence
<220> FEATURE:
<223> OTHER INFORMATION: o3Des(Pi GA2); omega 3 desaturase; Phytophthora
      infestans; codon optimized, 2nd version

<400> SEQUENCE: 18

```
Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
```

```
                210                 215                 220
Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
                260                 265                 270

Ile Asp Asn Leu Ser His Asn Ile Gly Thr His Gln Ile His His Leu
                275                 280                 285

Phe Pro Ile Ile Pro His Tyr Lys Leu Lys Lys Ala Thr Ala Ala Phe
290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
                340                 345                 350

Glu Ala Ala Ala Lys Thr Lys Ser Thr
                355                 360

<210> SEQ ID NO 19
<211> LENGTH: 1086
<212> TYPE: DNA
<213> ORGANISM: Artificial Sequence
<220> FEATURE:
<223> OTHER INFORMATION: o3Des(Pi GA); omega 3 desaturase; Phytophthora
      infestans; codon optimized

<400> SEQUENCE: 19
atggctacaa aggaggctta cgttttccca actctcaccg agatcaagag atctctccca      60
aaggattgct cgaggcttc tgtgcctttg tctctctact acactgtgag atgcttggtt     120
attgctgtgg cttttgacctt cggattgaac tacgctagag cttttgccaga ggttgagtct    180 ttctgggctt tggatgctgc tttgtgcact ggatatatcc tcctccaggg aattgtgttc     240
tggggattct tcactgttgg acacgatgct ggacatggag ctttctctag ataccacctc     300
ttgaacttcg ttgtgggaac cttcatgcat tctctcatct tgaccccatt cgagtcttgg    360
aagttgaccc atagacacca tcataagaac accggaaaca tcgatagaga tgaggtgttc     420
tacccacaga gaaaggctga tgatcatcca ttgtccagga acttgatctt ggctttggga    480
gctgcttggc ttgcttattt ggtggaggga ttcccaccaa gaaaggtgaa ccacttcaac    540
ccattcgagc cactttttgt gagacaagtg tccgctgtgg ttatctcttt gctcgctcac    600
ttcttcgttg ctggactctc tatctacttg tctctccagt tgggacttaa gaccatggct    660
atctactact acggaccagt tttcgtgttc ggatctatgt tggtgattac caccttcttg    720
caccataacg atgaggagac tccatggtat gctgattctg agtggactta cgtgaaggga    780
aacttgtcct ctgtggatag atcttacggt gctctcatcg ataacctctc cataacatc    840 ggaactcatc agatccatca cctcttccca attatcccac actacaagct caagaaggct    900
actgctgctt tccatcaagc tttcccagag cttgtgagaa agtccgatga gccaatcatc    960
aaggctttct tcagagtggg aaggttgtat gctaactacg gagtggttga tcaagaggct   1020
aagctcttca ctttgaagga ggctaaggct gctactgaag ctgctgctaa gaccaagtct   1080
acctga                                                              1086
```

```
<210> SEQ ID NO 20
<211> LENGTH: 18
<212> TYPE: DNA
<213> ORGANISM: Artificial Sequence
<220> FEATURE:
<223> OTHER INFORMATION: enhancer end sequence according to invention

<400> SEQUENCE: 20
accaatcacc accaaaaa                                                 18

<210> SEQ ID NO 21
<211> LENGTH: 18
<212> TYPE: DNA
<213> ORGANISM: Artificial Sequence
<220> FEATURE:
<223> OTHER INFORMATION: 5' untranslated region based on 6-tuples

<400> SEQUENCE: 21
aatcaccacc accaaaaa                                                 18

<210> SEQ ID NO 22
<211> LENGTH: 18
<212> TYPE: DNA
<213> ORGANISM: Artificial Sequence
<220> FEATURE:
<223> OTHER INFORMATION: 5' untranslated region based on 6-tuples

<400> SEQUENCE: 22
accaccaatc accaaaaa                                                 18

<210> SEQ ID NO 23
<211> LENGTH: 18
<212> TYPE: DNA
<213> ORGANISM: Artificial Sequence
<220> FEATURE:
<223> OTHER INFORMATION: 5' untranslated region based on 6-tuples

<400> SEQUENCE: 23
caccaccacc accaaaaa                                                 18

<210> SEQ ID NO 24
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 24
aaagaaccac caccaaaa                                                 18

<210> SEQ ID NO 25
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 25
aaccaatcac caccaaaa                                                 18

<210> SEQ ID NO 26
<211> LENGTH: 18
<212> TYPE: DNA
<213> ORGANISM: Artificial Sequence
<220> FEATURE:
<223> OTHER INFORMATION: 5' untranslated region based on 5-tuples
```

```
<400> SEQUENCE: 26
aactcaccac caccaaaa                                                 18

<210> SEQ ID NO 27
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 27
aatcaccacc accaaaaa                                                 18

<210> SEQ ID NO 28
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 28
accaatcaca caccaaaa                                                 18

<210> SEQ ID NO 29
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 29
actcacacac caccaaaa                                                 18

<210> SEQ ID NO 30
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 30
caactcacca caccaaaa                                                 18

<210> SEQ ID NO 31
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 31
caatcacacc accaaaaa                                                 18

<210> SEQ ID NO 32
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 32
cacaactcac accaaaaa                                                 18

<210> SEQ ID NO 33
<211> LENGTH: 18
```

```
<212> TYPE: DNA
<213> ORGANISM: Artificial Sequence
<220> FEATURE:
<223> OTHER INFORMATION: 5' untranslated region based on 5-tuples

<400> SEQUENCE: 33
cacaactcac caccaaaa                                                    18

<210> SEQ ID NO 34
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 34
caccaccaat caccaaaa                                                    18

<210> SEQ ID NO 35
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 35
ccaatcacca ccaaaaaa                                                    18

<210> SEQ ID NO 36
<211> LENGTH: 18
<212> TYPE: DNA
<213> ORGANISM: Artificial Sequence
<220> FEATURE:
<223> OTHER INFORMATION: 5' untranslated region based on 5-tuples

<400> SEQUENCE: 36
ccaccaatca caccaaaa                                                    18

<210> SEQ ID NO 37
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 37
accacactca caaccaaa                                                    18

<210> SEQ ID NO 38
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 38
actcaccaca accaaaaa                                                    18

<210> SEQ ID NO 39
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 39
```
cacaaccact caccaaaa                                            18

<210> SEQ ID NO 40
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 40
cacaactcac caccaaaa                                            18

<210> SEQ ID NO 41
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 41
caccacacaa tcaccaaa                                            18

<210> SEQ ID NO 42
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 42
caccaccaca caaccaaa                                            18

<210> SEQ ID NO 43
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 43
ccaactcaca ccacaaaa                                            18

<210> SEQ ID NO 44
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 44
ccaccaactc acaccaaa                                            18

<210> SEQ ID NO 45
<211> LENGTH: 18
<212> TYPE: DNA
<213> ORGANISM: Artificial Sequence
<220> FEATURE:
<223> OTHER INFORMATION: 5' untranslated region based on 4-tuples

<400> SEQUENCE: 45
ctcacaccac accacaaa                                            18

<210> SEQ ID NO 46
<211> LENGTH: 57
<212> TYPE: DNA
<213> ORGANISM: Artificial Sequence

```
<220> FEATURE:
<223> OTHER INFORMATION: longer enhancer

<400> SEQUENCE: 46
ccaccacaca actcacaact cactctcaca ccttaaagaa ccaatcacca ccaaaaa        57

<210> SEQ ID NO 47
<211> LENGTH: 57
<212> TYPE: DNA
<213> ORGANISM: Artificial Sequence
<220> FEATURE:
<223> OTHER INFORMATION: 5' untranslated region based on 6-tuples

<400> SEQUENCE: 47
acaactcaca actcacacct taaagaacca atcaccaatc accaccacca ccaaaaa        57

<210> SEQ ID NO 48
<211> LENGTH: 57
<212> TYPE: DNA
<213> ORGANISM: Artificial Sequence
<220> FEATURE:
<223> OTHER INFORMATION: 5' untranslated region based on 6-tuples

<400> SEQUENCE: 48
acaactcaca actcactctc acaactcaca ccttaaagaa ccaatcacca ccaaaaa        57

<210> SEQ ID NO 49
<211> LENGTH: 57
<212> TYPE: DNA
<213> ORGANISM: Artificial Sequence
<220> FEATURE:
<223> OTHER INFORMATION: 5' untranslated region based on 6-tuples

<400> SEQUENCE: 49
acaactcaca actcactctc acaccttaaa gaaccaatca ccaccaatca ccaaaaa        57

<210> SEQ ID NO 50
<211> LENGTH: 57
<212> TYPE: DNA
<213> ORGANISM: Artificial Sequence
<220> FEATURE:
<223> OTHER INFORMATION: 5' untranslated region based on 6-tuples

<400> SEQUENCE: 50
actctcacac cttaaagaac caatcaccaa tcaccaatca ccaatcacca ccaaaaa        57

<210> SEQ ID NO 51
<211> LENGTH: 57
<212> TYPE: DNA
<213> ORGANISM: Artificial Sequence
<220> FEATURE:
<223> OTHER INFORMATION: 5' untranslated region based on 6-tuples

<400> SEQUENCE: 51
atcaccacac aactcactct cacaccttaa agaaccaatc accaccacca ccaaaaa        57

<210> SEQ ID NO 52
<211> LENGTH: 57
<212> TYPE: DNA
<213> ORGANISM: Artificial Sequence
<220> FEATURE:
<223> OTHER INFORMATION: 5' untranslated region based on 6-tuples

<400> SEQUENCE: 52
caccttaaag aaccaatcac caccacacct taaagaacca atcaccacca ccaaaaa        57
```

<210> SEQ ID NO 53
<211> LENGTH: 57
<212> TYPE: DNA
<213> ORGANISM: Artificial Sequence
<220> FEATURE:
<223> OTHER INFORMATION: 5' untranslated region based on 6-tuples

<400> SEQUENCE: 53
ccaatcacca cacaactcac tctcacaact cactctcaca ccttaaagaa ccaaaaa    57

<210> SEQ ID NO 54
<211> LENGTH: 57
<212> TYPE: DNA
<213> ORGANISM: Artificial Sequence
<220> FEATURE:
<223> OTHER INFORMATION: 5' untranslated region based on 6-tuples

<400> SEQUENCE: 54
tcacacaact cacaccttaa agaaccaatc accaccacca ccaccaatca ccaaaaa    57

<210> SEQ ID NO 55
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 55
aactcactct cacaactctc acacaactca caccaatcac caccaatcac accaaaa    57

<210> SEQ ID NO 56
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 56
acacaactct cactcacaac tcacaactca caactcactc acaactcacc accaaaa    57

<210> SEQ ID NO 57
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 57
actcacaact ctcaccacca caactctcac accttaaaga accaatcaca ccaaaaa    57

<210> SEQ ID NO 58
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 58
actcactcac aactcacaac tctcacacac caccacacca atcaccacca ccaaaaa    57

<210> SEQ ID NO 59
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 59
agaaccaatc actcaccaat caccttaaag aaccaccacc aatcacacca ccaaaaa        57

<210> SEQ ID NO 60
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 60
atcacaactc tcactcacca ccaatcactc acaccaatca ccaatcacac accaaaa        57

<210> SEQ ID NO 61
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 61
caatcaccac acacaactca ctcactcaca actctcacac caatcaccac caaaaaa        57

<210> SEQ ID NO 62
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 62
cacacacaca actcacacac caatcactct caccaatcac aactcaccac accaaaa        57

<210> SEQ ID NO 63
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 63
ccacaactct caccacaact caccacctta aagaaccaat cacaactctc accaaaa        57

<210> SEQ ID NO 64
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 64
ccaccaatca ctcaccacac cacaactctc acaactcaca accaccaatc accaaaa        57

<210> SEQ ID NO 65
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 65
ccttaaagaa ccaatcacaa ctcacacacc aatcactctc acaactcaca ccaaaaa        57

<210> SEQ ID NO 66

```
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 66
cttaaagaac caatcacacc aatcactctc acaactcaca actcaccacc accaaaa        57

<210> SEQ ID NO 67
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 67 caaccaccctt aaagaaccac aactcacacc ttaaagaacc accaccaatc accaaaa       57

<210> SEQ ID NO 68
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 68
tcacaactct cactcactca ctctcacaac tcacaccttta aagaaccacc accaaaa       57

<210> SEQ ID NO 69
<211> LENGTH: 57
<212> TYPE: DNA
<213> ORGANISM: Artificial Sequence
<220> FEATURE:
<223> OTHER INFORMATION: 5' untranslated region based on 5-tuples

<400> SEQUENCE: 69
tctcacaact cacaccacaa ctcactctca ccaatcacaa ctcacacacc accaaaa        57

<210> SEQ ID NO 70
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 70
aactcacaac caactcacac tcaccacaac cacaaccaca ccacactcac aaccaaa        57

<210> SEQ ID NO 71
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 71
aagaactcac acaatcacca caatcaccac cacacaactc acaaccactc accaaaa        57

<210> SEQ ID NO 72
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 72
```
aagaactctc tcacacaaag aactcaccac tctcaccacc acaactcacc accaaaa     57

<210> SEQ ID NO 73
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 73
acacaactca cacaccacca aagaactcac caactctcac accacacaat caccaaa     57

<210> SEQ ID NO 74
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 74
accaccaaag aaccaatcac caccaccaac tctcaccaac caactcacac cacaaaa     57

<210> SEQ ID NO 75
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 75
cacaactcac cacaactctc tctcactcac accacaccac caccaactca caccaaa     57

<210> SEQ ID NO 76
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 76
caccaatcac caatcacaat cactcaccac aatcacaatc accaccacac aaccaaa     57

<210> SEQ ID NO 77
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 77
caccacaacc aatcacctta aagaactcac cttaaaagaa ctcaccacaa ccaaaaa     57

<210> SEQ ID NO 78
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 78
caccacactc tcaccaccaa ctcacactca ccacaccaac tcacaccaca ccacaaa     57

<210> SEQ ID NO 79
<211> LENGTH: 57
<212> TYPE: DNA

```
<213> ORGANISM: Artificial Sequence
<220> FEATURE:
<223> OTHER INFORMATION: 5' untranslated region based on 4-tuples

<400> SEQUENCE: 79
ccacaactca ctcacacacc accaaaaaga actcaccaat cacacaatca caaaaaa        57

<210> SEQ ID NO 80
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 80
ccaatcacct taaagaactc accttaaaga actcacaatc acaccaccaa ccacaaa        57

<210> SEQ ID NO 81
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 81
ccacaccaca actcaccaca caatcacaac tcaccaagaa ctctctcacc accaaaa        57

<210> SEQ ID NO 82
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 82
ccactcacaa ctcacaacac caccaactca ccacaactca caccaactca ccttaaa        57

<210> SEQ ID NO 83
<211> LENGTH: 57
<212> TYPE: DNA
<213> ORGANISM: Artificial Sequence
<220> FEATURE:
<223> OTHER INFORMATION: 5' untranslated region based on 4-tuples

<400> SEQUENCE: 83
ctcaccacca caatcaccac tcacaactct ctcacacacc aaccaatcac caccaaa        57

<210> SEQ ID NO 84
<211> LENGTH: 5
<212> TYPE: DNA
<213> ORGANISM: Artificial Sequence
<220> FEATURE:
<223> OTHER INFORMATION: tuples at end of 5' untranslated region

<400> SEQUENCE: 84 ccaat        5

<210> SEQ ID NO 85
<211> LENGTH: 5
<212> TYPE: DNA
<213> ORGANISM: Artificial Sequence
<220> FEATURE:
<223> OTHER INFORMATION: tuples at end of 5' untranslated region

<400> SEQUENCE: 85 ccaaa        5
```

<210> SEQ ID NO 86
<211> LENGTH: 5
<212> TYPE: DNA
<213> ORGANISM: Artificial Sequence
<220> FEATURE:
<223> OTHER INFORMATION: tuples at end of 5' untranslated region

<400> SEQUENCE: 86 caaaa                                                                    5

<210> SEQ ID NO 87
<211> LENGTH: 5
<212> TYPE: DNA
<213> ORGANISM: Artificial Sequence
<220> FEATURE:
<223> OTHER INFORMATION: tuples at end of 5' untranslated region

<400> SEQUENCE: 87 aaaaa                                                                    5

<210> SEQ ID NO 88
<211> LENGTH: 5
<212> TYPE: DNA
<213> ORGANISM: Artificial Sequence
<220> FEATURE:
<223> OTHER INFORMATION: tuples at end of 5' untranslated region

<400> SEQUENCE: 88 accaa                                                                    5

<210> SEQ ID NO 89
<211> LENGTH: 5
<212> TYPE: DNA
<213> ORGANISM: Artificial Sequence
<220> FEATURE:
<223> OTHER INFORMATION: tuples at end of 5' untranslated region

<400> SEQUENCE: 89 waaag                                                                    5

<210> SEQ ID NO 90
<211> LENGTH: 4
<212> TYPE: DNA
<213> ORGANISM: Artificial Sequence
<220> FEATURE:
<223> OTHER INFORMATION: artificial tuples in 5' untranslated region

<400> SEQUENCE: 90 actc                                                                     4

<210> SEQ ID NO 91
<211> LENGTH: 6
<212> TYPE: DNA
<213> ORGANISM: Artificial Sequence
<220> FEATURE:
<223> OTHER INFORMATION: tuples in 5' untranslated region

<400> SEQUENCE: 91 caactc                                                                   6

<210> SEQ ID NO 92
<211> LENGTH: 7
<212> TYPE: DNA
<213> ORGANISM: Artificial Sequence
<220> FEATURE:

```
<223> OTHER INFORMATION: tuples in 5' untranslated region

<400> SEQUENCE: 92 acaactc                                                                  7

<210> SEQ ID NO 93
<211> LENGTH: 7
<212> TYPE: DNA
<213> ORGANISM: Artificial Sequence
<220> FEATURE:
<223> OTHER INFORMATION: tuples in 5' untranslated region

<400> SEQUENCE: 93 cacaact                                                                  7

<210> SEQ ID NO 94
<211> LENGTH: 20
<212> TYPE: DNA
<213> ORGANISM: Artificial Sequence
<220> FEATURE:
<223> OTHER INFORMATION: 5' untranslated region

<400> SEQUENCE: 94
gaaccaatca ccaccaaaaa                                                   20

<210> SEQ ID NO 95
<211> LENGTH: 21
<212> TYPE: DNA
<213> ORGANISM: Artificial Sequence
<220> FEATURE:
<223> OTHER INFORMATION: 5' untranslated region

<400> SEQUENCE: 95
agaaccaatc accaccaaaa a                                                 21

<210> SEQ ID NO 96
<211> LENGTH: 36
<212> TYPE: DNA
<213> ORGANISM: Artificial Sequence
<220> FEATURE:
<223> OTHER INFORMATION: longer 5' untranslated region

<400> SEQUENCE: 96
actctcacac cttaaagaac caatcaccac caaaaa                                 36

<210> SEQ ID NO 97
<211> LENGTH: 15
<212> TYPE: DNA
<213> ORGANISM: Artificial Sequence
<220> FEATURE:
<223> OTHER INFORMATION: longer 5' untranslated region

<400> SEQUENCE: 97
actctcacac cttaa                                                        15

<210> SEQ ID NO 98
<211> LENGTH: 16
<212> TYPE: DNA
<213> ORGANISM: Artificial Sequence
<220> FEATURE:
<223> OTHER INFORMATION: longer 5' untranslated region

<400> SEQUENCE: 98
actctcacac cttaaa                                                       16
```

```
<210> SEQ ID NO 99
<211> LENGTH: 19
<212> TYPE: DNA
<213> ORGANISM: Artificial Sequence
<220> FEATURE:
<223> OTHER INFORMATION: longer 5' untranslated region

<400> SEQUENCE: 99
actctcacac cttaaagaa                                                19

<210> SEQ ID NO 100
<211> LENGTH: 4
<212> TYPE: DNA
<213> ORGANISM: Artificial Sequence
<220> FEATURE:
<223> OTHER INFORMATION: CCAAT-Box core

<400> SEQUENCE: 100 ccaa                                                                 4

<210> SEQ ID NO 101
<211> LENGTH: 9
<212> TYPE: DNA
<213> ORGANISM: Artificial Sequence
<220> FEATURE:
<223> OTHER INFORMATION: CCAAT-Box

<400> SEQUENCE: 101 aaccaatca                                                            9

<210> SEQ ID NO 102
<211> LENGTH: 4
<212> TYPE: DNA
<213> ORGANISM: Artificial Sequence
<220> FEATURE:
<223> OTHER INFORMATION: Dof1 core

<400> SEQUENCE: 102 aaag                                                                 4

<210> SEQ ID NO 103
<211> LENGTH: 17
<212> TYPE: DNA
<213> ORGANISM: Artificial Sequence
<220> FEATURE:
<223> OTHER INFORMATION: Dof1

<400> SEQUENCE: 103
cacaccttaa agaacca                                                  17

<210> SEQ ID NO 104
<211> LENGTH: 15
<212> TYPE: DNA
<213> ORGANISM: Artificial Sequence
<220> FEATURE:
<223> OTHER INFORMATION: SEF3, Soybean embryo factor 3

<400> SEQUENCE: 104
tataaaccca ccatc                                                    15

<210> SEQ ID NO 105
<211> LENGTH: 15
<212> TYPE: DNA
<213> ORGANISM: Artificial Sequence
<220> FEATURE:
<223> OTHER INFORMATION: SEF3, Soybean embryo factor 3
```

```
<400> SEQUENCE: 105
accaaaccca ccaca                                                    15

<210> SEQ ID NO 106
<211> LENGTH: 4
<212> TYPE: DNA
<213> ORGANISM: Artificial Sequence
<220> FEATURE:
<223> OTHER INFORMATION: SEF3, Soybean embryo factor 3 core

<400> SEQUENCE: 106 accc                                                                 4

<210> SEQ ID NO 107
<211> LENGTH: 19
<212> TYPE: DNA
<213> ORGANISM: Artificial Sequence
<220> FEATURE:
<223> OTHER INFORMATION: Plant TATA box

<400> SEQUENCE: 107
cactatataa acccaccat                                                19

<210> SEQ ID NO 108
<211> LENGTH: 5
<212> TYPE: DNA
<213> ORGANISM: Artificial Sequence
<220> FEATURE:
<223> OTHER INFORMATION: Plant TATA box core

<400> SEQUENCE: 108 tataa                                                                5

<210> SEQ ID NO 109
<211> LENGTH: 27
<212> TYPE: DNA
<213> ORGANISM: Artificial Sequence
<220> FEATURE:
<223> OTHER INFORMATION: RY and Sph motifs conserved in seed-specific
      promoters

<400> SEQUENCE: 109
gtgtagccca tgcaaagtta acactca                                       27

<210> SEQ ID NO 110
<211> LENGTH: 4
<212> TYPE: DNA
<213> ORGANISM: Artificial Sequence
<220> FEATURE:
<223> OTHER INFORMATION: RY and Sph motifs conserved in seed-specific
      promoters core

<400> SEQUENCE: 110 catg                                                                 4

<210> SEQ ID NO 111
<211> LENGTH: 17
<212> TYPE: DNA
<213> ORGANISM: Artificial Sequence
<220> FEATURE:
<223> OTHER INFORMATION: Prolamin box, conserved in cereal seed storage
      protein gene promoters

<400> SEQUENCE: 111
gcccatgcaa agttaac                                                  17
```

<210> SEQ ID NO 112
<211> LENGTH: 4
<212> TYPE: DNA
<213> ORGANISM: Artificial Sequence
<220> FEATURE:
<223> OTHER INFORMATION: Prolamin box, conserved in cereal seed storage
      protein gene promoters core

<400> SEQUENCE: 112 aaag                                                                    4

<210> SEQ ID NO 113
<211> LENGTH: 13
<212> TYPE: DNA
<213> ORGANISM: Artificial Sequence
<220> FEATURE:
<223> OTHER INFORMATION: Common plant regulatory factor (CPRF) from
      parsley

<400> SEQUENCE: 113
aagaacagcc cat                                                         13

<210> SEQ ID NO 114
<211> LENGTH: 4
<212> TYPE: DNA
<213> ORGANISM: Artificial Sequence
<220> FEATURE:
<223> OTHER INFORMATION: Common plant regulatory factor (CPRF) from
      parsley core

<400> SEQUENCE: 114 acgt                                                                    4

<210> SEQ ID NO 115
<211> LENGTH: 13
<212> TYPE: DNA
<213> ORGANISM: Artificial Sequence
<220> FEATURE:
<223> OTHER INFORMATION: TCP class I transcription factor (Arabidopsis)

<400> SEQUENCE: 115
gtaagcccaa aag                                                         13

<210> SEQ ID NO 116
<211> LENGTH: 4
<212> TYPE: DNA
<213> ORGANISM: Artificial Sequence
<220> FEATURE:
<223> OTHER INFORMATION: TCP class I transcription factor (Arabidopsis)
      core

<400> SEQUENCE: 116 gccc                                                                    4

<210> SEQ ID NO 117
<211> LENGTH: 21
<212> TYPE: DNA
<213> ORGANISM: Artificial Sequence
<220> FEATURE:
<223> OTHER INFORMATION: bZIP protein G-Box binding factor 1

<400> SEQUENCE: 117
ataatactac gtgtaagccc a                                                21

<210> SEQ ID NO 118
<211> LENGTH: 4

```
<212> TYPE: DNA
<213> ORGANISM: Artificial Sequence
<220> FEATURE:
<223> OTHER INFORMATION: bZIP protein G-Box binding factor 1 core

<400> SEQUENCE: 118 acgt                                                                    4

<210> SEQ ID NO 119
<211> LENGTH: 15
<212> TYPE: DNA
<213> ORGANISM: Artificial Sequence
<220> FEATURE:
<223> OTHER INFORMATION: Cis-element in the GAPDH promoters conferring
      light inducibility

<400> SEQUENCE: 119
ttgcatgaat aatac                                                       15

<210> SEQ ID NO 120
<211> LENGTH: 4
<212> TYPE: DNA
<213> ORGANISM: Artificial Sequence
<220> FEATURE:
<223> OTHER INFORMATION: Cis-element in the GAPDH promoters conferring
      light inducibility core

<400> SEQUENCE: 120 atga                                                                    4

<210> SEQ ID NO 121
<211> LENGTH: 17
<212> TYPE: DNA
<213> ORGANISM: Artificial Sequence
<220> FEATURE:
<223> OTHER INFORMATION: SBF-1

<400> SEQUENCE: 121
cacattatta aaatacc                                                     17

<210> SEQ ID NO 122
<211> LENGTH: 4
<212> TYPE: DNA
<213> ORGANISM: Artificial Sequence
<220> FEATURE:
<223> OTHER INFORMATION: SBF-1 core

<400> SEQUENCE: 122 ttaa                                                                    4

<210> SEQ ID NO 123
<211> LENGTH: 11
<212> TYPE: DNA
<213> ORGANISM: Artificial Sequence
<220> FEATURE:
<223> OTHER INFORMATION: Sunflower homeodomain leucine-zipper protein
      Hahb-4

<400> SEQUENCE: 123
cacattatta a                                                           11

<210> SEQ ID NO 124
<211> LENGTH: 4
<212> TYPE: DNA
<213> ORGANISM: Artificial Sequence
<220> FEATURE:
<223> OTHER INFORMATION: Sunflower homeodomain leucine-zipper protein
```

```
            Hahb-4 core

<400> SEQUENCE: 124 atta                                                                      4

<210> SEQ ID NO 125
<211> LENGTH: 11
<212> TYPE: DNA
<213> ORGANISM: Artificial Sequence
<220> FEATURE:
<223> OTHER INFORMATION: Transcriptional repressor BELLRINGER

<400> SEQUENCE: 125
aaaattagta a                                                             11

<210> SEQ ID NO 126
<211> LENGTH: 4
<212> TYPE: DNA
<213> ORGANISM: Artificial Sequence
<220> FEATURE:
<223> OTHER INFORMATION: Transcriptional repressor BELLRINGER core

<400> SEQUENCE: 126 atta                                                                      4

<210> SEQ ID NO 127
<211> LENGTH: 21
<212> TYPE: DNA
<213> ORGANISM: Artificial Sequence
<220> FEATURE:
<223> OTHER INFORMATION: Floral homeotic protein APETALA1

<400> SEQUENCE: 127
cattgccaaa attagtaaaa t                                                  21

<210> SEQ ID NO 128
<211> LENGTH: 4
<212> TYPE: DNA
<213> ORGANISM: Artificial Sequence
<220> FEATURE:
<223> OTHER INFORMATION: Floral homeotic protein APETALA1 core

<400> SEQUENCE: 128 caaa                                                                      4

<210> SEQ ID NO 129
<211> LENGTH: 15
<212> TYPE: DNA
<213> ORGANISM: Artificial Sequence
<220> FEATURE:
<223> OTHER INFORMATION: ICE (inducer of CBF expression 1), AtMYC2
      (rd22BP1)

<400> SEQUENCE: 129
aatgtacact tgtca                                                         15

<210> SEQ ID NO 130
<211> LENGTH: 4
<212> TYPE: DNA
<213> ORGANISM: Artificial Sequence
<220> FEATURE:
<223> OTHER INFORMATION: ICE (inducer of CBF expression 1), AtMYC2
      (rd22BP1) core

<400> SEQUENCE: 130 acac                                                                      4
```

<210> SEQ ID NO 131
<211> LENGTH: 11
<212> TYPE: DNA
<213> ORGANISM: Artificial Sequence
<220> FEATURE:
<223> OTHER INFORMATION: bZIP factors DPBF-1 and 2 (Dc3 promoter binding factor-1 and 2)

<400> SEQUENCE: 131
tacacttgtc a                                                              11

<210> SEQ ID NO 132
<211> LENGTH: 4
<212> TYPE: DNA
<213> ORGANISM: Artificial Sequence
<220> FEATURE:
<223> OTHER INFORMATION: bZIP factors DPBF-1 and 2 (Dc3 promoter binding factor-1 and 2) core

<400> SEQUENCE: 132 acac                                                                       4

<210> SEQ ID NO 133
<211> LENGTH: 17
<212> TYPE: DNA
<213> ORGANISM: Artificial Sequence
<220> FEATURE:
<223> OTHER INFORMATION: Class I GATA factors

<400> SEQUENCE: 133
agtaagataa tccaaat                                                        17

<210> SEQ ID NO 134
<211> LENGTH: 4
<212> TYPE: DNA
<213> ORGANISM: Artificial Sequence
<220> FEATURE:
<223> OTHER INFORMATION: Class I GATA factors core

<400> SEQUENCE: 134 gata                                                                       4

<210> SEQ ID NO 135
<211> LENGTH: 17
<212> TYPE: DNA
<213> ORGANISM: Artificial Sequence
<220> FEATURE:
<223> OTHER INFORMATION: Dof2 - single zinc finger transcription factor

<400> SEQUENCE: 135
tccaaattaa agcaaga                                                        17

<210> SEQ ID NO 136
<211> LENGTH: 4
<212> TYPE: DNA
<213> ORGANISM: Artificial Sequence
<220> FEATURE:
<223> OTHER INFORMATION: Dof2 - single zinc finger transcription factor core

<400> SEQUENCE: 136 aaag                                                                       4

<210> SEQ ID NO 137
<211> LENGTH: 21

```
<212> TYPE: DNA
<213> ORGANISM: Artificial Sequence
<220> FEATURE:
<223> OTHER INFORMATION: Transcription factor binding site box enhancer

<400> SEQUENCE: 137
cacaccttaa agaaccaatc a                                              21

<210> SEQ ID NO 138
<211> LENGTH: 43
<212> TYPE: DNA
<213> ORGANISM: Artificial Sequence
<220> FEATURE:
<223> OTHER INFORMATION: Transcription factor binding site box short
      promoter

<400> SEQUENCE: 138
ataatactac gtgtaagccc aaagaaccc acgtgtagcc cat                       43

<210> SEQ ID NO 139
<211> LENGTH: 69
<212> TYPE: DNA
<213> ORGANISM: Artificial Sequence
<220> FEATURE:
<223> OTHER INFORMATION: Transcription factor binding site box long
      promoter

<400> SEQUENCE: 139
tccaaattaa agcaagagag gccaagtaag ataatccaaa tgtacacttg tcattgccaa    60
aattagtaa                                                            69

<210> SEQ ID NO 140
<211> LENGTH: 17
<212> TYPE: DNA
<213> ORGANISM: Artificial Sequence
<220> FEATURE:
<223> OTHER INFORMATION: spacer

<400> SEQUENCE: 140
ccccaatctc accaaac                                                   17

<210> SEQ ID NO 141
<211> LENGTH: 98
<212> TYPE: DNA
<213> ORGANISM: Artificial Sequence
<220> FEATURE:
<223> OTHER INFORMATION: 98nt promoter

<400> SEQUENCE: 141
ataatactac gtgtaagccc aaaagaaccc acgtgtagcc catgcaaagt taacactcac    60
gaccccattc ctcagtctcc actatataaa cccaccat                            98

<210> SEQ ID NO 142
<211> LENGTH: 115
<212> TYPE: DNA
<213> ORGANISM: Artificial Sequence
<220> FEATURE:
<223> OTHER INFORMATION: 98nt promoter with spacer

<400> SEQUENCE: 142
ataatactac gtgtaagccc aaaagaaccc acgtgtagcc catgcaaagt taacactcac    60
gaccccattc ctcagtctcc actatataaa cccaccatcc ccaatctcac caaac        115

<210> SEQ ID NO 143
```

```
<211> LENGTH: 172
<212> TYPE: DNA
<213> ORGANISM: Artificial Sequence
<220> FEATURE:
<223> OTHER INFORMATION: 98nt promoter with spacer and enhancer

<400> SEQUENCE: 143
ataatactac gtgtaagccc aaaagaaccc acgtgtagcc catgcaaagt taacactcac      60
gaccccattc ctcagtctcc actatataaa cccaccatcc caatctcac caaacccacc     120 acacaactca caactcactc tcacaccttaa agaaccaat caccaccaaa aa            172

<210> SEQ ID NO 144
<211> LENGTH: 142
<212> TYPE: DNA
<213> ORGANISM: Artificial Sequence
<220> FEATURE:
<223> OTHER INFORMATION: 142nt promoter

<400> SEQUENCE: 144
cacattatta aaataccgta tatgtattgg ctgcatttgc atgaataata ctacgtgtaa     60
gcccaaaaga acccacgtgt agcccatgca aagttaacac tcacgacccc attcctcagt   120
ctccactata taaacccacc at                                            142

<210> SEQ ID NO 145
<211> LENGTH: 159
<212> TYPE: DNA
<213> ORGANISM: Artificial Sequence
<220> FEATURE:
<223> OTHER INFORMATION: 142nt promoter with spacer

<400> SEQUENCE: 145
cacattatta aaataccgta tatgtattgg ctgcatttgc atgaataata ctacgtgtaa     60
gcccaaaaga acccacgtgt agcccatgca aagttaacac tcacgacccc attcctcagt   120
ctccactata taaacccacc atccccaatc tcaccaaac                          159

<210> SEQ ID NO 146
<211> LENGTH: 216
<212> TYPE: DNA
<213> ORGANISM: Artificial Sequence
<220> FEATURE:
<223> OTHER INFORMATION: 142nt promoter with spacer and enhancer

<400> SEQUENCE: 146
cacattatta aaataccgta tatgtattgg ctgcatttgc atgaataata ctacgtgtaa     60
gcccaaaaga acccacgtgt agcccatgca aagttaacac tcacgacccc attcctcagt   120
ctccactata taaacccacc atccccaatc tcaccaaacc caccacacaa ctcacaactc   180
actctcacac cttaaagaac caatcaccac caaaaa                             216

<210> SEQ ID NO 147
<211> LENGTH: 160
<212> TYPE: DNA
<213> ORGANISM: Artificial Sequence
<220> FEATURE:
<223> OTHER INFORMATION: 160nt promoter

<400> SEQUENCE: 147
cggcatattg tattcccaca cattattaaa ataccgtata tgtattggct gcatttgcat     60
gaataatact acgtgtaagc ccaaaagaac ccacgtgtag cccatgcaaa gttaacactc   120
acgaccccat tcctcagtct ccactatata aacccaccat                         160
```

<210> SEQ ID NO 148
<211> LENGTH: 177
<212> TYPE: DNA
<213> ORGANISM: Artificial Sequence
<220> FEATURE:
<223> OTHER INFORMATION: 160nt promoter with spacer

<400> SEQUENCE: 148
cggcatattg tattcccaca cattattaaa ataccgtata tgtattggct gcatttgcat    60
gaataatact acgtgtaagc ccaaaagaac ccacgtgtag cccatgcaaa gttaacactc   120
acgaccccat tcctcagtct ccactatata aacccaccat ccccaatctc accaaac      177

<210> SEQ ID NO 149
<211> LENGTH: 234
<212> TYPE: DNA
<213> ORGANISM: Artificial Sequence
<220> FEATURE:
<223> OTHER INFORMATION: 160nt promoter with spacer and enhancer

<400> SEQUENCE: 149
cggcatattg tattcccaca cattattaaa ataccgtata tgtattggct gcatttgcat    60
gaataatact acgtgtaagc ccaaaagaac ccacgtgtag cccatgcaaa gttaacactc   120
acgaccccat tcctcagtct ccactatata aacccaccat ccccaatctc accaaaccca   180
ccacacaact cacaactcac tctcacacct taaagaacca atcaccacca aaaa         234

<210> SEQ ID NO 150
<211> LENGTH: 197
<212> TYPE: DNA
<213> ORGANISM: Artificial Sequence
<220> FEATURE:
<223> OTHER INFORMATION: 197nt promoter

<400> SEQUENCE: 150
aatgtacact tgtcattgcc aaaattagta aaatactcgg catattgtat tcccacacat    60
tattaaaata ccgtatatgt attggctgca tttgcatgaa taatactacg tgtaagccca   120
aaagaaccca cgtgtagccc atgcaaagtt aacactcacg accccattcc tcagtctcca   180
ctatataaac ccaccat                                                   197

<210> SEQ ID NO 151
<211> LENGTH: 214
<212> TYPE: DNA
<213> ORGANISM: Artificial Sequence
<220> FEATURE:
<223> OTHER INFORMATION: 197nt promoter with spacer

<400> SEQUENCE: 151
aatgtacact tgtcattgcc aaaattagta aaatactcgg catattgtat tcccacacat    60
tattaaaata ccgtatatgt attggctgca tttgcatgaa taatactacg tgtaagccca   120
aaagaaccca cgtgtagccc atgcaaagtt aacactcacg accccattcc tcagtctcca   180
ctatataaac ccaccatccc caatctcacc aaac                                214

<210> SEQ ID NO 152
<211> LENGTH: 271
<212> TYPE: DNA
<213> ORGANISM: Artificial Sequence
<220> FEATURE:
<223> OTHER INFORMATION: 197nt promoter with spacer and enhancer

```
<400> SEQUENCE: 152
aatgtacact tgtcattgcc aaaattagta aaatactcgg catattgtat tcccacacat      60
tattaaaata ccgtatatgt attggctgca tttgcatgaa taatactacg tgtaagccca     120
aaagaaccca cgtgtagccc atgcaaagtt aacactcacg accccattcc tcagtctcca     180
ctatataaac ccaccatccc caatctcacc aaacccacca cacaactcac aactcactct     240
cacaccttaa agaaccaatc accaccaaaa a                                    271

<210> SEQ ID NO 153
<211> LENGTH: 235
<212> TYPE: DNA
<213> ORGANISM: Artificial Sequence
<220> FEATURE:
<223> OTHER INFORMATION: 235nt promoter

<400> SEQUENCE: 153
tccaaattaa agcaagagag gccaagtaag ataatccaaa tgtacacttg tcattgccaa      60
aattagtaaa atactcggca tattgtattc ccacacatta ttaaaatacc gtatatgtat     120
tggctgcatt tgcatgaata atactacgtg taagcccaaa agaacccacg tgtagcccat     180
gcaaagttaa cactcacgac cccattcctc agtctccact atataaaccc accat          235

<210> SEQ ID NO 154
<211> LENGTH: 252
<212> TYPE: DNA
<213> ORGANISM: Artificial Sequence
<220> FEATURE:
<223> OTHER INFORMATION: 235nt promoter with spacer

<400> SEQUENCE: 154
tccaaattaa agcaagagag gccaagtaag ataatccaaa tgtacacttg tcattgccaa      60
aattagtaaa atactcggca tattgtattc ccacacatta ttaaaatacc gtatatgtat     120
tggctgcatt tgcatgaata atactacgtg taagcccaaa agaacccacg tgtagcccat     180
gcaaagttaa cactcacgac cccattcctc agtctccact atataaaccc accatcccca     240
atctcaccaa ac                                                         252

<210> SEQ ID NO 155
<211> LENGTH: 309
<212> TYPE: DNA
<213> ORGANISM: Artificial Sequence
<220> FEATURE:
<223> OTHER INFORMATION: 235nt promoter with spacer and enhancer

<400> SEQUENCE: 155
tccaaattaa agcaagagag gccaagtaag ataatccaaa tgtacacttg tcattgccaa      60
aattagtaaa atactcggca tattgtattc ccacacatta ttaaaatacc gtatatgtat     120
tggctgcatt tgcatgaata atactacgtg taagcccaaa agaacccacg tgtagcccat     180
gcaaagttaa cactcacgac cccattcctc agtctccact atataaaccc accatcccca     240
atctcaccaa acccaccaca caactcacaa ctcactctca caccttaaag aaccaatcac     300
caccaaaaa                                                             309

<210> SEQ ID NO 156
<211> LENGTH: 240
<212> TYPE: DNA
<213> ORGANISM: Artificial Sequence
<220> FEATURE:
<223> OTHER INFORMATION: 240nt promoter
```

<400> SEQUENCE: 156

| | | | | | |
|---|---|---|---|---|---|
| aataatccaa | attaaagcaa | gagaggccaa | gtaagataat | ccaaatgtac | acttgtcatt | 60
| gccaaaatta | gtaaaatact | cggcatattg | tattcccaca | cattattaaa | ataccgtata | 120
| tgtattggct | gcatttgcat | gaataatact | acgtgtaagc | ccaaaagaac | ccacgtgtag | 180
| cccatgcaaa | gttaacactc | acgaccccat | tcctcagtct | ccactatata | aacccaccat | 240

<210> SEQ ID NO 157
<211> LENGTH: 257
<212> TYPE: DNA
<213> ORGANISM: Artificial Sequence
<220> FEATURE:
<223> OTHER INFORMATION: 240nt promoter with spacer

<400> SEQUENCE: 157

| | | | | | |
|---|---|---|---|---|---|
| aataatccaa | attaaagcaa | gagaggccaa | gtaagataat | ccaaatgtac | acttgtcatt | 60
| gccaaaatta | gtaaaatact | cggcatattg | tattcccaca | cattattaaa | ataccgtata | 120
| tgtattggct | gcatttgcat | gaataatact | acgtgtaagc | ccaaaagaac | ccacgtgtag | 180
| cccatgcaaa | gttaacactc | acgaccccat | tcctcagtct | ccactatata | aacccaccat | 240
| ccccaatctc | accaaac | | | | | 257

<210> SEQ ID NO 158
<211> LENGTH: 314
<212> TYPE: DNA
<213> ORGANISM: Artificial Sequence
<220> FEATURE:
<223> OTHER INFORMATION: 240nt promoter with spacer and enhancer

<400> SEQUENCE: 158

| | | | | | |
|---|---|---|---|---|---|
| aataatccaa | attaaagcaa | gagaggccaa | gtaagataat | ccaaatgtac | acttgtcatt | 60
| gccaaaatta | gtaaaatact | cggcatattg | tattcccaca | cattattaaa | ataccgtata | 120
| tgtattggct | gcatttgcat | gaataatact | acgtgtaagc | ccaaaagaac | ccacgtgtag | 180
| cccatgcaaa | gttaacactc | acgaccccat | tcctcagtct | ccactatata | aacccaccat | 240
| ccccaatctc | accaaaccca | ccacacaact | cacaactcac | tctcacacct | taaagaacca | 300
| atcaccacca | aaaa | | | | | 314

<210> SEQ ID NO 159
<211> LENGTH: 989
<212> TYPE: DNA
<213> ORGANISM: Artificial Sequence
<220> FEATURE:
<223> OTHER INFORMATION: 1064nt promoter

<400> SEQUENCE: 159

| | | | | | |
|---|---|---|---|---|---|
| ttagcagata | tttggtgtct | aaatgtttat | tttgtgatat | gttcatgttt | gaaatggtgg | 60
| tttcgaaacc | agggacaacg | ttgggatctg | atagggtgtc | aaagagtatt | atggattggg | 120
| acaatttcgg | tcatgagttg | caaattcaag | tatatcgttc | gattatgaaa | attttcgaag | 180
| aatatcccat | ttgagagagt | ctttacctca | ttaatgtttt | tagattatga | aattttatca | 240
| tagttcatcg | tagtcttttt | ggtgtaaagg | ctgtaaaaag | aaattgttca | cttttgtttt | 300
| cgtttatgtg | aaggctgtaa | aagattgtaa | aagactattt | tggtgttttg | gataaaatga | 360
| tagttttat | agattctttt | gcttttagaa | gaaatacatt | tgaatttttt | tccatgttga | 420
| gtataaaata | ccgaaatcga | ttgaagatca | tagaaatatt | ttaactgaaa | acaaatttat | 480

```
aactgattca attctctcca tttttatacc tatttaaccg taatcgattc taatagatga     540 tcgattttt   atataatcct aattaaccaa cggcatgtat tggataatta accgatcaac    600
tctcacccct aatagaatca gtattttcct tcgacgttaa ttgatcctac actatgtagg    660
tcatatccat cgttttaatt tttggccacc attcaattct gtcttgcctt tagggatgtg    720
aatatgaacg gccaaggtaa gagaataaaa ataatccaaa ttaaagcaag agaggccaag    780
taagataatc caaatgtaca cttgtcattg ccaaaattag taaaatactc ggcatattgt    840
attcccacac attattaaaa taccgtatat gtattggctg catttgcatg aataatacta    900
cgtgtaagcc caaaagaacc cacgtgtagc catgcaaag ttaacactca cgaccccatt     960
cctcagtctc cactatataa acccaccat                                      989
```

<210> SEQ ID NO 160
<211> LENGTH: 1006
<212> TYPE: DNA
<213> ORGANISM: Artificial Sequence
<220> FEATURE:
<223> OTHER INFORMATION: 1064nt promoter with spacer but without enhancer

<400> SEQUENCE: 160

```
ttagcagata tttggtgtct aaatgtttat tttgtgatat gttcatgttt gaaatggtgg     60
tttcgaaacc agggacaacg ttgggatctg atagggtgtc aaagagtatt atggattggg    120
acaatttcgg tcatgagttg caaattcaag tatatcgttc gattatgaaa attttcgaag    180
aatatcccat ttgagagagt ctttacctca ttaatgtttt tagattatga aattttatca    240
tagttcatcg tagtcttttt ggtgtaaagg ctgtaaaaag aaattgttca cttttgtttt    300
cgtttatgtg aaggctgtaa aagattgtaa aagactattt tggtgttttg gataaaatga    360
tagtttttat agattctttt gcttttagaa gaaatacatt tgaaattttt tccatgttga    420
gtataaaata ccgaaatcga ttgaagatca tagaaatatt ttaactgaaa acaaatttat    480
aactgattca attctctcca tttttatacc tatttaaccg taatcgattc taatagatga    540 tcgattttt  atataatcct aattaaccaa cggcatgtat tggataatta accgatcaac     600
tctcacccct aatagaatca gtattttcct tcgacgttaa ttgatcctac actatgtagg    660
tcatatccat cgttttaatt tttggccacc attcaattct gtcttgcctt tagggatgtg    720
aatatgaacg gccaaggtaa gagaataaaa ataatccaaa ttaaagcaag agaggccaag    780
taagataatc caaatgtaca cttgtcattg ccaaaattag taaaatactc ggcatattgt    840
attcccacac attattaaaa taccgtatat gtattggctg catttgcatg aataatacta    900
cgtgtaagcc caaaagaacc cacgtgtagc catgcaaag ttaacactca cgaccccatt     960
cctcagtctc cactatataa acccaccatc cccaatctca ccaaac                   1006
```

<210> SEQ ID NO 161
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 161

```
ataatactac gtgtaagccc aaaagaaccc acgtgtagcc catgcaaagt taacactcat     60 gacccccattc ctcagtctcc actatataaa cccaccatcc cctatctcac caaacccacc   120
acacaactca caactcactc tcacaccctta aagaaccaat caccaccaaa aa           172
```

<210> SEQ ID NO 162
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 162

```
ataatactac gtgtaagccc aaaagaaccc acgtgtagcc catgcaaagt taacactcac      60
aaccccattc ctcagtctcc actatataaa cccaccatct tacttctcac caaacccacc     120
acacaactca caactcactc tcacacctta aagaaccaat caccaccaaa aa             172
```

<210> SEQ ID NO 163
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 163

```
ataatactac gtgtaagccc aaaagaaccc acgtgtagcc catgcaaagt taacactcaa      60
gaccccattc ctcagtctcc actatataaa cccaccatcc atcgtctcac caaacccacc     120
acacaactca caactcactc tcacacctta aagaaccaat caccaccaaa aa             172
```

<210> SEQ ID NO 164
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 164

```
ataatactac gtgtaagccc aaaagaaccc acgtgtagcc catgcaaagt taacactcat      60
aaccccattc ctcagtctcc actatataaa cccaccatca tctctctcac caaacccacc     120
acacaactca caactcactc tcacacctta aagaaccaat caccaccaaa aa             172
```

<210> SEQ ID NO 165
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 165

```
ataatactac gtgtaagccc aaaagaaccc acgtgtagcc catgcaaagt taacactcat      60
taccccattc ctcagtctcc actatataaa cccaccatcg aatttctcac caaacccacc     120
acacaactca caactcactc tcacacctta aagaaccaat caccaccaaa aa             172
```

<210> SEQ ID NO 166
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 166

```
ataatactac gtgtaagccc aaaagaaccc acgtgtagcc catgcaaagt taacactcag      60
caccccattc ctcagtctcc actatataaa cccaccatcc tcgctctcac caaacccacc     120
acacaactca caactcactc tcacacctta aagaaccaat caccaccaaa aa             172
```

```
<210> SEQ ID NO 167
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 167
ataatactac gtgtaagccc aaaagaaccc acgtgtagcc catgcaaagt taacactcag      60
gaccccattc ctcagtctcc actatataaa cccaccatcg gatgtctcac caaacccacc     120
acacaactca caactcactc tcacaccttta aagaaccaat caccaccaaa aa            172

<210> SEQ ID NO 168
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 168
ataatactac gtgtaagccc aaaagaaccc acgtgtagcc catgcaaagt taacactcac      60
caccccattc ctcagtctcc actatataaa cccaccatca catctctcac caaacccacc     120
acacaactca caactcactc tcacaccttta aagaaccaat caccaccaaa aa            172

<210> SEQ ID NO 169
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 169
ataatactac gtgtaagccc aaaagaaccc acgtgtagcc catgcaaagt taacactcag      60
gaccccattc ctcagtctcc actatataaa cccaccatca acaatctcac caaacccacc     120
acacaactca caactcactc tcacaccttta aagaaccaat caccaccaaa aa            172

<210> SEQ ID NO 170
<211> LENGTH: 172
<212> TYPE: DNA
<213> ORGANISM: Artificial Sequence
<220> FEATURE:
<223> OTHER INFORMATION: ProPer 98nt promoter with spacer and enhancer

<400> SEQUENCE: 170
ataatactac gtgtaagccc aaaagaaccc acgtgtagcc catgcaaagt taacactcac      60
taccccattc ctcagtctcc actatataaa cccaccatcc aacatctcac caaacccacc     120
acacaactca caactcactc tcacaccttta aagaaccaat caccaccaaa aa            172

<210> SEQ ID NO 171
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 171
attaaaatac cgtatataaa cccacgtgta gcccatgcaa agttaacact cacgacccca      60
ttcccacaca ttattaaaat actacgtgta agcccatgca aagttaacac tcaccatccc     120
```
cattcccaca cattattaaa ataccgtata taaacccacc aaaagaaccc accaaac    177

<210> SEQ ID NO 172
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 172
acgtgtaagc ccaatctcac catccccatt cctcagtctc cactatataa acccacgtgt    60
agcccatgca aagttaacac tcacgacccc atgcaaagtt aacactcacg accccaatct    120
caccatcccc attcctcagt ctccactata taaacccacc aaaagaaccc accaaac    177

<210> SEQ ID NO 173
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 173
ctacgtgtaa gcccaatctc acgaccccat gcaaagttaa cactcaccaa aagaacccac    60
caaaagaacc cacgtgtagc ccaatctcac gaccccattc tcagtctcc actatataaa    120 cccacacatt attaaaatac cgtatataaa cccacgtgta gcccaatctc accaaac    177

<210> SEQ ID NO 174
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 174
tcctcagtct ccactatatg tattgtattc ctcagtctcc actatataaa cccacgtgta    60
gcccattccc acacattatt aaaatactac gtgtagccca tgcaaagtta acactcacca    120
tccccattcc cacacattat taaaataccg tatataaacc cacgtgtaag cccaaac    177

<210> SEQ ID NO 175
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 175
tgtaagccca tgcaaagtta acactcacga ccccattccc acacattatt aaaataccgt    60
atataaaccc accatcccca aaagaaccca cgtgtagccc atgcaaagtt aacactcacg    120
accccattcc cacacattat taaaataccg tatataaacc cacgtgtaag cccaaac    177

<210> SEQ ID NO 176
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 176
acattattaa aataccgtat atgtattggc tgcatgaata atactacgtg tagcccatgc    60
aaagttaaca ctcaccatcc ccattcccac gtgtagccca tgcaaagtta acactcacca    120

```
tccccattcc tcagtctcca ctatataaac ccacgtgtaa gcccaatctc accaaac      177
```

<210> SEQ ID NO 177
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 177

```
cgaccccatg caaagttaac actcacgacc ccaatctcac caaaagaacc caccatcccc      60
atgcaaagtt aacactcacc atccccatgc aaagttaaca ctcaccatcc ccaaaagaac     120
ccacgtgtaa gcccattcct cagtctccac tatataaacc cacgtgtaag cccaaac         177
```

<210> SEQ ID NO 178
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 178

```
aacactcacg accccaatct cacgaccccca aaagaaccca cgtgtagccc aatctcacga      60
ccccatgcaa agttaacact caccatcccc attcctcagt ctccactata tgtattgtat     120
tcccacgtgt agcccattcc tcagtctcca ctatataaac ccacgtgtag cccaaac         177
```

<210> SEQ ID NO 179
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 179

```
aaaagaaccc acacattatt aaaataccgt atataaaccc acgtgtaagc ccaaaagaac      60
ccacacatta ttaaaatact acgtgtaagc ccatgcaaag ttaacactca ccaaaagaac     120
ccacacatta ttaaaatacc gtatataaac ccacgtgtaa gcccaatctc accaaac         177
```

<210> SEQ ID NO 180
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 180

```
cccacgtgta agcccaatct cacgacccca ttcccacaca ttattaaaat actacgtgta      60
agcccattcc cacgtgtagc ccatgcaaag ttaacactca cgaccccatt cctcagtctc     120
cactatatgt attcctcagt ctccactata taaacccacc aaaagaaccc accaaac         177
```

<210> SEQ ID NO 181
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 181

```
aacccacaca ttattaaaat accgtatatg tattcccacc atccccatgc aaagttaaca      60
```
ctcaccatcc ccaaaagaac ccacacatta ttaaaatacc gtatatgtat tcccacgtgt    120
agcccattcc tcagtctcca ctatataaac ccacgtgtaa gcccattccc accaaac       177

<210> SEQ ID NO 182
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 182
cccatgcaaa gttaacactc acgaccccaa aagaacccac acattattaa aataccgtat    60
atgtattcct cagtctccac tatataaacc cacgtgtaag cccattccca cacattatta   120
aaataccgta tatgtattcc tcagtctcca ctatataaac ccacgtgtag cccaaac      177

<210> SEQ ID NO 183
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 183
cgtatatgta ttgtattccc acgtgtaagc ccaatctcac gaccccatgc aaagttaaca    60
ctcacgaccc catgcaaagt taacactcac caaaagaacc cacacattat taaaatacta   120
cgtgtagccc attcctcagt tccactata taaacccacc aaaagaaccc accaaac       177

<210> SEQ ID NO 184
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 184
acacattatt aaaataccgt atataaaccc acgtgtagcc catgcaaagt taacactcac    60
gaccccaaaa gaaccacac attattaaaa tactacgtgt aagcccattc ctcagtctcc   120
actatatgta ttgtattcct cagtctccac tatataaacc cacgtgtaag cccaaac      177

<210> SEQ ID NO 185
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 185
tatatgtatt cccacacatt attaaaatac tacgtgtagc ccattcccac acattattaa    60
aatactacgt gtaagcccat tcctcagtct ccactatata aacccacgtg tagcccattc   120
ccacacatta ttaaaatacc gtatataaac ccacgtgtaa gcccattccc accaaac      177

<210> SEQ ID NO 186
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 186
taaacccacc atccccattc ctcagtctcc actatataaa cccacgtgta gcccatgcaa    60

```
agttaacact caccatcccc aatctcacca tccccaatct cacgacccca tgcaaagtta    120
acactcacga ccccattcct cagtctccac tatataaacc cacgtgtaag cccaaac      177

<210> SEQ ID NO 187
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 187
ctacgtgtag cccattccca cgtgtaagcc caatctcacg accccattcc cacgtgtaag    60
cccattccca cgtgtagccc atgcaaagtt aacactcacc atccccaatc tcaccatccc   120
caatctcacg accccattcc tcagtctcca ctatataaac ccacgtgtag cccaaac      177

<210> SEQ ID NO 188
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 188
atgcaaagtt aacactcacg accccatgca aagttaacac tcaccaaaag aacccacaca    60
ttattaaaat actacgtgta gcccattccc acgtgtaagc ccattcctca gtctccacta   120
tatgtattcc tcagtctcca ctatataaac ccacgtgtaa gcccaatctc accaaac      177

<210> SEQ ID NO 189
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 189
gaacccacac attattaaaa tactacgtgt agcccaatct caccatcccc aaaagaaccc    60
acacattatt aaaataccgt atatgtattg tattgtattg gctgcatttg catgaataat   120
actacgtgta agcccattcc tcagtctcca ctatataaac ccacgtgtag cccaaac      177

<210> SEQ ID NO 190
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 190
cctcagtctc cactatataa acccacgtgt agcccaatct caccatcccc atgcaaagtt    60
aacactcacc atccccaaaa gaacccacac attattaaaa taccgtatat gtattgtatt   120
cccacacatt attaaaatac cgtatataaa cccacgtgta gcccaatctc accaaac      177

<210> SEQ ID NO 191
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 191
```

```
agttaacact cacgacccca atctcaccat ccccattccc acgtgtagcc caatctcacg    60
accccaatct cacgacccca atctcaccaa aagaacccac gtgtaagccc atgcaaagtt   120
aacactcacg accccattcc tcagtctcca ctatataaac ccacgtgtag cccaaac      177

<210> SEQ ID NO 192
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 192
gcccatgcaa agttaacact caccatcccc attcctcagt ctccactata tgtattccca    60
cacattatta aaataccgta tataaaccca cgtgtagccc atgcaaagtt aacactcacg   120
accccattcc tcagtctcca ctatataaac ccacgtgtaa gcccaatctc accaaac      177

<210> SEQ ID NO 193
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 193
cattattaaa ataccgtata tgtattccca cgtgtaagcc caatctcacg accccatgca    60
aagttaacac tcaccatccc caatctcacg accccattcc tcagtctcca ctatatgtat   120
tgtattgtat tcctcagtct ccactatata aacccaccat ccccaatctc accaaac      177

<210> SEQ ID NO 194
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 194
cccattccca cgtgtaagcc catgcaaagt taacactcac gaccccaatc tcacgacccc    60
attcccacca aagaaccca cacattatta aaataccgta tatgtattgg ctgcatgaat   120
aataccgtat atgtattcct cagtctccac tatataaacc cacgtgtaag cccaaac      177

<210> SEQ ID NO 195
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 195
atgtattggc tgcatgaata ataccgtata tgtattcctc agtctccact atatgtattc    60
ctcagtctcc actatatgta ttggctgcat gaataatact acgtgtaagc ccaatctcac   120
gaccccattc ctcagtctcc actatataaa cccacgtgta gcccaatctc accaaac      177

<210> SEQ ID NO 196
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 196
```

```
ccatccccat tcctcagtct ccactatata aacccacaca ttattaaaat actacgtgta      60
gcccattccc acgtgtagcc catgcaaagt taacactcac gacccccaatc tcaccaaaag    120 aacccaccat ccccattcct cagtctccac tatataaacc cacgtgtaag cccaaac       177
```

<210> SEQ ID NO 197
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 197

```
accccatgca aagttaacac tcacgacccc attcccacac attattaaaa taccgtatat     60
gtattcctca gtctccacta tataaaccca ccaaaagaac ccacacatta ttaaaatacc    120
gtatatgtat tggctgcatg aataataccg tatataaacc cacgtgtaag cccaaac       177
```

<210> SEQ ID NO 198
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 198

```
cactatatgt attggctgca tttgcatttg catgaataat actacgtgta agcccaatct     60
cacgacccca aagaaccca cacattatta aataccgta tataaaccca cacattatta     120
aaataccgta tatgtattcc tcagtctcca ctatataaac ccacgtgtag cccaaac       177
```

<210> SEQ ID NO 199
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 199

```
cacgacccca aagaaccca cgtgtaagcc caatctcacg accccatgca aagttaacac      60
tcaccatccc catgcaaagt taacactcac caaaagaacc cacacattat aaaatacta    120 cgtgtagccc attcctcagt ctccactata aacccacc aaaagaaccc accaaac        177
```

<210> SEQ ID NO 200
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 200

```
actacgtgta gcccattcct cagtctccac tatatgtatt gtattcccac gtgtaagccc     60
atgcaaagtt aacactcacg accccaaaag aacccacaca ttattaaaat actacgtgta   120
agcccattcc cacacattat taaaataccg tatataaacc cacgtgtaag cccaaac       177
```

<210> SEQ ID NO 201
<211> LENGTH: 177
<212> TYPE: DNA
<213> ORGANISM: Artificial Sequence
<220> FEATURE:
<223> OTHER INFORMATION: synthetic 160nt promoter with spacer

```
<400> SEQUENCE: 201
aataataccg tatatgtatt ggctgcattt gcatgaataa tactacgtgt aagcccaatc      60
tcaccatccc cattcctcag tctccactat ataaacccac acattattaa aataccgtat     120
atgtattggc tgcatgaata ataccgtata taaacccacc aaaagaaccc accaaac       177

<210> SEQ ID NO 202
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 202
accgtatatg tattggctgc atttgcatga ataataccgt atataaaccc acgtgtaagc      60
ccatgcaaag ttaacactca ccatccccat tcctcagtct ccactatatg tattcctcag    120
tctccactat atgtattcct cagtctccac tatataaacc cacgtgtaag cccaaac       177

<210> SEQ ID NO 203
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 203
ccaaaagaac ccacgtgtaa gcccatgcaa agttaacact caccatcccc aatctcacca      60
tccccattcc cacacattat aaaataccg tatataaacc cacacattat aaaatacta     120 cgtgtagccc attcctcagt ctccactata taaacccacc aaaagaaccc accaaac       177

<210> SEQ ID NO 204
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 204
atgcaaagtt aacactcacg accccatgca aagttaacac tcaccatccc catgcaaagt      60
taacactcac caaagaacc caccatcccc atgcaaagtt aacactcacc atccccattc    120
ccacacatta ttaaaatacc gtatataaac ccacgtgtaa gcccaatctc accaaac       177

<210> SEQ ID NO 205
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 205
atactacgtg taagcccatt cctcagtctc cactatatgt attcccacgt gtaagcccaa      60
aagaacccac gtgtaagccc atgcaaagtt aacactcacg accccaatct caccatcccc    120
aatctcacga ccccattcct cagtctccac tatataaacc cacgtgtaag cccaaac       177

<210> SEQ ID NO 206
<211> LENGTH: 177
<212> TYPE: DNA
<213> ORGANISM: Artificial Sequence
<220> FEATURE:
<223> OTHER INFORMATION: synthetic 160nt promoter with spacer
```

<400> SEQUENCE: 206

```
cactcacgac cccatgcaaa gttaacactc acgaccccat gcaaagttaa cactcacgac        60
cccaatctca cgaccccatt cccacacatt attaaaatac cgtatataaa cccaccaaaa       120
gaacccacca tccccattcc tcagtctcca ctatataaac ccacgtgtag cccaaac          177
```

<210> SEQ ID NO 207
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 207

```
acattattaa ataccgtat ataaacccac acattattaa aatactacgt gtaagcccaa        60
aagaacccac catcccccaat ctcacgaccc caatctcacg accccattcc tcagtctcca    120
ctatataaac ccacacatta ttaaaatacc gtatataaac ccacgtgtag cccaaac          177
```

<210> SEQ ID NO 208
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 208

```
aaaataccgt atataaaccc acgtgtaagc ccaatctcac catccccatg caaagttaac        60
actcacgacc ccaatctcac gaccccatgc aaagttaaca ctcacgaccc cattcctcag      120
tctccactat atgtattcct cagtctccac tatataaacc cacgtgtaag cccaaac          177
```

<210> SEQ ID NO 209
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 209

```
taagcccaat ctcaccatcc ccattcctca gtctccacta tatgtattcc cacgtgtaag        60
cccaatctca cgaccccatg caaagttaac actcacgacc ccaaaagaac ccaccatccc      120
caaaagaacc cacacattat taaaataccg tatataaacc cacgtgtaag cccaaac          177
```

<210> SEQ ID NO 210
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 210

```
acattattaa aatactacgt gtaagcccat gcaaagttaa cactcaccat ccccaatctc        60
accaaaagaa cccacgtgta agcccaatct caccatcccc atgcaaagtt aacactcacg      120
accccattcc tcagtctcca ctatataaac ccacgtgtaa gcccattccc accaaac          177
```

<210> SEQ ID NO 211
<211> LENGTH: 177
<212> TYPE: DNA
<213> ORGANISM: Artificial Sequence
<220> FEATURE:

<223> OTHER INFORMATION: synthetic 160nt promoter with spacer

<400> SEQUENCE: 211

```
cactcaccaa aagaacccac catccccaaa agaacccacg tgtagcccaa tctcacgacc      60
ccattcccac catccccatg caaagttaac actcacgacc ccattcccac acattattaa     120
aataccgtat atgtattcct cagtctccac tatataaacc cacgtgtaag cccaaac        177
```

<210> SEQ ID NO 212
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 212

```
acccacgtgt agcccatgca aagttaacac tcaccatccc caaagaacc cacgtgtaag      60
cccattccca cacattatta aaataccgta tatgtattcc tcagtctcca ctatataaac    120
ccacacatta ttaaaatacc gtatataaac ccacgtgtaa gcccaatctc accaaac        177
```

<210> SEQ ID NO 213
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 213

```
atgtattcct cagtctccac tatatgtatt cccacgtgta agcccaatct caccatcccc     60
aaaagaaccc accaaaagaa cccacacatt attaaaatac tacgtgtagc ccaatctcac    120
gaccccattc ctcagtctcc actatataaa cccacgtgta gcccaatctc accaaac        177
```

<210> SEQ ID NO 214
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 214

```
attaaaatac cgtatatgta ttggctgcat gaataatacc gtatataaac ccacgtgtaa     60
gcccaaaaga acccacacat tattaaaata ccgtatataa acccacgtgt agcccaaaag    120
aacccacaca ttattaaaat accgtatata acccaccat ccccaatctc accaaac         177
```

<210> SEQ ID NO 215
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 215

```
cactatatgt attcctcagt ctccactata aacccacaca cattattaaa ataccgtata     60
tgtattggct gcatgaataa tactacgtgt agcccatgca aagttaacac tcaccatccc    120
caaagaacc cacacattat taaataccg tatataaacc cacgtgtaag cccaaac          177
```

<210> SEQ ID NO 216
<211> LENGTH: 177
<212> TYPE: DNA
<213> ORGANISM: Artificial Sequence

```
<220> FEATURE:
<223> OTHER INFORMATION: synthetic 160nt promoter with spacer

<400> SEQUENCE: 216
actacgtgta agcccatgca aagttaacac tcacgacccc atgcaaagtt aacactcacg      60
accccaatct cacgacccca ttcctcagtc tccactatat aaacccacgt gtaagcccat     120
tcccacgtgt agcccattcc tcagtctcca ctatataaac ccacgtgtag cccaaac        177

<210> SEQ ID NO 217
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 217
aagaacccac acattattaa aataccgtat ataaacccac acattattaa aataccgtat      60
atgtattcct cagtctccac tatataaacc caccatcccc atgcaaagtt aacactcacg     120
accccattcc tcagtctcca ctatataaac ccacgtgtaa gcccaatctc accaaac        177

<210> SEQ ID NO 218
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 218
acattattaa aatactacgt gtaagcccaa tctcaccaaa agaacccacg tgtaagccca      60
atctcacgac cccatgcaaa gttaacactc accaaaagaa cccacgtgta agcccaaaag    120
aacccacaca ttattaaaat accgtatata aacccaccat ccccattccc accaaac        177

<210> SEQ ID NO 219
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 219
ctcacgaccc cattcccacg tgtagcccat gcaaagttaa cactcaccat ccccaatctc      60
accaaaagaa cccaccatcc caaaagaac ccacacatta ttaaaatact acgtgtaagc     120
ccaaaagaac ccacacatta ttaaaatacc gtatataaac ccacgtgtag cccaaac        177

<210> SEQ ID NO 220
<211> LENGTH: 177
<212> TYPE: DNA
<213> ORGANISM: Artificial Sequence
<220> FEATURE:
<223> OTHER INFORMATION: synthetic 160nt promoter with spacer

<400> SEQUENCE: 220
tccccatgca aagttaacac tcaccatccc caatctcacc aaaagaaccc acacattatt      60
aaaataccgt atataaaccc acacattatt aaaatactac gtgtaagccc atgcaaagtt    120
aacactcacg accccattcc tcagtctcca ctatataaac ccacgtgtag cccaaac       177

<210> SEQ ID NO 221
<211> LENGTH: 234
<212> TYPE: DNA
```

<213> ORGANISM: Artificial Sequence
<220> FEATURE:
<223> OTHER INFORMATION: ProPer 160nt promoter with spacer and enhancer

<400> SEQUENCE: 221

```
aaggcatcgc tgaaagagca cattattaaa ataccgtata tgtattggct gcatttgcat      60
gaataatact acgtgtaagc ccaaaagaac ccacgtgtag cccatgcaaa gttaacactc     120
aggaccccat tcctcagtct ccactatata aacccaccat cggggttctc accaaaccca     180
ccacacaact cacaactcac tctcacacct taaagaacca atcaccacca aaaa           234
```

<210> SEQ ID NO 222
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 222

```
gaggcgaggg tctgtcgaca cattattaaa ataccgtata tgtattggct gcatttgcat      60
gaataatact acgtgtaagc ccaaaagaac ccacgtgtag cccatgcaaa gttaacactc     120
actaccccat tcctcagtct ccactatata aacccaccat cctctctctc accaaaccca     180
ccacacaact cacaactcac tctcacacct taaagaacca atcaccacca aaaa           234
```

<210> SEQ ID NO 223
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 223

```
ctggtgatgc cagggttgca cattattaaa ataccgtata tgtattggct gcatttgcat      60
gaataatact acgtgtaagc ccaaaagaac ccacgtgtag cccatgcaaa gttaacactc     120
aaaaccccat tcctcagtct ccactatata aacccaccat caacattctc accaaaccca     180
ccacacaact cacaactcac tctcacacct taaagaacca atcaccacca aaaa           234
```

<210> SEQ ID NO 224
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 224

```
cgagtgggaa ccgttcctca cattattaaa ataccgtata tgtattggct gcatttgcat      60
gaataatact acgtgtaagc ccaaaagaac ccacgtgtag cccatgcaaa gttaacactc     120
ataaccccat tcctcagtct ccactatata aacccaccat cagccctctc accaaaccca     180
ccacacaact cacaactcac tctcacacct taaagaacca atcaccacca aaaa           234
```

<210> SEQ ID NO 225
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 225

```
attctacggt tccctcaaca cattattaaa ataccgtata tgtattggct gcatttgcat      60
```

```
gaataatact acgtgtaagc ccaaaagaac ccacgtgtag cccatgcaaa gttaacactc    120
accaccccat tcctcagtct ccactatata aacccaccat ctctcttctc accaaaccca    180
ccacacaact cacaactcac tctcacacct taaagaacca atcaccacca aaaa          234

<210> SEQ ID NO 226
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 226
agatccgcgg cacaaagcca cattattaaa ataccgtata tgtattggct gcatttgcat    60
gaataatact acgtgtaagc ccaaaagaac ccacgtgtag cccatgcaaa gttaacactc    120
agcaccccat tcctcagtct ccactatata aacccaccat cggcaatctc accaaaccca    180
ccacacaact cacaactcac tctcacacct taaagaacca atcaccacca aaaa          234

<210> SEQ ID NO 227
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 227
agatacgcac ccaccctaca cattattaaa ataccgtata tgtattggct gcatttgcat    60
gaataatact acgtgtaagc ccaaaagaac ccacgtgtag cccatgcaaa gttaacactc    120
attaccccat tcctcagtct ccactatata aacccaccat ctgacttctc accaaaccca    180
ccacacaact cacaactcac tctcacacct taaagaacca atcaccacca aaaa          234

<210> SEQ ID NO 228
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 228
gacggtgccc tgcgtggcca cattattaaa ataccgtata tgtattggct gcatttgcat    60
gaataatact acgtgtaagc ccaaaagaac ccacgtgtag cccatgcaaa gttaacactc    120
aacaccccat tcctcagtct ccactatata aacccaccat cctagatctc accaaaccca    180
ccacacaact cacaactcac tctcacacct taaagaacca atcaccacca aaaa          234

<210> SEQ ID NO 229
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 229
cctgggagag gtctcttaca cattattaaa ataccgtata tgtattggct gcatttgcat    60
gaataatact acgtgtaagc ccaaaagaac ccacgtgtag cccatgcaaa gttaacactc    120
aaaaccccat tcctcagtct ccactatata aacccaccat ctgtaatctc accaaaccca    180
ccacacaact cacaactcac tctcacacct taaagaacca atcaccacca aaaa          234
```

<210> SEQ ID NO 230
<211> LENGTH: 234
<212> TYPE: DNA
<213> ORGANISM: Artificial Sequence
<220> FEATURE:
<223> OTHER INFORMATION: ProPer 160nt promoter with spacer and enhancer

<400> SEQUENCE: 230

```
gcagctttcc gttacgggca cattattaaa ataccgtata tgtattggct gcatttgcat        60
gaataatact acgtgtaagc ccaaaagaac ccacgtgtag cccatgcaaa gttaacactc       120
accaccccat tcctcagtct ccactatata aacccaccat ccttcctctc accaaaccca       180
ccacacaact cacaactcac tctcacacct taaagaacca atcaccacca aaaa            234
```

<210> SEQ ID NO 231
<211> LENGTH: 220
<212> TYPE: DNA
<213> ORGANISM: Artificial Sequence
<220> FEATURE:
<223> OTHER INFORMATION: synthetic 240nt promoter with spacer

<400> SEQUENCE: 231

```
ccaaattaaa gcaagagagg ccaagtaaaa ttagtaaaat actacgtgta gcccattccc        60
accatcccca atctcaccat ccccattcct cagtctccac tatatgtatt gtattcccac       120
gtgtagccca tgcaaagtta acactcacga ccccaaatta aaatactcgg catattgtat       180
tcctcagtct ccactatata aacccacgtg tagcccaaac                             220
```

<210> SEQ ID NO 232
<211> LENGTH: 248
<212> TYPE: DNA
<213> ORGANISM: Artificial Sequence
<220> FEATURE:
<223> OTHER INFORMATION: synthetic 240nt promoter with spacer

<400> SEQUENCE: 232

```
gtgtaagccc aaattaaaat accgtatata aacccacaca ttattaaagc aagagaggcc        60
aaaatactac gtgtagccca aaattaaaat accgtatata aacccacgtg tagcccaatc       120
tcacgacccc atgcaaagtt aacactcacg accccaaaag aacccacaca ttattaaagc       180
aagagaggcc aaatgtattg tattcctcag tctccactat ataaacccac gtgtaagata       240
atccaaac                                                                248
```

<210> SEQ ID NO 233
<211> LENGTH: 275
<212> TYPE: DNA
<213> ORGANISM: Artificial Sequence
<220> FEATURE:
<223> OTHER INFORMATION: synthetic 240nt promoter with spacer

<400> SEQUENCE: 233

```
gcatttgcat gaataatcca aaataccgta tatgtacact tgtcattgcc aagtaaaatt        60
aaaattaaag caagagaggc caaattaaaa tactacgtgt aagcccattc ccacgtgtag       120
cccatgcaaa gttaacactt gtcattgcca aattaaaata ctcggcatat tggctgcatg       180
aataatacta cgtgtagccc aatctcacga ccccaaaata ctacgtgtaa gataataccg       240
tatataaacc cacgtgtagc ccaatctcac caaac                                  275
```

<210> SEQ ID NO 234
<211> LENGTH: 282

```
<212> TYPE: DNA
<213> ORGANISM: Artificial Sequence
<220> FEATURE:
<223> OTHER INFORMATION: synthetic 240nt promoter with spacer

<400> SEQUENCE: 234
cacacattat taaagcaaga gaggccaaaa gaacccacac attattaaag caagagaggc    60
caagtaagat aatccaaatt aaaatactac gtgtagccca ttcccacgtg taagcccaat   120
ctcacgaccc cattcctcag tctccactat ataaacccac catccccatg caaagttaac   180
acttgtcatt gccaagtaaa attagtaaaa tactacgtgt aagcccattc ccacacatta   240
ttaaaatacc gtatataaac ccacgtgtaa gataatccaa ac                      282

<210> SEQ ID NO 235
<211> LENGTH: 302
<212> TYPE: DNA
<213> ORGANISM: Artificial Sequence
<220> FEATURE:
<223> OTHER INFORMATION: synthetic 240nt promoter with spacer

<400> SEQUENCE: 235
accaaaagaa cccacgtgta agcccaaaag aacccacgtg taagcccaaa tgtattccca    60
cacattatta aagcaagaga ggccaagtaa aatactacgt gtagcccatg caaagttaac   120
actcaccaaa tgtattccca ccaaattagt aaaatactac gtgtaagccc attcccacca   180
aaagaaccca cgtgtagccc atgcaaagtt aacacttgtc attgccaagt aaaatactcg   240
gcatattggc tgcatgaata ataccgtata taaacccacg tgtaagccca atctcaccaa   300
ac                                                                  302

<210> SEQ ID NO 236
<211> LENGTH: 324
<212> TYPE: DNA
<213> ORGANISM: Artificial Sequence
<220> FEATURE:
<223> OTHER INFORMATION: synthetic 240nt promoter with spacer

<400> SEQUENCE: 236
tcagtctcca ctatataaac ccacacatta ttaaagcaag agaggccaaa atactacgtg    60
taagcccatt cccacgtgta gcccaaatta gtaagcccat gcaaagttaa cactcacgac   120
cccattccca cgtgtaagat aatccaaatt agtaaaatac tcggcatatt gtattggctg   180
catgaataat ccaaaatact cggcatattg tattgtattc ccaccaaaat actcggcata   240
ttgtattgta ttcctcagtc tccactatat gtattgtatt cctcagtctc cactatataa   300
acccacgtgt aagataatcc aaac                                          324

<210> SEQ ID NO 237
<211> LENGTH: 343
<212> TYPE: DNA
<213> ORGANISM: Artificial Sequence
<220> FEATURE:
<223> OTHER INFORMATION: synthetic 240nt promoter with spacer

<400> SEQUENCE: 237
tgaataatcc aaaagaaccc acgtgtaaga taatactcgg catattgtat tggctgcatg    60
aataatccaa aagaacccac acattattaa agcaagagag gccaaaatac tacgtgtagc   120
ccaaatgtac acttgtcatt gccaaaagaa cccacgtgta gcccattccc acacattatt   180
aaagcaagag aggccaagta agcccatgca aagttaacac tcacgacccc attcccacgt   240
```

```
gtagcccaaa ttagtaagat aatccaaaat accgtatatg tacacttgtc attgccaagt      300
aagataatac cgtatataaa cccacgtgta agataatcca aac                        343

<210> SEQ ID NO 238
<211> LENGTH: 344
<212> TYPE: DNA
<213> ORGANISM: Artificial Sequence
<220> FEATURE:
<223> OTHER INFORMATION: synthetic 240nt promoter with spacer

<400> SEQUENCE: 238
tttgcatgaa taatactcgg catattgtat tggctgcatt tgcatttgca tttgcatgaa       60
taatccaaaa gaacccacca aaattaaaat taaagcaaga gaggccaagt aagataatac      120
tcggcatatt gtattggctg catgaataat actcggcata ttgtattggc tgcatgaata      180
atccaaaata ctacgtgtag cccattcctc agtctccact atatgtacac tcacgacccc      240
attcctcagt ctccactata taaacccacg tgtaagccca tgcaaagtta acactcacga      300
ccccaaaata ccgtatataa acccacgtgt aagataatcc aaac                      344

<210> SEQ ID NO 239
<211> LENGTH: 362
<212> TYPE: DNA
<213> ORGANISM: Artificial Sequence
<220> FEATURE:
<223> OTHER INFORMATION: synthetic 240nt promoter with spacer

<400> SEQUENCE: 239
taccgtatat aaacccacac attattaaag caagagaggc caagtaagat aatccaaatg       60
tacacttgtc attgccaagt aaaattagta aatactcgg catattggct gcatttgcat      120
gaataatacc gtatataaac ccaccaaaat taaaataccg tatataaacc cacacattat      180
taaaattaaa atactacgtg tagcccatgc aaagttaaca cttgtcattg ccaaaagaac      240
ccacgtgtaa gccatgcaa agttaacact tgtcattgcc aaaagaaccc acgtgtaagc      300
ccattcccac acattattaa ataccgtat ataaacccac gtgtagccca atctcaccaa      360
ac                                                                    362

<210> SEQ ID NO 240
<211> LENGTH: 363
<212> TYPE: DNA
<213> ORGANISM: Artificial Sequence
<220> FEATURE:
<223> OTHER INFORMATION: synthetic 240nt promoter with spacer

<400> SEQUENCE: 240
aagcaagaga ggccaagtaa gataatccaa atgtattccc acgtgtagcc catgcaaagt       60
taacacttgt cattgccaag taagcccaat ctcaccatcc ccattcctca gtctccacta      120
tatgtacact tgtcattgcc aagtaaaatt aaaataccgt atataaaccc accatcccca      180
tgcaaagtta acactcacga ccccaaaatt aaagcaagag aggccaagta aaatactacg      240
tgtagcccaa tctcaccaaa tgtattccca ccatcccat tcccacgtgt agcccatgca      300
aagttaacac tcaccaaatt agtaaaatac cgtatataaa cccacgtgta agataatcca      360
aac                                                                   363

<210> SEQ ID NO 241
<211> LENGTH: 368
<212> TYPE: DNA
<213> ORGANISM: Artificial Sequence
```

```
<220> FEATURE:
<223> OTHER INFORMATION: synthetic 240nt promoter with spacer

<400> SEQUENCE: 241
cacattatta aaattaaagc aagagaggcc aagtaagccc aaatgtacac ttgtcattgc      60
caaattaaaa tactcggcat attgtattgt attcccacac attattaaaa tactcggcat     120
attgtattgg ctgcatttgc atttgcatga ataatactac gtgtaagata atccaaaata     180
ctacgtgtag cccatgcaaa gttaacactc accaaaagaa cccacgtgta agcccatgca     240
aagttaacac tcaccaaatg tattcccaca cattattaaa attaaatta gtaaaatacc      300 gtatatgtat tcccacgtgt aagcccattc ctcagtctcc actatataaa cccacgtgta     360
gcccaaac                                                              368

<210> SEQ ID NO 242
<211> LENGTH: 369
<212> TYPE: DNA
<213> ORGANISM: Artificial Sequence
<220> FEATURE:
<223> OTHER INFORMATION: synthetic 240nt promoter with spacer

<400> SEQUENCE: 242
agcccaatct caccaaaaga acccacgtgt agcccatgca aagttaacac ttgtcattgc      60
caaaagaacc cacgtgtaag cccattccca cacattatta aagcaagaga ggccaagtaa     120
gcccaaatgt acacttgtca ttgccaagta aaatactacg tgtagcccat gcaaagttaa     180
cactcaccat ccccaatctc acgacccat tcccacgtgt aagataatcc aaattaaagc      240
aagagaggcc aaatgtattc ctcagtctcc actatataaa cccaccatcc ccatgcaaag     300
ttaacacttg tcattgccaa attagtaaga taataccgta tataaaccca cgtgtaagat     360
aatccaaac                                                             369

<210> SEQ ID NO 243
<211> LENGTH: 379
<212> TYPE: DNA
<213> ORGANISM: Artificial Sequence
<220> FEATURE:
<223> OTHER INFORMATION: synthetic 240nt promoter with spacer

<400> SEQUENCE: 243
aataatactc ggcatattgg ctgcatgaat aatactcggc atattgtatt gtattggctg      60
catttgcatg aataatactc ggcatattgt attgtattgt attcccacac attattaaag     120
caagagaggc caagtaaaat actcggcata ttggctgcat gaataatcca aattaaagca     180
agagaggcca aaatactacg tgtagcccaa attaaaatac tcggcatatt gtattcccac     240
caaatgtatt cctcagtctc cactatatgt attgtattcc tcagtctcca ctatataaac     300
ccacgtgtag cccatgcaaa gttaacactt gtcattgcca agtaaaatac cgtatataaa     360
cccacgtgta agcccaaac                                                  379

<210> SEQ ID NO 244
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 244
cattcccacc atccccaaaa gaacccacac attattaaag caagagaggc caaaatacta      60
```

```
cgtgtagccc attcctcagt ctccactata tgtattggct gcatttgcat ttgcatttgc    120
atttgcattt gcatttgcat ttgcatgaat aataccgtat ataaacccac caaaagaacc    180
cacacattat taaaatactc ggcatattgt attcccacgt gtagcccaat ctcaccaaat    240
gtattggctg catgaataat actacgtgta agcccaatct cacgacccca atctcaccat    300
ccccatgcaa agttaacact tgtcattgcc aaatgtattc ccacgtgtaa gataataccg    360
tatataaacc cacgtgtagc ccaaac                                         386
```

<210> SEQ ID NO 245
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 245

```
attaaagcaa gagaggccaa gtaaaatact acgtgtagcc caatctcacc atccccattc     60
ctcagtctcc actatatgta ttcccacaca ttattaaagc aagagaggcc aagtaaaata    120
ccgtatataa acccaccatc cccattccca cgtgtagccc atgcaaagtt aacacttgtc    180
attgccaaat gtacactcac catccccaaa ttagtaaaat accgtatata aacccaccaa    240
atgtacactc acgaccccat tcccaccatc cccatgcaaa gttaacactc accatcccca    300
ttcccaccaa aagaacccac gtgtagccca atctcacgac ccattcctc agtctccact     360 atataaaccc acgtgtaagc ccaaac                                         386
```

<210> SEQ ID NO 246
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 246

```
ctcagtctcc actatataaa cccacacatt attaaagcaa gagaggccaa gtaaaatact     60
acgtgtaagc ccaaatgtac actcaccaaa agaacccacc atcccaaaa gaacccacgt    120 gtagcccatg caaagttaac actcacgacc ccatgcaaag ttaacactca ccatcccat     180 tcctcagtct ccactatatg tacacttgtc attgccaagt aagcccaatc tcacgacccc    240
aatctcacga ccccaaatgt attcctcagt ctccactata tgtattgtat tcccaccaaa    300
ttagtaaaat actacgtgta gcccaatctc accatcccca ttcctcagtc tccactatat    360
aaacccacgt gtaagataat ccaaac                                         386
```

<210> SEQ ID NO 247
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 247

```
ttgtattcct cagtctccac tatataaacc cacacattat taaagcaaga gaggccaaaa     60
tactacgtgt agcccaaatg tattcccacg tgtagcccaa aagaacccac gtgtaagccc    120
attcccacgt gtaagcccat tcccacacat tattaaagca agagaggcca agtaaaatac    180
cgtatatgta ttcctcagtc tccactatat gtacacttgt cattgccaag taaaatactc    240
ggcatattgt attgtattcc tcagtctcca ctatataaac ccaccatccc caaaattagt    300
```

```
aagcccatgc aaagttaaca cttgtcattg ccaagtaaga taatccaaat taaaataccg    360
tatataaacc cacgtgtagc ccaaac                                         386

<210> SEQ ID NO 248
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 248
gataatactc ggcatattgg ctgcatgaat aatccaaaat tagtaaaatt aaagcaagag     60
aggccaagta aaatactacg tgtaagataa tactacgtgt agcccattcc tcagtctcca   120
ctatataaac ccacgtgtag cccatgcaaa gttaacactc acgacccaa atgtacactt    180 gtcattgcca agtaaaatta gtaaaattag taagataatc caaaatacta cgtgtagccc   240
aatctcacca tccccattcc tcagtctcca ctatataaac ccaccatccc cattcccaca   300
cattattaaa attagtaaaa taccgtatat aaacccacac attattaaaa taccgtatat   360
aaacccacgt gtaagataat ccaaac                                         386

<210> SEQ ID NO 249
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 249
attaaagcaa gagaggccaa gtaaaatact acgtgtaaga taatactacg tgtagcccaa     60
tctcacgacc ccaaaatact cggcatattg gctgcatgaa taatactacg tgtagcccaa   120
atgtattgta ttcctcagtc tccactatat gtattcctca gtctccacta tataaaccca   180
cgtgtagccc atgcaaagtt aacactcacc atccccaatc tcacgacccc attcctcagt   240
ctccactata taaacccaca cattattaaa ataccgtata taaacccacg tgtaagccca   300
tgcaaagtta acactcacca tccccaaatg tacacttgtc attgccaaat taaaataccg   360
tatataaacc cacgtgtagc ccaaac                                         386

<210> SEQ ID NO 250
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 250
taaacccaca cattattaaa gcaagagagg ccaagtaaaa ttaaaatact acgtgtaagc     60
ccaatctcac gacccaatc tcaccaaatg tacacttgtc attgccaagt aaaatactcg    120
gcatattggc tgcatttgca tgaataatac tacgtgtagc ccattcctca gtctccacta   180
tataaaccca cgtgtagccc atgcaaagtt aacacttgtc attgccaagt aagataaatac   240 tacgtgtaag ataatccaaa agaacccacg tgtagcccat gcaaagttaa cactcaccaa   300
atgtattcct cagtctccac tatataaacc cacacattat taaaataccg tatataaacc   360
caccaaatta gtaagataat ccaaac                                         386

<210> SEQ ID NO 251
```

```
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 251
ccactatata aacccacaca ttattaaagc aagagaggcc aaattagtaa aattaaagca      60
agagaggcca aaatactacg tgtaagccca aatgtacact caccaaaaga acccaccaaa     120
agaacccacg tgtaagataa tactacgtgt aagcccaatc tcaccatccc catgcaaagt     180
taacactcac catccccatt cccacgtgta gcccaatctc acgacccat gcaaagttaa      240 cactcacgac cccattcctc agtctccact atataaaccc acgtgtaagc ccatgcaaag     300
ttaacactca cgaccccaat ctcaccaaat gtattgtatt cctcagtctc cactatataa     360
acccaccatc cccattccca ccaaac                                          386

<210> SEQ ID NO 252
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 252
tagcccaatc tcaccaaaat accgtatatg tattcctcag tctccactat atgtattggc      60
tgcatgaata atccaaaatt aaagcaagag aggccaagta aaatactacg tgtaagccca     120
atctcacgac cccattccca ccaaaagaac ccacgtgtag cccaatctca ccaaaattag     180
taagataatc caaaatacta cgtgtaagcc catgcaaagt taacacttgt cattgccaaa     240
tgtacacttg tcattgccaa attaaagcaa gagaggccaa gtaagcccat gcaaagttaa     300
cacttgtcat tgccaaaata ctacgtgtaa gcccattcct cagtctccac tatataaacc     360
cacgtgtaag cccaatctca ccaaac                                          386

<210> SEQ ID NO 253
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 253
attattaaag caagagaggc caagtaaaat actacgtgta gcccattccc acgtgtagcc      60
catgcaaagt taacactcac catccccatg caaagttaac acttgtcatt gccaaattaa     120
aatactcggc atattggctg catttgcatt tgcatttgca tttgcatttg catgaataat     180
ccaaaagaac ccaccatccc cattcctcag tctccactat atgtacactc acgacccaa     240 tctcaccatc cccatgcaaa gttaacactc accaaaagaa cccacgtgta agcccaatct     300
caccaaatta agcaagaga ggccaaatta aaatactacg tgtaagataa taccgtatat      360
aaacccacgt gtaagataat ccaaac                                          386

<210> SEQ ID NO 254
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 254
```

```
acccattcc caccatcccc aatctcacga ccccatgcaa agttaacact tgtcattgcc      60
aagtaagccc attcctcagt ctccactata tgtacacttg tcattgccaa atgtattccc     120
accatcccca ttcctcagtc tccactatat aaacccacac attattaaag caagagaggc    180
caaattagta aaattagtaa gcccattccc accaaaatac cgtatatgta ttgtattgta    240
ttcccacgtg taagataata ctacgtgtag cccattccca cgtgtaagcc catgcaaagt    300
taacactcac catccccaat ctcacgaccc caaattagta agataatacc gtatataaac    360
ccacgtgtag cccaatctca ccaaac                                         386

<210> SEQ ID NO 255
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 255
gtaaaattaa agcaagagag gccaaaatac tacgtgtagc ccaatctcac gaccccaaat     60
taaaataccg tatatgtaca ctcacgaccc caatctcacg accccatgca agttaacac    120 tcacgacccc attcccacgt gtaagcccat gcaaagttaa cactcaccat ccccattccc   180
accaaatgta ttcctcagtc tccactatat aaacccacac attattaaaa tactacgtgt   240
aagcccaatc tcacgacccc atgcaaagtt aacacttgtc attgccaagt aagcccaaat    300
taaaataccg tatatgtatt ggctgcatga ataatccaaa attagtaaaa taccgtatat   360
aaacccacgt gtaagataat ccaaac                                         386

<210> SEQ ID NO 256
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 256
attaaaatta aagcaagaga ggccaagtaa gataatacta cgtgtagccc attcccacca     60
tccccaatct caccaaaatt aaaattagta aaatactcgg catattgtat tgtattggct   120
gcatttgcat ttgcatgaat aatactcggc atattgtatt cctcagtctc cactatataa    180
acccacacat tattaaagca agagaggcca agtaagccca tgcaaagtta acacttgtca    240
ttgccaaaat accgtatata aacccacgtg tagcccaatc tcacgacccc aaaataccgt   300
atataaaccc acgtgtagcc catgcaaagt taacacttgt cattgccaag taaaataccg    360
tatataaacc cacgtgtagc ccaaac                                         386

<210> SEQ ID NO 257
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 257
ttggctgcat ttgcatgaat aatccaaatt aaagcaagag aggccaaatt aaaatactac     60
gtgtagccca tgcaaagtta acactcacca tccccaatct cacgacccca ttcctcagtc    120
tccactatat aaacccacgt gtagcccaat ctcaccatcc ccattcctca gtctccacta   180
```

```
tataaaccca ccatccccaa tctcaccatc cccaatctca ccatccccat gcaaagttaa    240
cactcaccat ccccaaaata ctcggcatat tgtattcctc agtctccact atatgtacac    300
ttgtcattgc caagtaagcc caaatgtatt ggctgcattt gcatgaataa taccgtatat    360
aaacccacgt gtaagataat ccaaac                                        386
```

```
<210> SEQ ID NO 258
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 258
agagaggcca agtaaaatac cgtatatgta ttcccacaca ttattaaaat actacgtgta     60
gcccaaaaga acccacacat tattaaagca agagaggcca agtaagccca aaatactacg    120
tgtagcccat gcaaagttaa cacttgtcat tgccaagtaa gcccattccc acacattatt    180
aaaattaaag caagagaggc caaatgtaca cttgtcattg ccaaatgtat tgtattcctc    240
agtctccact atataaaccc acgtgtagcc catgcaaagt taacacttgt cattgccaag    300
taaaatactc ggcatattgt attcctcagt ctccactata tgtattcctc agtctccact    360
atataaaccc acgtgtaagc ccaaac                                        386
```

```
<210> SEQ ID NO 259
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 259
tgcaaagtta acacttgtca ttgccaagta agataatcca aattagtaag cccaaatgta     60
cactcaccat ccccaatctc accaaatgta ttcccaccat ccccatgcaa agttaacact    120
cacgacccca atctcacgac cccaaaatta agcaagaga ggccaaaaga acccacacat    180
tattaaagca agagaggcca agtaaaatta aaatactcgg catattgtat tggctgcatg    240
aataatacta cgtgtagccc aatctcacca aaagaaccca cgtgtaagcc caaaagaacc    300
cacgtgtaag cccatgcaaa gttaacactc accatcccca ttcctcagtc tccactatat    360
aaacccacgt gtaagataat ccaaac                                        386
```

```
<210> SEQ ID NO 260
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 260
attaaaatac tcggcatatt ggctgcatga ataataccgt atataaaccc acacattatt     60
aaagcaagag aggccaaaat actcggcata ttgtattgta ttggctgcat gaataatcca    120
aaataccgta tatgtacact tgtcattgcc aagtaaaatt agtaagataa tactacgtgt    180
agcccaatct caccaaaatt agtaagataa tactcggcat attgtattcc cacgtgtaag    240
cccaatctca ccatccccat tcccaccatc cccaaatgta cactcaccaa agaacccac    300 gtgtaagccc atgcaaagtt aacacttgtc attgccaaat aaaataccg tatataaacc    360 cacgtgtaag cccaatctca ccaaac                                        386
```

<210> SEQ ID NO 261
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 261

```
attgccaagt aagataatcc aaatgtattc ccaccaaaat actcggcata ttggctgcat      60
gaataatacc gtatataaac ccacacatta ttaaagcaag agaggccaag taaaatactc     120
ggcatattgg ctgcatttgc atgaataatc caaattaaag caagagaggc caaattagta     180
aaatactacg tgtaagccca aaattaaaat actcggcata ttgtattgta ttgtattggc     240
tgcatttgca tgaataatcc aaatgtacac ttgtcattgc caaaagaacc cacgtgtagc     300
ccatgcaaag ttaacacttg tcattgccaa atgtattgta ttcctcagtc tccactatat     360
aaacccacca aagaaccca ccaaac                                           386
```

<210> SEQ ID NO 262
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 262

```
acattattaa aattaaagca agagaggcca aatgtacact tgtcattgcc aagtaagata      60
atccaaatta gtaagataat ccaaaagaac ccacacatta ttaaagcaag agaggccaaa     120
ttaaaatact acgtgtaagc ccaaattagt aaaattaaaa ttagtaagat aatccaaatt     180
aaaatactac gtgtagccca tgcaaagtta acactcacga ccccattcct cagtctccac     240
tatataaacc caccaaaata ctacgtgtaa gcccattcct cagtctccac tatataaacc     300
cacgtgtagc ccatgcaaag ttaacacttg tcattgccaa atgtattcct cagtctccac     360
tatataaacc cacgtgtagc ccaaac                                          386
```

<210> SEQ ID NO 263
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 263

```
acattattaa agcaagagag gccaaattaa aattagtaaa atactacgtg taagataata      60
ctcggcatat tgtattcctc agtctccact atataaaccc acgtgtaagc ccatgcaaag     120
ttaacactca cgaccccatt cctcagtctc cactatataa acccacgtgt agcccatgca     180
aagttaacac tcacgacccc atgcaaagtt aacacttgtc attgccaagt aagataatac     240
cgtatatgta ttgtattccc acgtgtagcc caatctcacg accccaaaag aacccacaca     300
ttattaaagc aagagaggcc aaaatactac gtgtagccca ttcctcagtc tccactatat     360
aaacccacgt gtaagataat ccaaac                                          386
```

<210> SEQ ID NO 264
<211> LENGTH: 386
<212> TYPE: DNA
<213> ORGANISM: Artificial Sequence
<220> FEATURE:

<223> OTHER INFORMATION: synthetic 240nt promoter with spacer

<400> SEQUENCE: 264

| ggcatattgg ctgcatgaat atccaaatt aaagcaagag aggccaagta aaattagtaa | 60 |
| aatactacgt gtaagataat ccaaaattag taagcccaaa atactcggca tattggctgc | 120 |
| atttgcatga ataatccaaa tgtattgtat tgtattcctc agtctccact atatgtacac | 180 |
| tcacgacccc aaattaaaat actacgtgta agataatcca aattagtaag cccaaaagaa | 240 |
| cccacgtgta gcccaaaaga acccaccatc cccaaattag taagcccatg caaagttaac | 300 |
| acttgtcatt gccaagtaaa ataccgtata tgtattgtat tgtattcctc agtctccact | 360 |
| atataaaccc acgtgtaagc ccaaac | 386 |

<210> SEQ ID NO 265
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 265

| gaccccaatc tcaccatccc catgcaaagt taacacttgt cattgccaag taagcccaaa | 60 |
| agaacccacc aaatgtattg tattcccaca cattattaaa gcaagagagg ccaaatgtat | 120 |
| tcccaccaaa agaacccacc atccccaatc tcacgacccc aatctcacca aattagtaag | 180 |
| ataatactac gtgtaagccc attcctcagt ctccactata taaacccacc atccccaatc | 240 |
| tcacgacccc attcctcagt ctccactata taaacccaca cattattaaa ataccgtata | 300 |
| taaacccacg tgtagcccat gcaaagttaa cactcaccat ccccattcct cagtctccac | 360 |
| tatataaacc cacgtgtagc ccaaac | 386 |

<210> SEQ ID NO 266
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 266

| cccatgcaaa gttaacactc acgaccccaa tctcaccatc cccaatctca ccaaaagaac | 60 |
| ccaccatccc catgcaaagt taacactcac gaccccattc cacacatta ttaaagcaag | 120 |
| agaggccaaa ttagtaagat aataccgtat atgtacactc accaaattaa gcaagagag | 180 |
| gccaagtaag ataatactac gtgtagccca aaattaaagc aagagaggcc aagtaagata | 240 |
| atccaaatta gtaaaatact acgtgtagcc caatctcacc atcccaaaa gaacccacgt | 300 |
| gtaagcccat gcaaagttaa cacttgtcat tgccaaaatt agtaagataa taccgtatat | 360 |
| aaacccacgt gtaagataat ccaaac | 386 |

<210> SEQ ID NO 267
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 267

| ccacgtgtaa gataatactc ggcatattgg ctgcatttgc atttgcattt gcatttgcat | 60 |
| gaataatacc gtatatgtat tcccacgtgt aagataatcc aaattagtaa aatactcggc | 120 |

```
atattggctg catgaataat actacgtgta agataatacc gtatataaac ccacacatta      180
ttaaagcaag agaggccaag taagataatc caaattagta aaatactacg tgtaagccca      240
ttcccacgtg tagcccatgc aaagttaaca ctcaccaaaa tactcggcat attggctgca      300
tgaataatcc aaattagtaa gcccaatctc accatcccca ttcctcagtc tccactatat      360
aaacccacgt gtaagataat ccaaac                                           386

<210> SEQ ID NO 268
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 268
tccactatat gtacactcac gaccccaaat gtacacttgt cattgccaaa tgtattggct      60
gcatgaataa tccaaatgta ttcccacaca ttattaaagc aagagaggcc aagtaagata     120
ataccgtata tgtattggct gcatgaataa tccaaaatta gtaaaattag taagataata     180
ctacgtgtag cccattcctc agtctccact atataaaccc acgtgtagcc catgcaaagt     240
taacactcac gaccccaatc tcacgacccc aaaagaaccc accaaaagaa cccacacatt     300
attaaagcaa gagaggccaa atgtacactc acgaccccaa attagtaaaa taccgtatat     360
aaacccacgt gtaagataat ccaaac                                           386

<210> SEQ ID NO 269
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 269
ttaaaattaa agcaagagag gccaaatgta cactcacgac cccattcctc agtctccact     60
atataaaccc accatcccca tgcaaagtta acactcacca aattagtaag cccatgcaaa     120
gttaacactt gtcattgcca agtaaaatta gtaaaattag taaatactac gtgtagccc     180 aaaattagta aaattagtaa gcccattccc accaaaatac tacgtgtagc ccaaaagaac     240
ccacacatta ttaaaatacc gtatataaac ccacgtgtag cccatgcaaa gttaacactt     300
gtcattgcca agtaagataa tccaaaatta aagcaagaga ggccaagtaa gataataccg     360
tatataaacc cacgtgtagc ccaaac                                           386

<210> SEQ ID NO 270
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 270
caaaagaacc cacacattat taaagcaaga gaggccaaaa tactacgtgt agcccattcc      60
cacacattat taaagcaaga gaggccaagt aagataatcc aaattagtaa gcccaaaatt     120
aaaatactcg gcatattgta ttgtattccc acgtgtagcc catgcaaagt taacacttgt     180
cattgccaaa atactcggca tattgtattc ccacacatta ttaaagcaag agaggccaag     240
taagcccatg caaagttaac acttgtcatt gccaagtaaa attagtaagc ccaatctcac     300
```

```
gaccccaatc tcacgacccc aaattaaaat actcggcata ttgtattcct cagtctccac    360
tatataaacc cacgtgtagc ccaaac                                         386

<210> SEQ ID NO 271
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 271
gtacactcac caaaagaacc cacacattat taaagcaaga gaggccaagt aaaattaaaa     60
ttagtaagcc catgcaaagt taacacttgt cattgccaaa attagtaaaa ttaaaatacc    120
gtatataaac ccacgtgtaa gataatacta cgtgtagccc aatctcacga ccccaatctc    180
acgaccccat tcccacacat tattaaagca agagaggcca agtaagccca tgcaaagtta    240
acacttgtca ttgccaagta agataatcca aagaaccca cgtgtagccc atgcaaagtt     300
aacacttgtc attgccaagt aaaatactac gtgtagccca ttcctcagtc tccactatat    360
aaacccacgt gtaagataat ccaaac                                         386

<210> SEQ ID NO 272
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 272
tcagtctcca ctatataaac ccacacatta ttaaagcaag agaggccaag taagataata     60
ctacgtgtag cccatgcaaa gttaacactc accatcccca tgcaaagtta acacttgtca    120
ttgccaaaag aacccacgtg taagcccatg caaagttaac actcacgacc ccaaattagt    180
aagataatcc aaatgtacac tcaccatccc caaaattagt aaaattagta aaatactacg    240
tgtagcccat tcctcagtct ccactatata aacccaccaa atgtattcct cagtctccac    300
tatatgtatt cccaccaaaa taccgtatat aaacccacac attattaaaa taccgtatat    360
aaacccacca aaagaaccca ccaaac                                         386

<210> SEQ ID NO 273
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 273
tccactatat aaacccacac attattaaag caagagaggc caagtaaaat actacgtgta     60
gcccaatctc acgaccccaa tctcacgacc ccaatctcac gacccccatgc aaagttaaca   120 cttgtcattg ccaagtaaaa taccgtatat aaacccacgt gtaagataat ccaaattaaa    180
ataccgtata taaacccacc atccccaatc tcaccatccc catgcaaagt taacactcac    240
gaccccatgc aaagttaaca cttgtcattg ccaaatgtac acttgtcatt gccaaaatac    300
cgtatatgta ttgtattcct cagtctccac tatatgtatt ggctgcatga ataataccgt    360
atataaaccc acgtgtaagc ccaaac                                         386

<210> SEQ ID NO 274
<211> LENGTH: 386
```

```
<212> TYPE: DNA
<213> ORGANISM: Artificial Sequence
<220> FEATURE:
<223> OTHER INFORMATION: synthetic 240nt promoter with spacer

<400> SEQUENCE: 274
attgccaaaa gaacccacca aatgtacact tgtcattgcc aaaagaaccc acacattatt    60
aaagcaagag aggccaaaag acccacaca ttattaaaat tagtaagata atccaaaata   120
ctacgtgtag cccaatctca cgaccccatg caaagttaac acttgtcatt gccaagtaaa   180
ataccgtata taaacccacg tgtagcccat gcaaagttaa cactcacgac cccaatctca   240
cgaccccatt cctcagtctc cactatataa acccacgtgt aagataatcc aaatgtacac   300
ttgtcattgc caaaatacta cgtgtaagat aatccaaatt agtaagataa taccgtatat   360
aaacccacgt gtaagataat ccaaac                                         386

<210> SEQ ID NO 275
<211> LENGTH: 386
<212> TYPE: DNA
<213> ORGANISM: Artificial Sequence
<220> FEATURE:
<223> OTHER INFORMATION: synthetic 240nt promoter with spacer

<400> SEQUENCE: 275
cacattatta aagcaagaga ggccaaatta aaatactacg tgtagcccat gcaaagttaa    60
cactcacgac cccatgcaaa gttaacactc accatcccca ttcccaccat ccccattccc   120
accatcccca atctcacgac cccattcctc agtctccact atataaaccc acgtgtagcc   180
catgcaaagt taacacttgt cattgccaag taaaattagt aaaataccgt atatgtattg   240
gctgcatttg catgaataat accgtatatg tacactcacg accccaatct cacgacccca   300
tgcaaagtta acactcacca aaatactacg tgtaagccca ttcctcagtc tccactatat   360
aaacccacgt gtaagataat ccaaac                                         386

<210> SEQ ID NO 276
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 276
aataatccaa attaaagcaa gagtaggaaa gtaagataat ccaaatgtac acttgtcatt    60
gccaaaatta gtaaaatact cggcatattg tagaagcgca cattattaaa ataccgtata   120
tgtattggct gcatttgcat gaataatact acgtgtaagc ccaaaagaac cacgtgtag   180 cccatgcaaa gttaacactc agaacccat tcctcagtct ccactatata acccaccat   240 ctttcatctc accaaaccca ccacacaact cacaactcac tctcacacct aaagaacca   300 atcaccacca aaaa                                                      314

<210> SEQ ID NO 277
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 277
tataatccaa attaaagcaa gacctcgcaa gtaagataat ccaaatgtac acttgtcatt    60
```

```
gccaaaatta gtaaaatact cggcatattg tatgaggaca cattattaaa ataccgtata    120
tgtattggct gcatttgcat gaataatact acgtgtaagc ccaaaagaac ccacgtgtag    180
cccatgcaaa gttaacactc acgaccccat tcctcagtct ccactatata aacccaccat    240
cagcggtctc accaaaccca ccacacaact cacaactcac tctcacacct taaagaacca    300
atcaccacca aaaa                                                     314
```

<210> SEQ ID NO 278
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 278

```
tataatccaa attaaagcaa gacagtctaa gtaagataat ccaaatgtac acttgtcatt     60
gccaaaatta gtaaaatact cggcatattg taatgcgtca cattattaaa ataccgtata    120
tgtattggct gcatttgcat gaataatact acgtgtaagc ccaaaagaac ccacgtgtag    180
cccatgcaaa gttaacactc aaaaccccat tcctcagtct ccactatata aacccaccat    240
cttgagtctc accaaaccca ccacacaact cacaactcac tctcacacct taaagaacca    300
atcaccacca aaaa                                                     314
```

<210> SEQ ID NO 279
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 279

```
aataatccaa attaaagcaa gatgcgaaaa gtaagataat ccaaatgtac acttgtcatt     60
gccaaaatta gtaaaatact cggcatattg tattgtgcca cattattaaa ataccgtata    120
tgtattggct gcatttgcat gaataatact acgtgtaagc ccaaaagaac ccacgtgtag    180
cccatgcaaa gttaacactc actaccccat tcctcagtct ccactatata aacccaccat    240
catttatctc accaaaccca ccacacaact cacaactcac tctcacacct taaagaacca    300
atcaccacca aaaa                                                     314
```

<210> SEQ ID NO 280
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 280

```
tataatccaa attaaagcaa gacttttgca gtaagataat ccaaatgtac acttgtcatt     60
gccaaaatta gtaaaatact cggcatattg tactcactca cattattaaa ataccgtata    120
tgtattggct gcatttgcat gaataatact acgtgtaagc ccaaaagaac ccacgtgtag    180
cccatgcaaa gttaacactc aagaccccat tcctcagtct ccactatata aacccaccat    240
cttcggtctc accaaaccca ccacacaact cacaactcac tctcacacct taaagaacca    300
atcaccacca aaaa                                                     314
```

<210> SEQ ID NO 281
<211> LENGTH: 314

```
<212> TYPE: DNA
<213> ORGANISM: Artificial Sequence
<220> FEATURE:
<223> OTHER INFORMATION: ProPer 240nt with spacer and enhancer

<400> SEQUENCE: 281
aataatccaa attaaagcaa gaatatgtaa gtaagataat ccaaatgtac acttgtcatt      60
gccaaaatta gtaaaatact cggcatattg taatctgcca cattattaaa ataccgtata     120
tgtattggct gcatttgcat gaataatact acgtgtaagc ccaaaagaac ccacgtgtag     180
cccatgcaaa gttaacactc atcaccccat tcctcagtct ccactatata aacccaccat     240
ctccactctc accaaaccca ccacacaact cacaactcac tctcacacct taaagaacca     300
atcaccacca aaaa                                                       314

<210> SEQ ID NO 282
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 282
tataatccaa attaaagcaa gatcgtggaa gtaagataat ccaaatgtac acttgtcatt      60
gccaaaatta gtaaaatact cggcatattg tacttatcca cattattaaa ataccgtata     120
tgtattggct gcatttgcat gaataatact acgtgtaagc ccaaaagaac ccacgtgtag     180
cccatgcaaa gttaacactc agtaccccat tcctcagtct ccactatata aacccaccat     240
cccacttctc accaaaccca ccacacaact cacaactcac tctcacacct taaagaacca     300
atcaccacca aaaa                                                       314

<210> SEQ ID NO 283
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 283
aataatccaa attaaagcaa gagtacggca gtaagataat ccaaatgtac acttgtcatt      60
gccaaaatta gtaaaatact cggcatattg tagcaattca cattattaaa ataccgtata     120
tgtattggct gcatttgcat gaataatact acgtgtaagc ccaaaagaac ccacgtgtag     180
cccatgcaaa gttaacactc aggaccccat tcctcagtct ccactatata aacccaccat     240
catctatctc accaaaccca ccacacaact cacaactcac tctcacacct taaagaacca     300
atcaccacca aaaa                                                       314

<210> SEQ ID NO 284
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 284
aataatccaa attaaagcaa gagcgacata gtaagataat ccaaatgtac acttgtcatt      60
gccaaaatta gtaaaatact cggcatattg taaagtctca cattattaaa ataccgtata     120
tgtattggct gcatttgcat gaataatact acgtgtaagc ccaaaagaac ccacgtgtag     180
```

```
cccatgcaaa gttaacactc actaccccat tcctcagtct ccactatata aacccaccat    240
caaacatctc accaaaccca ccacacaact cacaactcac tctcacacct taaagaacca    300
atcaccacca aaaa                                                      314

<210> SEQ ID NO 285
<211> LENGTH: 314
<212> TYPE: DNA
<213> ORGANISM: Artificial Sequence
<220> FEATURE:
<223> OTHER INFORMATION: ProPer 240nt with spacer and enhancer

<400> SEQUENCE: 285
aataatccaa attaaagcaa gattagagaa gtaagataat ccaaatgtac acttgtcatt     60
gccaaaatta gtaaaatact cggcatattg taaggcccca cattattaaa ataccgtata    120
tgtattggct gcatttgcat gaataatact acgtgtaagc ccaaaagaac ccacgtgtag    180
cccatgcaaa gttaacactc atcaccccat tcctcagtct ccactatata aacccaccat    240
cgtaactctc accaaaccca ccacacaact cacaactcac tctcacacct taaagaacca    300
atcaccacca aaaa                                                      314

<210> SEQ ID NO 286
<211> LENGTH: 1037
<212> TYPE: DNA
<213> ORGANISM: Artificial Sequence
<220> FEATURE:
<223> OTHER INFORMATION: synthetic 1064 promoter with spacer

<400> SEQUENCE: 286
atgtgaaggc tgtaaaatga tcgattgatc ctaatagatt atgaaaattt tataaaaatt     60
aaagcaagag tatatgtatt tttaatgttt ttatataact gaaatactc ggcatgtttg     120 agttgcaaat gtacactttt attattttgg ccaccatccc caatctcacc atcgtttata    180
gattattttg gccaagtatt ttggtgtcat attgggacaa ttttcgttta tagatgatat    240
gaatatccca cgtgtaaaat gttcatgagt attggattgg ataaaatacc gaaattctct    300
caccattcaa gtaaactga ttcttttaac cgtatatcgt ttataaaatg ttttttatata    360 actgaaatga tcctaattaa ttgtaaaaga tcaactctca ccattccttc gattatgaac    420
ggcatgtttg aaaatatgta ttattaaaat attttagaaa tcgattgtat tggctgtaaa    480
ggctgtaaaa attttggcca aggtaagata tttttttcctc attgccttta cctatttat    540 aaaaatgttc acttttgtt catgtttgaa aacaaatgat cgattctgtc taaatgatat    600
gaaaacaaat taaggctgt aaaagaataa tccaaagac tatttttaac caaattctaa    660
tactacgtgt aaaatacatt aacactatgt attatggatt ggataaaatt tttggtgtaa    720
gattatgaaa ttgttcactt ttggataata gaatcagtct ttagattcta attagtaagc    780
ccatgtttat atgttttaga agaacccacg tgtaaaggct gtaaaattga tcctaataga    840
aatcgattgt attggccaag gtaagcccaa tctcacgacc ccatgcaaat tctgtctttt    900
aacacttgtc aaagttaatg ttcactttta taaaataccg taatcgattc aattctgtct    960
ttacctattt atagaataat ccaaaatact cggcatgaac ggcatgagta taaaaagaac   1020
ccacgtgtag cccaaac                                                  1037

<210> SEQ ID NO 287
<211> LENGTH: 1129
<212> TYPE: DNA
<213> ORGANISM: Artificial Sequence
```

```
<220> FEATURE:
<223> OTHER INFORMATION: synthetic 1064 promoter with spacer

<400> SEQUENCE: 287
ccaaggtaag atcaactctc cactatataa aagatcaact ctccatttgc tttttatga      60
aaattctaat accgtaatcc taatagatta tgaaatgatc taattaatt aaagcaagag     120
aataaaattt tcgattatgg ataatagatt atgtattgga ttggattgga taatcgattt    180
tatgaataat tagtaaaaat gatcgattat gaaattaatt gttcatgagt tgcatgagtt    240
gcaaattttc catgcaaatt ctgtctaatt ttcgacgttg ggatctgata gttcactttt    300
gcaaagttaa ttgaaggctg taaaattttg gataaaattt cgttcgaaga ttcaagtatt    360
aatttcgacg ttaattaaag gctgtaagat catagattct aaatgatatg tgatattgtt    420
tgaagaaccc acgtgtagcc catgcaaatg tttgaaattt cgaagaaata ccgtatatcc    480
ccaatctcac gaccoctaat accgaaacca gggacaacgt taactgattc tctccatcgt    540
tttggtgtca agttaacac tatgtacact cacgacccct aatagaaatt gtaaaatact    600
acgtgtagcc catgcaaatt taatgtacac ttttttggtg gtttcgttta ttttagatga    660
tcctaatact acgtgtaaaa taccgtaatc gattggataa tccaaatgta ttggccacca    720
aatttatatc cccatgcaaa ttgtaaaaga aattaaccaa cggcatatcc cacgtgtaaa    780
gcaagagtct tttagaagaa tatgtgatat gtgatagttc atcgttcgaa gataatagaa    840
gatcatagtt tttgcttttg caaagactat ataatccaaa ataccgaaat gtaggtcatg    900
aaaataccga tcaactctcc atcgttcgaa gaaatggtgt catgtacact tttaatgtat    960
ttaatgtttg aaaataaaaa ttaacactat ataaaatatc gttcgacgtt gggacaacgt   1020
taatgtttat ttttccattc ccatgcaaag aaatttttat atcgttcgaa atcgattatg   1080
aatattttcg tttataccctc agtatataaa atactcggca tatccaaac              1129

<210> SEQ ID NO 288
<211> LENGTH: 1240
<212> TYPE: DNA
<213> ORGANISM: Artificial Sequence
<220> FEATURE:
<223> OTHER INFORMATION: synthetic 1064 promoter with spacer

<400> SEQUENCE: 288
aaagcaagag tattggataa tcctaatttt gtgaaggctg taagagagta tatgtacact     60
ttttggtgtt tgaaattaaa gcaagagagt ctttagaaga aatcgattgt attattatga    120
ataatacatt atgtgaataa tccaaattca atttcgttcg aagaaattaa aattttatca    180
tatcgttcga ttggccaagt aagcccaatc tcacgacccc atgtacacta tgtttttaa    240
cactatgtac actcacccct aatactacgt gtaaatatt tgcatgtttt cgaaaccca    300
cacatttgag aggccaagta aaggctgtaa aaagattgta aaaagactat ttttagggt    360
gtctaaatgt acactatatg aataatccta cactcaccat ttgaaggctg catttgcttt    420
taactgatat tggataatta gtaaaatttt ttatcataga tgatagttca tgtattgtaa    480
aattctaatt aaagcaagag tcttgccttt acctatttat acctcattgc caaggtaagc    540
ccaaaagaac ccacacattt gaatactcg gcatgtattc ccacacatta ttaaccgtaa    600
tcgattctaa tagattgaaa tgatagggtg tcaaagacta tgtgaataaa cccacgtgta    660
ggtcatgaaa ttttatataga atcagtcttt agggatctga tagggatctg ataggggtc    720
aaagactatg ttttaaccga tcaactctcc atttgctttt agatgatagt tcatgagttg    780
```

-continued

```
cattttcctt cgattttaac tgatattggc tgtaaaaaga gtataaaaat actacgtgta    840
aaaagatcaa ctctcacgac cccatttggt gtcaaagtta attaaaatac attaatgttg    900
agaggccaag gtaagatcat agttttttat aatccaaatt aaccagggat ctgatatgaa    960
atactacgtg taaaagacta tataaaagac tatatcccca atctcacgac cccaatctca   1020
cgaccccctaa tagattgaaa tactcggcat gtatttgaaa atgatcctac actcaccccca  1080
aaagaaccca cacattatga aatcgattct aaatgttttt tgtgatattt gcaaagttaa   1140
cactcacgac ccctaattaa ttgtaaaggc tgtaaagcaa gagtctccat gcaaattttt   1200
tgcttttata actgataggg acaattctct caccccaaac                         1240
```

<210> SEQ ID NO 289
<211> LENGTH: 1266
<212> TYPE: DNA
<213> ORGANISM: Artificial Sequence
<220> FEATURE:
<223> OTHER INFORMATION: synthetic 1064 promoter with spacer

<400> SEQUENCE: 289

```
tgttcatcgt agtctttaa ccgaaatttt gcttttggtg taagataaac caacgttaat     60
gtattgggac aacgttaatg tttgaaaaca aatttaactg atagttttcg aagatcatat    120
tgggatgtga tagggatgtg atagttcatg tttttttttgg ataatcctac actatatgaa   180
tatgaatatc ccacacattt gaaatgtttt tatgtttttg ttcacttgtc atatcgttta   240
tcatatcgta gtcttgccaa atttaattta ttttattaa ttagtaagat tatgaacggc    300
caaggtaaga ttattatgaa tatttatcat agttcacttt tggtgtaaag gctgtaagag   360
tcttttatat aactgaaaat gatagttttt cggtcataga tgatagttca cttgtcatta   420
aagcaagagt ataattagta aaatttttta ttaacacttt taaccgtaat cctacacttg   480
tcatagtttt ggctgtaaaa gactatgtac actcaccccca tgttttggct gtaaaattga   540
agaacccaca cattatgaaa tactacgtgt aggtcatagt tttggtggtt tcgaaaccca   600
cacatttgaa aattttttgct ttttggtgta gcccattccc accatcgtag tctttaccta   660
ttttatagat gatcgatttt cctcattgcc aaatttttttg gtgtcaaagt taaccaaatt   720
taattgtaaa atttcgacgt tgggacaatt ctctccattt tatacctcat tgcctttacc   780
tcattaaagc aagagagagt ctttagggat gtgaaggctg catgagttgc atttgagaga    840
gtctccatcc ccattttcgt tcgacgttaa cactcacgac cccatgcaaa tgatcgattt    900
tgtttatttt atgaacggcc aaggtaagag aggccaagta tatccatttg cttttttgctt   960
ttgtgaatat cgtagtctcc actatttttgt tcatcgtttt agaagaataa tccattccca  1020
ccatccccat ttgaaaataa ttgtaagatt caattctaat agatgatatt gggacaattc  1080
tgtctaatta gtaagcccat tccttcgaag aacccacgtg tagcccatgc aaattttcct  1140
cattattaac cgtaatccta cactatgttg agaggccaag gtaagagtat ttaatgttta   1200
tttgcatttg aagaacccac gtgtagccca ttttataaaa tacctcagta ttcctcattg  1260
ccaaac                                                             1266
```

<210> SEQ ID NO 290
<211> LENGTH: 1269
<212> TYPE: DNA
<213> ORGANISM: Artificial Sequence
<220> FEATURE:
<223> OTHER INFORMATION: synthetic 1064 promoter with spacer

<400> SEQUENCE: 290

```
ccatgttcac ttttttttc cttcgacgtt gggacaacgg ccaagtaagc ccatgcaaag      60
ttaattagta agatcaactc tccactatat aactgatagt tttccttcga aaccaaaata    120
ccgaaattct ctcacgaccc caaaagacta tgtatttgaa atactcggca tgtttatttg    180
aaataccgta tatgaaaatt gatcgattgt attgtttatc atatttaatt tttcgttttc    240
gtttatggat aatccaaatg tacacttttg cttttggtgt agcccaaatt aaaatggtgt    300
aggtcatgaa taaaaagaga ggccaaggta agagaatcag tcttgccttt acctcattat    360
taaaagaaat tttccatccc caatctcacc aaattaaagg ctgcatgttt ttccatcgtt    420
ttttcggtca tatttgaaat cgattctaat taaagcaaga gtcttttgtg aagaataatc    480
gattcaattc ttttggtgta ggtcattatg gataatccaa agaataatc caaatttcga    540 cgttaatgta ttttttccatt caagtattat tatgaaatcg attgggacaa cgttgggaca    600
attctttaga atatcgttcg attctgtctt tagaatcagt cttgccttta gaaatcgatt    660
gatcctacac tatatcccca tgcaaatggt gtagcccaaa atatgtatta accgtaatcc    720
aaaatactac gtgtaagccc aaatgtttga aaacaaatgg tgtctaatag atgatagttt    780 tggtggttttc ggtcatatttt atataaaata ctcggcatgt ttgaagaaat ttcgttcgaa    840
ataccgaaat actacgtgta aaagaaatt ttcgttcgac gttaatttcg acgttaactg    900
aaataatttt cggtcatgag tattggccac cattcaattt ttggtgtctt tacctcagtc    960
ttttggtggt ttcgacgttg ggatgtgaag gctgtaaaag atcatatttt tatgaatatt   1020
ttggtggttt cgacgttggg atgtgaagaa cccacgtgta aaattttaac cgaaaccaaa   1080
agaaattgtt ttaaccgtat ataatcgatt ttttttagaag aacccacaca tttgagtata   1140
tcccacacat taaagcaaga gaatatcccc atgcaaagaa cccaccattc aattttttaga   1200 atcagtcttt tataccgatc atagattctt ttatagaatc agtataaaat actacgtgta   1260
agcccaaac                                                              1269
```

<210> SEQ ID NO 291
<211> LENGTH: 1360
<212> TYPE: DNA
<213> ORGANISM: Artificial Sequence
<220> FEATURE:
<223> OTHER INFORMATION: synthetic 1064 promoter with spacer

<400> SEQUENCE: 291

```
gcaaattttt tcctcattaa aggctgtaaa agagtattgg ctgtaaaaga acccacacat      60
taaaggctgc attttagat tctctcacca ttcaagtaaa aatactacgt gtaaaagagt    120
atataaaaga gaataaaaat tgatcgatta tgaatatcgt agtctttaga ttgatcgatt    180
ctctccatgc aaagaaattc aattcttttg tgaataatcc aaattaaccg aaacccacca    240
tccccaatct cacgaccct aatagatgat agttcatgtt tgaaggctgc atgaaatggt    300 gtaaaatac attttatcat atccccaatc tcacgacccc attttaggga tgtgaatatg    360
tagcccatgc aaattaaaag aacccacgtg taaagcaaga gaatcagtct tttggtggtt    420
tcgaagataa taccgtatat ccaaaagatt gggacaacgg ccaccatcgt ttatgaataa    480
tccaaattta tggataatcc atgcaaagaa attgtaaaag aacccacgtg taaaatactc    540
ggcatatttt ggtgtcaaag agtcttgcct ttagaagaaa tacctcatta tgtgaaggct    600
gtaaaagact atttttaacc gtataaacca acggcatgta ttttcggtca tattttggtg    660
gtttcggtca ttaaccgatc aactctccac tatgtgaata ttgttttgtg aagattgatc    720
```

```
ctacactttt ggccaccatt cccatgtagg tcatagttca tgaaaacaaa ttgatcgatt      780
ctctcaccaa cgttgggaca acggcatgtt catcgttttt atgaataaaa tttcgttcga      840
agattcaagt aaaggctgta aaatactacg tgtaggtcat agaaatcgat tttggataaa      900
cccaccatcg ttcgacgttg ggacaacgtt gggacaacgg ccaaattttt taaccgtata      960
tccaaatgat cgattatgaa cggcatatcc catgtattaa agaatcagt attcctcatt      1020 gccaaggtaa gcccaatctc acgacccta atacattatg aacggccaaa ataattgaaa     1080
acaaatttcg aaacccacgt gtaaaaattt attaaccgaa attcttttgc tttttaattt     1140
cgacgttggg acaattcaat tcaagtaaaa tttcggtcat atttgaaatt gaaatcgatt     1200
gatcctacac tattttgcat ttgctttta tgtattttt aactgattct gtctaataga      1260
agaatattgg attgggacaa cgttaactga ttctctccat gcaaagaaat acctcattgc     1320
ctttacctca gtataactga aattaatttt atatccaaac                           1360

<210> SEQ ID NO 292
<211> LENGTH: 1432
<212> TYPE: DNA
<213> ORGANISM: Artificial Sequence
<220> FEATURE:
<223> OTHER INFORMATION: synthetic 1064 promoter with spacer

<400> SEQUENCE: 292
tctccatttg agaggccaag gtaagagaga atatcgtagt ctccattcaa ttctctccac       60 tattttcct tcgaagaacc cacacatttt tgcaaattta ttaacactat gtattttgt      120 gaaggctgta aagcaagaga atatccatgc aaattaattg atcctacact tgtcaaagaa     180
atacatttga aggctgtaaa agaatatttt ttcggtcatg aaatactacg tgtaaaatac     240
attatggatt gtttatcata gttcatgttt ttggtgtaaa atgatcctac actcaccatc     300
gttttagatt gtaaaagatc atattggcca ccatcccaca cattaacact cacgaccct      360 aatagatgat cgattttata cctcattaat tgttcatcgt tcgaaattaa ccgatcaact     420
ctccactatt ttggctgcat gagttgcatt tttatagaat cagtctttta ttaattttgt     480
ttttaaccga tcaactctcc atcgtttatg gataatcgat tatgaatatt gtaaaagaaa     540
taatagatga tatgtagccc attcctcagt cttttgttca tcgtttatag aaatgtattg     600
ggacaatttt ggccaccatc gttcgaaatt tttggtgtca aagagtattt tggtgttta      660 taaaagaaat tgatcctaca ctcaccccaa atttaatttt tagaagaatc agtattggga     720
tctgattctg tcttgccaag taaagcaaga gagtatataa ctgaaattaa aaatatccat     780
ccccaatctc acgaccccaa aataccgaaa cccacgtgta gcccaaaaga ctatataact     840
gatattggct gtaaaaatgg tgtcttgcct ttagaatcag tcttgccttt agattgtatt     900
atgtaggtca tagttcactt gtcattgcct ttacctattt aaccgtatat gtttttatgg     960
ataatagaaa tactcggcat gagttgcatg tttttggtgg tttcggtcat tatgaaataa     1020
tccatgcaaa gagtatatga atgaaatt tttatcatag ttcatgaaaa ttttcgaag      1080 aataaaaga acccaccatc gtttttatag aataatccta attaaattg atcctacact     1140 cacccctaat agaatcagta tataactgaa attttgcatt tgagagtata taactgaaat     1200
actacgtgta agattgggac aattcaattc aagtattgga ttgaaaacaa atttatcata     1260
gaataatcga ttttggataa tcctacactt ttttaaccgt atataaaaat accgatcaac     1320 tctccaccatt ttccttcgac gttgggacaa ttctctccat gcaaagttaa tgtattaaaa     1380
tactacgtgt aggtcatgag tatataaacc aggacaacg gcatatccaa ac             1432
```

<210> SEQ ID NO 293
<211> LENGTH: 1509
<212> TYPE: DNA
<213> ORGANISM: Artificial Sequence
<220> FEATURE:
<223> OTHER INFORMATION: synthetic 1064 promoter with spacer

<400> SEQUENCE: 293

```
ctatataaac caaaatggtg tttgagagag aatattttat tatgaacggc atgagttgca      60
tttgcaaatg atagttcatg agtattccca ccaacgttaa ctgatagggt gtaggtcata     120
tccaaaatac cgtaatccaa atttaacact attttcggtc atagattatt tatgtgaata     180
attaaagcaa gagagtcttt tatcatatcc ccaaattaaa ggctgtaagc ccaaattttt     240
aacactcacg acccattttt tgttttcct tcgaaataat cctacactat gtacactcac      300
gaccccatgt ttatatcccc aaatggtggt ttcgacgttg ggacaacggc caccatcgtt     360
ttggtgtcaa agttaacact tttggtgttt ataccgtaat cctaatagat tcaattctct     420
caccaacggc atgagttgca tttgcttttt gcatttggtg taaaagacta tttgaaatac     480
tacgtgtagg tcattaattt aaccgtatat cgtttataga tgatcctaca ctcaccccaa     540
tctcacgacc cctaatttat accgtaatcc aaattgtaaa agattcaatt caattttttg     600
gtgtagccca ttttatgaaa tggtgtaaaa gaataatact acgtgtaaaa gaaatttatc     660
atagattatg aaatttaacc gtaatcctaa tagaaattct aaatgtttat accgatcata     720
gttttgtgaa taaaaagact attttataga ttcaattttta taaagagag aataaaagac     780
tatgtacact tgtcaaagtt aactgattct ctcaccccat gcaaattctt ttaactgaaa     840
tttataatag atgatagggt gtcattgcct ttacctcagt attccttcga agaaataccg     900
atcatagttc acttttcct cagtctccac tatgtatttt gtgaataaac ccacgtgtaa      960
aatacattat gaaatatgta ttcccattcc tcattaaccg taatccatgc aaagagtctt    1020
ttatatgaaa tttatagatt gtattccttc gaagaaattt cgtttataga tgatcgatta    1080
tgaatatcgt tcgaagaaat tctaattgta ttccttcgat tatttaacac tattttataa    1140
tactcggcat atcccattca attttccatt cccattcctt cgaagaaatt tatataaaat    1200
accgatcata gttttagatg atcgattatg gataatagat gatagttcat gttcatcgtt    1260
tatatgaaaa tacattatgg ataatcgatt ctgtcttttt tggctgcatg ttcatcgtag    1320
tctccactat gttttataga tgatattttt tgtgaataat cctacacttg tcatagttca    1380
cttttttgttc atgagttgca aagactatgt tttataattt ttattattat gaacggcatg    1440
aaaatttcga ttctctcacg accectaatt aaccgtatat aaaccaggga caacggcata    1500
tccccaaac                                                            1509
```

<210> SEQ ID NO 294
<211> LENGTH: 1509
<212> TYPE: DNA
<213> ORGANISM: Artificial Sequence
<220> FEATURE:
<223> OTHER INFORMATION: synthetic 1064 promoter with spacer

<400> SEQUENCE: 294

```
aatctcaccc cattccttcg aagaacccac caaaatggtg tcatagaaga atatcccatg      60
caaattaaaa ttttttcctca ttaaagcaag agaggccaag taagagtctt tacctcattg    120
ccaagtaaaa ttttaacact tgtcaaagtt aaccagggat gtgatagttc atgtacacta    180
```

```
tttgcatttg aaatcgattt ttggattggc tgtaaaggct gtaaaagac tatatcccac    240 acatttgcat gttgagagtc tttacctatt tttcgattca attttaggg caacgttgg    300 gatgtgaata atactacgtg taaaatacat ttgaaaacaa attaaaggct gtaaaagata    360
atcgattctt tagaagaata aacccacgtg taagcccaat ctcaccatcc cacgtgtaag    420
cccatgcaaa tgatatgtac actcacgacc cctaattttt ggtggtttcg aaataataca    480
ttatgaaaat actacgtgta agcccaatct cacgacccca aaataatcca aaagagagta    540
ttggctgtaa aatattttgc ttttttgctt ttggtgtttg aagaaatttt tttaacactt    600
gtcaaagtta accgaaaccc acgtgtaagc ccatttgaag atcaactctc acgaccccaa    660
tctcacgacc cctaattaac acttttggtg taaaagatt atgaatatcg ttttagaata    720
atcctaatag aaattgaaat ttcgacgttg ggatgtgaat atccccattt gaaataccga    780
tcaactctca ccatttgctt ttagaaatcg attctttta actgataggg tgtaaaattt    840
atatgtattt taaccaggga caacgttggg atgtgaataa acccaccatt cccacgtgta    900
ggtcatagat tggataaacc aaaatactac gtgtaaaaga gtatttaact gaaataccct    960 attgcctttta cctattttta acactatata atccatcgtt tatatccaaa agagagtctt    1020
ttgtgatatt tttccatcgt agtctttaga agaaataccg taatcctaca ctttggata    1080 attagtaaga tcatagtttt gtgaataaac ccaccattcc tcagtctcca tcgtttataa    1140
ctgaaatttt atcatatttt agattggcca aggtaagaga atattttagg gtgtttatta    1200
attaaaatta accaaaagag agtataaaaa tactcggcat atcgtttttt agggatgtga    1260
ataaaccaac gttaactgaa aacaaattct gtctaaatgg tggtttcgaa gaaatactcg    1320
gcatgagttg caaattcaag tatatgtatt cctcattaat taaagcaaga gagtctttag    1380
attattttgg tgtcaaagat caactctcac gaccccattt tccttcgacg ttaattgtat    1440
tgtaaaatgg tgtcattaat taattgtaaa agagtatata aatgataggt gtgttttcca    1500
tccccaaac                                                            1509

<210> SEQ ID NO 295
<211> LENGTH: 1509
<212> TYPE: DNA
<213> ORGANISM: Artificial Sequence
<220> FEATURE:
<223> OTHER INFORMATION: synthetic 1064 promoter with spacer

<400> SEQUENCE: 295
cattcaattt tttatcatag atgatagttt ttcgaaatcg attctaatag aaatactacg     60
tgtaagagta ttaatgtttt tccattcaat tcaatttag aagataaaag aatatcccca    120
aatttaaccg taatcgattc aattctgtct tgccaagtat atgaataatc caaattagta    180
aagcaagaga gtctccattt gaaggctgta aaggctgtaa aggctgtaaa atactacgtg    240
taaaggctgt aaaagacta tatgaataat cctaatagat tatgaaattt cgttcgacgt    300
tgggatctga ttctgtcttg cctttaccta tttaattgat cgattttcg acgttaatgt    360 acactatatg ttcactttg tgaagaaatt ttttagatg atcgattatg aaatactacg    420
tgtaaaagaa taattaaaag aaatcgattt ttattgaa acaaatttt ggtgtcatag    480 aagataattt atagattgta aaattaacac tatgttcatg agtattggcc aagtaagccc    540
attcccattt ggataaaaag actatatccc acgtgtaaaa ataatcctac acttgtcaaa    600
gagaataaaa gattatgtga ataattgaag gctgtaaaat actacgtgta aagcaagaga    660
gtattggctg catgagtata actgataggg tgtttataga ttatgaaaat atcgttttcg    720
```

```
tttttggtgt catatcccac gtgtaaaatg tttgaaaaca aattttttcgg tcatagtttt      780 tgcttttttgg tgttttatat aatccaaatg tttatcatag ttcacttgtc atagttttttg     840 ttcatgttca tcgtagtctc cactatataa aatacctcag tattggctgt aaaagactat      900
tttgcatttt tggtgtcata tccccattcc tcattaacca gggatctgat tctctcacga      960
ccccatttgc atttggtggt ttcgttcgaa atgtaggtca ttatgtattc ctcagtattg     1020
taaaaatttc gattgggatc tgattcaatt ctaatagatt gtaaaaatgg tgtctaaatg     1080
ttcacttgtc aaagaaccca cgtgtaggtc atatcccatg caaagattga tcctaatact     1140
acgtgtaaaa ttttccatgt acactttttgg tgttttaggg tgtcatgagt attatggata    1200
atcgattgaa attttaggga caacggcatg aataatccaa atttcgatta tgaacggcca     1260
agtattggcc accaacggcc aagtatttta gattattaaa agaaatacct cagtataaac     1320
ccacgtgtaa aattgtatta tgaaaacaaa ttaaaggctg catttgaagg ctgtaaagca     1380
agagaataaa agaataatcg attgaaaaca aatttatcat agttcacttg tcaaagttaa     1440
ttagtaagag agaggccacc atttgcaaat tgatcctaca ctatataatc caaattagta     1500
agcccaaac                                                             1509
```

<210> SEQ ID NO 296
<211> LENGTH: 1509
<212> TYPE: DNA
<213> ORGANISM: Artificial Sequence
<220> FEATURE:
<223> OTHER INFORMATION: synthetic 1064 promoter with spacer

<400> SEQUENCE: 296

```
gggacaattt atgaataatc ctaatagatt atggataatc catgttcatg tatttttagg       60
gtgtttgaaa ttttgctttt ggtgttttttg gtgtcaaagt taattttcgg tcattgccaa     120
ggtaagatca actctccact atataaaaga aatgtaggtc atgaatatgt tgagttgcat     180
gttgagagta ttaaccaacg gccaccaacg ttgggacaac gttgggatct gattctctcc     240
atttggtggt ttcgattatg aaatggtgtt tatagaagat aatccatgca aagttaatgt     300
ttgagtattc ctcagtatat gtagcccatg caaatgttca tcgtagtctt ttgtgatagg     360
gacaacggcc aaggtaagcc catttgcttt tggtgttttt agaagatcat agttcacttg     420
tcaaagagag agaataatcg attatgaaat actacgtgta aaatgatagg gtgtcaaaga     480
acccaccaaa ttaaagcaag agaggccacc attcaagtaa aatgatcgat tttagggatc     540
tgatagtttt gttttttggct gcatgaaaac aaattagtaa gagagtctcc actatttaac     600
cgaaaccagg gatctgattc aagtataaaa gactatgtag gtcatagaag aatcagtctt     660
ttttagatta ttttaaccga aacccacgtg taggtcattg ccaaaatact cggcatatcg     720
tttattttat aatcctacac tattttgtga ataattaaag gctgtaagat tatgaaaata     780
ctacgtgtaa gcccattccc acacattttc gaagaaccca cgtgtaggtc atgaaattct     840
ctcaccatcc caccattcaa gtattgggac aattctaatt aactgaaatt aaaatatgta     900
cactcacccc taatacatta tggattgtaa gcccatgttt gaaggctgca tgagttgcaa     960
attctgtcta atagattcta atagaaataa tcgattggga tgtgaataat tttccatgta    1020 ggtcatatt atcatagaaa ttgtattggc caaggtaaga ttgtaaaata atcgattatt     1080
aaaggctgta aaataccat ttataataga ttcctttagat tgggatgtga aggctgtaaa     1140
ggctgtaaaa tacctatttta tatccatcgt tcgacgttaa ccgtataaaa gatcaactct     1200
```

```
caccattttc cttcgaagaa taattttta tcatagttca cttgtcaaag ttaatgtagg    1260
tcatagattc aagtaaaaag actatgtagg tcatgagtat tcccatgcaa attgatccta    1320
atttaatgtt catgtattgt aagatcatag aagaaatttt ggccaccatt caatttcggt    1380
catgtattcc cacgtgtagg tcatgtttat aactgattct gtctaaatgt tgagttgcaa    1440
atgtaggtca ttgccaagta aataccgta tatgttttcg tttatataaa atactcggca    1500
tatccaaac                                                           1509

<210> SEQ ID NO 297
<211> LENGTH: 1509
<212> TYPE: DNA
<213> ORGANISM: Artificial Sequence
<220> FEATURE:
<223> OTHER INFORMATION: synthetic 1064 promoter with spacer

<400> SEQUENCE: 297
actattttaa cactattttg gtgtcatagt ttttggataa tcgattatta attagtaagc     60
ccaatctcac gaccctaat agaagattct gtctaatacc gtaaactga tatgtattcc     120 catgtattcc ttcgaaaccc acgtgtaaaa gaacccacca ttttagggtg taaaagacta    180 tataaattt tcggtcatgt attaaccagg gatctgatat gtattggata aacccaccat    240
ttgagagtat tttggctgta aaagagaata aaattagtaa gagagaatat cgtttattaa    300
aatgatagtt ttccttcgac gttaattaac caaaagacta tgtacacttg tcattgcctt    360
tacctcatta acactatgta ttttggataa tcctaataga ataaaatggt gtaaaattaa    420
ccagggatct gattcttta taccgtatat ccatcgttcg aaatatcgta gtcttgccaa    480
gtatataaac cagggacaac gttaattaaa gcaagagtat tatgaacggc atgttgagta    540
ttccttcgat tctaaatgta ggtcatagaa taatcctaca ctattttata cctatttta    600 taccgtaatc gattctgtct aatactacgt gtagcccaat ctcaccatt gaaattttag    660 atgatcctaa ttgaaattta tcatagttca tcgttcgaaa ccaaaagaac ccacgtgtaa    720
gagagtcttt ttccatcgtt tttaaccgta taaaataccg aaatatttt tcggtcattg    780 ccaaggtaag cccaatctca ccccatttgg ataatcctaa tagatgatcg attttccatg    840
tagcccaaaa gactatttga gaggccacca aaagaaatcg attatgaaat taaaagaaa    900 tactacgtgt aaaggctgta aaagactatg tgaaggctgt aaattttgt gaaggctgta    960 aaagaatcag tctccactat ttggtggttt cgaagattga aatatcgttt atagattgaa    1020
atgtattaac cgtatataaa ccagggatgt gatagttttt taaccaggga tgtgaataat    1080
ccaaatgatc ctaattgaaa atacctcagt ctccattcaa ttcttttgct tttggtggtt    1140
tcgaagaaat taaccgtata aaagaaatt agtaaaggct gcattttgtg aataaaccca    1200
cgtgtagccc aatctcaccc catgcaaaga tcaactctcc atccccattt gaaatcgatt    1260
tttatgtatt gtattcctca ttatgaacgg catatttgag ttgcatgaac ggcatgttg    1320 aaggctgtaa aaattaatgt tcatcgtagt cttgccttta cctatttgct ttttagggac    1380
aacggccaag gtaagattct tttaactgat agttcacttg tcaaagttaa tgtttgaaaa    1440 caattaacc gaaattaaag gctgtaaaag aatcagtctc cactatataa ttagtaagag    1500
aggccaaac                                                           1509

<210> SEQ ID NO 298
<211> LENGTH: 1509
<212> TYPE: DNA
<213> ORGANISM: Artificial Sequence
```

<220> FEATURE:
<223> OTHER INFORMATION: synthetic 1064 promoter with spacer

<400> SEQUENCE: 298

```
aaggctgcat ttgaaggctg taagatcata gttcatcgtt tatacctcat tgcctttacc      60
tattttccat cgttcgaaat tttcgtttat ggataataga ttgtaaaaag aaatcgatta     120
tgaataaaat aaaagattat taattaattg aaggctgcat gtttttaggg tgtctaatac     180
tcggcatatc gtagtctttt aacactattt tggtgtcttt tataactgaa aacaaatttt     240
atagattctc tcacgacccc taatagaata tcgttcgatt caattcaagt aagcccatgc     300
aaagttaatt tatgaataaa agactatttt ccatcgtttt tatgaacggc caccatcgta     360
gtctccacta tgtatttgag tattccttcg attctttacc tcagtattcc cacacatttg     420
aaatggtgtc atgagtattg taaagcaaga gaggccacca tcgttttggt gtaagagtat     480
tcctcagtat ataaacccac acattttatt aaccgaaacc agggacaacg gcatgagtat     540
taacactttt gtgatagggt gtaggtcatg ttgagagagt ataatccaaa ttctgtctaa     600
atggtgtttt tggtggtttc gaaaccaggg atctgattct aaatgatatg tgaagaaatt     660
aattttcgtt tataccgtat aactgattct aaatgttcac ttttggataa ttaatttata     720
tgtattgtat ttaattttcg aaattttcca tccccatgca aagttaatgt ttgaaatacc     780
gtatataaac ccacgtgtaa aagaatatga aaacaaattt tcgaagaaat ttttaaccaa     840
aattaaccgt aatccaaaag aaattttat ggataataga tgatcctaca cttttcgat      900
tggccaccaa atttagaag aaatcgatta tgaacggcca aggtaagagt cttttggtgt      960
aaggctgta aatactacg tgtaaaatac tacgtgtaag cccatttgaa aacaaatgtt     1020
catcgtagtc ttttgttcac ttgtcaaagt taacacttgt caaagttaat gtttgagagt     1080
attgtttgag agaatcagta ttaaaaatac tacgtgtagc ccatgttttt cgattatgaa     1140
tatgtacact ttttggctgt aagagtcttg ccaaggtaag agtattggct gtaaaatgtt     1200
ttggtgtttt cgaaatgttt gaaatcgatt atgaaataat cctacactat ttaattgtaa     1260
aatactacgt gtaaaggctg taaaatatgt tttttatttt ataaaattttt cgaagaaccc     1320
accattcaat tcaattctct ccactatta attgtaaagg ctgtaaaaga ctatataaaa     1380
gactatttat atgtattgga ttgtaaaaga acccacgtgt aagcccatgc aaattttcgt     1440
tttggattgg gacaatttcg aagaaatttt tcgtttataa tagaagatat tggattggat     1500
aatccaaac                                                            1509
```

<210> SEQ ID NO 299
<211> LENGTH: 1509
<212> TYPE: DNA
<213> ORGANISM: Artificial Sequence
<220> FEATURE:
<223> OTHER INFORMATION: synthetic 1064 promoter with spacer

<400> SEQUENCE: 299

```
aactgattct gtcttttggc caccattcaa gtaagagtct tttgttttgg tgtttatacc      60
gatcaactct ccactatgtg aatatcgtag tctccatgca aattttggt gtaaaaagaa     120
tcagtatatc gtagtctta cctcagtctt gcctttacct attttatacc gaaatttcga     180
aacccacaca ttatgaacgg catgaaatta attaaagcaa gagaggccaa attgaaggct     240
gcatgttgag agtattggat aatagattca attctgtcta atacattatg ttttggataa     300
tcgattatga ataatccaaa ataccgaaac ccaccaaaag aacccaccat cgtagtctcc     360
```

```
attcctcatt aaaaatacct cagtatataa aatgtttatc atagttcatc gttttggcca      420
agtattaaaa taatcgatta tgaaaataat agatgatagg gtgtctaata ctcggcatga      480
aattttcctc agtataaaat taaaaagatt ctgtctttag attcttttta tatgtattgg      540
ccaccatttg caaagttaat gtacactttt gtgaataatc catcgtagtc ttttttccatt    600 tttatatgtg aataaaccaa aagatatgaa cggcatgttt attatgaata tgaaatattg     660
gctgcatttg aaaataatcg attggataat cgattttcct tcgacgttgg gacaacggcc    720
aagtattgga ttggccaagg taagcccaat ctcacgaccc taattgtat tcccatttga      780 aaatgatcct acactcaccc cattcaattc aattttttata ccgtataact gattcttttg    840
gtgtaagagt ctccactatt taaccgtaat cctacactat tttagaagaa atatgtacac     900
ttttggataa tagaaatact acgtgtaaaa tactacgtgt agcccaaaag actatataaa     960
atactcggca tgaatatgaa taattaaagg ctgtaaaata ctacgtgtaa aatactacgt    1020
gtaaaagaaa tactacgtgt aaaattctaa tagaaattaa aatgttgagt tgcaaagtta    1080
accagggaca atttatatcg ttttttgtga tagggtgttt ataaacccac gtgtagccca    1140
aaattgtaaa aagataatcc aaaatactac gtgtaaaatt gatcgatttt tggtgtcaaa    1200
gttaattaac cgtataactg aaatcgatta ttaaccaaaa tatttggata aacccaccat    1260
ttggtgtctt tacctcatta ttttccatgt tcatcgtttt agaagattat gaatatgtag    1320
cccatgcaaa ttttcgttcg attattaaaa ttgatcgatt gaaaacaaat ttcgaagaac    1380
ccacacatta atgtattatg tagcccaaat ggtgtcatag aataatagaa tatccaaaat    1440
ttttataact gaaatcgatt gttcatgaac ggcatgagta tataaaccca ccaaattgta    1500
agcccaaac                                                            1509

<210> SEQ ID NO 300
<211> LENGTH: 1509
<212> TYPE: DNA
<213> ORGANISM: Artificial Sequence
<220> FEATURE:
<223> OTHER INFORMATION: synthetic 1064 promoter with spacer

<400> SEQUENCE: 300
cttcgaagat caactctcac gacccctaat taaaggctgt aaagcaagag aggccaccat     60
cccaccattt gaaatacatt atgaaaacaa attttcctca ttgccaaatt ctgtcttgcc     120
tttacctatt ttggtggttt cggtcatgaa atcgattatg aaatcgattg aaaattgtat     180
tggattgatc ctacactcac gacccctaat tagtaagaga gaggccaagg taagatcata    240
gttcatcgta gtctccacta tttgagaggc caagtatttt ggctgtaagc ccattcctca    300
ttatgaaaac aaattttcga ttgatcgatt ttttgctttt ggtgtttatg gataatttcg    360
ttcgaaacca gggatgtgaa tatcgtttta aaaaatact acgtgtagcc cattcaattc    420
tttttatacc tcagtatata aaatacatta attaattttt atggataatc catcccaat     480 ctcacccta atagaagaac ccacacatta tgtgaagaat atcgtagtct tgccaaggta     540
agcccaaaat ttaaccgtaa tcgattttt aaccaaaata ccgtatataa ttaaaataca    600
ttaaccgtaa tcctacacta ttttaatgt tttccatgta ggtcatgttg agaggccaaa    660
ttagtaaaat aatccattcc tcattgcctt tagaagaaat aaaatacctc attatttgag    720
aggccaaggt aagcccatgt attggctgta aaaatgatcg attgaaaata tttataccga    780
aacccacgtg taagattcaa ttcaagtaag atcaactctc acgaccccta attttggtg    840 tctaatagat tggctgtaaa ataccctagt ctccactatt tttggtgttt cgaaattta    900
```

```
tacctcatta accagggaca acgttaaccg taatccaaat gatatttaat tttaaccagg        960
gatgtgatag ttcatgagtt gcaaatggtg tcatatccca tttggtggtt tcgaaatgtt       1020
tgaaataaaa agataatcca aaataaaaga gagtattttg gtggtttcga agaaatgata       1080
gggatgtgaa gaacccacgt gtaagcccaa tctcacgacc cctaattagt aagcccaatc       1140
tcaccccatt cccacgtgta aaatggtgt tttggctgta aaatggtgta aagaataat         1200 cgattggctg taagcccaat ctcaccccta atagaatatt gttcatgaat aatccaaaat      1260
ttatagaata attaaccagg gatgtgaagg ctgcatgagt tgcatttgct ttttatataa      1320
ctgaaatacc tcagtataaa ccaaaataat cctacactca cgaccccatg caaagagaga      1380
gtctccattc aatttcgacg ttaaccaggg atgtgatatt ggccaaattt aatttatgta      1440
ttgtattgtt ttaactgaaa tgtacactat atcgttttta taactgaaat aaaataccgt      1500
aatccaaac                                                              1509

<210> SEQ ID NO 301
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 301
atcgcagata tttggtgtct aaatgtttat tgtcctgtat gttcatttgg gacaaattag         60
ctgaacagcc agggacaacg ttgggatctg atagggtgtc aaagagtatt ataaactggg        120
acaatttcgg tcatgagttg caaattcaag tatatagctc tgccgggggg attttcgaag        180
aatatcccat ttgacgagtc acctggctca ttaatgtttt tagattatga aattttatca        240
tagtaagggg acagttattt ggtgtaaagg ctgtaaaaag aaattgttca cttttgtttt        300
cgtttatgtg aaggccctaa aagattgtgt aagactattt tggtgttttg gataaaatga       360
tagtttttat agattctttt gctttttagaa gaaatacatt tgaaattttt tccatgttga      420
gtataaacgc atttatcgta ttgaagatca tagaaatatt ttaactgaaa ataatttat        480 aactgattca attctctcca tttttatacc tatttaaccg taatcgtggc gagatcccgt       540
caggaccagc caagcatcct aattaaccaa cggcatgtat tggataatta accgatcaac      600
tctcacccct aatagaatca gagcgacact tcgacgttaa ttgatcctac actacggggg      660
tcatatccat cgttttaatt tttcgccacc attcaattct gtcttgcctt tagggatgtg      720
aatatgaacg gccaaggtcc gggtgcaaaa ataatccaaa ttaaagcaag aaaccgggag      780
taagataatc caaatgtaca cttgtcattg ccaaaattag taaaatactc ggcatattgt      840
actaggccac attattaaaa taccgtatat gtattggctg catttgcatg aataatacta      900
cgtgtaagcc caaaagaacc cacgtgtagc ccatgcaaag ttaacactca atccccatt       960 cctcagtctc cactatataa acccaccatc ggcactctca ccaaacccac cacacaactc     1020
acaactcact ctcacacctt aaagaaccaa tcaccaccaa aaa                        1063

<210> SEQ ID NO 302
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 302
```

| | |
|---|---:|
| acagcagata tttggtgtct aaatgtttat tgttggctat gttcatgtga ttctggttac | 60 |
| gcaatgcttc agggacaacg ttgggatctg atagggtgtc aaagagtatt gtgctctggg | 120 |
| acaatttcgg tcatgagttg caaattcaag tatatacatt agtcgcacca gatttcgaag | 180 |
| aatatcccat ttgacgaccc acaatgctca ttaatgtttt tagattatga aattttatca | 240 |
| tagttagaac acaatggttt ggtgtaaagg ctgtaaaaag aaattgttca cttttgtttt | 300 |
| cgtttatgtg aaggctataa aagattgtat aagactattt tggtgttttg gataaaatga | 360 |
| tagtttttat agattctttt gcttttagaa gaaatacatt tgaaattttt tccatgttga | 420 |
| gtataaagac cattgtataa ttgaagatca tagaaatatt ttaactgaaa actcatttat | 480 |
| aactgattca attctctcca tttttatacc tatttaaccg taatcgtacc ctcggtacta | 540 |
| cgctaggaag cagccgtcct aattaaccaa cggcatgtat tggataatta accgatcaac | 600 |
| tctcacccct aatagaatca tctcgaaagt tcgacgttaa ttgatcctac actagtttgg | 660 |
| tcatatccat cgttttaatt ttttgccacc attcaattct gtcttgcctt tagggatgtg | 720 |
| aatatgaacg gccaagacgg agagtaaaaa ataatccaaa ttaaagcaag aaactggcag | 780 |
| taagataatc caaatgtaca cttgtcattg ccaaaattag taaaatactc ggcatattgt | 840 |
| acaaggccac attattaaaa taccgtatat gtattggctg catttgcatg aataatacta | 900 |
| cgtgtaagcc caaagaaacc cacgtgtagc ccatgcaaag ttaacactca tgacccatt | 960 |
| cctcagtctc cactatataa acccaccatc acgactctca ccaaacccac cacacaactc | 1020 |
| acaactcact ctcacacctt aaagaaccaa tcaccaccaa aaa | 1063 |

<210> SEQ ID NO 303
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 303

| | |
|---|---:|
| tgtgcagata tttggtgtct aaatgtttat ttcaaaatat gttcatgacg ccgctgaacg | 60 |
| aagaaaggac agggacaacg ttgggatctg atagggtgtc aaagagtatt agtcgatggg | 120 |
| acaatttcgg tcatgagttg caaattcaag tatatggggt atctcagcaa tctttcgaag | 180 |
| aatatcccat ttgaagcatt ttactcctca ttaatgtttt tagattatga aattttatca | 240 |
| tagtataggg gtgttttttt ggtgtaaagg ctgtaaaaag aaattgttca cttttgtttt | 300 |
| cgtttatgtg aaggccctaa aagattgtac aagactattt tggtgttttg gataaaatga | 360 |
| tagtttttat agattctttt gcttttagaa gaaatacatt tgaaattttt tccatgttga | 420 |
| gtataaaagg gttcttctcc ttgaagatca tagaaatatt ttaactgaaa acccatttat | 480 |
| aactgattca attctctcca tttttatacc tatttaaccg taatcgctaa gttcgtcaag | 540 |
| gaaataactt ttaacctcct aattaaccaa cggcatgtat tggataatta accgatcaac | 600 |
| tctcacccct aatagaatca gtcgatgtct tcgacgttaa ttgatcctac actacgtcgg | 660 |
| tcatatccat cgttttaatt ttttgccacc attcaattct gtcttgcctt tagggatgtg | 720 |
| aatatgaacg gccaagctag ttgtcgaaaa ataatccaaa ttaaagcaag atagtctcag | 780 |
| taagataatc caaatgtaca cttgtcattg ccaaaattag taaaatactc ggcatattgt | 840 |
| aattttgcac attattaaaa taccgtatat gtattggctg catttgcatg aataatacta | 900 |
| cgtgtaagcc caaagaaacc cacgtgtagc ccatgcaaag ttaacactca ctaccccatt | 960 |
| cctcagtctc cactatataa acccaccatc agctatctca ccaaacccac cacacaactc | 1020 | acaactcact ctcacacctt aaagaaccaa tcaccaccaa aaa            1063

<210> SEQ ID NO 304
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 304
cgtgcagata tttggtgtct aaatgtttat tctggcatat gttcatttgt catgatttat   60
ccgccccttc agggacaacg ttgggatctg atagggtgtc aaagagtatt ttctgttggg  120
acaatttcgg tcatgagttg caaattcaag tatatagttc gccgtgctgc gttttcgaag  180
aatatcccat ttgagactgg tcgttcctca ttaatgtttt tagattatga aattttatca  240
tagtcgcacc cattgtcttt ggtgtaaagg ctgtaaaaag aaattgttca cttttgtttt  300
cgtttatgtg aaggctgtaa aagattgttc aagactattt ggtgttttg gataaaatga   360
tagtttttat agattctttt gcttttagaa gaaatacatt tgaaattttt tccatgttga  420
gtataaactt gatcgttcgg ttgaagatca tagaaatatt ttaactgaaa agaaatttat  480
aactgattca attctctcca tttttatacc tatttaaccg taatcgaagc cgaaatgagc  540
caacgcctac gctatttcct aattaaccaa cggcatgtat tggataatta accgatcaac  600
tctcacccct aatagaatca atttcccgct tcgacgttaa ttgatcctac actaggtggg  660
tcatatccat cgttttaatt tttagccacc attcaattct gtcttgcctt tagggatgtg  720
aatatgaacg gccaagcaag ctttgaaaaa ataatccaaa ttaaagcaag aaacaccaag  780
taagataatc caaatgtaca cttgtcattg ccaaaattag taaaatactc ggcatattgt  840
agaacgccac attattaaaa taccgtatat gtattggctg catttgcatg aataatacta  900
cgtgtaagcc caaagaaacc cacgtgtagc ccatgcaaag ttaacactca taccccatt  960
cctcagtctc cactatataa acccaccatc tcggatctca ccaaacccac cacacaactc 1020
acaactcact ctcacacctt aaagaaccaa tcaccaccaa aaa            1063

<210> SEQ ID NO 305
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 305
agagcagata tttggtgtct aaatgtttat tggttcgtat gttcatagtc cgagtatgta   60
cgagaaagcc agggacaacg ttgggatctg atagggtgtc aaagagtatt gtacgttggg  120
acaatttcgg tcatgagttg caaattcaag tatatgctca aggaagctca agtttcgaag  180
aatatcccat ttgagacgac cgacgcctca ttaatgtttt tagattatga aattttatca  240
tagttcaccc cgaagatttt ggtgtaaagg ctgtaaaaag aaattgttca cttttgtttt  300
cgtttatgtg aaggctataa aagattgtat aagactattt ggtgttttg gataaaatga   360
tagtttttat agattctttt gcttttagaa gaaatacatt tgaaattttt tccatgttga  420
gtataaaagg cacgggagtg ttgaagatca tagaaatatt ttaactgaaa ataatttat   480
aactgattca attctctcca tttttatacc tatttaaccg taatcgcagt gatggacgcg  540
ggcatcggta ggactatcct aattaaccaa cggcatgtat tggataatta accgatcaac  600

```
tctcacccct aatagaatca gcaaataagt tcgacgttaa ttgatcctac actatcaggg        660
tcatatccat cgtttttaatt tttggccacc attcaattct gtcttgcctt tagggatgtg      720
aatatgaacg gccaaggact ccattaaaaa ataatccaaa ttaaagcaag aactcttcag       780
taagataatc caaatgtaca cttgtcattg ccaaaattag taaaatactc ggcatattgt       840
acagccccac attattaaaa taccgtatat gtattggctg catttgcatg aataatacta       900
cgtgtaagcc caaagaacc cacgtgtagc ccatgcaaag ttaacactca gcaccccatt        960
cctcagtctc cactatataa acccaccatc tcttttctca ccaaacccac cacacaactc      1020
acaactcact ctcacacctt aaagaaccaa tcaccaccaa aaa                        1063
```

<210> SEQ ID NO 306
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 306

```
cgagcagata tttggtgtct aaatgtttat tgtagtatat gttcattttt aacttatgtt        60
aggtgtcaac agggacaacg ttgggatctg atagggtgtc aaagagtatt aataagtggg       120
acaatttcgg tcatgagttg caaattcaag tatattccta ctcgtagtgg gttttcgaag       180
aatatcccat ttgaacgtaa tcataactca ttaatgtttt tagattatga aattttatca       240
tagtagacat gctttgattt ggtgtaaagg ctgtaaaaag aaattgttca cttttgtttt       300
cgtttatgtg aaggcggtaa aagattgttc aagactattt tggtgttttg gataaaatga      360
tagtttttat agattctttt gcttttagaa gaaatacatt tgaaattttt tccatgttga      420
gtataaaagg cacgaatcaa ttgaagatca tagaaatatt ttaactgaaa agcgatttat      480
aactgattca attctctcca tttttatacc tatttaaccg taatcgggtg caccaactga      540
attgctttaa tgatactcct aattaaccaa cggcatgtat tggataatta accgatcaac      600
tctcacccct aatagaatca gtagcggttt tcgacgttaa ttgatcctac actattaggg     660
tcatatccat cgtttttaatt tttggccacc attcaattct gtcttgcctt tagggatgtg    720
aatatgaacg gccaagcgca cgacgcaaaa ataatccaaa ttaaagcaag acctgcaaag    780
taagataatc caaatgtaca cttgtcattg ccaaaattag taaaatactc ggcatattgt    840
aatcgctcac attattaaaa taccgtatat gtattggctg catttgcatg aataatacta    900
cgtgtaagcc caaagaacc cacgtgtagc ccatgcaaag ttaacactca caccccatt     960 cctcagtctc cactatataa acccaccatc gaatttctca ccaaacccac cacacaactc  1020
acaactcact ctcacacctt aaagaaccaa tcaccaccaa aaa                    1063
```

<210> SEQ ID NO 307
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 307

```
gatgcagata tttggtgtct aaatgtttat tcgaggatat gttcatgggg accgtcaagg       60
tagatgacac agggacaacg ttgggatctg atagggtgtc aaagagtatt ccctgatggg     120
acaatttcgg tcatgagttg caaattcaag tatatcggaa caggtcatgg gctttcgaag     180
aatatcccat ttgatcgttt aaaggactca ttaatgtttt tagattatga aattttatca     240
```

```
tagtagcgcg tgtccggttt ggtgtaaagg ctgtaaaaag aaattgttca cttttgtttt      300
cgtttatgtg aaggccgtaa aagattgtaa aagactattt tggtgttttg gataaaatga      360
tagtttttat agattctttt gcttttagaa gaaatacatt tgaaattttt tccatgttga      420
gtataaacgt gaggttgtcc ttgaagatca tagaaatatt ttaactgaaa atctatttat      480
aactgattca attctctcca tttttatacc tatttaaccg taatcgcaca tttaagggat      540
ggcgacagca cccgcttcct aattaaccaa cggcatgtat tggataatta accgatcaac      600
tctcacccct aatagaatca gttttggtgt tcgacgttaa ttgatcctac actatccggg      660
tcatatccat cgtttttaatt tttggccacc attcaattct gtcttgcctt tagggatgtg     720
aatatgaacg gccaagcaat gccttgaaaa ataatccaaa ttaaagcaag atctctaaag      780
taagataatc caaatgtaca cttgtcattg ccaaaattag taaaatactc ggcatattgt      840
agttctccac attattaaaa taccgtatat gtattggctg catttgcatg aataatacta      900
cgtgtaagcc caaaagaacc cacgtgtagc ccatgcaaag ttaacactca agacccatt      960 cctcagtctc cactatataa acccaccatc atagctctca ccaaacccac cacacaactc     1020
acaactcact ctcacacctt aaagaaccaa tcaccaccaa aaa                        1063
```

<210> SEQ ID NO 308
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 308

```
catgcagata tttggtgtct aaatgtttat ttacccttat gttcattcca cgctagggga       60
gtgaatcacc agggacaacg ttgggatctg atagggtgtc aaagagtatt ctcccgtggg      120
acaatttcgg tcatgagttg caaattcaag tatatgacag ggctgggaca cttttcgaag      180
aatatcccat ttgattaatc aagagactca ttaatgtttt tagattatga aattttatca      240
tagtgattct ctgttacttt ggtgtaaagg ctgtaaaaag aaattgttca cttttgtttt      300
cgtttatgtg aaggccctaa aagattgtgc aagactattt tggtgttttg gataaaatga      360
tagtttttat agattctttt gcttttagaa gaaatacatt tgaaattttt tccatgttga      420
gtataaaggc gggctgggtc ttgaagatca tagaaatatt ttaactgaaa agccatttat      480
aactgattca attctctcca tttttatacc tatttaaccg taatcgcagc ggaggaatgt      540
cactgacaaa tgaacgtcct aattaaccaa cggcatgtat tggataatta accgatcaac      600
tctcacccct aatagaatca gttccgtcat tcgacgttaa ttgatcctac actacgacgg      660
tcatatccat cgtttttaatt tttagccacc attcaattct gtcttgcctt tagggatgtg     720
aatatgaacg gccaagttac gtcaacaaaa ataatccaaa ttaaagcaag aaaaccctag      780
taagataatc caaatgtaca cttgtcattg ccaaaattag taaaatactc ggcatattgt      840
atcgagacac attattaaaa taccgtatat gtattggctg catttgcatg aataatacta      900
cgtgtaagcc caaaagaacc cacgtgtagc ccatgcaaag ttaacactca atacccatt      960 cctcagtctc cactatataa acccaccatc agccttctca ccaaacccac cacacaactc     1020
acaactcact ctcacacctt aaagaaccaa tcaccaccaa aaa                        1063
```

<210> SEQ ID NO 309
<211> LENGTH: 1063
<212> TYPE: DNA

<213> ORGANISM: Artificial Sequence
<220> FEATURE:
<223> OTHER INFORMATION: ProPer full promoter with spacer and enhancer

<400> SEQUENCE: 309

| | | | | | |
|---|---|---|---|---|---|
| gtggcagata | tttggtgtct | aaatgtttat | tcctagatat | gttcattgcg | gaattgcttc | 60 |
| tcaccgtgac | agggacaacg | ttgggatctg | atagggtgtc | aaagagtatt | tcgacgtggg | 120 |
| acaatttcgg | tcatgagttg | caaattcaag | tatattcggt | ccaccttgtt | agtttcgaag | 180 |
| aatatcccat | ttgacatggg | cgcgcgctca | ttaatgtttt | tagattatga | aatttttatca | 240 |
| tagttagcgc | ctgcctattt | ggtgtaaagg | ctgtaaaaag | aaattgttca | cttttgtttt | 300 |
| cgtttatgtg | aaggccgtaa | aagattgtta | aagactattt | tggtgttttg | gataaaatga | 360 |
| tagttttat | agattctttt | gcttttagaa | gaaatacatt | tgaaatttt | tccatgttga | 420 |
| gtataaagcc | gaactgacac | ttgaagatca | tagaaatatt | ttaactgaaa | atacatttat | 480 |
| aactgattca | attctctcca | tttttatacc | tatttaaccg | taatcgggat | tagacgatat | 540 |
| ttccgcgtca | tgccggtcct | aattaaccaa | cggcatgtat | tggataatta | accgatcaac | 600 |
| tctcacccct | aatagaatca | gaatatttat | tcgacgttaa | ttgatcctac | actaacatgg | 660 |
| tcatatccat | cgttttaatt | tttggccacc | attcaattct | gtcttgcctt | tagggatgtg | 720 |
| aatatgaacg | gccaagatcc | catttcaaaa | ataatccaaa | ttaaagcaag | atttcagtag | 780 |
| taagataatc | caaatgtaca | cttgtcattg | ccaaaattag | taaaatactc | ggcatattgt | 840 |
| atgtgttcac | attattaaaa | taccgtatat | gtattggctg | catttgcatg | aataatacta | 900 |
| cgtgtaagcc | caaagaacc | cacgtgtagc | ccatgcaaag | ttaacactca | cgaccccatt | 960 |
| cctcagtctc | cactatataa | acccaccatc | tgtagtctca | ccaaacccac | cacacaactc | 1020 |
| acaactcact | ctcacacctt | aaagaaccaa | tcaccaccaa | aaa | | 1063 |

<210> SEQ ID NO 310
<211> LENGTH: 1063
<212> TYPE: DNA
<213> ORGANISM: Artificial Sequence
<220> FEATURE:
<223> OTHER INFORMATION: ProPer full promoter with spacer and enhancer

<400> SEQUENCE: 310

| | | | | | |
|---|---|---|---|---|---|
| atggcagata | tttggtgtct | aaatgtttat | tgggtggtat | gttcatcttc | aatttagtgg | 60 |
| tgtcaccggc | agggacaacg | ttgggatctg | atagggtgtc | aaagagtatt | aaattttggg | 120 |
| acaatttcgg | tcatgagttg | caaattcaag | tatatcgacc | cgccccaat | tatttcgaag | 180 |
| aatatcccat | ttgagtggat | agacgtctca | ttaatgtttt | tagattatga | aatttttatca | 240 |
| tagtaccggt | aaccctgttt | ggtgtaaagg | ctgtaaaaag | aaattgttca | cttttgtttt | 300 |
| cgtttatgtg | aaggcgttaa | aagattgttg | aagactattt | tggtgttttg | gataaaatga | 360 |
| tagttttat | agattctttt | gcttttagaa | gaaatacatt | tgaaatttt | tccatgttga | 420 |
| gtataaagac | cgtggtatag | ttgaagatca | tagaaatatt | ttaactgaaa | agcaatttat | 480 |
| aactgattca | attctctcca | tttttatacc | tatttaaccg | taatcgaata | atcccaaaaa | 540 |
| gtatcgttag | tttggctcct | aattaaccaa | cggcatgtat | tggataatta | accgatcaac | 600 |
| tctcacccct | aatagaatca | ttcgtcgctt | tcgacgttaa | ttgatcctac | actatcttgg | 660 |
| tcatatccat | cgttttaatt | tttcgccacc | attcaattct | gtcttgcctt | tagggatgtg | 720 |
| aatatgaacg | gccaagtgat | ccgcataaaa | ataatccaaa | ttaaagcaag | atatttcaag | 780 |
| taagataatc | caaatgtaca | cttgtcattg | ccaaaattag | taaaatactc | ggcatattgt | 840 |

```
agcgactcac attattaaaa taccgtatat gtattggctg catttgcatg aataatacta    900
cgtgtaagcc caaaagaacc cacgtgtagc ccatgcaaag ttaacactca tgaccccatt    960
cctcagtctc cactatataa acccaccatc ggtgctctca ccaaacccac cacacaactc   1020
acaactcact ctcacacctt aaagaaccaa tcaccaccaa aaa                     1063
```

<210> SEQ ID NO 311
<211> LENGTH: 398
<212> TYPE: DNA
<213> ORGANISM: Artificial Sequence
<220> FEATURE:
<223> OTHER INFORMATION: WO0116340-GUS data

<400> SEQUENCE: 311

```
tccactatgt aggtcatatc catcatttta attttggggc accattcaat tccatcttgc     60
ctttagggat gtgaatatga acggccaagg taagagaata aaaataatcc aaattaaagc    120
aagagaggcc aagtaagata atccaaatgt acacttgtca tcgccgaaat tagtaaaata    180
cgcggcatat tgtattccca cacattatta aaataccgta tatgtattgg ctgcatttgc    240
atgaataata ctacgtgtaa gcccaaaaga acccacgtgt agcccatgca aagttaacac    300
tcacgacccc attcctcagt ctccactata taaacccacc atccccaatc ttaccaaacc    360
caccacacga ctcacaactc gactctcaca ccttaaag                            398
```

<210> SEQ ID NO 312
<211> LENGTH: 417
<212> TYPE: DNA
<213> ORGANISM: Artificial Sequence
<220> FEATURE:
<223> OTHER INFORMATION: WO0116340-SEQ-006UTR

<400> SEQUENCE: 312

```
tccactatgt aggtcatatc catcatttta attttggggc accattcaat tccatcttgc     60
ctttagggat gtgaatatga acggccaagg taagagaata aaaataatcc aaattaaagc    120
aagagaggcc aagtaagata atccaaatgt acacttgtca tcgccgaaat tagtaaaata    180
cgcggcatat tgtattccca cacattatta aaataccgta tatgtattgg ctgcatttgc    240
atgaataata ctacgtgtaa gcccaaaaga acccacgtgt agcccatgca aagttaacac    300
tcacgacccc attcctcagt ctccactata taaacccacc atccccaatc ttaccaaacc    360
caccacacga ctcacaactc gactctcaca ccttaaagaa ccaatcacca ccaaaaa      417
```

<210> SEQ ID NO 313
<211> LENGTH: 1676
<212> TYPE: DNA
<213> ORGANISM: Artificial Sequence
<220> FEATURE:
<223> OTHER INFORMATION: WO0116340-SEQ-006

<400> SEQUENCE: 313

```
tccactatgt aggtcatatc catcatttta attttggggc accattcaat tccatcttgc     60
ctttagggat gtgaatatga acggccaagg taagagaata aaaataatcc aaattaaagc    120
aagagaggcc aagtaagata atccaaatgt acacttgtca tcgccgaaat tagtaaaata    180
cgcggcatat tgtattccca cacattatta aaataccgta tatgtattgg ctgcatttgc    240
atgaataata ctacgtgtaa gcccaaaaga acccacgtgt agcccatgca aagttaacac    300
tcacgacccc attcctcagt ctccactata taaacccacc atccccaatc ttaccaaacc    360
```

```
caccacacga ctcacaactc gactctcaca ccttaaagaa ccaatcacca ccaaaaaatg      420
gcaaagctga tgagcctagc agccgtagca acgcagttcc tcttcctgat cgtggtggac      480
gcatccgtcc gaaccacagt gattatcgac gaggagacca accaaggccg cggtggaggc      540
aaggtggcag ggacagcagc agtctgcgag cagcagatcc agcagcgaga cttcctgagg      600
agctgccagc agttcatgtg ggagaaagtc cagaggggcg gccacagcca ctattacaac      660
cagggccgtg gaggaggcga acagagccag tacttcgaac agctgtttgt gacgacctta      720
agcaattgcg caccgcggtg caccatgcca ggggacttga agcgtgccat cggccaaatg      780
aggcaggaaa tccagcagca gggacagcag cagggacagc agcaggaagt tcagaggtgg      840
atccagcaag ctaaacaaat cgctaaggac ctccccggac agtgccgcac ccagcctagc      900
caatgccagt tccagggcca gcagcaatct gcatggtttt gaaggggtga tcgattatga      960
gatcgtacaa agacactgct aggtgttaag gatggataat aataataata atgagatgaa     1020
tgtgttttaa gttagtgtaa cagctgtaat aaagagagag agagagagag agagagagag     1080
agagagagag agagagagag agaggctgat gaaatgttat gtatgtttct ggttttttaa     1140
aataaatgaa agcacatgct cgtgtggttc tatcgaatta ttcggcggtt cctgtgggaa     1200
aaagtccaga agggcggccg cagctactac tacaaccaag gccgtggagg agggcaacag     1260
agccagcact tcgatagctg ctgcgatgat cttaagcaat tgaggagcga gtgcacatgc     1320
aggggactgg agcgtgcaat cggccagatg aggcaggaca tccagcagca gggacagcag     1380
caggaagttg agaggtggtc ccatcaatct aaacaagtcg ctagggacct tccgggacag     1440
tgcggcaccc agcctagccg atgccagctc caggggcagc agcagtctgc atggttttga     1500
agtggtgatc gatgagatcg tataaagaca ctgctaggtg ttaaggatgg gataataaga     1560
tgtgttttaa gtcattaacc gtaataaaaa gagagagagg ctgatggaat gttatgtatg     1620
tatgtttctt ggttttttaaa attaaatgga aagcacatgc tcgtgtgggt tctatc        1676
```

<210> SEQ ID NO 314
<211> LENGTH: 1121
<212> TYPE: DNA
<213> ORGANISM: Artificial Sequence
<220> FEATURE:
<223> OTHER INFORMATION: WO2002102970-pConlinin-1

<400> SEQUENCE: 314

```
caacggttcc ggcggtatag agttgggtaa ttcgaaaccg cacagatcca attcgattag       60
cagatatttg gtgtctaaat gtttattttg tgatatgttc atgttgaaa tggtggtttc      120 gaaaccaggg acaacgttgg gatctgatag ggtgtcaaag agtattatgg attgggacaa      180
tttcggtcat gagttgcaaa ttcaagtata tcgttcgatt atgaaaattt tcgaagaata      240
tcccatttga gagagtcttt acctcattaa tgttttttaga ttatgaaatt ttatcatagt      300
tcatcgtagt cttttttggtg taaaggctgt aaaaagaaat tgttcacttt tgttttcgtt      360
tatgtgaagg ctgtaaaaga ttgtaaaaga ctattttggt gttttggata aaatgatagt      420
ttttatagat tcttttgctt ttagaagaaa tacatttgaa attttttcca tgttgagtat      480
aaaataccga aatcgattga agatcataga aatatttttaa ctgaaaacaa atttataact      540
gattcaattc tctccatttt tatacctatt taaccgtaat cgattctaat agatgatcga      600
ttttttatat aatcctaatt aaccaacggc atgtatggat aattaaccga tcaactctca      660
cccctaatag aatcagtatt ttccttcgac gttaattgat cctacactat gtaggtcata      720
tccatcgttt taattttttgg ccaccattca attctgtctt gcctttaggg atgtgaatat      780
```

```
gaacggccaa ggtaagagaa taaaaataat ccaaattaaa gcaagagagg ccaagtaaga        840
taatccaaat gtacacttgt cattgccaaa attagtaaaa tactcggcat attgtattcc        900
cacacattat taaaataccg tatatgtatt ggctgcattt gcatgaataa tactacgtgt        960
aagcccaaaa gaacccacgt gtagcccatg caaagttaac actcacgacc ccattcctca       1020
gtctccacta tataaaccca ccatccccaa tctcaccaaa cccaccacac aactcacaac       1080
tcactctcac accttaaaga accaatcacc accaaaaaat g                           1121

<210> SEQ ID NO 315
<211> LENGTH: 1017
<212> TYPE: DNA
<213> ORGANISM: Artificial Sequence
<220> FEATURE:
<223> OTHER INFORMATION: WO2002102970-pConlinin-2

<400> SEQUENCE: 315
aactgatata tattactttg ttggttggtt aatagattaa cctattttc ataaaattat          60 aattaataaa aaaattgagt ttttgaaatt ttgagctttc ttgtattatg ttggaacttc        120
ttgttccatt gcaataaaat cagttataaa aaaattacaa acgaagtgca ctcagtaatt       180
aaccacctca aacagactct cacttactca tagtaggatc aatattttcc ttcggcgata       240
atcgttcctc cactatgtag gtcattattt taatttttgg tgatttatta tgtgtctaat       300
tttaaaaatt aattattcga taaatattac ttttatgtat tgttagtttg ttttggaatt       360
ttaaagtttg agttggtctt aagagttatc ttgtttaacc gatattaatt gtaatactag       420
aaaaataaag cttataaaaa acctttta tt tgtacataga tagggaatc gaagaagaaa      480 aaaattcaaa gtttaaatta tttatttat atttatgtta tttactttaa attttctaat        540
ttctattaaa tattaatcat atacgtcaaa gcgtaatata atgggcacct tacacaaaca       600
ttcgatagaa gggatgtgaa tatgaaggga ccaaagtgag atcttgccct cagctcctag       660
tgcgcctctt gctgttgctc cacgtgttaa tccaagtggc gagaaaagga gaataataac       720
gcaaaaaaac aggccaagta agataatcca agtgtacact tgtcatcgcc aaacttacta       780
aaatacgcgg caaattgtat acccacacat tattaccata ccatatattg gctgcatttg       840
catgtataat actacgtgta agctcagaaa attccacgtg tcgcccatgc aaaattaaca       900
ctcacgaccc attcctaaat ctccactata taaacccccca ctccccca tc ttaccaaacc     960 caccacacaa ctcacaactt agaaaaacca atcataacca aaatggcaaa gctgatg        1017

<210> SEQ ID NO 316
<211> LENGTH: 673
<212> TYPE: DNA
<213> ORGANISM: Artificial Sequence
<220> FEATURE:
<223> OTHER INFORMATION: WO02102970-SEQ-001-cDNA-Conlinin-1

<400> SEQUENCE: 316
gaaaaaccaa tcataaccaa aatggcaaag ctgatgagcc tagcagccgt agcaacggca         60
ttcctcttcc tcattgtggt ggacgcatcc gtccgaacca cagtgatcat cgacgaggac       120
accaaccaag gccgcggtgg ccaaggtggg caaggacagc agcagcaatg cgagaagcag       180
atccaggagc aagactacct gaggagctgc cagcagttcc tgtgggagaa agtccagaag       240
ggcggccgca gctactacta caaccaaggc cgtggaggag gcaacagag ccagcacttc        300 gatagctgct gcgatgatct taagcaattg gaggagcgagt gcacatgcag gggactggag       360
```

```
cgtgcaatcg gccagatgag gcaggacatc cagcagcagg acagcagca ggaagttgag      420 aggtgggtcc agcaagctaa acaagtcgct agggaccttc cgggacagtg cggcacccag      480
cctagccgat gccagctcca ggggcagcag cagtctgcat ggttttgaag tggtgatcga      540
tgagatcgta taaagacact tgctaggtgt taaggatggg ataataagat gtgttttaag      600
tcattaaccc gtaattaaaa ggagagagag cttgatggaa tggtattgat gttccttggg      660
ttttaaaaaa aaa                                                         673
```

<210> SEQ ID NO 317
<211> LENGTH: 21
<212> TYPE: DNA
<213> ORGANISM: Artificial Sequence
<220> FEATURE:
<223> OTHER INFORMATION: WO02102970-UTR-SEQ-001-cDNA-Conlinin-1

<400> SEQUENCE: 317

```
gaaaaaccaa tcataaccaa a                                                 21
```

<210> SEQ ID NO 318
<211> LENGTH: 676
<212> TYPE: DNA
<213> ORGANISM: Artificial Sequence
<220> FEATURE:
<223> OTHER INFORMATION: WO02102970-SEQ-003-cDNA-Conlinin-2

<400> SEQUENCE: 318

```
aagaaccaat caccaccaaa aaatggcaaa gctgatgagc ctggcagccg tagcaacggc       60
attcctcttc ctgatcgtgg tggacgcatc cgtccgaacc acagtgatta tcgacgagga      120
gaccaaccaa ggccgcggtg gaggccaagg tggccaggga cagcagcagt cttgcgagca      180
gcagatccag cagcaagact tcctgaggag ctgccagcag ttcatgtggg agaaagtcca      240
gaggggcggc cgcagccact attacaacca gggccgtgga ggaggcgaac agagccagta      300
cttcgacagc tgttgtgacg accttaagca attgagcacc gggtgcacat gcaggggact      360
tgagcgtgcc atcggccaaa tgaggcagga aatccagcag cagggacagc agcaggaagt      420
tcagaggtgg atccagcaag ctaaacaaat cgctaaggac ctccccggac agtgccgacc      480
cagcctagcc aatgccagtt ccagggccag cagcaatctg catggttttg aagggggtgat      540 cgattatgag atcgtacaaa gacactgcta ggtgttaagg atggataata ataataataa      600
tgagatggat gtgttttaag ttaatgtaac agcttaataa agagagagag agagagagag      660
agagagagtc aaaaaa                                                     676
```

<210> SEQ ID NO 319
<211> LENGTH: 22
<212> TYPE: DNA
<213> ORGANISM: Artificial Sequence
<220> FEATURE:
<223> OTHER INFORMATION: WO02102970-UTR-SEQ-003-cDNA-Conlinin-2

<400> SEQUENCE: 319

```
aagaaccaat caccaccaaa aa                                                22
```

<210> SEQ ID NO 320
<211> LENGTH: 1039
<212> TYPE: DNA
<213> ORGANISM: Artificial Sequence
<220> FEATURE:
<223> OTHER INFORMATION: WO2009130291-SEQ-026-pCnl1

<400> SEQUENCE: 320

```
ttagcagata tttggtgtct aaatgtttat tttgtgatat gttcatgttt gaaatggtgg      60
tttcgaaacc agggacaacg ttgggatctg atagggtgtc aaagagtatt atggattggg     120
acaatttcgg tcatgagttg caaattcaag tatatcgttc gattatgaaa attttcgaag     180
aatatcccat ttgagagagt ctttacctca ttaatgtttt tagattatga aattttatca     240
tagttcatcg tagtcttttt ggtgtaaagg ctgtaaaaag aaattgttca cttttgtttt     300
cgtttatgtg aaggctgtaa aagattgtaa aagactattt tggtgttttg gataaaatga     360
tagtttttat agattctttt gcttttagaa gaaatacatt tgaaattttt tccatgttga     420
gtataaaata ccgaaatcga ttgaagatca tagaaatatt ttaactgaaa acaaatttat     480
aactgattca attctctcca ttttatacc tatttaaccg taatcgattc taatagatga     540
tcgatttttt atataatcct aattaaccaa cggcatgtat tggataatta accgatcaac     600
tctcacccct aatagaatca gtattttcct tcgacgttaa ttgatcctac actatgtagg     660
tcatatccat cgttttaatt tttggccacc attcaattct gtcttgcctt tagggatgtg     720
aatatgaacg gccaaggtaa gagaataaaa ataatccaaa ttaaagcaag agaggccaag     780
taagataatc caaatgtaca cttgtcattg ccaaaattag taaaatactc ggcatattgt     840
attcccacac attattaaaa taccgtatat gtattggctg catttgcatg aataatacta     900
cgtgtaagcc caaagaacc cacgtgtagc ccatgcaaag ttaacactca cgaccccatt     960
cctcagtctc cactatataa acccaccatc cccaatctca ccaaacccac cacacaactc    1020
acaactcact ctcacacct                                                 1039

<210> SEQ ID NO 321
<211> LENGTH: 109
<212> TYPE: DNA
<213> ORGANISM: Artificial Sequence
<220> FEATURE:
<223> OTHER INFORMATION: WO2009130291-SEQ-015-part

<400> SEQUENCE: 321
cccaccatcc ccaatctcac caaacccacc acacaactca caactcactc tcacaccta      60 aagaaccaat caccaccaaa aaaccatggg aaaaggatct gagggaaga                109

<210> SEQ ID NO 322
<211> LENGTH: 1080
<212> TYPE: DNA
<213> ORGANISM: Artificial Sequence
<220> FEATURE:
<223> OTHER INFORMATION: WO2009130291-SEQ-016-reverse part

<400> SEQUENCE: 322
ttagcagata tttggtgtct aaatgtttat tttgtgatat gttcatgttt gaaatggtgg      60
tttcgaaacc agggacaacg ttgggatctg atagggtgtc aaagagtatt atggattggg     120
acaatttcgg tcatgagttg caaattcaag tatatcgttc gattatgaaa attttcgaag     180
aatatcccat ttgagagagt ctttacctca ttaatgtttt tagattatga aattttatca     240
tagttcatcg tagtcttttt ggtgtaaagg ctgtaaaaag aaattgttca cttttgtttt     300
cgtttatgtg aaggctgtaa aagattgtaa aagactattt tggtgttttg gataaaatga     360
tagtttttat agattctttt gcttttagaa gaaatacatt tgaaattttt tccatgttga     420
gtataaaata ccgaaatcga ttgaagatca tagaaatatt ttaactgaaa acaaatttat     480
aactgattca attctctcca ttttatacc tatttaaccg taatcgattc taatagatga     540
```

```
tcgatttttt atataatcct aattaaccaa cggcatgtat tggataatta accgatcaac    600
tctcacccct aatagaatca gtattttcct tcgacgttaa ttgatcctac actatgtagg    660
tcatatccat cgttttaatt tttggccacc attcaattct gtcttgcctt tagggatgtg    720
aatatgaacg gccaaggtaa gagaataaaa ataatccaaa ttaaagcaag agaggccaag    780
taagataatc caaatgtaca cttgtcattg ccaaaattag taaaatactc ggcatattgt    840
attcccacac attattaaaa taccgtatat gtattggctg catttgcatg aataatacta    900
cgtgtaagcc caaaagaacc cacgtgtagc ccatgcaaag ttaacactca cgaccccatt    960
cctcagtctc cactatataa acccaccatc cccaatctca ccaaaccacc cacacaactc   1020
acaactcact ctcacacctt aaagaaccaa tcaccaccaa aaaaccatgg gaaaaggatc   1080

<210> SEQ ID NO 323
<211> LENGTH: 635
<212> TYPE: DNA
<213> ORGANISM: Artificial Sequence
<220> FEATURE:
<223> OTHER INFORMATION: AJ414732-Truska-Linum mRNA Cnl1

<400> SEQUENCE: 323
aagaaccaat caccaccaaa aaatggcaaa gctgatgagc ctggcagccg tagcaacggc     60
attcctcttc ctgatcgtgg tggacgcatc cgtccgaacc acagtgatta tcgacgagga    120
gaccaaccaa ggccgcggtg gaggccaagg tggccaggga cagcagcagt cttgcgagca    180
gcagatccag cagcaagact tcctgaggag ctgccagcag ttcatgtggg agaaagtcca    240
gaggggcggc cgcagccact attacaacca gggccgtgga ggaggcgaac agagccagta    300
cttcgacagc tgttgtgacg accttaagca attgagcacc gggtgcacat gcaggggact    360
tgagcgtgcc atcggccaaa tgaggcagga atccagcag cagggacagc agcaggaagt    420
tcagaggtgg atccagcaag ctaaacaaat cgctaaggac ctccccggac agtgccgcac    480
ccagcctagc caatgccagt tccagggcca gcagcaatct gcatggtttt gaaggggtga    540
tcgattatga gatcgtacaa agacactgct aggtgttaag gatggataat aataataata    600
atgagatgga tgtgttttaa gttaatgtaa cagct                               635

<210> SEQ ID NO 324
<211> LENGTH: 88
<212> TYPE: DNA
<213> ORGANISM: Artificial Sequence
<220> FEATURE:
<223> OTHER INFORMATION: promotor p1039+38 UTR

<400> SEQUENCE: 324
ccccaatctc accaaaccca ccacacaact cacaactcac tctcacacct tctagaggat     60
ctgatatctg cggccgcggc gcgccacc                                       88

<210> SEQ ID NO 325
<211> LENGTH: 38
<212> TYPE: DNA
<213> ORGANISM: Artificial Sequence
<220> FEATURE:
<223> OTHER INFORMATION: promotor p1039+38 differing part

<400> SEQUENCE: 325
tctagaggat ctgatatctg cggccgcggc gcgccacc                             38

<210> SEQ ID NO 326
<211> LENGTH: 52
```

<212> TYPE: DNA
<213> ORGANISM: Artificial Sequence
<220> FEATURE:
<223> OTHER INFORMATION: promotor p1039+2 UTR

<400> SEQUENCE: 326

```
ccccaatctc accaaaccca ccacacaact cacaactcac tctcacacct cc          52
```

<210> SEQ ID NO 327
<211> LENGTH: 1064
<212> TYPE: DNA
<213> ORGANISM: Artificial Sequence
<220> FEATURE:
<223> OTHER INFORMATION: SEQ ID NO: 1 plus A

<400> SEQUENCE: 327

```
ttagcagata tttggtgtct aaatgtttat tttgtgatat gttcatgttt gaaatggtgg    60
tttcgaaacc agggacaacg ttgggatctg atagggtgtc aaagagtatt atggattggg   120
acaatttcgg tcatgagttg caaattcaag tatatcgttc gattatgaaa attttcgaag   180
aatatcccat ttgagagagt ctttacctca ttaatgtttt tagattatga aattttatca   240
tagttcatcg tagtcttttt ggtgtaaagg ctgtaaaaag aaattgttca cttttgtttt   300
cgtttatgtg aaggctgtaa aagattgtaa aagactattt tggtgttttg gataaaatga   360
tagtttttat agattctttt gcttttagaa gaaatacatt tgaaattttt tccatgttga   420
gtataaaata ccgaaatcga ttgaagatca tagaaatatt ttaactgaaa acaaatttat   480
aactgattca attctctcca tttttatacc tatttaaccg taatcgattc taatagatga   540
tcgattttt atataatcct aattaaccaa cggcatgtat tggataatta accgatcaac   600
tctcacccct aatagaatca gtattttcct tcgacgttaa ttgatcctac actatgtagg   660
tcatatccat cgttttaatt tttggccacc attcaattct gtcttgcctt tagggatgtg   720
aatatgaacg gccaaggtaa gagaataaaa ataatccaaa ttaaagcaag agaggccaag   780
taagataatc caaatgtaca cttgtcattg ccaaaattag taaaatactc ggcatattgt   840
attcccacac attattaaaa taccgtatat gtattggctg catttgcatg aataatacta   900
cgtgtaagcc caaagaaacc cacgtgtagc ccatgcaaag ttaacactca cgaccccatt   960
cctcagtctc cactatataa acccaccatc cccaatctca ccaaacccac cacacaactc  1020
acaactcact ctcacacctt aaagaaccaa tcaccaccaa aaaa                  1064
```

<210> SEQ ID NO 328
<211> LENGTH: 1072
<212> TYPE: DNA
<213> ORGANISM: Artificial Sequence
<220> FEATURE:
<223> OTHER INFORMATION: SEQ ID NO: 1 Kozak ATG

<400> SEQUENCE: 328

```
ttagcagata tttggtgtct aaatgtttat tttgtgatat gttcatgttt gaaatggtgg    60
tttcgaaacc agggacaacg ttgggatctg atagggtgtc aaagagtatt atggattggg   120
acaatttcgg tcatgagttg caaattcaag tatatcgttc gattatgaaa attttcgaag   180
aatatcccat ttgagagagt ctttacctca ttaatgtttt tagattatga aattttatca   240
tagttcatcg tagtcttttt ggtgtaaagg ctgtaaaaag aaattgttca cttttgtttt   300
cgtttatgtg aaggctgtaa aagattgtaa aagactattt tggtgttttg gataaaatga   360
tagtttttat agattctttt gcttttagaa gaaatacatt tgaaattttt tccatgttga   420
```

```
gtataaaata ccgaaatcga ttgaagatca tagaaatatt ttaactgaaa acaaatttat      480
aactgattca attctctcca tttttatacc tatttaaccg taatcgattc taatagatga      540 tcgattttt  atataatcct aattaaccaa cggcatgtat tggataatta accgatcaac      600
tctcacccct aatagaatca gtattttcct tcgacgttaa ttgatcctac actatgtagg      660
tcatatccat cgttttaatt tttggccacc attcaattct gtcttgcctt tagggatgtg      720
aatatgaacg gccaaggtaa gagaataaaa ataatccaaa ttaaagcaag agaggccaag      780
taagataatc caaatgtaca cttgtcattg ccaaaattag taaaatactc ggcatattgt      840
attcccacac attattaaaa taccgtatat gtattggctg catttgcatg aataatacta      900
cgtgtaagcc caaaagaacc cacgtgtagc ccatgcaaag ttaacactca cgaccccatt      960
cctcagtctc cactatataa acccaccatc cccaatctca ccaaacccac cacacaactc     1020
acaactcact ctcacacctt aaagaaccaa tcaccaccaa aaaaccatgg ga             1072
```

GENE EXPRESSION OR ACTIVITY ENHANCING ELEMENTS

CROSS-REFERENCE TO RELATED APPLICATIONS

This application is a National Stage application of International Application No. PCT/IB2014/062816 filed Jul. 3, 2014, which claims priority under 35 U.S.C. § 119 to European Patent Application No. 13175398.0, filed Jul. 5, 2013, which is incorporated herein by reference in its entirety. The present invention relates to transgenic nucleic acids, expression cassettes, vectors, plant cells, plant organs and plants. The invention also relates to methods for increasing expression or activity of a target gene, particularly in a plant cell or plant organ, and also to uses of recombinant nucleic acids and expression cassettes to increase expression or activity of a target gene or for manufacturing of a vector, plant cell, plant organ or plant. Incidentally, the invention relates to enhancers for achieving increased expression or activity of a target gene, particularly in a plant cell or plant organ, when operably linked to a promoter functional in such plant cell, plant organ or plant. The invention is described herein with reference to the technical field of production of polyunsaturated fatty acids (PUFAs), without being limited to this technical field.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "75088_SubSeqListing.txt" created on Sep. 2, 2016, and is 203,780 bytes in size. The sequence listing contained in this .txt file is part of the specification and is hereby incorporated by reference herein in its entirety.

For the production of desired molecules in plant cells, e.g. PUFAs, it is frequently required to express a target gene heterologous to the plant cell, or to overexpress a target gene naturally found in said plant cell.

WO 02/102970 discloses two Conlinin genes (Conlinin 1 and 2) and their respective promoter regions obtained from flax which can be utilized to improve seed traits, modify the fatty acid composition of seed oil and amino acid composition of seed storage protein, and produce bioactive compounds in plant seeds. The document also mentions methods based on using theses promoters to direct seed-specific expression of a gene of interest, which for example might be involved in lipid biosynthesis like e.g. acyl carrier protein, saturases, desaturases, and elongases.

WO 01/16340 discloses methods allowing the seed-specific expression of heterologous genes in flax and other plants. Of particular interest were promoters associated with fatty acid metabolism, such as acyl carrier protein, saturases, desaturases, elongases and the like.

Promoters function to initiate transcription of DNA into mRNA. Generally, transcribed mRNA comprises a translated region, also called a gene sequence, and upstream thereof an untranslated region. This untranslated region is generally believed not to have any profound influence on the translation of the gene sequence or the stability of the mRNA. Thus, the region between a promoter TATA box and a start codon is normally treated as being unimportant. For example, WO 01/16340 discloses a putative conlinin promoter, but the only GUS expression construct disclosed (herein reproduced as SEQ ID NO. 311) in this document is shortened on the 3' side of the putative promoter sequence.

Finding enhancer genetic elements which can improve the expression or activity of a target gene in a cell of interest is an ongoing demand for the development of improved agronomic traits. Specifically, oilseed crops producing modified fatty acid composition of the seed oil is a demand which makes the identification of further enhancing elements necessary; preferably, promoters are needed further improving the expression of genes of the fatty acid biosynthesis.

It has now been unexpectedly found that certain nucleic acids can improve expression or activity of a target or reporter gene when the gene is operably linked to a promoter.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list.

To overcome, reduce or mitigate the aforementioned disadvantages and/or to further the aforementioned goals and/or improve the aforementioned advantages, the invention provides a recombinant nucleic acid comprising a target gene and an untranslated region adjacent to the target gene, wherein the untranslated region comprises an enhancer of at least 18 consecutive nucleotides, wherein at least 14 nucleotides are adenosine or cytidine.

Describing the invention from another perspective, the invention provides a recombinant nucleic acid comprising a plant promoter and an untranslated region adjacent to the promoter, wherein the untranslated region comprises an enhancer of at least 18 consecutive nucleotides, wherein at least 14 nucleotides are adenosine or cytidine.

According to the invention is also provided an enhancer comprising
a) a CCAAT-Box comprising SEQ ID NO. 100, preferably comprising a sequence having at least 90% identity to SEQ ID NO. 101 and comprising SEQ ID NO. 100, and more preferably SEQ ID NO. 101, and/or
b) a Dof1/MNB1a binding site comprising SEQ ID NO. 102, preferably comprising a sequence having at least 90% identity to SEQ ID NO. 103 and comprising SEQ ID NO. 102, and more preferably SEQ ID NO. 103.

Further according to the invention is provided an expression cassette comprising a recombinant nucleic acid according to the invention, and, if not already comprised in the recombinant nucleic acid, a plant promoter, wherein the promoter comprises a TATA-box, preferably comprising SEQ ID NO. 108, more preferably comprising a sequence having at least 90% identity to SEQ ID NO. 107 and comprising SEQ ID NO. 108, and more preferably comprising SEQ ID NO. 107, and a CPRF factor binding site, preferably comprising SEQ ID NO. 114, more preferably comprising a sequence having at least 90% identity to SEQ ID NO. 113 and comprising SEQ ID NO. 114, and more preferably comprising SEQ ID NO. 113, and a TCP class I transcription factor binding site, preferably comprising SEQ ID NO. 116, more preferably comprising a sequence having at least 90% identity to SEQ ID NO. 115 and comprising SEQ ID NO. 116, and more preferably comprising SEQ ID NO. 115, and a bZIP protein G-Box binding factor 1 binding site, preferably comprising SEQ ID NO. 118, more preferably comprising a sequence having at least 90% identity to SEQ ID NO. 117 and comprising SEQ ID NO. 118, and more preferably comprising SEQ ID NO. 117.

The invention also provides a vector comprising the expression cassette of the present invention.

Further, the invention provides plants, plant organs or plant cells comprising a recombinant nucleic acid according to the present invention or an expression cassette according to the present invention.

The invention also teaches a method of increasing expression or activity of a target gene, comprising the steps of
i) providing, upstream of the target gene, an untranslated region and a plant promoter to obtain an expression cassette according to any of claims 9 to 11, and
ii) introducing the expression cassette into a plant cell to allow expression of the target gene.

According to the invention, an enhancer as described herein according to the invention or an expression cassette according to the invention can be used for
increasing expression or activity of a target gene,
producing a vector according to claim 15, or for
producing a plant, plant organ or plant cell according to claim 16.

The invention is hereinafter described in more detail. Unless specifically stated otherwise, the definitions of the chapter "definitions" apply throughout all of this text.

DETAILED DESCRIPTION OF THE INVENTION

One way to look at the invention is to understand that according to the present invention a recombinant nucleic acid is provided, said nucleic acid comprising a target gene and an untranslated region adjacent to the target gene. According to the invention, the untranslated region comprises an enhancer of at least 18 consecutive nucleotides, wherein at least 14 nucleotides are adenosine or cytidine.

The inventors have found that a particular section of a nucleic acid—preferred embodiments of which will be described hereinafter—functions as an enhancer in host cells, particularly plant cells, that is, activity of a target or reporter gene product can be increased by operably linking the reporter gene with the enhancer. The enhancer and the target gene are thus functionally linked, i.e. the enhancer influences or modifies transcription or translation of the target gene. Increase of activity by the enhancer of the present invention can be achieved by an increase in production of mRNA by the host cell, or can be achieved by an increased rate of translation of the mRNA, e.g. by improving the binding of ribosomes to the mRNA, or by protection of the mRNA against degradation. The invention, however, is not limited by any of these mechanisms.

The enhancer is preferably heterologous to the target gene and/or a promoter driving expression of the target gene. Thus, the following sequences are not part of the present invention: SEQ ID NO. 311 to 323 which are particularly comprised in WO0116340, WO2002102970, WO2009130291

The target gene can be any gene whose activity in a plant is desired to be increased. Increase is determined by comparison of the activity of the target gene being expressed in the same type of cell, e.g. seed cells, root cells and so on, without being functionally linked to the enhancer. Examples of useful target genes are fatty acid desaturase and fatty acid elongase genes, particularly d12d15Des(Ac_GA) (cf. WO 2007042510), d12Des(Ce_GA) (cf. US 2003172398), d12Des(Co_GA2) (cf. WO 200185968), d12Des(Fg) (cf. WO 2007133425), d12Des(Ps_GA) (cf. WO 2006100241), d12Des(Tp_GA) (cf. WO 2006069710), d6Des(Ol_febit) (cf. WO 2008040787), d6Des(Ol_febit)2 (cf. WO 2008040787), d6Des(Ot_febit) (cf. WO 2008040787), d6Des(Ot_GA) (cf. WO 2005083093), d6Des(Ot_GA2) (cf. WO 2005083093), d6Des(Pir) (cf. WO 2002026946), d6Des (Pir_GAI) (cf. WO 2002026946), d6Des(Plu) (cf. WO 2007051577), d6Elo(Pp_GA) (cf. WO 2001059128), d6Elo (Pp_GA2) (cf. WO 2001059128), d6Elo(Pp_GA3) (cf. WO 2001059128), d6Elo(Tp_GA) (cf. WO 2005012316) and d6Elo(Tp_GA2) (cf. WO 2005012316).

The enhancer is comprised in or forms an untranslated region adjacent to the target gene. For the present invention, the untranslated region is considered adjacent to the target gene if no translated region other than a region belonging to the target gene is located between the untranslated region comprising or consisting of the enhancer and the target gene. Thus, for example, in cases where the target gene comprises several exons, the untranslated region is considered to be located adjacent to the target gene when the untranslated region us located upstream of the first exon such that no translated region is located between the untranslated region comprising or being the enhancer and the first exon. For the sake of the present invention, exons are counted in 5' to 3' direction, so that the first exon is the one comprising the start codon of the target gene.

It is to be noted that the untranslated region may comprise, in addition to the enhancer of the present invention, further functional units including transcription or translation enhancing sequences. Regardless of whether the untranslated region comprises such further functional units the untranslated region is, for the purposes of the present invention, located adjacent to the target gene under the aforementioned conditions, that is, no translated region is located between the untranslated region and the target gene. It is preferred but not required that the enhancer of the present invention as such is adjacent to the translation start codon of the target gene.

The untranslated region may or may not be transcribed in a cell. In particular, the untranslated region may comprise translation enhancing sequences or mRNA stability enhancing sequences which are transcribed but not translated.

The untranslated region and the enhancer are preferably located upstream of the target gene. If the nucleobases of the target gene were numbered starting from 1 for the 5'-most nucleobase of the first translated codon (normally "A" of the codon "ATG" of a DNA sequence corresponding to "AUG" of the target gene mRNA) and incrementing the number in 3' direction, then nucleobases of the enhancer would be designated by negative numbers, as the untranslated region is preferably located in 5' direction of the target gene.

It is particularly preferred that the untranslated region comprises, in 5' to 3' direction, the enhancer of the present invention and one or more further functional units, particularly one or more NEENAs or RENAs as described for example in WO2013038294.

At the junction of the untranslated region and the target gene preferably a Kozak sequence is located. Preferably a Kozak sequence comprises the nucleotide sequence "ATGG", wherein the "ATG" is the start codon of the target gene. Kozak sequences facilitate the translation of the target gene. The skilled person can adapt the exact nucleotide sequence of the Kozak sequence according to the cell he would like to use, and also according to the expression needs of the target gene. For example, the skilled person could create all 256 variants of the sequence "NNATGNN", where "N" designates any nucleobase "A", "C", "G" or "T", and clone these variants in the cell he intends to use. By analyzing the activity of the target gene he will find the Kozak sequence optimal for his needs. The number of variants can be significantly reduced if the second amino acid is important for the functioning of the target gene, because in such cases at least the first nucleotide after (that is, in 3' direction of) the "ATG" start codon is limited to one or two alternatives. A preferred Kozak sequence is "CCATGG", as this sequence is also recognized by the restriction enzymes NcoI or Bsp19I, thus facilitating cloning of the target gene adjacent to the untranslated region. For the purposes of the present invention the leading "CC" nucleobases are considered to belong to the untranslated region.

The enhancer of the present invention comprises or consists of at least 18 consecutive nucleotides. The enhancer is thus not interrupted by any other element, be it a functional element or a non-functional element. As is described below, the enhancer and also the untranslated region can be substantially longer than 18 nucleotides, and preferably the enhancer consists of 57 or 58 consecutive nucleotides as described below.

The enhancer of the present invention has several beneficial features. For one, the enhancer sequence is short compared to other expression inducing sequences like NEENAs as described for example in WO2011023537, WO 2011023539, WO2011023800 or WO2013/005152. The enhancer thus can be incorporated with ease also in such constructs which are under severe size limitation, e.g. due to the number and/or size of genes to be incorporated in the respective construct.

Also, the enhancer has been shown to be active for a huge number of different target genes, particularly for desaturase and elongase genes of highly disparate sequence. Thus, the present invention provides a universally applicable enhancer for use in plants.

The enhancer of the present invention also is functional not only in *Arabidopsis* but also in other plants, particularly crop plants as described below, particularly in plant cells of the Brassicaceae family, even more in plant cells of genus *Brassica* and even more in particular in cells of *Brassica napus*, *Brassica oleracea*, *Brassica carinata*, *Brassica nigra*, *Brassica juncea* and *Brassica rapa*.

Another advantage of the enhancer of the present invention is that it is useful for increasing expression or activity of a target gene expressed under the control of a seed-specific promoter. Particularly the enhancer of the present invention can be combined with a Conlinin-type promoter to achieve seed-specific expression as described in WO2002102970. However, the enhancer of the present invention can also be combined with other promoters to increase expression or activity of a target gene.

The untranslated region or enhancer of the present invention preferably comprises any nucleotide sequence according to SEQ ID NO. 84, 85, 86, 87, 88 or 89. It is particularly preferred that the untranslated region or enhancer comprises two copies of one or more of the aforementioned sequences. The nucleotide sequences according to SEQ ID NO. 84, 85, 86, 87, 88 or 89 can be present in the untranslated region or enhancer in an overlapping form. For example, a nucleotide sequence of two cytidines followed by five adenosine nucleobases would simultaneously embody the sequences according to SEQ ID NO. 85, 86 and 87.

It is particularly preferred that the enhancer comprises the nucleotide sequence according to SEQ ID NO. 84. This sequence comprises the core motif SEQ ID NO. 100 of the plant CCAAT-box found in plant promoters. Thus, the presence of the sequence according to SEQ ID NO. 84 is particularly suitable for achieving the effects of transcription factor binding to this sequence. It is particularly preferred that the enhancer or untranslated region comprises two copies of SEQ ID NO. 84 separated by approximately 5 turns in a DNA helix, that is, a DNA sequence comprising the enhancer or untranslated region preferably comprises two instances of SEQ ID NO. 84 separated by 52, 53, 54, 55, 56, 57 or 58 nucleotides counting from the 1st nucleotide of the first (i.e. 5'-most) instance of SEQ ID NO. 84 to the last nucleotide in 5' direction in front of the second instance of SEQ ID NO. 84, preferably they are separated by 54, 55 or 56 nucleotides and most preferably by 55 nucleotides. For example, in the nucleotide sequence according to SEQ ID NO. 143 the instances of SEQ ID NO. 84 of the untranslated region are separated by 55 nucleotides.

It is also particularly preferred that the enhancer is functionally linked to a promoter such that the enhancer can be transcribed in a cell. This aspect of the invention is described in greater detail below. In such cases it is particularly preferred that the enhancer comprises at least one copy or instance of SEQ ID NO. 84.

According to the present invention, the enhancer preferably comprises or consists of 18 consecutive nucleotides, of which at least 15, preferably at least 17 nucleotides are adenosine or cytidine, and most preferably at most 1 nucleotide is neither adenosine nor cytidine. Preferred embodiments of such enhancers are described in SEQ ID NO. 20 to SEQ ID NO. 45. Of these, the sequences according to SEQ ID NO. 20, 22, 25, 28, 34, 35 and 36 are preferred as they comprise an instance of SEQ ID NO. 84. Particularly preferred is the sequence according to SEQ ID NO. 25, as this sequence comprises all of SEQ ID NO. 84, 100 and 101 and thus closely resembles a plant CCAAT box.

It is also preferred that the enhancer comprises or consists of 21 consecutive nucleotides, of which at least 15, preferably at least 16 nucleotides are adenosine or cytidine, and most preferably at most 2 nucleotides are neither adenosine nor cytidine. A correspondingly preferred sequence is given by SEQ ID NO. 95 and by the last 21 nucleotides of any of SEQ ID NO. 46, 96 161-170, 221-230, 276-285 and 301-310.

It is also preferred that the enhancer comprises or consists of 22 consecutive nucleotides, of which at least 16, preferably at least 17 nucleotides are adenosine or cytidine, and most preferably at most 2 nucleotides are neither adenosine nor cytidine. A preferred instance of such sequence is given by the last 22 nucleotides of any of SEQ ID NO. 46, 96 161-170, 221-230, 276-285 and 301-310.

It is also preferred that the enhancer comprises or consists of 24 consecutive nucleotides, of which at least 18, preferably at least 19 nucleotides are adenosine or cytidine, and most preferably at most 3 nucleotides are neither adenosine nor cytidine. A preferred instance of such sequence is given by the last 24 nucleotides of any of SEQ ID NO. 46, 96 161-170, 221-230, 276-285 and 301-310.

It is also preferred that the enhancer comprises or consists of 36 consecutive nucleotides, of which at least 27, preferably at least 28 nucleotides are adenosine or cytidine, and most preferably at most 6 nucleotides are neither adenosine nor cytidine. A preferred instance of such sequence is given by SEQ ID NO. 96 and by the last 36 nucleotides of any of SEQ ID NO. 46, 161-170, 221-230, 276-285 and 301-310.

It is also preferred that the enhancer comprises or consists of 57 consecutive nucleotides, of which at least 42, preferably at least 45 nucleotides are adenosine or cytidine, and most preferably at most 8 nucleotides are neither adenosine nor cytidine. Preferred examples of such enhancer are given by any of SEQ ID NO. 46 to 83, or the last 57 nucleotides of any of SEQ ID NO. 46, 96 161-170, 221-230, 276-285 and 301-310.

It is also preferred that the enhancer comprises or consists of 83 consecutive nucleotides, of which at least 62, preferably at least 65 nucleotides are adenosine or cytidine, and most preferably at most 8 nucleotides are neither adenosine nor cytidine. A preferred instance of such sequence is given by the last 83 nucleotides of any of SEQ ID NO. 161-170, 221-230, 276-285 and 301-310. Further preferred instances of such sequence are given by the last (i.e. counting from the 3' end) 83 nucleotides of a combination of SEQ ID NO. 140 and any of SEQ ID NO. 46 to 83, wherein the sequence of SEQ ID NO. 140 is fused immediately to the 5' end of any of SEQ ID NO. 46 to 83.

The sequences of SEQ ID NO. 161-170, 221-230, 276-285 and 301-310 are, for each group, sorted in descending order of preference. For example SEQ ID NO. 161 is more preferred than SEQ ID NO. 162, and SEQ ID NO. 221 is more preferred than SEQ ID NO. 230. The groups, however, are sorted in ascending order of preference, such that for example SEQ ID NO. 221 is more preferred than SEQ ID NO. 161 or SEQ ID NO. 170.

Among the sequences disclosed in the present application, the sequences of SEQ ID NO. 161-170, 221-230, 276-285 and 301-310 are special, because these sequences were checked not to affect major known or predicted cis-regulatory elements of the sequence according to SEQ ID NO. 1. The cis-regulatory elements that were checked comprise those mentioned below in greater detail, i.e. TATA-box, CPRF factor binding site, TCP class I transcription factor binding site, bZIP protein G-Box binding factor 1 binding site, Ry motif, prolamin box, Cis-element as in GAPDH promoters conferring light inducibility, SBF-1 binding site and Sunflower homeodomain leucine-zipper protein Hahb-4 binding site. This approach has been demonstrated to provide functional variants of the seed-specific p-PvARC5, the p-VfSBP and the p-BnNapin promoters in a GUS reporter gene assay and is described in more details in WO2012077020, which is incorporated herein by reference.

According to the present invention it is thus preferred if the enhancer comprises any sequence according to
a) any of SEQ ID NO. 20 to SEQ ID NO. 45, or any sequence according to
b) the last 18, 21, 22, 24, 36 or 57 nucleotides of any of SEQ ID NO.46-83, 161-170, 221-230, 276-285 or 301-310, or
c) any of SEQ ID NO. 90, 91, 92, 93, 94, 95, 96, 97, 98, 99, 100, 101, 102, 103 or 137, or
d) a sequence according to b) or c) with 1 additional base inserted therein.

It is to be understood that preferably regardless of the number of A, C, G and T nucleotides an enhancer is considered an enhancer of the present invention if it consists of or comprises SEQ ID NO. 137.

Another way to look at the invention is to understand that according to the present invention a recombinant nucleic acid is provided, said nucleic acid comprising a plant promoter and an untranslated region adjacent to the promoter, wherein the untranslated region comprises an enhancer of the present invention. As described above, the enhancer consists of or comprises at least 18 consecutive nucleotides, wherein at least 14 nucleotides are adenosine or cytidine. Preferred enhancers and untranslated regions are described particularly above in greater detail. As described above, the enhancer is preferably heterologous to the promoter.

According to the present invention the untranslated region or enhancer is adjacent to a promoter as long as no translated region is present between the 3'-most TATA box of the promoter and the 5' end of the untranslated region or enhancer. Preferably, the enhancer is located immediately contiguous to the promoter 3' end, or is preferably separated from the promoter 3' end by at most 56 nucleotides, even more preferably by at most 39 nucleotides and even more preferably by at most 17 nucleotides. A preferred spacer sequence of 17 nucleotides length is given in SEQ ID NO. 140.

The promoter of the present invention preferably is a minimal promoter, and thus preferably consists only of the minimum length and nucleotide sequence required to achieve expression of a target gene functionally linked to said promoter and enhancer or untranslated region. This way the advantages described above due to the short length of the enhancer of the present invention are preserved. Particularly, a combination of a minimal promoter and the enhancer of the present invention allows to provide an expression cassette as described below that is not much longer than the target gene. Thus, the combination of a minimal promoter and the enhancer of the present invention allows cloning of long nucleotide sequences also in vectors and using transformation means which are restricted in size. This is particularly important when trying to establish, in plants, new metabolic pathways which require the introduction of multiple genes. Such pathways are for example described in WO2005083093, WO2007017419, WO2007042510 and WO2007096387.

The promoter can also be minimal in the sense that it consists only of the minimum length an nucleotide sequence required to function as a promoter under specific circumstances, e.g. driving expression of a gene functionally linked to said promoter only in specific plant tissues, developmental stages or under specific environmental conditions like heat stress or attempted pathogen infection. The promoter can, according to the present invention, also be longer or comprise more transcription influencing elements (e.g. transcription factor binding sites) than a minimal promoter. Suitable promoters are described e.g. in WO2002102970, WO2009077478, WO2010000708 and WO2012077020, the contents of which are incorporated herein by reference.

A preferred promoter comprises a TATA-box, preferably comprising SEQ ID NO. 108, more preferably comprising a sequence having at least 89% identity to SEQ ID NO. 107 and comprising SEQ ID NO. 108, and more preferably comprising SEQ ID NO. 107. Such TATA box facilitates onset of transcription particularly in plant cells. As the TATA box at least comprises the core motif SEQ ID NO. 108 of plant TATA boxes, at least a minimal activity of the promoter in plant can be achieved. If the promoter does not comprise the exact sequence SEQ ID NO. 107, then the promoter preferably comprises at least a sequence similar thereto. Such similar sequence contains the exact sequence SEQ ID NO. 108 and has a minimum of 89% identity to SEQ ID NO. 107 and thus preferably differs by at most two nucleotides from the sequence of SEQ ID NO. 107, and even more preferably differs by at most one nucleotide from the sequence of SEQ ID NO 107.

A preferred promoter comprises a CPRF factor binding site, preferably comprising SEQ ID NO. 114, more preferably comprising a sequence having at least 90% identity to SEQ ID NO. 113 and comprising SEQ ID NO. 114, and more preferably comprising SEQ ID NO. 113. Where such promoter does not comprise the exact sequence SEQ ID NO. 113, it comprises a sequence differing from SEQ ID NO. 113 by at most one nucleotide and contains in this sequence the exact sequence SEQ ID NO. 114.

A preferred promoter comprises a TCP class I transcription factor binding site, preferably comprising SEQ ID NO. 116, more preferably comprising a sequence having at least 90% identity to SEQ ID NO. 115 and comprising SEQ ID NO. 116, and more preferably comprising SEQ ID NO. 115. Where such promoter does not comprise the exact sequence SEQ ID NO. 115, it comprises a sequence differing from SEQ ID NO. 115 by at most one nucleotide and contains in this sequence the exact sequence SEQ ID NO. 116.

A preferred promoter comprises a bZIP protein G-Box binding factor 1 binding site, preferably comprising SEQ ID NO. 118, more preferably comprising a sequence having at least 85% identity to SEQ ID NO. 117 and comprising SEQ ID NO. 118, and more preferably comprising SEQ ID NO. 117. If the promoter does not comprise the exact sequence SEQ ID NO. 117, then the promoter preferably comprises at least a sequence similar thereto. Such similar sequence contains the exact sequence SEQ ID NO. 118 and has a minimum of 85% identity to SEQ ID NO. 117 and thus preferably differs by at most three nucleotides from the sequence of SEQ ID NO. 117, more preferably differs by at most two nucleotides from the sequence of SEQ ID NO 117 and even more preferably differs by at most one nucleotide from the sequence of SEQ ID NO 117.

A preferred promoter comprises a Ry motif, preferably comprising SEQ ID NO. 110, more preferably comprising a sequence having at least 88% identity to SEQ ID NO. 109 and comprising SEQ ID NO. 110, and more preferably comprising SEQ ID NO. 109. Where such promoter does not comprise the exact sequence SEQ ID NO. 109, contains the exact sequence SEQ ID NO. 110 and has a minimum of 88% identity to SEQ ID NO. 109 and thus preferably differs by at most three nucleotides from the sequence of SEQ ID NO. 109, more preferably differs by at most two nucleotides from the sequence of SEQ ID NO 109 and even more preferably differs by at most one nucleotide from the sequence of SEQ ID NO 109.

A preferred promoter comprises a prolamin box, preferably comprising SEQ ID NO. 112, more preferably comprising a sequence having at least 90% identity to SEQ ID NO. 111 and comprising SEQ ID NO. 112, and more preferably comprising SEQ ID NO. 111. Where such promoter does not comprise the exact sequence SEQ ID NO. 111, contains the exact sequence SEQ ID NO. 112 and has a minimum of 90% identity to SEQ ID NO. 111 and thus preferably differs by at most two nucleotides from the sequence of SEQ ID NO 111 and even more preferably differs by at most one nucleotide from the sequence of SEQ ID NO 111.

A preferred promoter comprises a Cis-element as in GAPDH promoters conferring light inducibility, preferably comprising SEQ ID NO. 120, more preferably comprising a sequence having at least 90% identity to SEQ ID NO. 119 and comprising SEQ ID NO. 120, and more preferably comprising SEQ ID NO. 119. Where such promoter does not comprise the exact sequence SEQ ID NO. 119, contains the exact sequence SEQ ID NO. 120 and has a minimum of 90% identity to SEQ ID NO. 119 and thus preferably differs by at most two nucleotides from the sequence of SEQ ID NO 119 and even more preferably differs by at most one nucleotide from the sequence of SEQ ID NO 119.

A preferred promoter comprises a SBF-1 binding site, preferably comprising SEQ ID NO. 122, more preferably comprising a sequence having at least 90% identity to SEQ ID NO. 121 and comprising SEQ ID NO. 122, and more preferably comprising SEQ ID NO. 121. Where such promoter does not comprise the exact sequence SEQ ID NO. 121, contains the exact sequence SEQ ID NO. 122 and has a minimum of 90% identity to SEQ ID NO. 121 and thus preferably differs by at most two nucleotides from the sequence of SEQ ID NO 121 and even more preferably differs by at most one nucleotide from the sequence of SEQ ID NO 121.

A preferred promoter comprises a Sunflower homeodomain leucine-zipper protein Hahb-4 binding site, preferably comprising SEQ ID NO. 124, more preferably comprising a sequence having at least 80% identity to SEQ ID NO. 123 and comprising SEQ ID NO. 124, and more preferably comprising SEQ ID NO. 123. Where such promoter does not comprise the exact sequence SEQ ID NO. 123, contains the exact sequence SEQ ID NO. 124 and has a minimum of 80% identity to SEQ ID NO. 123 and thus preferably differs by at most two nucleotides from the sequence of SEQ ID NO 123 and even more preferably differs by at most one nucleotide from the sequence of SEQ ID NO 123.

A preferred promoter comprises a Transcriptional repressor BELLRINGER, preferably comprising SEQ ID NO. 126, more preferably comprising a sequence having at least 80% identity to SEQ ID NO. 125 and comprising SEQ ID NO. 126, and more preferably comprising SEQ ID NO. 125. Where such promoter does not comprise the exact sequence SEQ ID NO. 125, contains the exact sequence SEQ ID NO. 126 and has a minimum of 80% identity to SEQ ID NO. 125 and thus preferably differs by at most two nucleotides from the sequence of SEQ ID NO 125 and even more preferably differs by at most one nucleotide from the sequence of SEQ ID NO 125.

A preferred promoter comprises a Floral homeotic protein APETALA1, preferably comprising SEQ ID NO. 128, more preferably comprising a sequence having at least 85% identity to SEQ ID NO. 127 and comprising SEQ ID NO. 128, and more preferably comprising SEQ ID NO. 127. Where such promoter does not comprise the exact sequence SEQ ID NO. 127, contains the exact sequence SEQ ID NO. 128 and has a minimum of 85% identity to SEQ ID NO. 127 and thus preferably differs by at most three nucleotides from the sequence of SEQ ID NO 127, more preferably by at most two nucleotides from the sequence of SEQ ID NO 127 and even more preferably differs by at most one nucleotide from the sequence of SEQ ID NO 127.

A preferred promoter comprises an inducer of CBF expression 1, also called AtMYC2 (rd22BP1), preferably comprising SEQ ID NO. 130, more preferably comprising a sequence having at least 85% identity to SEQ ID NO. 129 and comprising SEQ ID NO. 130, and more preferably comprising SEQ ID NO. 129. Where such promoter does not comprise the exact sequence SEQ ID NO. 129, contains the exact sequence SEQ ID NO. 130 and has a minimum of 85% identity to SEQ ID NO. 129 and thus preferably differs by at most two nucleotides from the sequence of SEQ ID NO 129 and even more preferably differs by at most one nucleotide from the sequence of SEQ ID NO 129.

A preferred promoter comprises a binding site for bZIP factors DPBF-1 and/or 2, preferably comprising SEQ ID NO. 132, more preferably comprising a sequence having at least 81% identity to SEQ ID NO. 131 and comprising SEQ ID NO. 132, and more preferably comprising SEQ ID NO. 131. Where such promoter does not comprise the exact sequence SEQ ID NO. 131, contains the exact sequence SEQ ID NO. 132 and has a minimum of 81% identity to SEQ ID NO. 131 and thus preferably differs by at most two nucleotides from the sequence of SEQ ID NO 131 and even more preferably differs by at most one nucleotide from the sequence of SEQ ID NO 131.

A preferred promoter comprises a binding site for Class I GATA factors, preferably comprising SEQ ID NO. 134, more preferably comprising a sequence having at least 88% identity to SEQ ID NO. 133 and comprising SEQ ID NO. 134, and more preferably comprising SEQ ID NO. 133. Where such promoter does not comprise the exact sequence SEQ ID NO. 133, contains the exact sequence SEQ ID NO. 134 and has a minimum of 88% identity to SEQ ID NO. 133 and thus preferably differs by at most two nucleotides from the sequence of SEQ ID NO 133 and even more preferably differs by at most one nucleotide from the sequence of SEQ ID NO 133.

A preferred promoter comprises a binding site for Dof2 single zinc finger transcription factor, preferably comprising SEQ ID NO. 136, more preferably comprising a sequence having at least 88% identity to SEQ ID NO. 135 and comprising SEQ ID NO. 136, and more preferably comprising SEQ ID NO. 135. Where such promoter does not comprise the exact sequence SEQ ID NO. 135, contains the exact sequence SEQ ID NO. 136 and has a minimum of 88% identity to SEQ ID NO. 135 and thus preferably differs by at most two nucleotides from the sequence of SEQ ID NO 135 and even more preferably differs by at most one nucleotide from the sequence of SEQ ID NO 135.

A preferred promoter comprises a combination of two or more of the aforementioned transcription factor binding sites or cis-active elements. Preferably, the promoter comprises a TATA-box, a CPRF binding site, a TCP class I transcription factor binding site and a bZIP protein G-Box binding factor 1 binding site, each as defined above. Particularly preferred is a promoter comprising the sequence SEQ ID NO. 138 and/or SEQ ID NO. 139, or a sequence being at least 70% identical, preferably 80% identical, more preferably at least 90% identical to any of these sequences, and even more preferably differing from any of these sequences by at most 10 nucleotides, even more preferably by at most 9 nucleotides, even more preferably by at most 8 nucleotides, even more preferably by at most 7 nucleotides, even more preferably by at most 6 nucleotides, even more preferably by at most 5 nucleotides, even more preferably by at most 4 nucleotides, even more preferably by at most 3 nucleotides, even more preferably by at most 2 nucleotides, even more preferably by at most 1 nucleotide. Where such promoter comprises a sequence being at least 70% identical to SEQ ID NO. 138, the promoter preferably comprises at least one binding site for each of the transcription factors CPRF, TCP class I transcription factor and bZIP protein G-Box binding factor 1 as defined above, and preferably comprises at least each sequence according to SEQ ID NO. 114, 118 and 120. Where such promoter comprises a sequence being at least 70% identical to SEQ ID NO. 139, the promoter preferably comprises at least one binding site for each of the transcription factors BELLRINGER, APETALA1, CBF expression inducer 1, DPBF-1 and 2, Class I GATA factors and Dof2 as defined above, and preferably comprises at least each sequence according to SEQ ID NO. 126, 128, 130, 132, 134 and 136.

The function of the transcription factors referred herein are known to the skilled person. By providing the corresponding transcription factor binding sites, e.g. as defined above, the skilled person achieves the benefits inherent in the action of these transcription factors. Particularly, the skilled person can combine two or more and preferably all of the aforementioned transcription factor binding sites.

With respect to the present invention the difference between nucleic acid sequences is calculated as the minimum number of substitutions, insertions or deletions required to transform one sequence into the other. Thus, for example, a sequence "ACGT" and "ATGT" differ by one nucleotide and have 75% sequence identity relative to the first sequence, and the sequences "AACCGGTT" and "AACTGTT" differ by two nucleotides, i.e one deletion and one substitution, and have 87.5% sequence identity relative to the first sequence. For the purposes of the present invention, sequences are given in the form of DNA sequences, the corresponding RNA sequences being considered identical, such that a substitution of "T" by "U" and vice versa is disregarded.

The promoter preferably has a length of at least or exactly 98 nucleotides, even more preferably at least or exactly 142 nucleotides, even more preferably at least or exactly 160 nucleotides, even more preferably at least or exactly 197 nucleotides, even more preferably at least or exactly 235 nucleotides and even more preferably at least or exactly 1063 nucleotides. A promoter having a length of not more than 98 nucleotides is particularly suitable for cloning of target genes under severe size limitation, a promoter of not more than 142 nucleotides is also still useful for cloning of target genes under severe size limitation, a promoter of not more than 160 nucleotides is also still useful for cloning of target genes under severe size limitation but is less preferred due to its larger size, a promoter of not more than 197 nucleotides is also still useful for cloning of target genes under severe size limitation but is less preferred due to its larger size, a promoter of not more than 235 nucleotides is also still useful for cloning of target genes under severe size limitation but is less preferred due to its larger size. Suitable promoters are selected preferably among those given in any of SEQ ID NO. 141, 144, 147, 150, 153, 156 and 159, and also in any of SEQ ID NO. 171-220, 231-275 and 286-300. Suitable promoters are also selected preferably among those having at least 70%, more preferably at least 80% and more preferably at least 90% sequence identity to any of SEQ ID NO. 141, 144, 147, 150, 153, 156, 159, 171-220, 231-275 and 286-300, and preferably comprise two or more transcription factor binding sites as described above.

Preferred nucleic acid sequences comprising a combination of a promoter and an enhancer of the present invention are selected from those of SEQ ID NO. 143, 146, 149, 152, 155, 158 and 1, and also from those of SEQ ID NO. 161-170, 221-230, 276-285 and 301-310. The order of preference for the sequences of SEQ ID NO. 161-170, 221-230, 276-285 and 301-310 and the reasons therefore are given above.

The invention also provides an expression cassette, comprising or consisting of a recombinant nucleic acid as described above. Where such recombinant nucleic acid does not already comprise a promoter, the expression cassette additionally comprises a promoter, preferably a plant promoter as described above. Thus, an expression cassette according to the present invention comprises, in 5' to 3' direction, a promoter, an untranslated region being or comprising the enhancer of the present invention, a target gene and optionally a terminator or other elements. The expression cassette of the present invention preferably comprises a promoter as defined above and an untranslated region or enhancer as described above. This way, the advantages attributed supra to the promoter and enhancer can be achieved using the expression cassette of the present invention. The expression cassette allows an easy transfer of a target gene into an organism, preferably a cell and preferably a plant cell.

Thus, the expression cassette of the present invention preferably comprises a promoter which in turn comprises
- a TATA-box, preferably comprising SEQ ID NO. 108, more preferably comprising a sequence having at least 89% identity to SEQ ID NO. 107 and comprising SEQ ID NO. 108, and more preferably comprising SEQ ID NO. 107, and
- a CPRF factor binding site, preferably comprising SEQ ID NO. 114, more preferably comprising a sequence having at least 90% identity to SEQ ID NO. 113 and comprising SEQ ID NO. 114, and more preferably comprising SEQ ID NO. 113, and
- a TCP class I transcription factor binding site, preferably comprising SEQ ID NO. 116, more preferably comprising a sequence having at least 90% identity to SEQ ID NO. 115 and comprising SEQ ID NO. 116, and more preferably comprising SEQ ID NO. 115, and
- a bZIP protein G-Box binding factor 1 binding site, preferably comprising SEQ ID NO. 118, more preferably comprising a sequence having at least 85% identity to SEQ ID NO. 117 and comprising SEQ ID NO. 118, and more preferably comprising SEQ ID NO. 117, and preferably also comprises at least one, preferably at least two, more preferably at least three and most preferably all of the following elements:
- a Ry motif, preferably comprising SEQ ID NO. 110, more preferably comprising a sequence having at least 88% identity to SEQ ID NO. 109 and comprising SEQ ID NO. 110, and more preferably comprising SEQ ID NO. 109,
- a prolamin box, preferably comprising SEQ ID NO. 112, more preferably comprising a sequence having at least 90% identity to SEQ ID NO. 111 and comprising SEQ ID NO. 112, and more preferably comprising SEQ ID NO. 111,
- a Cis-element as in GAPDH promoters conferring light inducibility, preferably comprising SEQ ID NO. 120, more preferably comprising a sequence having at least 90% identity to SEQ ID NO. 119 and comprising SEQ ID NO. 120, and more preferably comprising SEQ ID NO. 119,
- a SBF-1 binding site, preferably comprising SEQ ID NO. 122, more preferably comprising a sequence having at least 90% identity to SEQ ID NO. 121 and comprising SEQ ID NO. 122, and more preferably comprising SEQ ID NO. 121, and
- a Sunflower homeodomain leucine-zipper protein Hahb-4 binding site, preferably comprising SEQ ID NO. 124, more preferably comprising a sequence having at least 90% identity to SEQ ID NO. 123 and comprising SEQ ID NO. 124, and more preferably comprising SEQ ID NO. 123.

Also preferably the promotor comprises or consists of
a) a nucleic acid according to any of SEQ ID NO. 141, 142, 144, 145, 147, 148, 150, 151, 153, 154, 156, 157, 159 to 310, or
b) a nucleic acid having at least 70% sequence identity to any of the nucleic acid sequences according to a).

The advantages conferred with such promoters are described above.

Most preferred is a promoter-enhancer combination comprising or consisting of the sequence according to SEQ ID NO 1 or of a sequence having at least 70% sequence identity to the sequence of SEQ ID NO. 1. Such sequence is found flax (*Linum usitatissimum*) and allows for seed specific and highly active expression of more or less any target gene expressible in plant seeds. Interestingly the advantages conferred by the combination of a promoter, particularly the promoter found in SEQ ID NO. 1, and the enhancer of the present invention had not been noticed despite attempts in the prior art to analyze the characteristics of the promoter. For example, in WO0116340 a construct is created comprising the promoter found in SEQ ID NO. 1, but the enhancer region had been deleted. Thus, only a sequence as given in SEQ ID NO. 311 has been fused in this document to a GUS reporter gene. However, it has now been found that by including the enhancer of the present invention a substantial increase of reporter gene activity can be achieved.

The expression cassette of the present invention is preferably comprised in a vector. Thus, the vector of the present invention allows to transform a cell, preferably a plant cell, with a long target gene or a combination of multiple genes while achieving a high expression or activity of the target gene functionally linked to the enhancer of the present invention.

Correspondingly the invention provides a plant, plant organ or plant cell comprising an expression cassette according to the present invention or a recombinant nucleic acid according to the present invention. Of course the recombinant nucleic acid should also comprise a promoter such as to allow for the expression of the target gene, because an increase of expression or activity of the target gene by the enhancer of the present invention obviously cannot be effected if the target gene is not expressed at all due to lack of a promoter. The plant, plant organ or plant cell makes use of the advantages conferred by the enhancer, recombinant nucleic acid or expression cassette of the present invention such that expression or activity of the target gene is increased compared to a plant, plant organ or plant cell comprising the same promoter and target gene combination without the enhancer of the present invention.

From what is given above it is clear that the invention also provides a method of increasing expression or activity of a target gene, comprising the steps of
i) providing, upstream of the target gene, an untranslated region and a plant promotor to obtain an expression cassette according to the present invention, and
ii) introducing the expression cassette into a plant cell.

The enhancer is, corresponding to the indications given above, preferably heterologous to the promoter and/or to the target gene. The expression cassette is introduced into the plant cell to allow for expression of the target gene in the plant cell or in plant cells derived from the exact plant cell that was subjected to introduction of the expression cassette. Thus, the above method of the invention encompasses the introduction of the expression cassette into a first plant cell and growth of further cells from the first cells, wherein the further cells can form for example a full plant or a plant organ, preferably a seed. Depending on the promoter of the expression cassette, the target gene is expressed in one or more of the further cells or during a selected stage of growth, for example during seed formation, or under selected environmental conditions, for example heat or drought stress or pathogen infection.

Also as described above the enhancer or expression cassette of the present invention is used for
increasing expression or activity of a target gene,
producing a vector according to the present invention, and/or for
producing a plant, plant organ or plant cell according to the present invention.

The advantages conferred by the above uses have been described supra in detail.

Unless indicated otherwise, the following definitions apply for the current invention:

The term "nucleic acid" refers to deoxyribonucleotides or ribonucleotides and polymers thereof ("polynucleotides") in either single- or double-stranded form, composed of monomers (nucleotides) containing a sugar, phosphate and a base, which is either a purine or pyrimidine. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated.

A "codon" is a nucleotide sequence of three nucleotides which encodes a specific amino acid.

One nucleotide sequence can be "complementary" to another sequence, meaning that they have the base on each position is the complementary (i.e. A to T, C to G) and in the reverse order. If one strand of the double-stranded DNA is considered the "sense" strand, then the other strand, considered the "antisense" strand, will have the complementary sequence to the sense strand. This distinction is due to "sense" sequences which code for proteins, and the complementary "antisense" sequences which are by nature non-functional.

A "nucleic acid fragment" is a fragment of a given nucleic acid molecule.

"Genetic elements" are nucleic acid fragments of solitary building blocks like genes, introns, promoters etc.

In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid" or "nucleic acid sequence" or "polynucleotide sequence" are used interchangeably.

The "degeneracy code" is reflecting the redundancy of the genetic code characterized by its non-ambiguity. For example, although codons GAA and GAG both specify glutamic acid (redundancy), neither of them specifies any other amino acid (no ambiguity). Degeneracy results because there are more codons than amino acids to be encoded. Degenerate codon substitutions may be achieved by generating sequences in which the third position of one or more selected (or all) codons is substituted with mixed-base and/or deoxyinosine residues (Batzer 1991; Ohtsuka 1985; Rossolini 1994).

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The terms "genome" or "genomic DNA" is referring to the heritable genetic information of a host organism. Said genomic DNA comprises the DNA of the nucleus (also referred to as chromosomal DNA) but also the DNA of the plastids (e.g. chloroplasts) and other cellular organelles (e.g. mitochondria). Preferably the terms genome or genomic DNA is referring to the chromosomal DNA of the nucleus.

The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

"Coding sequence" refers to a DNA or RNA molecule that codes for a specific amino acid molecule and excludes the "non-coding sequences". It may constitute an "uninterrupted coding sequence", i.e., lacking an intron, such as in a cDNA or it may include one or more introns bounded by appropriate splice junctions. An "intron" is a molecule of RNA which is contained in the primary transcript but which is removed through cleavage and re-ligation of the RNA within the cell to create the mature mRNA that can be translated into a protein.

A "regulatory sequence" refers to nucleotide molecules influencing the transcription, RNA processing or stability, or translation of the associated (or functionally linked) nucleotide molecules to be transcribed. The transcription regulating nucleotide molecule may have various localizations with respect to the nucleotide molecules to be transcribed. The transcription regulating nucleotide molecule may be located upstream (5' non-coding sequences), within, or downstream (3' non-coding sequences) of the molecule to be transcribed (e.g., a coding sequence). The transcription regulating nucleotide molecule may be selected from the group comprising enhancers, promoters, translation leader sequences, introns, 5'-untranslated sequences, 3'-untranslated sequences, and polyadenylation signal sequences. They include natural and synthetic molecules as well as molecules, which may be a combination of synthetic and natural molecules. The term "transcription regulating nucleotide molecule" is not limited to promoters. However, preferably a transcription regulating nucleotide molecule of the invention comprises at least one promoter molecule (e.g., a molecule localized upstream of the transcription start of a gene capable to induce transcription of the downstream molecules). In one preferred embodiment the transcription regulating nucleotide molecule of the invention comprises the promoter molecule of the corresponding gene and—optionally and preferably—the native 5'-untranslated region of said gene. Furthermore, the 3'-untranslated region and/or the polyadenylation region of said gene may also be employed. As used herein, the term "cis-element" or "promoter motif" refers to a cis-acting transcriptional regulatory element that confers an aspect of the overall control of gene expression. A cis-element may function to bind transcription factors, transacting protein factors that regulate transcription. Some cis-elements bind more than one transcription factor, and transcription factors may interact with different affinities with more than one cis-element.

A "functional RNA" refers to an antisense RNA, microRNA, siRNA, ribozyme, or other RNA that is not translated.

"Transcription" takes place when RNA polymerase makes a copy from the DNA to mRNA. "mRNA" conveys genetic information from DNA to the ribosome, where they specify the amino acid sequence of the protein products of gene expression. Non-eukaryotic mRNA is, in essence, mature upon transcription and normally requires no processing. Eukaryotic pre-mRNA, requires "processing", meaning that the pre-mRNA is modified post-transcriptionally. Processing includes e.g. 5' cap addition, splicing, polyadenylation.

The term "RNA transcript" refers to the product resulting from RNA polymerase catalyzed transcription of a DNA molecule. When the RNA transcript is a perfect complementary copy of the DNA molecule, it is referred to as the primary transcript or it may be a RNA molecule derived from post-transcriptional processing of the primary transcript and is referred to as the mature RNA.

"Messenger RNA" (mRNA) refers to the RNA that is without introns and that can be translated into protein by the cell.

"cDNA" refers to a single- or a double-stranded DNA that is complementary to and derived from mRNA.

The terms "open reading frame" and "ORF" refer to the amino acid sequence encoded between translation initiation and termination codons of a coding sequence. "Translation" proceeds in four phases: initiation, elongation, translocation and termination. The terms "initiation codon" and "termination codon" refer to a unit of three adjacent nucleotides ("codon") in a coding sequence that specifies initiation and chain termination, respectively, of protein synthesis (mRNA translation). Initiation involves the small subunit of the ribosome binding to the 5' end of mRNA with the help of initiation factors (IF). The start codon is the first codon of a mRNA transcript translated by a ribosome. The start codon always codes for methionine in eukaryotes and a modified Met (fMet) in prokaryotes. The most common start codon is AUG. Termination of the polypeptide happens when the A site of the ribosome faces a stop codon (UAA, UAG, or UGA).

"5' non-coding sequence" or "5'-untranslated sequence" or "-region" refers to a sequence of a nucleotide molecule located 5' (upstream) to the codikeine ahnungng sequence. It is present in the fully processed mRNA upstream of the initiation codon and may affect processing of the primary transcript to mRNA, mRNA stability or translation efficiency.

"3' non-coding sequence" or "3'-untranslated sequence" or "-region" refers to a sequence of a nucleotide molecule located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

"Promoter" refers to a nucleotide molecule, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide molecule that includes a minimal promoter plus regulatory elements that is capable of controlling the expression of a coding sequence or functional RNA. This type of promoter molecule consists of proximal and more distal upstream elements, the latter elements often referred to as enhancers. Accordingly, such an "enhancer" is a DNA molecule which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors, which control the effectiveness of transcription initiation in response to physiological or developmental conditions. A person skilled in the art is aware of methods for rendering a unidirectional to a bidirectional promoter and of methods to use the complement or reverse complement of a promoter sequence for creating a promoter having the same promoter specificity as the original sequence. Such methods are for example described for constitutive as well as inducible promoters by Xie et al. (2001) "Bidirectionalization of polar promoters in plants" nature biotechnology 19 pages 677-679. The authors describe that it is sufficient to add a minimal promoter to the 5' prime end of any given promoter to receive a promoter controlling expression in both directions with same promoter specificity. The promoters of the present invention desirably contain cis-elements that can confer or modulate gene expression, also called transcription factor binding sites. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequent manipulation.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive promoter" refers to a promoter that is able to express the open reading frame (ORF) that it controls in all or nearly all of the plant tissues during all or nearly all developmental stages of the plant. Each of the transcdankmachs gut, and fühl dich gedrücktription-activating elements do not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic molecules as well as molecules which may be a combination of synthetic and natural molecules. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as epidermis, green tissue, embryo or cotyledon), or specific cell types (such as leaf parenchyma or seed storage cells). These also include promoters that are temporally regulated, such as in early or late embryogenesis, during leaf expansion fruit ripening in developing seeds or fruit, in fully differentiated leaf, or at the onset of senescence.

"Tissue-specific transcription" in the context of this invention means the transcription of a nucleic acid molecule by a transcription regulating nucleic acid molecule in a way that transcription of said nucleic acid molecule in said tissue contribute to more than 90%, preferably more than 95%, more preferably more than 99% of the entire quantity of the RNA transcribed from said nucleic acid molecule in the entire plant during any of its developmental stage. The transcription regulating nucleotide molecules specifically disclosed herein are considered to be tissue-specific transcription regulating nucleotide molecules.

"Tissue-preferential transcription" in the context of this invention means the transcription of a nucleic acid molecule by a transcription regulating nucleic acid molecule in a way that transcription of said nucleic acid sequence in the said tissue contribute to more than 50%, preferably more than 70%, more preferably more than 80% of the entire quantity of the RNA transcribed from said nucleic acid sequence in the entire plant during any of its developmental stage.

"Inducible promoter" refers to those regulated promoters that can be turned on in one or more cell types or that cause increased expression upon an external stimulus, such as a chemical, light, hormone, stress, or a pathogen.

A terminator, or transcription terminator is a section of genetic sequence that marks the end of gene or operon on genomic DNA for transcription.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

As part of gene expression, "translation" is the process through which cellular ribosomes manufacture proteins. In translation, messenger RNA (mRNA) produced by transcription is decoded by the ribosome to produce a specific amino acid chain, or polypeptide, that will later fold into an active protein. In bacteria, translation occurs in the cell's cytoplasm, where the large and small subunits of the ribosome are located, and bind to the mRNA. In eukaryotes, translation occurs across the membrane of the endoplasmic reticulum in a process called vectorial synthesis. The ribosome facilitates decoding by inducing the binding of transfer RNAs (tRNA) with complementary anticodon sequences to that of the mRNA.

The Kozak sequence on an mRNA molecule is recognized by the ribosome as the translational start site, from which a protein is coded by that mRNA molecule. The ribosome requires this sequence, or a possible variation to initiate translation. The sequence is identified by the notation (gcc) gccRccAUGG,
which summarizes data analysed by Kozak from a wide variety of sources (about 699 in all; Kozak M (October 1987). "An analysis of 5'-noncoding sequences from 699 vertebrate messenger RNAs". Nucleic Acids Res. 15 (20): 8125-8148.) as follows: a lower case letter denotes the most common base at a position where the base can nevertheless vary; upper case letters indicate highly-conserved bases, i.e. the 'AUGG' sequence is constant or rarely changes, 'R' which indicates that a purine (adenine or guanine) is always observed at this position (with adenine being claimed by Kozak to be more frequent); and the sequence in brackets ((gcc)) is of uncertain significance. Preferably, the Kozak consensus sequence it that of *Arabidopsis thaliana* AAA-AUG-GC.

A transfer RNA (tRNA) is an adaptor molecule composed of RNA that serves as the physical link between the nucleotide sequence of nucleic acids (DNA and RNA) and the amino acid sequence of proteins. It does this by carrying an amino acid to the protein synthetic machinery of a cell (i.e. the ribosome) as directed by a codon in the mRNA.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

The "expression pattern" of a promoter (with or without enhancer) is the pattern of expression levels, which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the "steady state" concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates. The rate of degradation can however be considered to proceed at a fixed rate when the transcribed molecules are identical, and thus this value can serve as a measure of synthesis rates. When promoters are compared in this way, techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA. The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter molecules that the sequence surrounding the initiation site ("initiator") plays an important role in determining the level of RNA expression directed by that specific promoter. This includes also part of the transcribed sequences. The direct fusion of promoter to reporter molecules would therefore lead to suboptimal levels of transcription. A commonly used procedure to analyze expression patterns and levels is through determination of the "steady state" level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression. Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

Preferably, the level of expression of a promoter of the current invention is analyzed on the basis of the target gene activity (conversion efficiency) as calculated by the sum of target gene products (in the examples below: ARA and EPA) divided by the total of target gene substrates and products (in the examples below: 20:3n-6, 20:4n-3, ARA and EPA).

"Constitutive expression" refers to expression using a constitutive or regulated promoter. "Conditional" and "regulated expression" refer to expression controlled by a regulated promoter.

"Specific expression" is the expression of gene products, which is limited to one or a few tissues (spatial limitation) and/or to one or a few developmental stages (temporal limitation) e.g. of a plant. It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The terms "polypeptide", "peptide", "oligopeptide", "gene product", "expression product" and "protein" are used interchangeably herein to refer to a polymer or oligomer of consecutive amino acid residues. As used herein, the term "amino acid sequence" or a "polypeptide sequence" refers to a list of abbreviations, letters, characters or words representing amino acid residues. Amino acids may be referred to herein by either their commonly known three letter symbols or by the one-letter symbols recommended by the IUPAC-IUB Biochemical Nomenclature Commission. The abbreviations used herein are conventional one letter codes for the amino acids: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid (see L. Stryer, Biochemistry, 1988, W. H. Freeman and Company, New York. The letter "x" as used herein within an amino acid sequence can stand for any amino acid residue.

The term "wild-type", "natural" or "natural origin" means with respect to an organism, polypeptide, or nucleic acid sequence that said organism is naturally occurring or available in at least one naturally occurring organism which is not changed, mutated, or otherwise manipulated by man.

"Recombinant DNA molecule" is a combination of DNA sequences that are joined together using recombinant DNA technology and procedures used to join together DNA sequences as described, for example, in Sambrook et al., 1989.

"Genetic modification" is the result of recombinant DNA modification, meaning an organism is recombinantly modified resulting in modified characteristics compared to the wild-type organism, which has not been genetically modified.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The terms "heterologous DNA molecule", or "heterologous nucleic acid," as used herein, each refer to a molecule that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA molecule. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous DNA molecule" is a DNA molecule that is naturally associated with a host cell into which it is introduced.

The heterologous nucleotide molecule to be expressed in e.g. a plant tissue, plant organ, plant, seed or plant cell is preferably operably linked to one or more introns having expression enhancing effects, NEENAs (WO2011023537, WO 2011023539), 5' and or 3'-untranslated regions, transcription termination and/or polyadenylation signals. 3'-untranslated regions are suitable to stabilize mRNA expression and structure. This can result in prolonged presence of the mRNA and thus enhanced expression levels. Termination and polyadenylation signals are suitable to stabilize mRNA expression (e.g., by stabilization of the RNA transcript and thereby the RNA level) to ensure constant mRNA transcript length and to prevent read-through transcription. Especially in multigene expression constructs this is an important feature. Furthermore correct termination of transcription is linked to re-initiation of transcription from the regulatory 5' nucleotide sequence resulting in enhanced expression levels. The above-mentioned signals can be any signal functional in plants and can for example be isolated from plant genes, plant virus genes or other plant pathogens. However, in a preferred embodiment the 3'-untranslated regions, transcription termination and polyadenylation signals are from the genes employed as the source for the promoters of this invention.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

A "reporter gene" is a special target gene. Meaning that such reporter genes are often attached to regulatory sequences because the characteristics they confer on organisms expressing them are easily identified and measured, or because they are selectable markers. Reporter genes are often used as an indication of whether a certain gene has been taken up by or expressed in the cell or organism. A "marker gene" encodes a selectable trait to be screened for.

The term "chimeric gene" refers to any gene that contains
  DNA sequences, including regulatory and coding sequences, that are not functionally linked together in nature, or
  sequences encoding parts of proteins not naturally adjoined, or
  parts of promoters that are not naturally adjoined.

Accordingly, a chimeric gene may comprise regulatory molecules and coding sequences that are derived from different sources, or comprise regulatory molecules, and coding sequences derived from the same source, but arranged in a manner different from that found in nature.

"Chimeric transacting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

An "oligonucleotide" corresponding to a nucleotide sequence of the invention, e.g., for use in probing or amplification reactions, may be about 30 or fewer nucleotides in length (e.g., 9, 12, 15, 18, 20, 21, 22, 23, or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

An "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals. The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a non-translated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development. In a preferred embodiment, such expression cassettes will comprise the transcriptional initiation region of the invention linked to a nucleotide sequence of interest. Such an expression cassette is preferably provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such, as the octopine synthase and nopaline synthase termination regions and others described below (see also, Guerineau 1991; Proudfoot 1991; Sanfacon 1991; Mogen 1990; Munroe 1990; Ballas 1989; Joshi 1987).

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Operably-linked" or "functionally linked" refers preferably to the association of nucleic acid molecules on single nucleic acid fragment so that the function of one is affected by the other. For example, a regulatory DNA molecule is said to be "operably linked to" or "associated with" a DNA molecule that codes for an RNA or a polypeptide if the two molecules are situated such that the regulatory DNA molecule affects expression of the coding DNA molecule (i.e., that the coding sequence or functional RNA is under the transcriptional control of the promoter). Coding sequences can be operably-linked to regulatory molecules in sense or antisense orientation.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

The term "transformation" refers to the transfer of a nucleic acid fragment into the genome of a host cell, resulting in genetically stable inheritance. Host cells containing the transformed nucleic acid fragments are referred to as "transgenic cells", and organisms comprising transgenic cells are referred to as "transgenic organisms". Examples of methods of transformation of plants and plant cells include *Agrobacterium*-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed", "transgenic", and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed", "transformant", and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as *Agrobacterium*-mediated transformation or biolistic bombardment), but not selected for stable maintenance. "Stably transformed" refers to cells that have been selected and regenerated on a selection media following transformation.

"Genetically stable" and "heritable" refer to chromosomally-integrated genetic elements that are stably maintained in the plant and stably inherited by progeny through successive generations.

"Chromosomally-integrated" refers to the integration of a foreign gene or DNA construct into the host DNA by covalent bonds. Where genes are not "chromosomally integrated", they may be "transiently expressed." Transient expression of a gene refers to the expression of a gene that is not integrated into the host chromosome but functions independently, either as part of an autonomously replicating plasmid or expression cassette, for example, or as part of another biological system such as a virus. "Transient expression" refers to expression in cells in which a virus or a transgene is introduced by viral infection or by such methods as *Agrobacterium*-mediated transformation, electroporation, or biolistic bombardment, but not selected for its stable maintenance.

"Overexpression" refers to the level of expression in transgenic cells or organisms that exceeds levels of expression in normal or untransformed (non-transgenic) cells or organisms.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide. The term "transit peptide" as used herein refers part of an expressed polypeptide (preferably to the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

The activity of a transcription regulating nucleotide molecule is considered equivalent if transcription is initiated in the same tissues as is by the reference molecule. Such expression profile is preferably demonstrated using reporter genes operably linked to said transcription regulating nucleotide sequence. Preferred reporter genes (Schenborn 1999) in this context are green fluorescence protein (GFP) (Chuff 1996; Leffel 1997), chloramphenicol transferase, luciferase (Millar 1992), β-glucuronidase or β-galactosidase. Especially preferred is β-glucuronidase (Jefferson 1987).

Beside this the transcription regulating activity of a functional equivalent homolog or fragment of the transcription regulating nucleotide molecule may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences, which—in comparison with its parent sequence—does, not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase by at least 50%, more preferably by at least 100%, most preferably by at least 500%.

What is meant by "substantially the same activity" or "the same activity" when used in reference to a polynucleotide fragment or a homolog is that the fragment or homolog has at least 90% or more, e.g., 91%, 92%, 93%, 94%, 95%, 96%, 97%, 98%, up to at least 99% of the expression regulating activity of the full length polynucleotide.

"Significant increase" is an increase that is larger than the margin of error inherent in the measurement technique, preferably an increase by about 2-fold or greater.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae. Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and clubmosses; gymnosperms such as conifers, cycads, ginkgo and Gnetaeae; algae such as Chlorophyceae, Phaeophpyceae, Rhodophyceae, Myxophyceae, Xanthophyceae, Bacillariophyceae (diatoms) and Euglenophyceae. Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Indaceae such as gladioli, iris, freesia and crocus, Compositae such as marigold, Geraniaceae such as geraniums, Lillaceae such as Drachaena, Moraceae such as ficus, Araceae such as philodendron and many others. The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidogsis*, very particularly the species *thaliana* and many others; the family of the Compositae, particularly the genus *Lactuca*, very particularly the species *sativa* (lettuce) and many others. The transgenic plants according to the invention may be selected among monocotyledonous crop plants, such as, for example, cereals such as wheat, barley, sorghum and millet, rye, triticale, maize, rice or oats, and sugarcane. Further preferred are trees such as apple, pear, quince, plum, cherry, peach, nectarine, apricot, *papaya*, mango, and other woody species including coniferous and deciduous trees such as poplar, pine, *sequoia*, cedar, oak, etc. Especially preferred are *Arabidopsis thaliana, Nicotiana tabacum*, oilseed rape, soybean, corn (maize), wheat, *Linum usitatissimum* (linseed and flax), *Camelina sativa, Brassica juncea*, potato and tagetes. *Brassica napus* is used synonymously with rapeseed and canola herein.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

"Mature seed" is a seed that has fully developed and has undergone all the stages of its development successfully. Such a seed can germinate into a seedling if provided with the necessary physical conditions. What are harvested are usually mature seeds.

The term "altered plant trait" means any phenotypic or genotypic change in a transgenic plant relative to the wild-type or non-transgenic plant host.

A "transgenic plant" is a plant having one or more plant cells that contain an expression vector or recombinant expression construct.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

The term "variant" or "homolog" with respect to a sequence (e.g., a polypeptide or nucleic acid sequence such as—for example—a transcription regulating nucleotide molecule of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

Sequence comparisons maybe carried out using a Smith-Waterman sequence alignment algorithm (see e.g., Waterman (1995)). The localS program, version 1.16, is preferably used with following parameters: match: 1, mismatch penalty: 0.33, open-gap penalty: 2, extended-gap penalty: 2.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

As used herein, "reference sequence" is a defined sequence used as a basis for sequence comparison. A reference sequence may be a subset or the entirety of a specified sequence; for example, as a segment of a full length cDNA or gene sequence or isolated nucleic acid sequence capable of regulating expression in plants, preferably the complete cDNA or gene sequence or isolated nucleic acid sequence capable of regulating expression in plants is the reference sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. In a preferred embodiment the comparison window defining the homology of sequence consists of the entire query sequence. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similaritymethod of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul, supra. Multiple alignments (i.e. of more than 2 sequences) are preferably performed using the Clustal W algorithm (Thompson 1994; e.g., in the software VectorNTI™, version 9; Invitrogen Inc.) with the scoring matrix BLOSUM62MT2 with the default settings (gap opening penalty 15/19, gap extension penalty 6.66/0.05; gap separation penalty range 8; % identity for alignment delay 40; using residue specific gaps and hydrophilic residue gaps).

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See http://www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, preferably the complete query or reference sequence as defined by SEQ ID NO: x, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 90%, 95%, and most preferably at least 98%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The term "substantial identity" in the context of a polypeptide indicates that a peptide comprises a sequence with at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. The reference sequences of the invention is defined by SEQ ID NO: x.

An indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m=81.5° C.+16.6(\log_{10} M)+0.41(\% \ GC)-0.61(\% \ \text{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, 4, 5, 6, 7, 8, 9, or 10° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

The term "fatty acid" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in WO 2004/101757.

Fatty acids are described herein by a simple notation system of "X:Y", wherein the number before the colon indicates the number of carbon atoms in the fatty acid and the number after the colon is the number of double bonds that are present. The number following the fatty acid designation indicates the position of the double bond from the carboxyl end of the fatty acid with the "c" affix for the cis configuration of the double bond [e.g., palmitic acid (16:0), stearic acid (18:0), oleic acid (18:1, 9c), petroselinic acid (18:1, 6c), LA (18:2, 9c, 12c), GLA (18:3, 6c,9c, 12c) and ALA (18:3, 9c,12c,15c)]. Unless otherwise specified 18:1, 18:2 and 18:3 refer to oleic, LA and linolenic fatty acids. If not specifically written as otherwise, double bonds are assumed to be of the cis configuration. For instance, the double bonds in 18:2 (9, 12) would be assumed to be in the cis configuration.

Nomenclature of Polyunsaturated Fatty Acids (PUFAs):

| Common name | | Chemical name | |
|---|---|---|---|
| linoleic acid | LA | cis-9,12-octadecadienoic acid | 18:2 ω-6 |
| gamma-linoleic acid | GLA | cis-6,9,12-octadecatrienoic acid | 18:3 ω-6 |
| alpha-linoleic acid | ALA | cis-9,12,15-octadecatrienoic acid | 18:3 ω-3 |
| stearidonic acid | STA | cis-6,9,12,15-octadecatetraenoic acid | 18:4 ω-3 |
| eicosadienoic acid | EDA | cis-11,14-eicosadienoic acid | 20:2 ω-6 |
| dihomo-gamma linoleic acid | DGLA | cis-8,11,14-eicosatrienoic acid | 20:3 ω-6 |
| eicosatrienoic acid | ETrA | cis-11,14,17-eicosatrienoic acid | 20:3 ω-3 |
| arachidonic acid | AA | cis-5,8,11,14-eicosatetraenoic acid | 20:4 ω-6 |
| eicosatetraenoic acid | ETA | cis-8,11,14,17-eicosatetraenoic acid | 20:4 ω-3 |
| eicosapentaenoic acid | ETA | cis-5,8,11,14,17-eicosapentaenoic acid | 20:5 ω-3 |
| docosapentaenoic acid | DPA | cis-7,10,13,16,19-docosapentaenoic acid | 22:5 ω-3 |
| docosahexaenoic acid | DHA | cis-4,7,10,13,16,19-docosapentaenoic acid | 22:6 ω-3 |

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan. Such oils can contain long chain PUFAs.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see WO 2005/003322). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a $C_{14/16}$ elongase, a $C_{16/18}$ elongase, a $C_{18/20}$ elongase and/or a $C_{20/22}$ elongase.

"Desaturase" is a polypeptide which can desaturate one or more fatty acids to produce a mono- or poly-unsaturated fatty acid or precursor which is of interest. Of particular interest herein are delta-8 desaturases that will desaturate a fatty acid between the 8$^{th}$ and 9$^{th}$ carbon atom numbered from the carboxyl-terminal end of the molecule and that can, for example, catalyze the conversion of EDA to DGLA and/or ETrA to ETA Other useful fatty acid desaturases include, for example:

a. delta-5 desaturases that catalyze the conversion of DGLA to ARA and/or ETA to EPA;
b. delta-6 desaturases that catalyze the conversion of LA to GLA and/or ALA to STA;
c. delta-4 desaturases that catalyze the conversion of DPA to DHA;
d. delta-12 desaturases that catalyze the conversion of oleic acid to LA;
e. delta-15 desaturases that catalyze the conversion of LA to ALA and/or GLA to STA;
f. delta-17 desaturases that catalyze the conversion of ARA to EPA and/or DGLA to ETA; and
g. delta-9 desaturases that catalyze the conversion of palmitate to palmitoleic acid (16:1) and/or stearate to oleic acid (18:1).

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., The Plant Cell 8:281-292 (1996)). In the first step, which has been found to be both substrate-specific and also rate-limiting, malonyl-GoA is condensed with a long-chain acyl-CoA to yield $CO_2$ and a beta-ketoacyl-CoA (where the acyl moiety has been elongated by two carbon atoms). Subsequent reactions include reduction to beta-hydroxyacyl-CoA, dehydration to an enoyl-CoA and a second reduction to yield the elongated acyl-CoA. Examples of reactions catalyzed by elongase systems are the conversion of GLA to DGLA, STA to ETA and EPA to DPA. For the purposes herein, an enzyme catalyzing the first condensation reaction (i.e., conversion of malonyl-GoA to beta-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{16/18}$ elongase will utilize a $C_{16}$ substrate (e.g., palmitate), a $C_{18/20}$ elongase will utilize a $C_{18}$ substrate (e.g., GLA, STA) and a $C_{20-22}$ elongase will utilize a $C_{20}$ substrate (e.g., EPA). In like manner, a delta-9 elongase is able to catalyze the conversion of LA and ALA to EDA and ETrA, respectively (see WO 2002/077213). It is important to note that some elongases have broad specificity and thus a single enzyme may be capable of catalyzing several elongase reactions (e.g., thereby acting as both a $C_{16/18}$ elongase and a $C_{18/20}$ elongase).

The following figures and examples describe the invention in further detail. The figures and examples are not meant to limit the scope of the invention or of the claims in any way.

Figure 3:
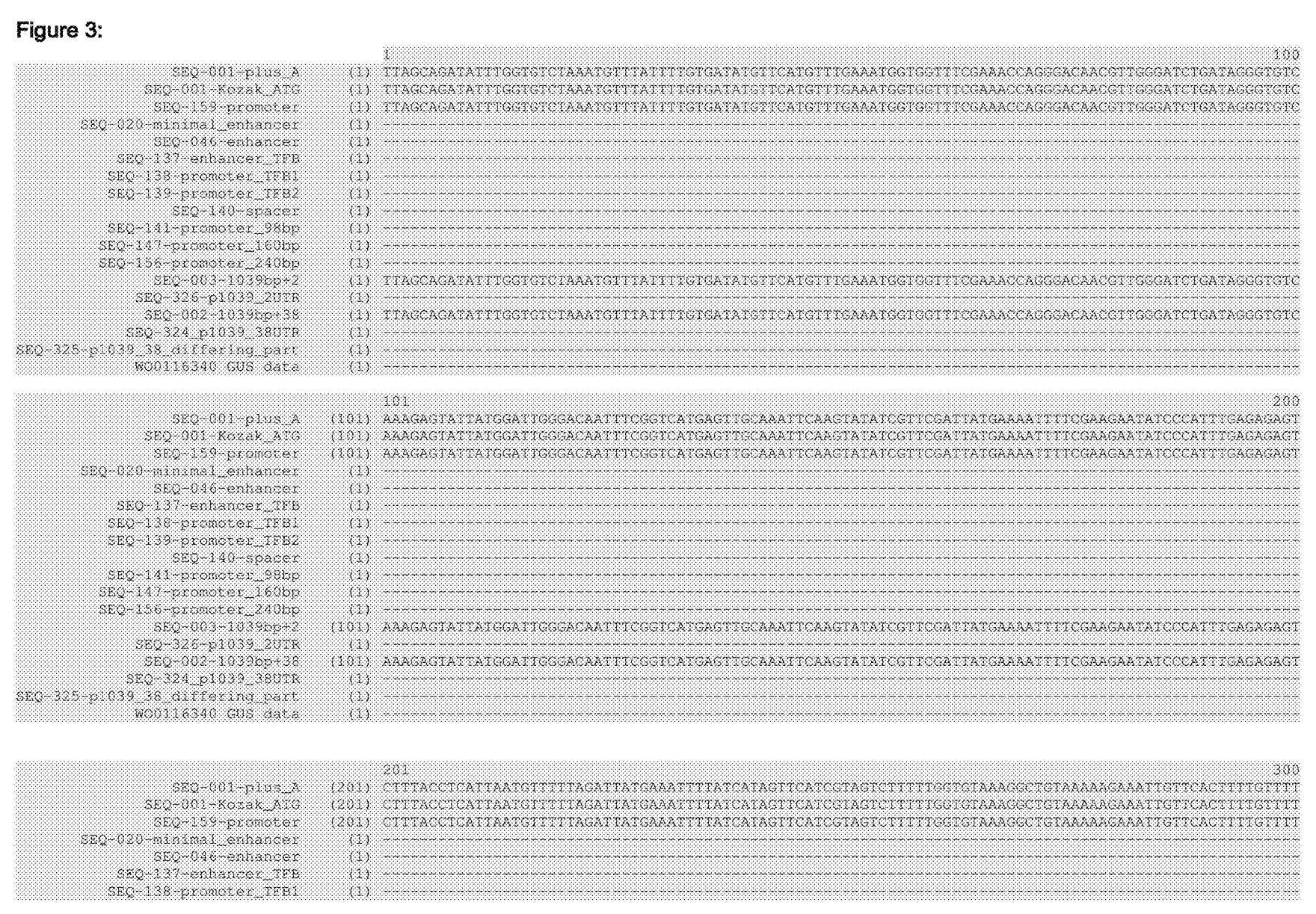
Figure 3:
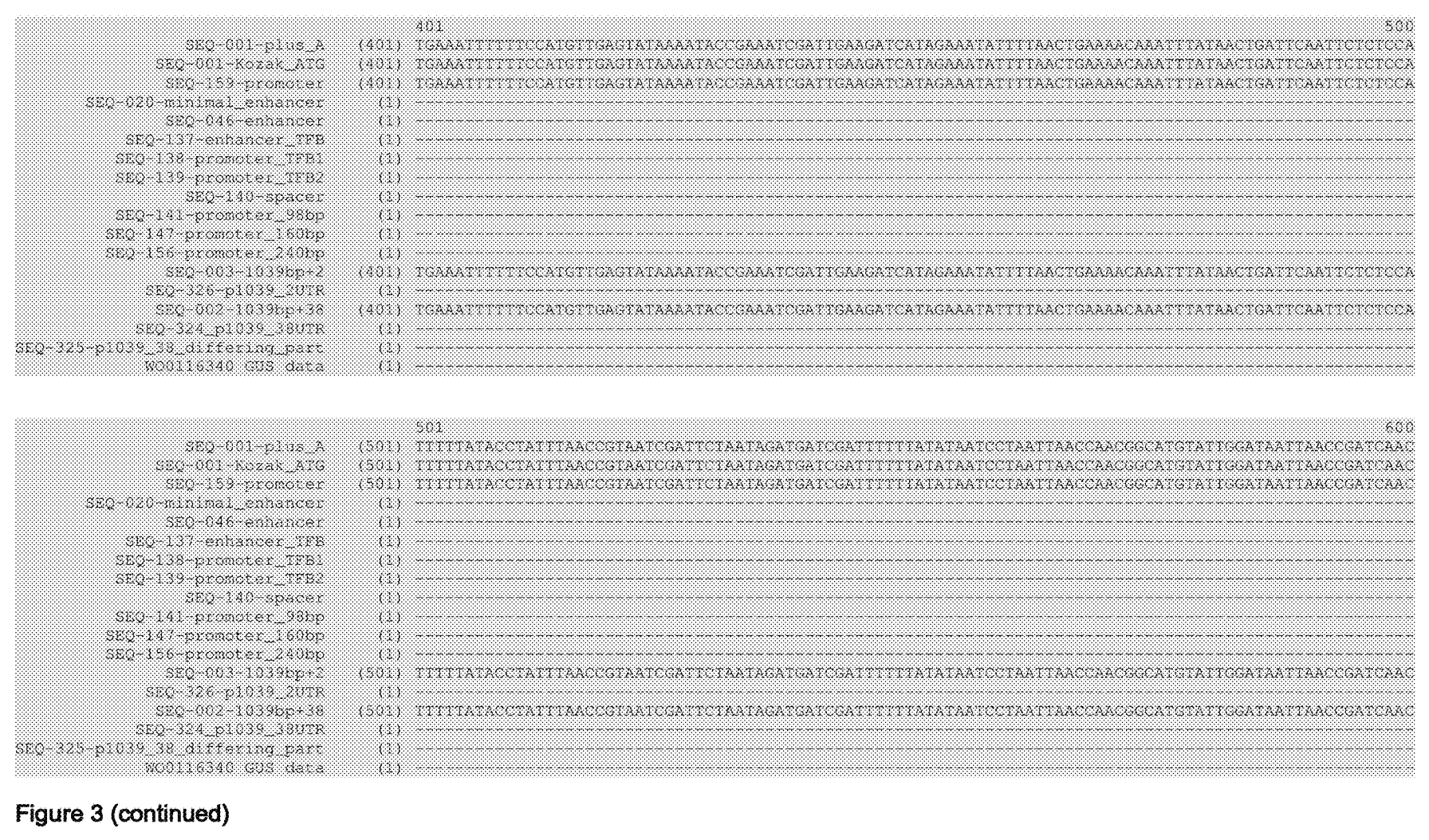
Figure 3:
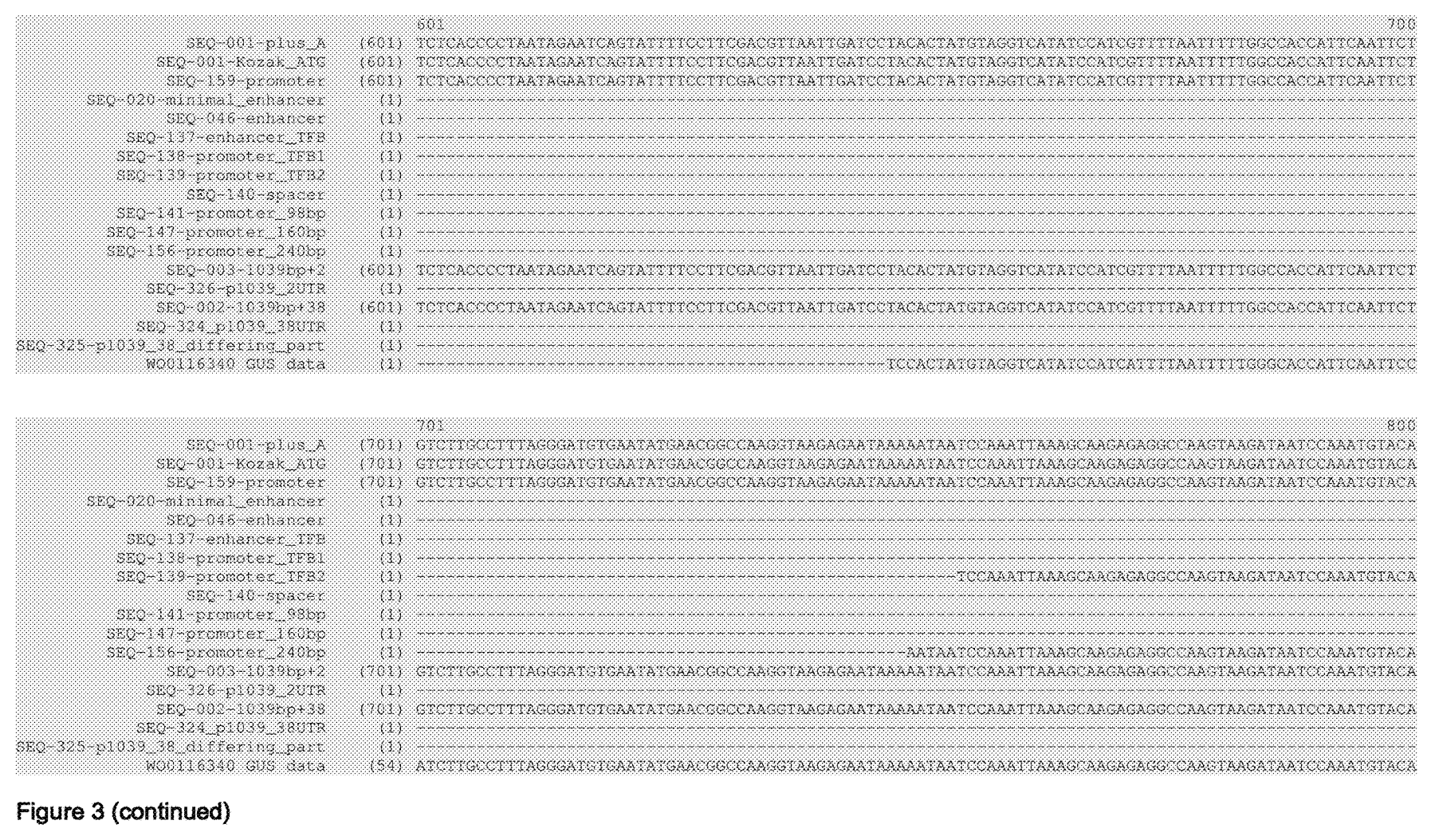
Figure 3:
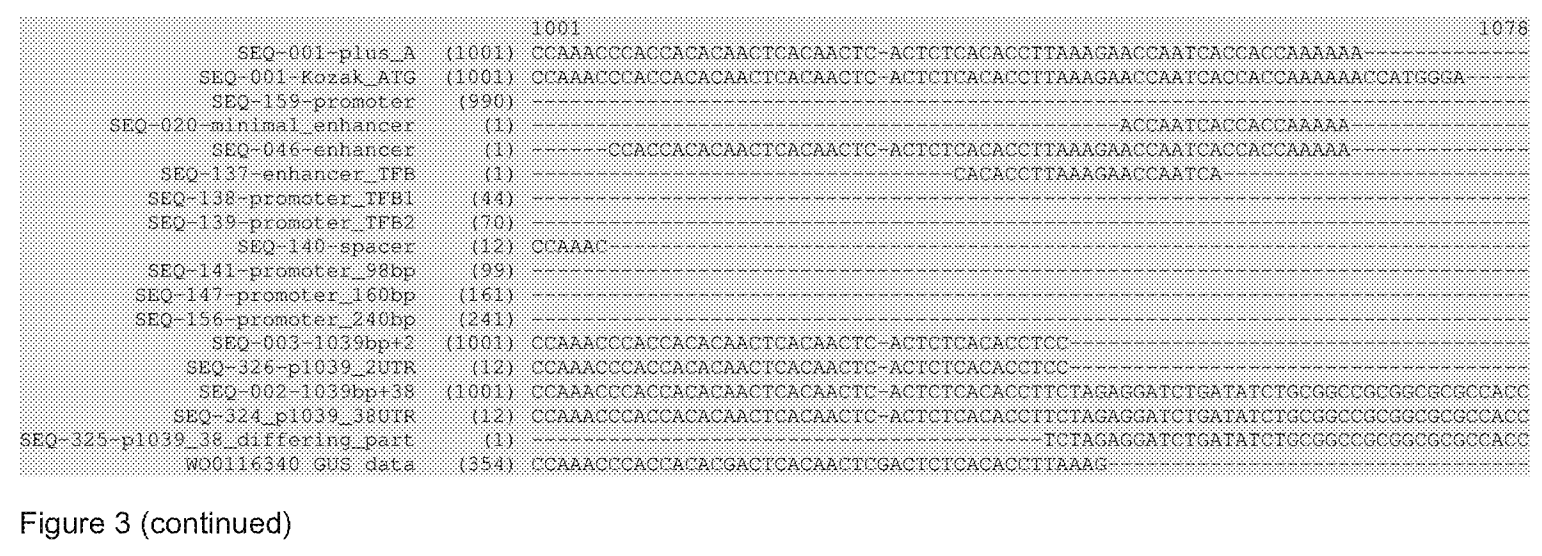

FIG. 3 depicts an alignment of sequences according to the present invention and a prior art sequence (SEQ-001-plus_A (SEQ ID NO: 327); SEQ-001-Kozak_ATG (SEQ ID NO: 328); SEQ-159-promoter (SEQ ID NO: 159); SEQ-020-minimal_enhancer (SEQ ID NO: 20); SEQ-046-enhancer (SEQ ID NO: 46); SEQ-137-enhancer_TFB (SEQ ID NO: 137); SEQ-138-promoter_TFB1 (SEQ ID NO: 138); SEQ-139-promoter_TFB2 (SEQ ID NO: 139); SEQ-140-spacer (SEQ ID NO: 140); SEQ-141-promoter_98bp (SEQ ID NO: 141); SEQ-147-promoter_160bp (SEQ ID NO: 147); SEQ-156-promoter_240bp (SEQ ID NO: 156); SEQ-003-1039bp+2 (SEQ ID NO: 3); SEQ-326-p1039_2UTR (SEQ ID NO: 326); SEQ-002-1039bp+38 (SEQ ID NO: 2); SEQ-324_p1039_38UTR (SEQ ID NO: 324); SEQ-325-p1039_38 differing part (SEQ ID NO: 325); and WO0116340 GUS data (SEQ ID NO: 311).

FIG. 4 depicts the sequences referred to in the present application.

EXAMPLES

With regards to the present invention, the terms "binary vector, "T-DNA containing plasmid" and "T-plasmid" are used interchangeably. An overview of binary vectors and their usage is given by Hellens et al, Trends in Plant Science (2000) 5: 446-451.

Example 1

General Cloning Methods

Cloning methods, e.g. use of restriction endonucleases to cut double stranded DNA at specific sites, agarose gel electrophoreses, purification of DNA fragments, transfer of nucleic acids onto nitrocellulose and nylon membranes, joining of DNA-fragments, transformation of E. coli cells and culture of bacteria, were performed as described in Sambrook et al. (1989) (Cold Spring Harbor Laboratory Press: ISBN 0-87965-309-6). Polymerase chain reaction was performed using Phusion™ High-Fidelity DNA Polymerase (NEB, Frankfurt, Germany) according to the manufacturer's instructions. In general, primers used in PCR were designed such that at least 20 nucleotides of the 3' end of the primer anneal perfectly with the template to amplify. Restriction sites were added by attaching the corresponding nucleotides of the recognition sites to the 5' end of the primer. Fusion PCR, for example described by K. Heckman and L. R. Pease, Nature Protocols (2007) 2, 924-932, was used as an alternative method to join two fragments of interest, e.g. a promoter to a gene or a gene to a terminator.

Example 2

Assembly of Genes Required for EPA and DHA Synthesis within Binary Vectors

Figure 2:
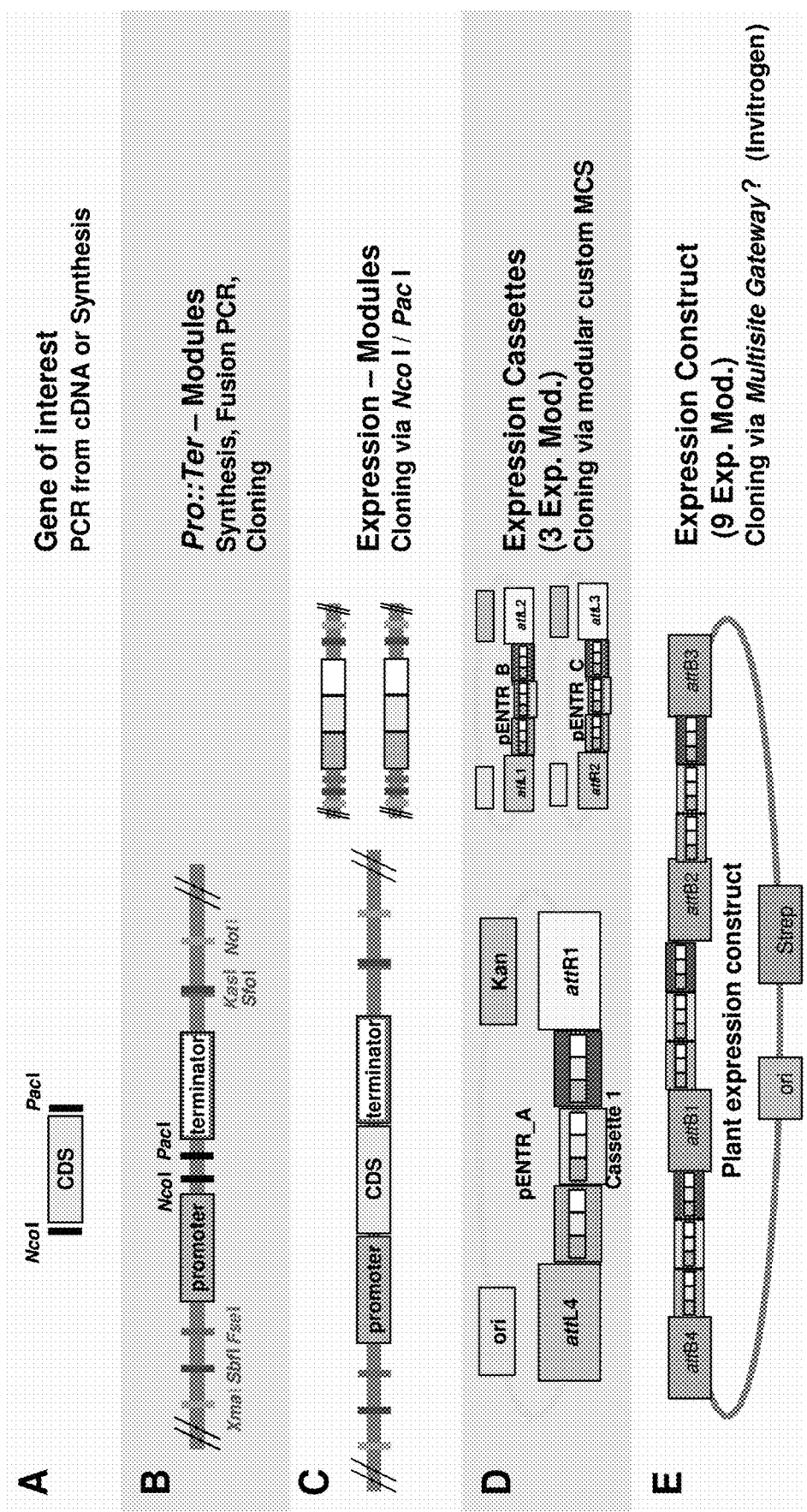
FIG. 2 depicts the general cloning strategy applied in the examples.

The general cloning strategy is depicted in FIG. 2.

Following the modular cloning scheme depicted in FIG. 2, genes were either synthesized by GeneArt (Regensburg) or PCR-amplified using Phusion™ High-Fidelity DNA Polymerase (NEB, Frankfurt, Germany) according to the manufacturer's instructions from cDNA. In both cases a Nco I and/or Asc I restriction site at the 5' terminus, and a Pac I restriction site at the 3' terminus (FIG. 2A) were introduced to enable cloning of these genes between functional elements such as promoters and terminators using these restriction sites such that the genes are functionally linked to both the respective promoter and terminator (see below in this example).

Promoter-terminator modules were created by complete synthesis by GeneArt (Regensburg) or by joining the corresponding expression elements using fusion PCR as described in example 1 and cloning the PCR-product into the TOPO-vector pCR2.1 (Invitrogen) according to the manufacturer's instructions (FIG. 2B). While joining terminator sequences to promoter sequences, recognition sequences for the restriction endonucleases Xma I, Sbf I, Fse I, Kas I, Fso I, Not I were added to either side of the modules in FIG. 2B, and the recognition sites for the restriction endonucleases Nco I, Asc I and Pac I were introduced between promoter and terminator (see FIG. 2B).

To obtain the final expression modules, PCR-amplified genes were cloned between promoter and terminator or intron and terminator via Nco I and/or Pac I restriction sites (FIG. 2C)

Employing the custom multiple cloning site (MCS) containing the recognition sequences for the restriction endonucleases Xma I, Sbf I, Fse I, Kas I, Fso I, Not I, up to three of expression modules were combined as desired to yield expression cassettes harbored by either one of pENTR/A, pENTR/B or pENTR/C constructs (FIG. 2D).

Finally, the Multisite Gateway™ System (Invitrogen) was used to combine three expression cassette harbored by pENTR/A, pENTR/B and pENTR/C (FIG. 2E) to obtain the final binary T-plasmids for plant transformation. Besides features for maintenance of the binary plasmid in E. coli and agrobacteria, the binary T-plasmid contains an acetohydroxyacid synthase (AHAS) gene to allow selection of transgenic plants.

To demonstrate the effectiveness of the enhancer of the invention, particularly of SEQ ID NO. 20 and SEQ ID NO. 46, three different promoter-enhancer combinations (SEQ ID NO. 1-3) based on the Conlinin-1 promoter as described in WO02102970 (FIG. 8) were prepared as described above.

The nucleic acid sequence A comprises a conlinin-1 promoter of SEQ ID NO. 159, a delta-5-desaturase as target gene coding for the amino acid sequence SEQ ID NO. 11 and between the promoter and the target gene an untranslated region of the sequence of SEQ ID NO. 140 fused with the enhancer of SEQ ID NO. 46. SEQ ID NO. 1 thus comprises the promotor and UTR up to the start codon.

The nucleic acid sequence B comprises the conlinin-1 promoter of SEQ ID NO. 159 and the delta-5 desaturase target gene coding for the polypeptide of SEQ ID NO. 11, and between the promoter and the target gene an untranslated region according to SEQ ID NO. 324. This sequence lacks the last 24 nucleotides of the enhancer of the invention according to SEQ ID NO. 46 and completely lacks the enhancer sequence SEQ ID NO. 20. Instead, the last 24 nucleotides of SEQ ID NO. 46 have been replaced by the 38 nucleotides of SEQ ID NO. 325. Even though the sequences A and B are of similar length, the latter sequence has the enhancer of the invention replaced by a sequence of significantly different number of G and T nucleotides. SEQ ID NO. 2 thus comprises the promotor and UTR up to the start codon.

The nucleic acid sequence C comprises the conlinin-1 promoter of SEQ ID NO. 159 and the delta-5 desaturase target gene coding for the polypeptide of SEQ ID NO. 11, and between the promoter and the target gene an untranslated region according to SEQ ID NO. 326. This sequence has the last 24 nucleotides of the enhancer of the invention according to SEQ ID NO. 46 replaced by the sequence "CC". SEQ ID NO. 3 thus comprises the promotor and UTR up to the start codon.

The delta-5 desaturase target gene converts the fatty acid 20:3n-6 to 20:4n-6 (arachidonic acid, ARA) and 20:4n-3 to 20:5n-3 (eicosapentaenoic acid, EPA). The reaction scheme is given in FIG. 1. In order to provide the substrates 20:3n-6 and 20:4n-3 for the delta-5-desaturase reporter gene in Brassica napus seeds, the constructs comprised in addition to the sequences A, B or C, respectively, further desaturase and elongase genes driven by other seed specific promoters in various combinations. This way it is assured that the activity and expression of the target gene is not dependent on any interaction with the desaturase and elongase genes or enzymes necessary for providing the substrates of the target gene. Among the desaturase and elongase genes used where d12d15Des(Ac_GA) (cf. WO 2007042510), d12Des (Ce_GA) (cf. US 2003172398), d12Des(Co_GA2) (cf. WO 200185968), d12Des(Fg) (cf. WO 2007133425), d12Des (Ps_GA) (cf. WO 2006100241), d12Des(Tp_GA) (cf. WO 2006069710), d6Des(Ol_febit) (cf. WO 2008040787), d6Des(Ol_febit)2 (cf. WO 2008040787), d6Des(Ot_febit) (cf. WO 2008040787), d6Des(Ot_GA) (cf. WO 2005083093), d6Des(Ot_GA2) (cf. WO 2005083093), d6Des(Pir) (cf. WO 2002026946), d6Des(Pir_GA1) (cf. WO 2002026946), d6Des(Plu) (cf. WO 2007051577), d6Elo (Pp_GA) (cf. WO 2001059128), d6Elo(Pp_GA2) (cf. WO 2001059128), d6Elo(Pp_GA3) (cf. WO 2001059128), d6Elo(Tp_GA) (cf. WO 2005012316) and d6Elo(Tp_GA2) (cf. WO 2005012316).

Figure 1:
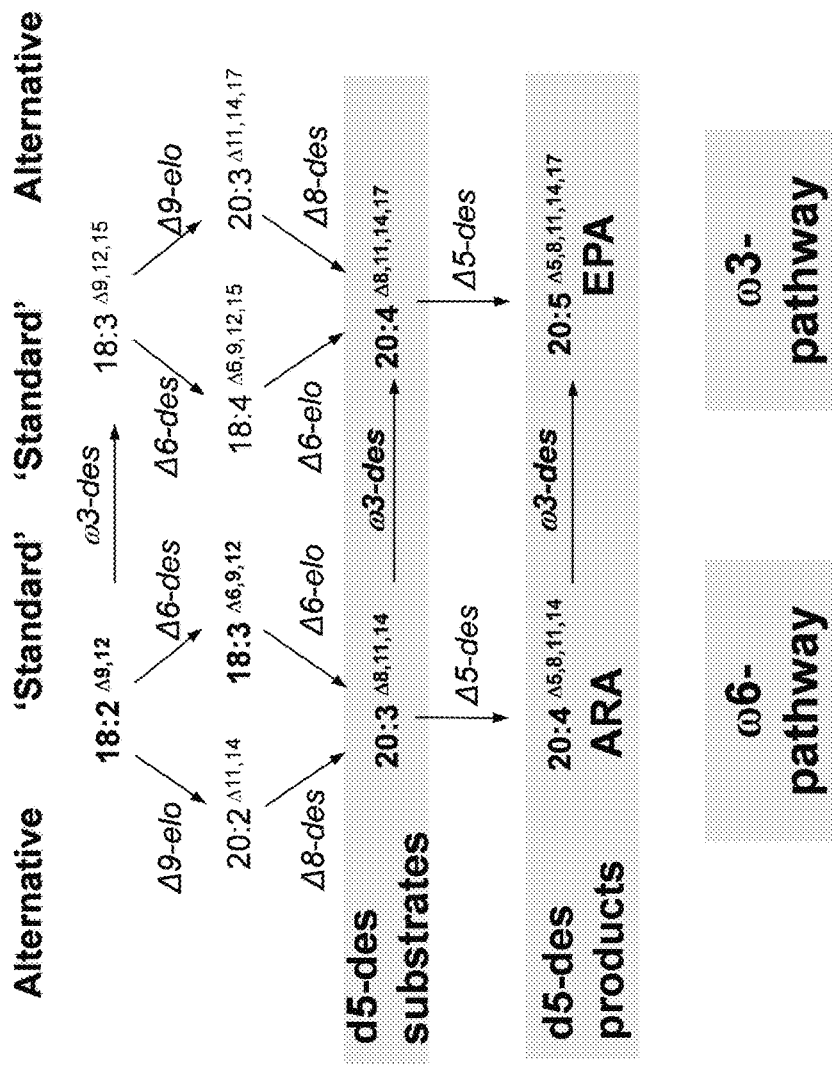
FIG. 1 depicts the general pathways for polyunsaturated fatty acid synthesis up to arachidonic acid and eicosapentaenoic acid.

Activity of the delta-5 desaturase was analyzed by measuring fatty acid concentrations in seeds as described in example 4 and calculating the sum of desaturated products (ARA and EPA) divided by the total of desaturase substrates and products (20:3n-6, 20:4n-3, ARA and EPA) to obtain the conversion efficiency. The constructs frequently comprised genes for omega-3 desaturases. Presence of omega-3-desaturase genes was not motivated by the invention; the respective genes were present to answer questions unrelated to the present invention. Omega-3 desaturase only shift the ratio of the substrates between each other, as well as the ratios of the products between each other; their mode of action is depicted in FIG. 1. Thus, the presence of omega-3 desaturases does not influence the analysis of conversion efficiency nor does it perceptibly influence the activity of the target gene or any other fatty acid desaturase activity.

An alignment of the sequences found in the constructs of the present invention is shown in FIG. 3. An overview of genetic elements employed in the constructs is given in Table 1. The delta-5 desaturase gene sequences SEQ ID NO. 10 and SEQ ID NO. 12 code for the identical polypeptide sequence. The activity of the desaturase is not dependent on either gene sequence. Instead, the sequences can be arbitrarily exchanged without altering the outcome of the comparison experiments.

TABLE 1

Overview of genetic elements. "p-...": Promoter; "d5Des": delta-5 desaturase; "o3Des": omega-3 desaturase

| Genetic element | SEQ ID NO. DNA | SEQ ID NO. Prot |
| --- | --- | --- |
| p-(1064bp) | 1 | |
| p-(1039bp + 38) | 2 | |
| p-(1039bp + 2) | 3 | |
| p-BnNapin | 4 | |
| p-LuPXR | 5 | |
| p-PvArc | 6 | |
| p-VfSBP | 7 | |
| p-BnFAE1 | 8 | |
| p-VfUSP | 9 | |
| d5Des(Tc_GA) | 10 | 11 |
| d5Des(Tc_GA2) | 12 | 11 |
| o3Des(Cp_GA) | 13 | 14 |
| o3Des(Cp_GA2)_V282L | 15 | 16 |
| o3Des(Pi_GA2) | 17 | 18 |
| o3Des(Pi_GA) | 19 | 18 |

Example 3

General Procedure for Production of Transgenic Plants

In general, the transgenic rapeseed plants were generated by a modified protocol according to Moloney et al. 1992, Plant Cell Reports, 8:238-242). For the generation rapeseed plants, the binary vectors described in example 2 were transformed into *Agrobacterium tumefaciens* C58C1: pGV2260 (Deblaere et al. 1984, Nucl. Acids. Res. 13: 4777-4788).

Overnight cultures of agrobacteria harbouring the binary vectors described in example 2 were grown in Murashige-Skoog Medium (Murashige and Skoog 1962 Physiol. Plant. 15, 473) supplemented by 3% saccharose (3MS-Medium). Hypocotyls of sterile rapeseed plants were incubated in a petri dish in a 1:50 diluted agrobacterial suspension obtained from the overnight cultures for 5-10 minutes. This was followed by a three day co-incubation in darkness at 25° C. on 3MS-Medium with 0.8% bacto-agar. After three days the culture was transferred on MS-medium containing 500 mg/l Claforan (Cefotaxime-Natrium), 100 nM Imazethapyr, 20 microM Benzylaminopurin (BAP) and 1.6 g/l Glucose where they were cultivated for 7 days at 25° C. under 16 hours light/8 hours darkness conditions. Growing sprouts—indicating the presence of the T-DNA harboring the AHAS selectable marker, were transferred to MS-Medium containing 2% saccharose, 250 mg/l Claforan and 0.8% Bacto-Agar. Rooting could be stimulated by adding a growth hormone, for example 2-indolbutyl acid.

Regenerated sprouts have been obtained on 2MS-Medium with Imazetapyr and Claforan and were transferred to the greenhouse for further development. After flowering, the mature seeds were harvested and analysed for expression of the genes listed in example 2 via lipid analysis as described in example 4.

Example 4

Lipid Extraction and Lipid Analysis of Plant Oils

Total lipids were extracted from fresh or freeze-dried homogenized plant material (seed or cotyledons) by liquid/liquid extraction using tert-butyl methyl ether.

The fatty acid composition of the extracted lipids was subsequently determined by the means of gas chromatography with flame-ionization detection or mass-selective detection after derivatization of the extracted lipids with trimethylsulfonium hydroxide.

Gas chromatographic separation of the so generated fatty acid methyl esters was performed on a suitable capillary column (50%-Cyanopropylphenyl)-dimethylpolysiloxane as stationary phase).

Identification and quantification of the separated chromatographic signals is accomplished by comparison of the respective retention times and signal intensities to chromatograms of standard solutions with known composition and content of fatty acid methyl esters.

To generate transgenic plants containing the genetic element described in example 2 for production of ARA and EPA in seeds, Canola (*Brassica napus*) was transformed as described in example 3. Selected plants containing the genetic elements described in example 2 where grown until development of mature seeds (Day/night cycle: 16 h at 200 mE and 21° C., 8 h at darkness and 19° C.). Fatty acids from harvested seeds were extracted and analyzed using gas chromatography.

Example 5

Comparison of Construct Containing the Promoter According to the Invention with Construct Containing Promoter not According to the Invention Two constructs (LJB950=comprising SEQ ID NO. 2 without any omega-3 desaturase and LJB997=comprising SEQ ID NO. 1 without any omega-3 desaturase) were evaluated which were identical in all genetic elements and their arrangement in the construct, apart from the promoter-untranslated region combination driving the reporter gene expression. Table 2 shows the result of the three independent transgenic plants (events) obtained for each of the two constructs.

TABLE 2

Comparison of conversion efficiency resulting from the use of two different versions of the Conlinin promoter.

| | 20:3n-6 + 20:4n-3 | ARA + EPA | Convertion Efficiency (%) | n (# of Events) | N = (# of constructs) |
|---|---|---|---|---|---|
| B) LJB950 (Conlinin 1039bp + 38) | 6.9 | 6.9 | 50 | 3 | 1 |
| A) LJB997 (Conlinin 1064bp) | 3.6 | 8.7 | 71 | 3 | 1 |

Surprisingly, use of sequence SEQ ID NO: 1 resulted in significantly higher conversion efficiency compared to SEQ ID NO: 2.

Example 6

Comparison of Constructs Containing the Promoter According to the Invention with Constructs Containing Promoters not According to the Invention A total of 69 constructs were evaluated which all express the delta-5-desaturase protein as shown in SEQ ID NO: 11 as a reporter gene. The reporter gene was functionally linked to SEQ ID NO: 1, SEQ ID NO: 2 or SEQ ID NO: 3. The differences between these three promoter versions are depicted in FIG. 3. In order to provide the substrates 20:3n-6 and 20:4n-3 for the delta-5-desaturase reporter gene in *Brassica napus* seeds, the constructs further contained desaturase and elongase genes driven by other seed specific promoters in various combinations as described in example 2 and table 1.

Table 3 shows that constructs using the SEQ ID NO: 1 constantly display a significantly higher conversion efficiency compared to constructs using SEQ ID NO: 2 or SEQ ID NO:3. This was particularly unexpected as WO 0116340 taught the uses of the promoter similar to SEQ ID NO: 3 using a reporter gene.

TABLE 3

Comparison of conversion efficiency resulting from the use of different constructs; delta-5 desaturase according to SEQ ID NO. 11 was the target gene for all constructs

|  | 20:3n-6 + 20:4n-3 | ARA + EPA | Convertion Efficiency (%) | n (# of Events) | N = (# of constructs) |
|---|---|---|---|---|---|
| constructs comprising SEQ ID NO. 2 and an omega-3 desaturase | 2 | 2.6 | 57 | 425 | 16 |
| constructs comprising SEQ ID NO. 2 without an omega-3 desaturase | 4.1 | 3.3 | 45 | 363 | 10 |
| constructs comprising SEQ ID NO. 3 and an omega-3 desaturase | 1.8 | 2 | 53 | 448 | 16 |
| constructs comprising SEQ ID NO. 1 and an omega-3 desaturase | 1.3 | 3.1 | 70 | 143 | 7 |
| constructs comprising SEQ ID NO. 1 without an omega-3 desaturase | 1.8 | 4 | 69 | 797 | 20 |

We claim:

1. A recombinant nucleic acid comprising a plant promoter, a target gene, and an untranslated region adjacent to the target gene, wherein the untranslated region comprises an enhancer of at least 18 consecutive nucleotides, wherein at least 14 nucleotides are adenosine or cytidine, wherein the enhancer is heterologous to the promoter and to the target gene, wherein the enhancer, promoter, and target gene are operably linked, wherein the enhancer comprises the last 24, 36 or 57 nucleotides of SEQ ID NO: 46; and wherein the promoter comprises or consists of i) nucleic acid of SEQ ID NO: 159 or ii) a nucleic acid having at least 95% sequence identity to the nucleic acid of i), wherein the recombinant nucleic acid does not comprise a nucleic acid sequence according to any of SEQ ID NOS: 311-323.

2. The recombinant nucleic acid of claim 1, wherein the target gene is a fatty acid desaturase or elongase gene.

3. An expression cassette comprising the recombinant nucleic acid of claim 1,
   wherein the promoter comprises
   a) a TATA-box, and
   b) a CPRF factor binding site, and
   c) a TCP class I transcription factor binding site, and
   d) a bZIP protein G-Box binding factor 1 binding site.

4. The expression cassette of claim 3, wherein the promoter further comprises one or more of the following sequences:
   a) a Ry motif,
   b) a prolamin box,
   c) a Cis-element conferring light inducibility,
   d) a SBF-1 binding site, or
   e) a Sunflower homeodomain leucine-zipper protein Hahb-4 binding site.

5. A vector comprising the expression cassette of claim 3.

6. A plant, plant organ or plant cell comprising the recombinant nucleic acid of claim 1, wherein the plant, plant organ or plant cell is of the genus *Brassica*.

7. A method of increasing expression or activity of a target gene, comprising the steps of
   a) providing, upstream of the target gene, an untranslated region and a plant promoter to obtain the expression cassette of claim 3, and
   b) introducing the expression cassette into a plant cell.

8. The expression cassette of claim 4, wherein the Cis-element conferring light inducibility is from a GAPDH promoter.

* * * * *